(12) United States Patent
McCall et al.

(10) Patent No.: US 10,392,389 B2
(45) Date of Patent: *Aug. 27, 2019

(54) HETEROCYCLIC COMPOUNDS FOR THE INHIBITION OF PASK

(71) Applicants: BioEnergenix, LLC, San Francisco, CA (US); John McCall, Boca Grande, FL (US); Robert C. Kelly, Port Charlotte, FL (US); Donna L. Romero, Chesterfield, MO (US)

(72) Inventors: John McCall, Boca Grande, FL (US); Robert C. Kelly, Port Charlotte, FL (US); Donna L. Romero, Chesterfield, MO (US)

(73) Assignee: BioEnergenix LLC, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/438,261

(22) PCT Filed: Oct. 25, 2013

(86) PCT No.: PCT/US2013/066869
§ 371 (c)(1),
(2) Date: Apr. 24, 2015

(87) PCT Pub. No.: WO2014/066795
PCT Pub. Date: May 1, 2014

(65) Prior Publication Data
US 2015/0284395 A1    Oct. 8, 2015

Related U.S. Application Data

(60) Provisional application No. 61/718,356, filed on Oct. 25, 2012.

(51) Int. Cl.
| | | |
|---|---|---|
| *C07D 487/04* | (2006.01) | |
| *A61K 31/519* | (2006.01) | |
| *A61P 3/06* | (2006.01) | |
| *A61K 45/06* | (2006.01) | |
| *A61P 35/04* | (2006.01) | |
| *A61P 3/10* | (2006.01) | |
| *A61P 3/04* | (2006.01) | |

(52) U.S. Cl.
CPC .......... *C07D 487/04* (2013.01); *A61K 31/519* (2013.01); *A61K 45/06* (2013.01); *A61P 3/06* (2018.01)

(58) Field of Classification Search
CPC ............................ C07D 487/04; A61K 31/519
See application file for complete search history.

(56) References Cited

U.S. PATENT DOCUMENTS

| 5,420,128 A | 5/1995 | Kiyokawa et al. |
|---|---|---|
| 5,843,951 A | 12/1998 | Inoue et al. |
| 6,197,774 B1 | 3/2001 | Yamada et al. |
| 9,278,973 B2 | 3/2016 | McCall |
| 2005/0004159 A1 | 1/2005 | Hibi |
| 2005/0136065 A1 | 6/2005 | Valiante et al. |
| 2005/0282827 A1 | 12/2005 | Goetschi et al. |
| 2006/0025426 A1 | 2/2006 | Fraley et al. |
| 2006/0040958 A1 | 2/2006 | Guzi et al. |
| 2006/0041131 A1 | 2/2006 | Guzi et al. |
| 2006/0089362 A1 | 4/2006 | Seno et al. |
| 2006/0094706 A1 | 5/2006 | Paruch et al. |
| 2006/0128725 A1 | 6/2006 | Guzi et al. |
| 2007/0072879 A1 | 3/2007 | McArthur et al. |
| 2007/0281951 A1 | 12/2007 | Guzi et al. |
| 2008/0050384 A1 | 2/2008 | Guzi et al. |
| 2009/0176778 A1 | 7/2009 | Schmitz et al. |
| 2009/0182142 A1 | 7/2009 | Furukubo et al. |
| 2009/0215778 A1 | 8/2009 | Nitz et al. |
| 2010/0152205 A1 | 6/2010 | Hunt et al. |
| 2012/0277224 A1 | 11/2012 | McCall et al. |
| 2015/0274740 A1 | 10/2015 | McCall |
| 2016/0235755 A1 | 8/2016 | McCall |

FOREIGN PATENT DOCUMENTS

| JP | 2004277337 | 10/2004 |
|---|---|---|
| JP | 2005008581 | 1/2005 |
| JP | 2006045156 | 2/2006 |
| WO | 9808847 A1 | 3/1998 |
| WO | WO9841526 | 9/1998 |
| WO | WO2004022062 | 3/2004 |
| WO | WO2004022559 | 3/2004 |
| WO | WO2004022560 | 3/2004 |
| WO | WO2004026229 | 4/2004 |
| WO | WO2007015866 | 2/2007 |
| WO | WO2007048066 | 4/2007 |
| WO | 2008057601 | 5/2008 |

(Continued)

OTHER PUBLICATIONS

Auzzi et al. (Farmaco, 1990, 45(11), pp. 1193-1205).*
Stella (J. Pharmaceutical Sciences, 2010, 99(12), pp. 4755-4765).*
Borisov et al. (J. of Comb. Chem., 2009, 11(6), pp. 1023-1029).*
STN structure database search (Registry# 1338651-46-9, Oct. 28, 2011, p. 1).*
Senga, K., et al., Synthesis and Antischistosomal Activity of Certain Pyrazolo[1,5-a]pyrimidines. J. Med. Chem., 1981, 24(5), 610-13.
Gavrin, L.K. et al., "Synthesis of Pyrazolo[1,5-a]pyrimidinone Regioisomers," J. Org. Chem., 2007, vol. 72, p. 1043-1046.

(Continued)

*Primary Examiner* — Susanna Moore
(74) *Attorney, Agent, or Firm* — Dennis A. Bennett; Brock Levin

(57) ABSTRACT

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

14 Claims, No Drawings

(56) References Cited

FOREIGN PATENT DOCUMENTS

| WO | WO2008057601 | 5/2008 |
| --- | --- | --- |
| WO | WO2008130569 | 10/2008 |
| WO | WO2008134035 | 11/2008 |
| WO | 2010056631 | 5/2010 |
| WO | WO2010056631 | 5/2010 |
| WO | 2011028947 A2 | 3/2011 |
| WO | 2011114148 | 9/2011 |
| WO | 2012149157 | 11/2012 |
| WO | 2014066743 | 5/2014 |
| WO | 2014066795 | 5/2014 |

OTHER PUBLICATIONS

Gavrilenko, B. B., "Syntheses with 3-aminopyrazole. I. Ways to synthesize hydroxy- and amino derivatives of pyrazolo[1,5-a]pyrimidines;" Zhurnal Organicheskoi Khimii (1982), 18(5), 1079-84. (partial translation and compounds).

Hao, H-X, et al. 'PAS kinase is required for normal cellular energy balance.' Proceedings of the National Academy of Sciences 104.39 (2007): 15466-15471.

PCT Patent Application No. PCT/US2013/066782, International Preliminary Report on Patentability, dated Apr. 28, 2015, 7 pages.

PCT Patent Application No. PCT/US2013/066782, International Search Report, dated Feb. 21, 2014, 4 pages.

International Application No. PCT/US2012/035209; International Preliminary Report on Patentability, dated Oct. 29, 2013; 7 pages.

International Application No. PCT/US2012/035209; International Preliminary Report or Patentability, dated Oct. 29, 2013; 07 pages.

International Application No. PCT/US2012/035209; International Search Report and Written Opinion of the International Search Authority, dated Jan. 3, 2013; 12 pages.

International Application No. PCT/US2013/066782; Written Opinion of the International Search Authority, dated Feb. 21, 2014; 06 pages.

International Application No. PCT/US2013/066869; International Preliminary Report or Patentability, dated Apr. 28, 2015; 07 pages.

International Application No. PCT/US2013/066869; International Search Report and Written Opinion of the International Search Authority, dated Feb. 21, 2014; 10 pages.

PubChem (SID#4262975, pp. 1-8, downloaded May 5, 2018/).

U.S. Appl. No. 13/456,838; Advisory Action dated Jul. 26, 2017; 02 pages.

U.S. Appl. No. 13/456,838; Advisory Action dated May 31, 2018; 2 pages.

U.S. Appl. No. 13/456,838; Applicant Initiated Interview Summary dated Aug. 14, 2014; 03 pages.

U.S. Appl. No. 13/456,838; Final Office Action dated Aug. 25, 2015; 09 pages.

U.S. Appl. No. 13/456,838; Final Office Action dated Mar. 16, 2017; 08 pages.

U.S. Appl. No. 13/456,838; Final Office Action dated Mar. 28, 2018; 06 pages.

U.S. Appl. No. 13/456,838; Non-Final Office Action dated Jan. 16, 2015; 08 pages.

U.S. Appl. No. 13/456,838; Non-Final Office Action dated Jun. 30, 2016; 07 pages.

U.S. Appl. No. 13/456,838; Non-Final Office Action dated Sep. 8, 2017; 07 pages.

U.S. Appl. No. 14/438,268; Notice of Allowance dated Oct. 30, 2015; 08 pages.

U.S. Appl. No. 15/010,619; Final Office Action dated Sep. 27, 2017; 06 pages.

U.S. Appl. No. 15/010,619; Non-Final Office Action dated Feb. 24, 2017; 10 pages.

U.S. Appl. No. 15/010,619; Non-Final Office Action dated May 11, 2018; 06 pages.

PubChem (SID#4260883, pp. 1-8, downloaded May 5, 2018).

U.S. Appl. No. 13/456,838; Non-Final Office Action dated Sep. 13, 2018; 16 pages.

U.S. Appl. No. 15/010,619; Final Office Action dated Aug. 30, 2018; 12 pages.

\* cited by examiner

HETEROCYCLIC COMPOUNDS FOR THE INHIBITION OF PASK

This application claims the benefit of priority under 35 U.S.C. § 371 of PCT International Application No. PCT/US2013/066869, filed Oct. 25, 2013, which in turn claims the benefit of priority of U.S. Provisional Application No. 61/718,356, filed Oct. 25, 2012, the disclosures of which are hereby incorporated by reference as if written herein in their entireties.

Disclosed herein are new heterocyclic compounds and compositions and their application as pharmaceuticals for the treatment of disease. Methods of inhibiting PAS Kinase (PASK) activity in a human or animal subject are also provided for the treatment of diseases such as diabetes mellitus.

The regulation of glycogen metabolism is critical for the maintenance of glucose and energy homeostasis in mammals. Glycogen, a large branched polymer of glucose, acts as a reserve of carbon and energy in a variety of organisms. In mammals, the most important stores are found in the liver and skeletal muscle (1). Liver glycogen is required to efficiently buffer blood glucose levels during fasting, whereas muscle glycogen is primarily used locally as a fuel for muscle contraction (2). Dysregulation of glycogen metabolism has been implicated in the development of many diseases, including type 2 diabetes mellitus (3, 4).

The synthesis of glycogen is primarily controlled through regulation of the enzyme glycogen synthase (GYS, various isoforms), which catalyzes bulk glycogen synthesis (5, 6, 7). The muscle isoform of glycogen synthase (GYS1) is inactivated by reversible phosphorylation that occurs at nine distinct sites within the enzyme (8, 9, 10). In the best characterized form of glycogen synthase, the phosphorylation sites are clustered at the N and C termini (14). Glycogen synthase kinase-3 (GSK-3), an insulin-dependent kinase which has long been implicated in the stepwise phosphorylation of four key sites in the C terminus of glycogen synthase including Ser-640 (one of the most important endogenous regulatory phosphorylation sites in mammalian glycogen synthase (15, 32) and Ser-644 (10, 11-13, 24, 25). GSK-3, however, is not the sole kinase that phosphorylates C-terminal regulatory sites; GSK-3-independent mechanisms also exist, since serine-to-alanine substitutions at Ser-7 and Ser-10 block GS K-3-mediated phosphorylation of the important regulatory sites Ser-640 and Ser-644, and phosphorylation at these sites still occurs.

PASK (purine-analog sensitive kinase, PAS kinase) is a PAS domain-containing serine/threonine kinase, and genetic experiments in *S. cerevisiae* yeast have implicated PASK as a physiological regulator of glycogen synthase and glycogen accumulation (16, 17). As with the entire glycogen synthase regulatory system, PASK is highly conserved from yeast to man. Human PASK (hPASK) phosphorylates glycogen synthase primarily at Ser-640, causing near complete inactivation. It is interesting to note that the exact site of PASK-dependent phosphorylation is similar but not identical in yeast and mammalian glycogen synthase (18, 19); yeast PASK phosphorylates glycogen synthase at the site analogous to Ser-644, four residues C-terminal (18). It appears that the hPASK mid region (residues 444-955) is required for efficient phosphorylation of glycogen synthase in vitro and for interaction with glycogen synthase in cells: an hPASK mutant (4955) lacking the noncatalytic N terminus was unable to efficiently phosphorylate glycogen synthase. Since this region is not required for the phosphorylation of generic, nonphysiological substrates, such as histones and synthetic peptides, it has been proposed that the mid region of hPASK is essential for substrate-targeting. A similar substrate region has been discovered in many protein kinases (26-29). Unlike GSK-3, the activity of hPASK has been shown to be independent of insulin and probably regulated instead by a more direct metabolic signal (23).

Genetic and proteomic screens using yeast PASK identified a number of substrates and implicated this kinase in the regulation of carbohydrate metabolism and translation (18). It has previously been shown that yeast PASK phosphorylates glycogen synthase in vitro and that strains lacking the PASK genes (PSK1 and PSK2) had elevated glycogen synthase activity and an approximately 5- to 10-fold accumulation of glycogen relative to wild-type strains, consistent with impaired ability to phosphorylate glycogen synthase in vivo (18). Because glycogen synthesis and translation are two processes tightly regulated in response to nutrient availability and because PAS domains are frequently involved in metabolic sensing, a role for PASK in the cellular response to metabolic status has been proposed. Indeed, it was recently demonstrated that mammalian PASK plays a role in the cellular response to nutrients. The catalytic activity of PASK in pancreatic islet β-cells is rapidly increased in response to glucose addition, and PASK is required for the glucose-responsive expression of some β-cell genes, including preproinsulin (23).

PASK catalytic activity is not responsive to glucose alone, however. The interaction between the hPASK midregion and glycogen synthase is regulated by at least two factors. First, the PAS domain of PAS kinase plays a negative role in regulating this interaction. If the PAS domain is deleted or disrupted, hPASK associates more stably with glycogen synthase. PAS domain function is usually controlled by the metabolic status of the host cell, as has been suggested for the PASK PAS domain (23). This observation raises the intriguing possibility that the hPASK-glycogen synthase interaction is regulated by the metabolic status of the cell, thereby enabling an additional layer of metabolic regulation of glycogen synthesis. Second, glycogen negatively regulates the hPASK-glycogen synthase interaction, which would initially seem counterintuitive, since glycogen would thereby stimulate its own continued synthesis. It is possible, however, that this mechanism exists to spatially coordinate the synthesis of glycogen. It is becoming increasingly apparent that glycogen is synthesized in cells in a highly organized spatial pattern (30). Perhaps one function of hPASK is to maintain free, unlocalized glycogen synthase in a phosphorylated, inactive form until it is properly localized to an existing, properly organized glycogen particle. These data strongly suggest that the hPASK midregion plays an important role in targeting hPASK catalytic activity to specific substrates within the cell.

Since hPASK has been recently implicated in glucose-sensing and glucose-responsive transcription, it appears likely that glucose signaling by means of hPASK affects glycogen metabolism in vivo. It is well-established that derangement in glycogen metabolism is one of the hallmarks of both Type 1 and Type 2 diabetes (20) and related conditions (21), including a panoply of life-threatening cardiovascular conditions (22). Using PASK1 mice, it has further been demonstrated that PASK is indeed required for normal insulin secretion by pancreatic β cells, and that PASK deletion results in nearly complete resistance to the phenotypes caused by a high-fat diet, including obesity, insulin resistance and hepatic fat accumulation. Therefore, PASK inhibition would comprise a system for the metabolic control of glucose utilization and storage in mammalian cells, and offer a new method to treat metabolic diseases including but not limited to diabetes and its complications, the metabolic syndrome, insulin resistance, and various cardiovascular conditions.

Novel compounds and pharmaceutical compositions, certain of which have been found to inhibit PASK have been discovered, together with methods of synthesizing and using the compounds including methods for the treatment of PAS K-mediated diseases in a patient by administering the compounds.

Disclosed herein is a compound of structural Formula I

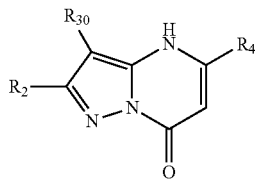

(I)

or a pharmaceutically acceptable salt, ester, or prodrug thereof, wherein:

$R_{30}$ is chosen from cyano, $CH_2CN$, $(CH_2)_yC(O)NR_{31}R_{32}$, and heteroaryl;

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{20}$ is chosen from lower alkyl, arylalkyl, aryl, heteroaryl, and heteroarylalkyl;

$R_{31}$ and $R_{32}$ are each independently chosen from hydrogen, lower alkyl, and aryl; and y is an integer from 0-3.

Certain compounds disclosed herein may possess useful PASK modulating activity, and may be used in the treatment or prophylaxis of a disease or condition in which PASK plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for modulating PASK. Other embodiments provide methods for treating a PAS K-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PASK.

In an embodiment, compounds have structural Formula II

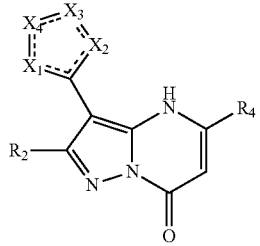

(II)

or a pharmaceutically acceptable salt, ester, or prodrug thereof, wherein:

$X_1$ is chosen from N, O, S, and $CR_{10}$;

$X_2$ is chosen from N, O, S, and $CR_{11}$;

$X_3$ is chosen from $NR_{14}$ and $CR_{12}$;

$X_4$ is chosen from O, $NR_{15}$ and $CR_{13}$;

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{10}$, $R_{11}$, $R_{12}$, and $R_{13}$, are each independently chosen from null, hydrogen, lower alkyl, aryl, lower alkoxy, hydroxy, and halo, or optionally, $R_{12}$ and $R_{13}$ can be taken together to form an aryl or heteroaryl, or $R_{11}$ and $R_{12}$ can be taken together to form an aryl or heteroaryl;

$R_{14}$, and $R_{15}$ are each independently chosen from null, hydrogen, lower alkyl, aryl, lower alkoxy, hydroxy, halo, and $COR_{20}$, $SO_2R_{20}$; and $R_{20}$ is chosen from lower alkyl, arylalkyl, aryl, heteroaryl, and heteroarylalkyl;

wherein at least two of $X_1$-$X_4$ are heteroatoms.

In an embodiment, $R_2$ is chosen from hydrogen, hydroxyl, alkoxy, lower alkyl, lower haloalkyl, any of which may be optionally substituted.

In an embodiment, $R_4$ is chosen from aryl and heteroaryl, either of which may be optionally substituted.

In an embodiment, compounds have structural formula III:

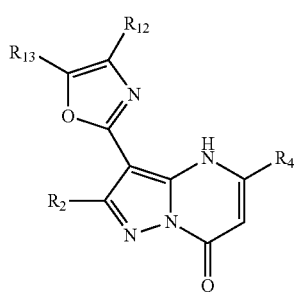

(III)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

R₄ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{12}$ and $R_{13}$ are each independently chosen from hydrogen, lower alkyl, aryl, lower alkoxy, hydroxy, and halo, or optionally, $R_{12}$ and $R_{13}$ can be taken together to form an aryl or heteroaryl; and $R_{20}$ is chosen from lower alkyl, arylalkyl, aryl, heteroaryl, and heteroarylalkyl.

In an embodiment, $R_2$ is chosen from hydrogen, hydroxyl, alkoxy, lower alkyl, lower haloalkyl, any of which may be optionally substituted.

In an embodiment, $R_4$ is chosen from aryl and heteroaryl, either of which may be optionally substituted.

In an embodiment, compounds have structural formula IV:

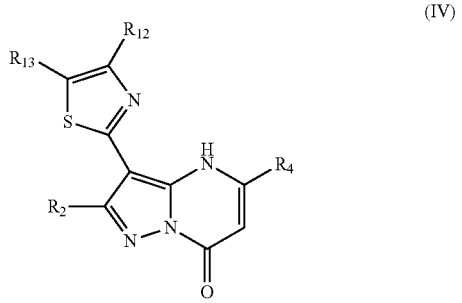

(IV)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{12}$ and $R_{13}$ are each independently chosen from hydrogen, lower alkyl, aryl, lower alkoxy, hydroxy, and halo, or optionally, $R_{12}$ and $R_{13}$ can be taken together to form an aryl or heteroaryl; and $R_{20}$ is chosen from lower alkyl, arylalkyl, aryl, heteroaryl, and heteroarylalkyl.

In an embodiment, compounds have structural formula V:

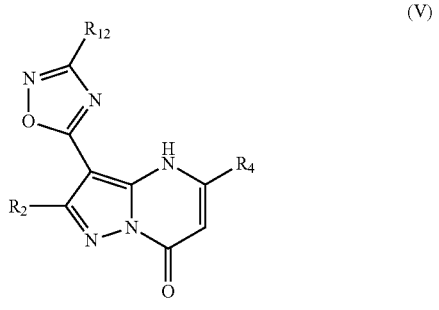

(V)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{12}$ is chosen from hydrogen, lower alkyl, aryl, lower alkoxy, hydroxy, and halo, or optionally, $R_{12}$ and $R_{13}$ can be taken together to form an aryl or heteroaryl; and $R_{20}$ is chosen from lower alkyl, arylalkyl, aryl, heteroaryl, and heteroarylalkyl.

In an embodiment, compounds have structural formula VI:

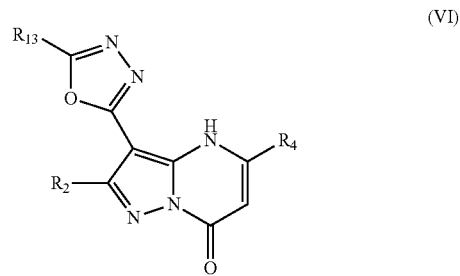

(VI)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{13}$ is chosen from hydrogen, lower alkyl, aryl, lower alkoxy, hydroxy, and halo, or optionally, $R_{12}$ and $R_{13}$ can be taken together to form an aryl or heteroaryl; and $R_{20}$ is chosen from lower alkyl, arylalkyl, aryl, heteroaryl, and heteroarylalkyl.

In an embodiment, compounds have structural formula VII:

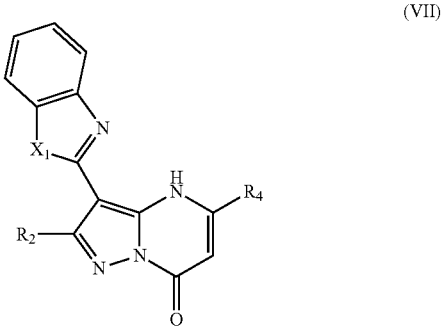

(VII)

or a salt, ester or prodrug thereof, wherein:

$X_1$ is chosen from O and S;

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl; and $R_{20}$ is chosen from lower alkyl, arylalkyl, aryl, heteroaryl, and heteroarylalkyl.

In an embodiment, compounds have structural formula VIII:

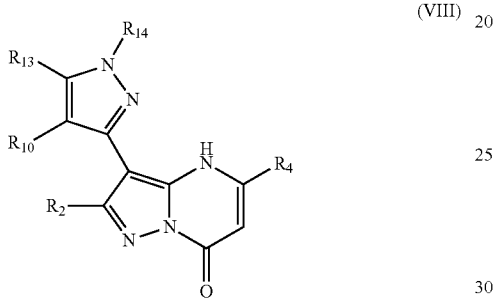

(VIII)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{10}$, $R_{13}$ and $R_{14}$ are each independently chosen from hydrogen, lower alkyl, aryl, lower alkoxy, hydroxy, and halo; and $R_{20}$ is chosen from lower alkyl, arylalkyl, aryl, heteroaryl, and heteroarylalkyl.

In an embodiment, compounds have structural formula IX:

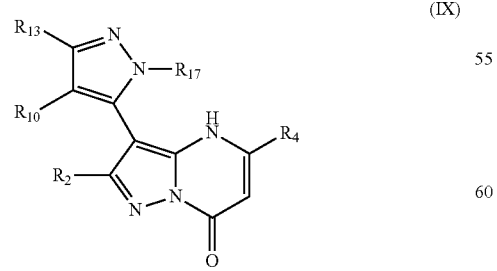

(IX)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{10}$ and $R_{13}$ are each independently chosen from hydrogen, lower alkyl, aryl, lower alkoxy, hydroxy, and halo;

$R_{17}$ is chosen from hydrogen and lower alkyl; and $R_{20}$ is chosen from lower alkyl, arylalkyl, aryl, heteroaryl, and heteroarylalkyl.

In an embodiment, compounds have structural formula X:

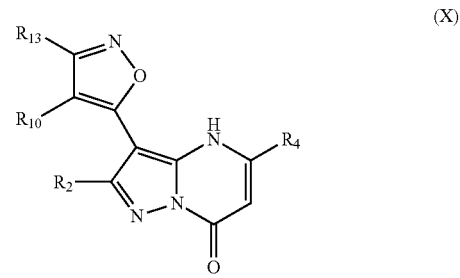

(X)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

$R_4$ is chosen from lower alkyl, $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{10}$ and $R_{13}$ are each independently chosen from hydrogen, lower alkyl, aryl, lower alkoxy, hydroxy, and halo; and $R_{20}$ is chosen from lower alkyl, arylalkyl, aryl, heteroaryl, and heteroarylalkyl.

In an embodiment, compounds have structural formula XI:

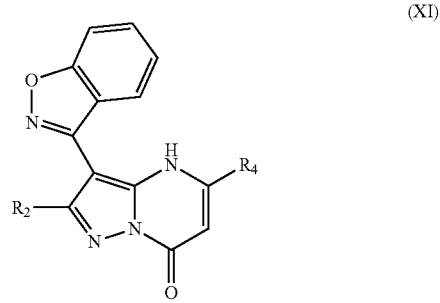

(XI)

or a salt, ester or prodrug thereof, wherein:

$R_2$ is chosen from hydrogen, hydroxy, alkoxy, amino, alkylamino, dialkylamino, $NHCOR_{20}$, lower alkyl, lower haloalkyl, aryl, arylalkyl, heteroaryl and heteroarylalkyl, any of which may be optionally substituted;

R$_4$ is chosen from lower alkyl, CH$_2$CO$_2$R$_5$, alkoxyalkyl, aryl, heteroaryl, cycloalkyl, arylalkyl, heteroarylalkyl, and cycloalkylalkyl, any of which may be optionally substituted;

R$_5$ is chosen from hydrogen and lower alkyl; and

R$_{20}$ is chosen from lower alkyl, arylalkyl, aryl, heteroaryl, and heteroarylalkyl.

Further provided is a compound as disclosed herein together with a pharmaceutically acceptable carrier Further provided is a compound as disclosed herein for use as a medicament.

Further provided is a compound as disclosed herein for use in the manufacture of a medicament for the prevention or treatment of a disease or condition ameliorated by the inhibition of PASK.

Further provided is a compound as disclosed herein for use in the manufacture of a medicament for the prevention or treatment of a disease or condition ameliorated by the inhibition of PASK.

Provided herein is a compound as disclosed herein for use in the prevention or treatment of a disease or condition ameliorated by the inhibition of PASK.

Further provided is a pharmaceutical composition comprising a compound as recited above together with a pharmaceutically acceptable carrier.

Further provided is a method of inhibiting PASK comprising contacting PASK with a compound as disclosed herein.

Further provided is a method of treatment of a disease comprising the administration of a therapeutically effective amount of a compound as disclosed herein to a patient in need thereof.

Further provided is the method as recited above wherein said disease is chosen from cancer and a metabolic disease.

Further provided is the method as recited above wherein said disease is a metabolic disease.

Further provided is the method as recited above wherein said metabolic disease is chosen from metabolic syndrome, diabetes, dyslipidemia, fatty liver disease, non-alcoholic steatohepatitis, obesity, and insulin resistance.

Further provided is the method disclosed herein wherein said diabetes is Type II diabetes.

Further provided is the method as disclosed herein wherein said dyslipidemia is hyperlipidemia.

In an embodiment, said hyperlipidemia is hypertriglyceridemia

Further provided is a method for achieving an effect in a patient comprising the administration of a therapeutically effective amount of a compound as disclosed herein to a patient, wherein the effect is selected from the group consisting of reduction of triglycerides, reduction of cholesterol, and reduction of hemoglobin A1c.

Further provided is the method as disclosed herein wherein said cholesterol is chosen from LDL and VLDL cholesterol.

Further provided is the method as disclosed herein wherein said triglycerides are chosen from plasma triglycerides and liver triglycerides.

Further provided is a method of treatment of a PASK-mediated disease comprising the administration of:
  a. a therapeutically effective amount of a compound as disclosed herein; and
  b. another therapeutic agent.

Not to be bound by any theory or mechanism, the compounds disclosed herein can be used to treat or modulate metabolic disease (including but not limited to diabetes, metabolic disorder, dyslipidemia, fatty liver disease, non-alcoholic steatohepatitis, obesity, and insulin resistance, as well as to reduce triglycerides, cholesterol, and hemoglobin A1c) and cancer.

Further provided is a method of inhibiting CK2 in a cell, comprising contacting the cell, in which inhibition of CK2 is desired with a compound having structural formula I.

Further provided is a method of treating a disease or condition that involves CK2 comprising administering to a patient, in need of said treatment with a compound having structural formula I.

Further provided is a method of treating a disease or condition that involves CK2 comprising administering to a patient, in need of said treatment, a pharmaceutical composition comprising a compound having structural formula I and a pharmaceutically acceptable carrier, excipient, or diluent.

Further provided is a method of treating a disease or condition that involves CK2, wherein the disease or condition is ovarian cancer, cervical cancer, breast cancer, colorectal cancer, or glioblastomas.

Further provided is a compound as disclosed herein for use in the manufacture of a medicament for the prevention or treatment of a disease or condition ameliorated by the inhibition of CK2.

Further provided is a compound as disclosed herein for use in the manufacture of a medicament for the prevention or treatment of a disease or condition ameliorated by the inhibition of CK2.

Provided herein is a compound as disclosed herein for use in the prevention or treatment of a disease or condition ameliorated by the inhibition of CK2.

Further provided is a method of inhibiting PIM1 in a cell, comprising contacting the cell, in which inhibition of PIM1 is desired with a compound having structural formula I.

Further provided is a method of treating a disease or condition that involves PIM1 comprising administering to a patient, in need of said treatment with a compound having structural formula I.

Further provided is a method of treating a disease or condition that involves PIM1 comprising administering to a patient, in need of said treatment, a pharmaceutical composition comprising a compound having structural formula I and a pharmaceutically acceptable carrier, excipient, or diluent.

Further provided is a method of treating a disease or condition that involves PIM1, wherein the disease or condition is ovarian cancer, cervical cancer, breast cancer, colorectal cancer, or glioblastomas.

Further provided is a compound as disclosed herein for use in the manufacture of a medicament for the prevention or treatment of a disease or condition ameliorated by the inhibition of PIM1.

Further provided is a compound as disclosed herein for use in the manufacture of a medicament for the prevention or treatment of a disease or condition ameliorated by the inhibition of PIM1.

Provided herein is a compound as disclosed herein for use in the prevention or treatment of a disease or condition ameliorated by the inhibition of PIM1.

As used herein, the terms below have the meanings indicated.

When ranges of values are disclosed, and the notation "from n$_1$ . . . to n$_2$" is used, where n$_1$ and n$_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 3 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be substituted or quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N— and not embodied in a ring.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethoxy" refers to a X$_3$CO— group where X is a halogen.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R$^n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PASK inhibitor" as used herein refers to a compound that exhibits an (IC$_{50}$/EC$_{50}$) with respect to PASK activity of no more than about 100 μM and more typically not more than about 50 μM, as measured in the PASK assay described generally hereinbelow. IC$_{50}$ is that concentration of inhibitors which reduces the activity of PASK to half-maximal level. Certain compounds disclosed herein have been discovered to exhibit inhibition against PASK.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of a compound as disclosed herein, and at least one other agent selected from the group comprising:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipetidyl peptidase IV) inhibitors such as DPP728, LAF237 (vildagliptin—Example 1 of WO 00/34241), MK-0431, saxagliptin, GSK23A; an AGE breaker; a thiazolidinedione derivative (glitazone) such as pioglitazone or rosiglitazone; and a non-glitazone type PPARδ agonist e.g. GI-262570;

b) hypolipidemic agents such as 3-hydroxy-3-methylglutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine or cannabinoid receptor antagonists;

d) anti-hypertensive agents, e.g., loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutral endopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin n antagonists such as candesartan, eprosartan, irbesartan, losartan, tehnisartan and valsartan, in particular valsartan; renin inhibitors such as aliskiren, terlakiren, ditekiren, RO 66-1132, RO-66-1168; -adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;

e) an HDL increasing compound;

f) cholesterol absorption modulator such as etizimibe and KT6-971;

g) Apo-A1 analogues and mimetics;

h) thrombin inhibitors such as Ximelagatran;

i) aldosterone inhibitors such as anastrazole, fadrazole, and eplerenone;

j) inhibitors of platelet aggregation such as aspirin, and clopidogrel bisulfate;

k) estrogen, testosterone, a selective estrogen receptor modulator, and a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, and compounds decreasing the protein kinase activity such as a PDGF receptor tyrosine kinase inhibitor such as miatinib; and m) an agent interacting with a 5-HT3 receptor and/or an agent interacting with 5-HT4 receptor such as tegaserod described in the U.S. Pat. No. 5,510,353 as example 13, tegaserod hydrogen maleate, cisapride, and cilansetron.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PASK-mediated disorders in a human or animal subject in need of such treatment comprising administering to said subject an amount of a compound disclosed herein effective to reduce or prevent said disorder in the subject, optionally in combination with at least one additional agent that is known in the art. In a related aspect, certain embodiments provide therapeutic compositions comprising at least one compound disclosed herein in combination with one or more additional agents for the treatment of PASK-mediated disorders.

Recent studies have found that elevated medium glucose concentrations caused post-translational activation of PASK. It has also been demonstrated that PASK activity is required for glucose-stimulated insulin expression, as shown by studies in PASK1 mice. It has also been demonstrated that PASK deletion results in nearly complete resistance to the phenotypes caused by a high-fat diet, including obesity, insulin resistance and hepatic fat accumulation. It has been postulated that this protection may be due to an increase in AMPK expression in each of the relevant tissues. PASK deletion abrogates nearly all of the maladaptive phenotype associated with a high-fat diet, possibly in part via maintenance of AMPK expression. Increasing AMPK signaling is a proven therapeutic strategy, as illustrated by Metformin, which acts by increasing the phosphorylation and activation of AMPK Inhibition of PASK signaling elicits similar beneficial effects, but through a distinct mechanism. This complementary therapeutic strategy, either alone or in combination, can be efficacious in the treatment of metabolic diseases. In any case, it appears that PASK inhibition can provide an effective therapeutic strategy for the treatment of diseases, for example Type 2 diabetes, insulin resistance in general, and the metabolic syndrome.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g. high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels—often for decades, before overt diabetes develops. Eventually the beta cells of the pancreas are unable to overcome insulin resistance through hypersecretion. Glucose levels rise, and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with type 2 diabetes includes increased serum very-low-density lipoprotein cholesterol and triglyceride levels and, sometimes, a decreased low-density lipoprotein cholesterol level. Insulin resistance has been found in persons with low levels of high-density lipoprotein. Insulin levels have also been linked to very-low-density lipoprotein synthesis and plasma triglyceride levels.

Accordingly, also disclosed are methods of treating insulin resistance in a subject comprising selecting a subject in need of treatment for insulin resistance; and administering to the subject an effective amount of a compound that inhibits PAS K.

Specific diseases to be treated by the compounds, compositions, and methods disclosed herein are those mediated at least in part by PASK. Accordingly, disclosed herein are methods: for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; or for treating disease; all comprising the administration of a therapeutic amount of a compound as described herein, to a patient in need thereof. In further embodiments, the disease to be treated may be a metabolic disease. In further embodiment, the metabolic disease may be selected from the group consisting of: obesity, diabetes melitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be selected from the group consisting of: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Additionally, the PASK modulators disclosed herein may be used to treat proliferative disorders such as cancers. Hematological and non-hematological cancers which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CLL), lymphomas, including Hodgkin's lymphoma and non-Hodgkin's lymphoma (low, intermediate, and high grade), malignancies of the brain, head and neck, breast, lung, reproductive tract, upper digestive tract, pancreas, liver, renal, bladder, prostate and colon/rectum.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

REFERENCES CITED

The following is a list of references cited herein which, while not necessarily comprehensive, is provided for the convenience of the reader. All references, patents, and patent applications cited herein are hereby incorporated by reference as if written herein in their entireties. When the teachings of these references contradict the teachings presented expressly herein, the present disclosure controls.

1. Roach, P. J. et al. (2001) in The Endocrine Pancreas and Regulation of Metabolism, eds. Cherrington, A. D. & Jefferson, L. S. (Oxford Univ. Press, New York), pp. 609-647.
2. Bergstrom, J. et al. (1967) Acta Physiol. Scand. 71, 140-150.

3. Cline, G. W. et al. (1994) J. Clin. Invest. 94, 2369-2376.
4. Shulman, G. I. et al. G. (1990) N. Engl. J. Med. 322, 223-228.
5. Cohen, P. (1982) Nature 296, 613-620.
6. Roach, P. J. (1986) in The Enzymes, eds. Boyer, P. D. & Krebs, E. G. (Academic, Orlando, Fla.), Vol. 17, pp. 499-539.
7. Cohen, P. (1986) in The Enzymes, eds. Boyer, P. D. & Krebs, E. G. (Academic, Orlando, Fla.), Vol. 17, pp. 461-497.
8. Friedman, D. L. & Larner, J. (1963) Biochemistry 128, 669-675.
9. Larner, J. (1990) Adv. Enzymol. Relat. Areas Mol. Biol. 63, 173-231.
10. Roach, P. J. (1990) FASEB J. 4, 2961-2968.
11. Skurat, A. V., et al. (1994) J. Biol. Chem. 269, 25534-25542.
12. Flotow, H. & Roach, P. J. (1989) J. Biol. Chem. 264, 9126-9128.
13. Nakielny, S., Campbell, D. G. & Cohen, P. (1991) Eur. J. Biochem. 199, 713-722.
14. Wilson W A et al., *Proc Natl Acad Sci USA*. 2005 Nov. 15; 102(46):16596-601, FIG. 6
15. Skurat, A. V. & Roach, P. J. (1995) J. Biol. Chem. 270, 12491-12497.
16. Hardy, T. A. & Roach, P. J. (1993) J. Biol. Chem. 268, 23799-23805
17. Francois, J. & Parrou, J. L. (2001) FEMS Microbiol. Rev. 25, 125-145.
18. Rutter, J., Probst, B. L. & McKnight, S. L. (2002) Cell 111, 17-28.
19. Rutter, J et al. (2001) Proc. Natl. Acad. Sci. USA 98, 8991-8996.
20. Roden M, Bernroider E: *Best Pract Res Clin Endocrinol Metab*. 2003 September; 17(3):365-83
21. Van Steenbergen W, Lanckmans S: *Int J Obes Relat Metab Disord*. 1995 September; 19 Suppl 3:S27-36.
22. Arad M et al., *Circ Res*. 2007 March 2; 100(4):474-88
23. da Silva Xavier, G. et al. (2004) Proc. Natl. Acad. Sci. USA 101, 8319-8324.
24. 33Picton, C. et al. (1982) FEBS Lett. 150, 191-196.
25. DePaoli-Roach, A. A. et al., (1983) J. Biol. Chem. 258, 10702-10709.
26. Elia, A. E. et al. (2003) Science 299, 1228-1231.
27. Gao, T. et al. (1997) Neuron 19, 185-196.
28. Wilson, W. A. et al. (1999) Mol. Cell. Biol. 19, 7020-7030.
29. Yedovitzky, M. et al. (1997) J. Biol. Chem. 272, 1417-1420.
30. Fernandez-Novell, J. M., et al. (2002) FEBS Lett. 531, 222-228.

General Synthetic Methods for Preparing Compounds

The following schemes can generally be used to practice the present invention.

Scheme I

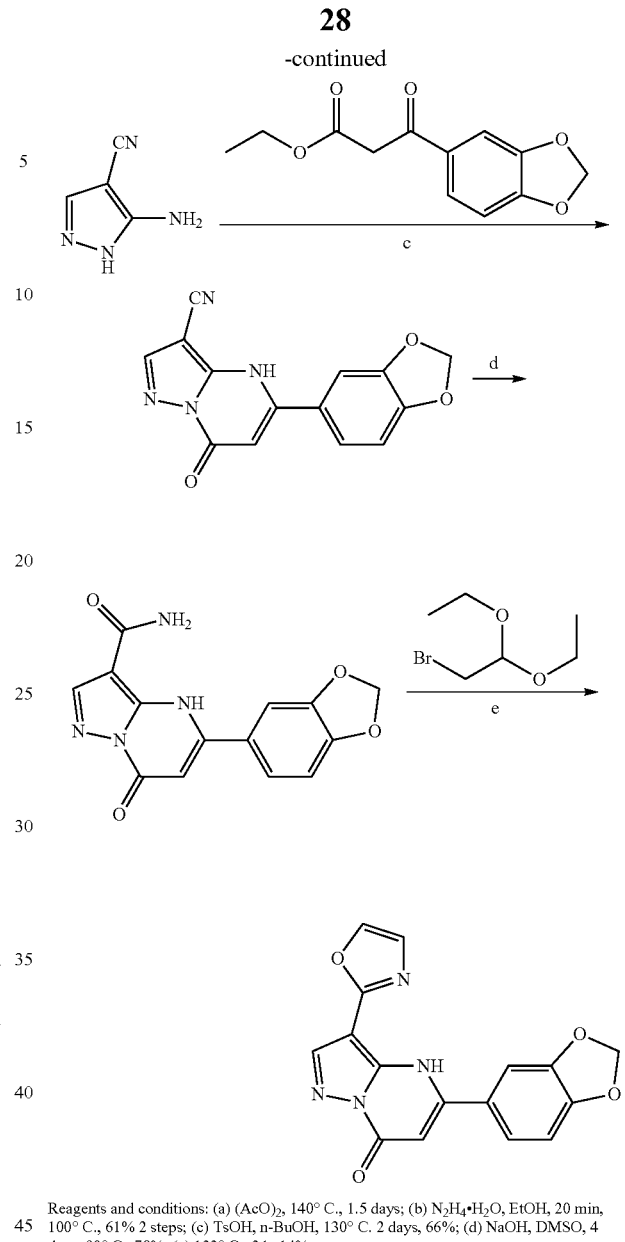

Reagents and conditions: (a) (AcO)₂, 140° C., 1.5 days; (b) N₂H₄·H₂O, EtOH, 20 min, 100° C., 61% 2 steps; (c) TsOH, n-BuOH, 130° C. 2 days, 66%; (d) NaOH, DMSO, 4 days, 90° C., 78%; (e) 132° C., 2 h, 14%.

Scheme II

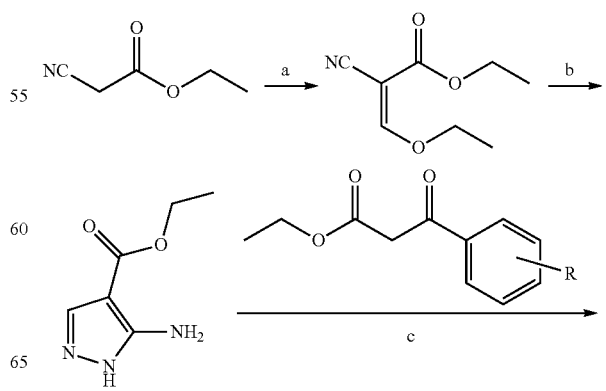

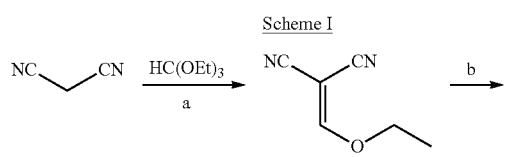

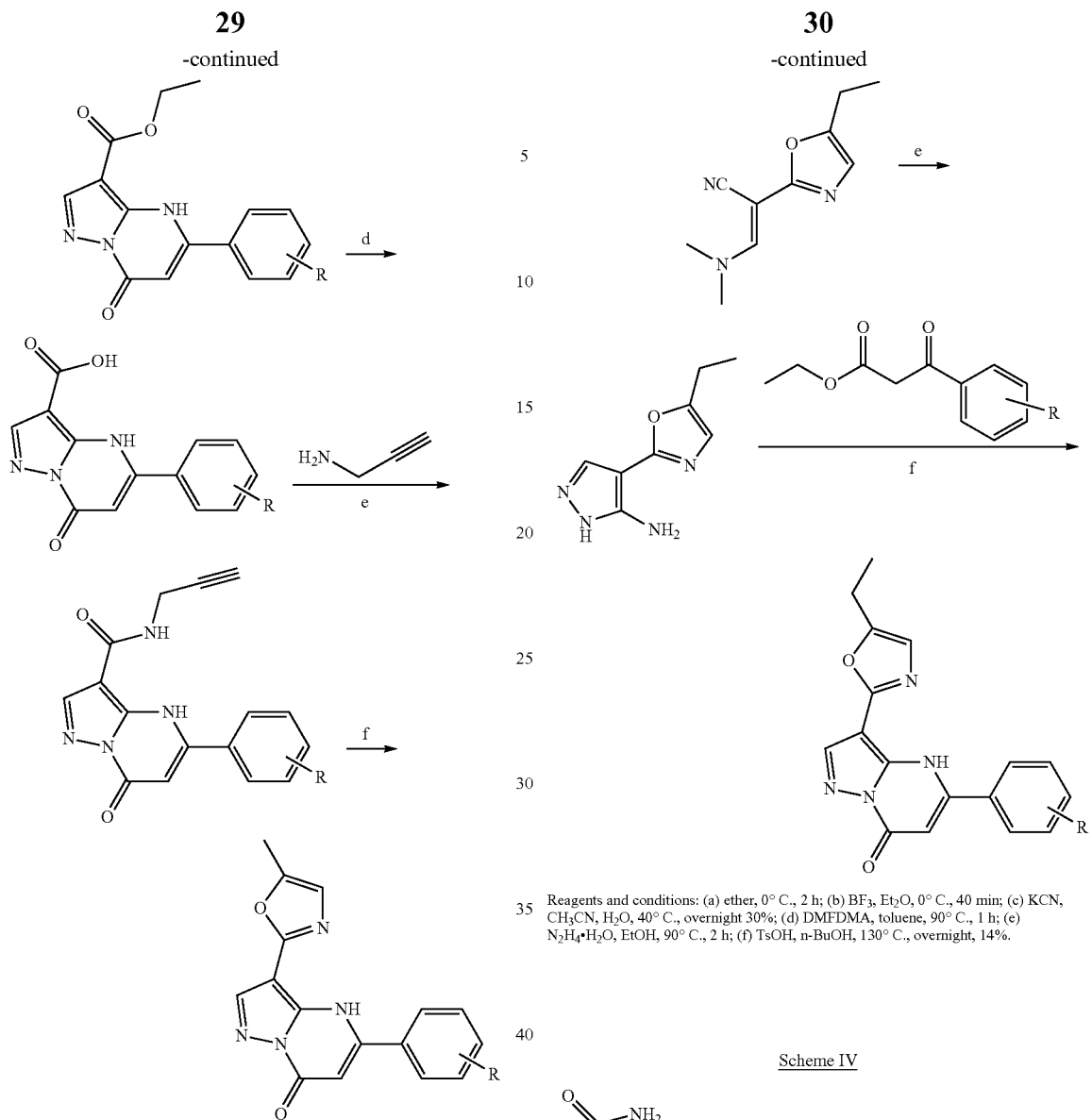
Reagents and conditions: (a) CH(OEt)₃, Ac₂O, 140° C., 24 h; (b) N₂H₄·H₂O, EtOH, 95° C., overnight 42%; (c) TsOH, n-BuOH, 130° C., 20 h, 85%; (d) NaOH, H₂O, DMSO, 70° C., 1 h, 80%; (e) CDI, DMF, 50° C., 20 h, 27%; (f) NaH, DMSO, 25° C., 2 h, 17%
Reagents and conditions: (a) ether, 0° C., 2 h; (b) BF₃, Et₂O, 0° C., 40 min; (c) KCN, CH₃CN, H₂O, 40° C., overnight 30%; (d) DMFDMA, toluene, 90° C., 1 h; (e) N₂H₄·H₂O, EtOH, 90° C., 2 h; (f) TsOH, n-BuOH, 130° C., overnight, 14%.
Scheme III
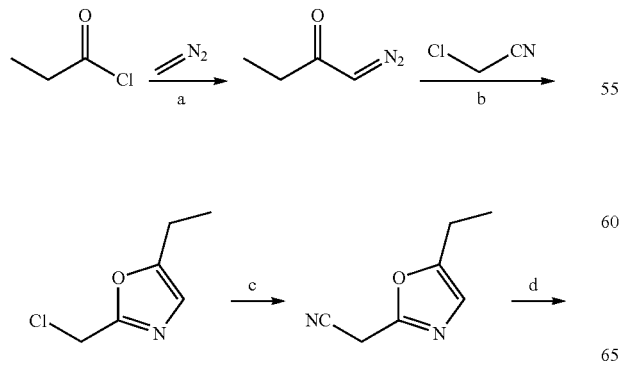
Scheme IV
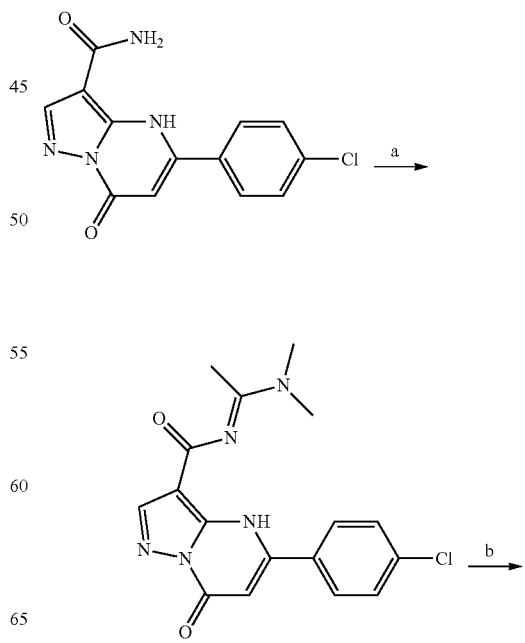

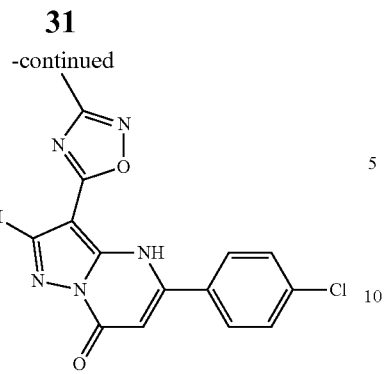

Reagents and conditions: (a) DMADMA, toluene, 130° C., 1.5 h, 50%; (b) NH₂OH•HCl, AcOH, NaOH(10%aq), dioxane, 100° C., 27%.

Scheme V

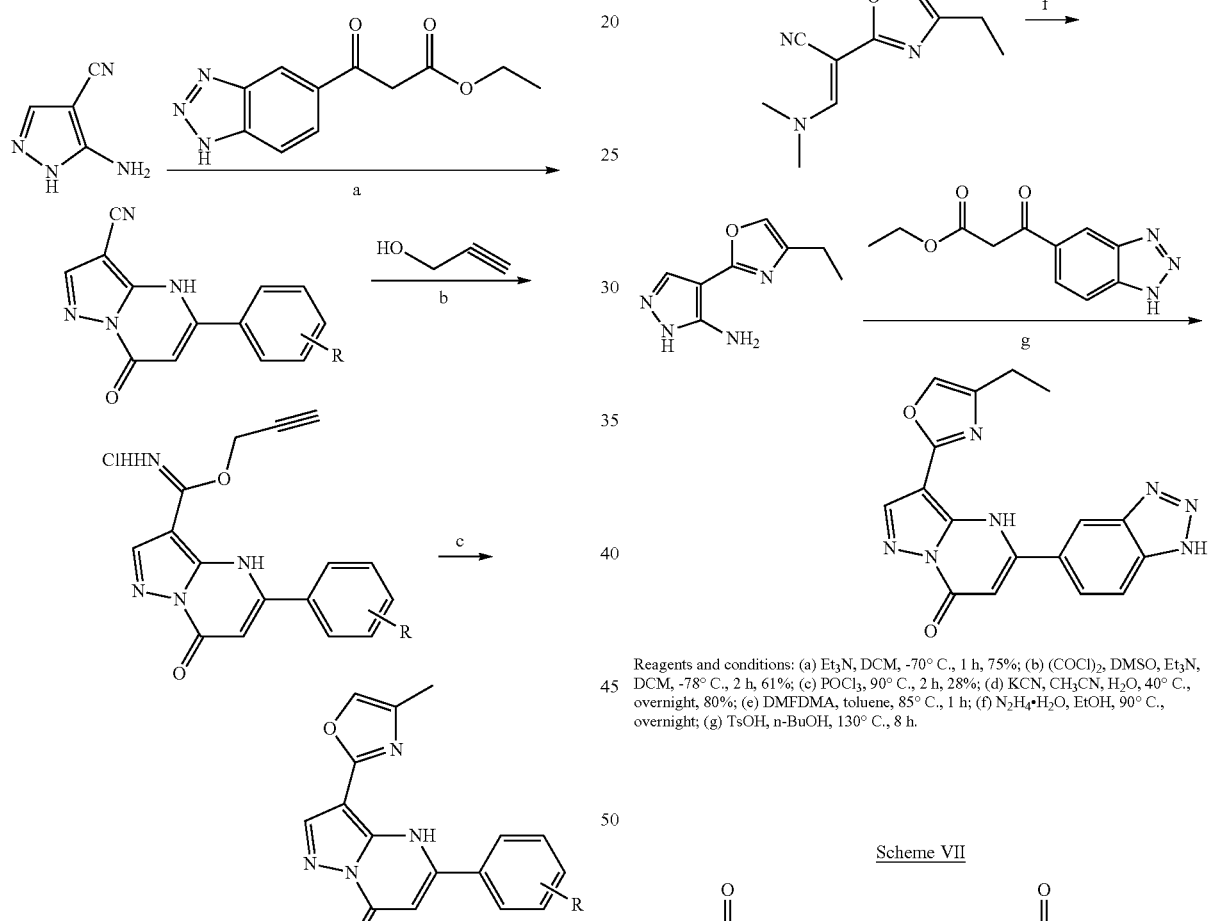

Reagents and conditions: (a) TsOH, n-BuOH, reflux, overnight, 82% (b) HCl(g), no solvent, rt, 2h; (c) DIEA, TsOAg, xylene, 70° C., 3 h, 13% 2 steps.

Scheme VI

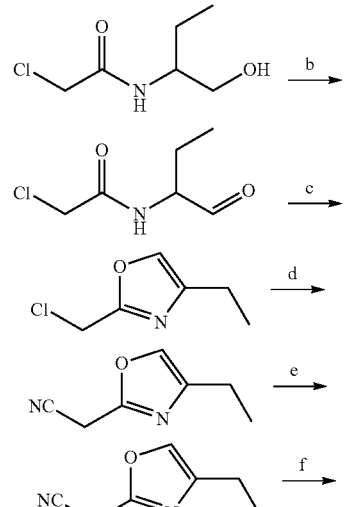

Reagents and conditions: (a) Et₃N, DCM, -70° C., 1 h, 75%; (b) (COCl)₂, DMSO, Et₃N, DCM, -78° C., 2 h, 61%; (c) POCl₃, 90° C., 2 h, 28%; (d) KCN, CH₃CN, H₂O, 40° C., overnight, 80%; (e) DMFDMA, toluene, 85° C., 1 h, 61%; (f) N₂H₄•H₂O, EtOH, 90° C., overnight; (g) TsOH, n-BuOH, 130° C., 8 h.

Scheme VII

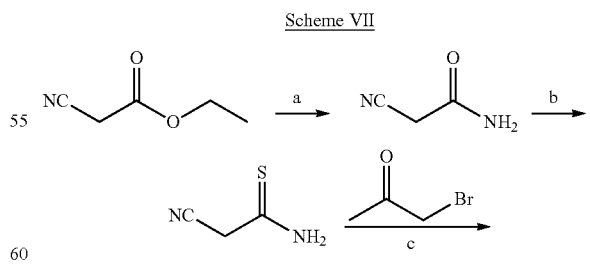

-continued

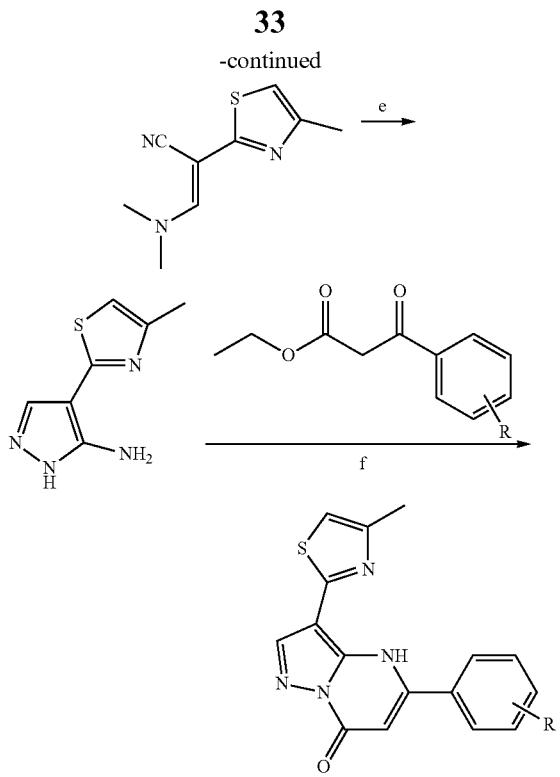

Reagents and conditions: (a) NH₃•H₂O, rt, 1 h, 84%; (b) Lawesson's Reagent, THF, rt, overnight, 53%; (c) Et₃N, EtOH, 50° C., 2 h; (d) DMFDMA, toluene, 85° C., 1 h; (e) N₂H₄•H₂O, EtOH, 90° C., 2 h, 6% 3 steps; (f) n-BuOH, TsOH, 130° C., 5 h 10%.

Scheme VIII

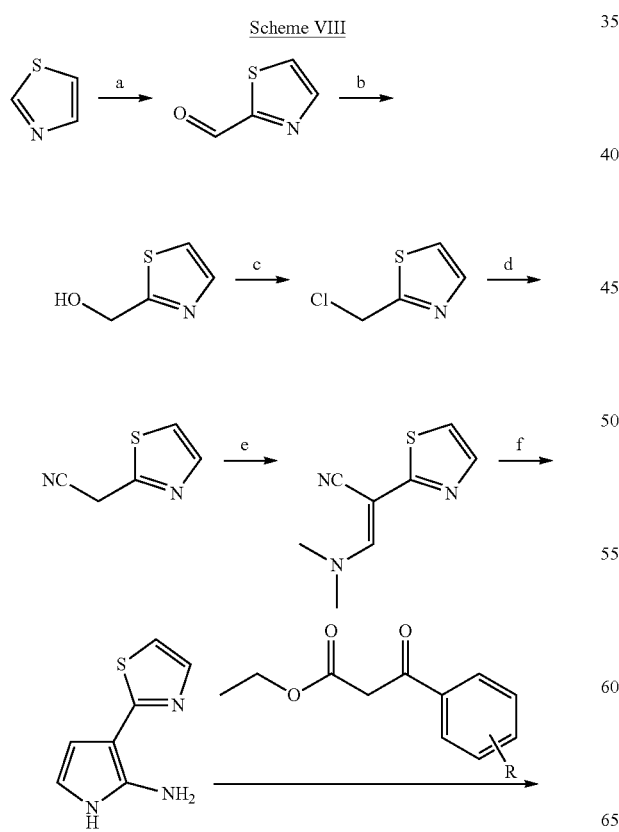

-continued

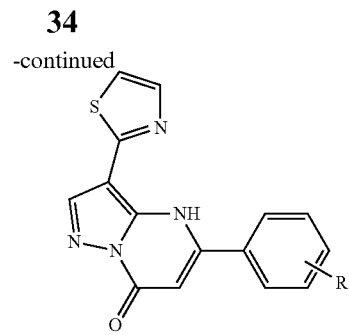

Reagents and conditions: (a) n-BuLi, DMF, THF, rt, 3 h; (b) NaBH4, MeOH, rt, overnight, 12% 2steps; (c) SOCl₂, DCM, rt, 2 h, 61%; (d) KCN, H₂O, KCN, 50° C., 10 h, 43%; (e) DMF-DMA, toluene, 85° C., 2 h; (f) N₂H₄•H₂O, AcOH, reflux, 4 h, 37%, 2 steps.

The invention is further illustrated by the following examples, which can be made by the methods described herein or by one skilled in the art without undue experimentation, or can be purchased from commercial sources.

EXAMPLE 1

5-(2H-1,3-benzodioxol-5-yl)-3-(1,3-oxazol-2-yl)-4H,7H-pyrazolo[1,5-a]pyrimidin-7-one

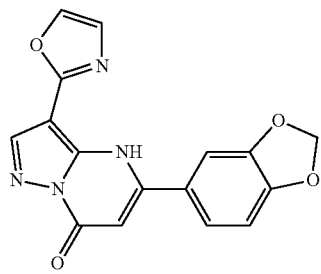 [SMILES: O=c1cc(-c2ccc3c(c2)OCO3)[nH]c2c(-c3ncco3)cnn12]

Step 1: 2-(ethoxymethylidene)propanedinitrile

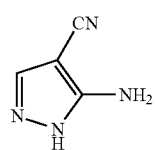

To a solution of propanedinitrile (5 g, 75.69 mmol) in (AcO)₂O (10 ml) was added triethoxymethane (11.6 g, 78.27 mmol), and the reaction mixture was stirred for 1.5 days at 140° C. in an oil bath. The resulting mixture was concentrated in vacuo to afford 2-(ethoxymethylidene)propanedinitrile as a red crude solid (11 g, crude).

Step 2: 5-amino-1H-pyrazole-4-carbonitrile

To a solution of 2-(ethoxymethylidene)propanedinitrile (11 g, crude) in ethanol (250 ml) was added N₂H₄.H₂O (3.9 g, 78.00 mmol), and the reaction mixture was stirred for 20 min at 100° C. in an oil bath and then concentrated in vacuo to give a residue, which was purified by a silica gel column chromatography with 2% to 10% methanol in dichloromethane to afford 5-amino-1H-pyrazole-4-carbonitrile as a red solid (5 g, 61% 2 steps).

LC/MS (ES, m/z): [M+H]⁺ 109.1

¹H NMR (300 MHz, DMSO): δ 11.52 (d, J=4.2 Hz, 1H), 7.78 (s, 1H), 6.03 (s, 2H)

Step 3: 5-(2H-1,3-benzodioxol-5-yl)-7-oxo-4H,7H-pyrazolo[1,5-a]pyrimidine-3-carbonitrile

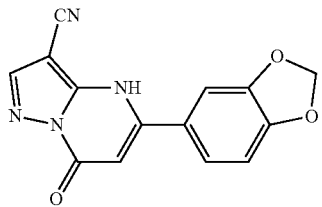 [SMILES: N#Cc1cnn2c(=O)cc(-c3ccc4c(c3)OCO4)[nH]c12]

To a solution of 5-amino-1H-pyrazole-4-carbonitrile (500 mg, 4.63 mmol) in n-BuOH (10 ml) was added 4-methylbenzene-1-sulfonic acid (60 mg, 0.35 mmol), ethyl 3-(2H-1,3-benzodioxol-5-yl)-3-oxopropanoate (2.08 g, 8.81 mmol), and the reaction mixture was stirred for 2 days at 130° C. in an oil bath. The solid was collected by filtration and washed with methanol (10 ml) to afford 5-(2H-1,3-benzodioxol-5-yl)-7-oxo-4H,7H-pyrazolo[1,5-a]pyrimidine-3-carbonitrile as an off-white solid (860 mg, 66%).

LC/MS (ES, m/z): [M+H]⁺ 281.1

¹H NMR (300 MHz, DMSO): δ 13.39 (s, 1H), 8.42 (s, 1H), 7.38-7.45 (m, 2H), 7.11-7.15 (m, 1H), 6.19 (s, 1H), 6.13 (s, 2H)

Step 4: 5-(2H-1,3-benzodioxol-5-yl)-7-oxo-4H,7H-pyrazolo[1,5-a]pyrimidine-3-carboxamide

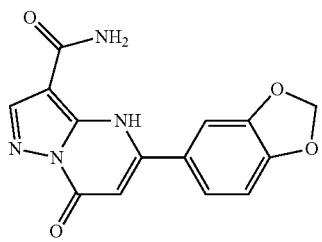 [SMILES: NC(=O)c1cnn2c(=O)cc(-c3ccc4c(c3)OCO4)[nH]c12]

To a solution of 5-(2H-1,3-benzodioxol-5-yl)-7-oxo-4H,7H-pyrazolo[1,5-a]pyrimidine-3-carbonitrile (660 mg, 2.36 mmol) in DMSO (5 ml) was added NaOH (171 mg, 4.28 mmol) in water (0.5 ml), and the reaction mixture was stirred for 4 days at 90° C. in an oil bath. The reaction was then quenched by the addition of water (20 ml) and adjusted to pH 7 with aqueous HCl (2N). The solids were collected by filtration and washed with water (10 ml) to afford 5-(2H-1,3-benzodioxol-5-yl)-7-oxo-4H,7H-pyrazolo[1,5-a]pyrimidine-3-carboxamide as a gray solid (550 mg, 78%).

LC/MS (ES, m/z): [M+H]⁺ 299.1

¹H NMR (300 MHz, DMSO): δ 7.96 (s, 1H), 7.57 (d, J=1.8 Hz, 2H), 7.54 (s, 1H), 6.97 (d, J=8.1 Hz, 1H), 6.07 (s, 1H), 6.04 (s, 1H)

Step 5: 5-(2H-1,3-benzodioxol-5-yl)-3-(1,3-oxazol-2-yl)-4H,7H-pyrazolo[1,5-a]pyrimidin-7-one

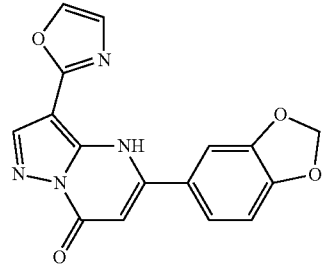 [SMILES: O=c1cc(-c2ccc3c(c2)OCO3)[nH]c2c(-c3ncco3)cnn12]

A solution of 5-(2H-1,3-benzodioxol-5-yl)-7-oxo-4H,7H-pyrazolo[1,5-a]pyrimidine-3-carboxamide (200 mg, 0.67 mmol) in 2-bromo-1,1-diethoxyethane (3 ml) was stirred for 6 h at 132° C. in an oil bath. The solids were collected by filtration, dissolved in methanol (20 ml), and filtered out the solid. The filtration was concentrated in vacuo to give a residue, which was purified by Prep-HPLC under the following conditions (Column, XBidge shield RP C18 150*19 mm 5 uL; mobile phase, water with 0.05% ammonia and CH3CN (25% CH3CN up to 45% in 10 min); Detector, 254 nm) to afford 5-(2H-1,3-benzodioxol-5-yl)-3-(1,3-oxazol-2-yl)-4H,7H-pyrazolo[1,5-a]pyrimidin-7-one as a gray solid (29.2 mg, 14%).

LC/MS (ES, m/z): [M+H]⁺ 323.0

¹H NMR (300 MHz, DMSO): δ 8.28 (s, 1H), 8.13 (s, 1H), 7.53-7.59 (m, 2H), 7.32 (s, 1H), 7.06 (d, J=7.8 Hz, 1H), 6.21 (s, 1H), 6.12 (s, 2H)

EXAMPLE 2

5-(2H-1,3-benzodioxol-5-yl)-2-methyl-3-(1,3-oxazol-2-yl)-4H,7H-pyrazolo[1,5-a]pyrimidin-7-one

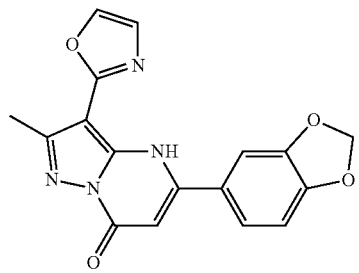 [SMILES: Cc1nn2c(=O)cc(-c3ccc4c(c3)OCO4)[nH]c2c1-c1ncco1]

Step 1: 2-(1-ethoxyethylidene)propanedinitrile

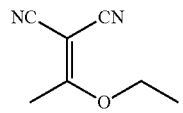

A solution of propanedinitrile (6 g, 90.9 mmol) in 1,1,1-triethoxyethane (13.5 g, 83.22 mmol) was stirred for 2 h at 95° C. in an oil bath. The reaction mixture was cooled to room temperature to afford 2-(1-ethoxyethylidene)propanedinitrile as a yellow crude solid (11 g, crude)

Step 2:
5-amino-3-methyl-1H-pyrazole-4-carbonitrile

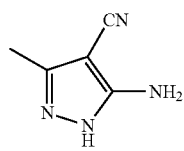

To a solution of 2-(1-ethoxyethylidene)propanedinitrile (17 g, crude) in ethanol (100 ml) was added N$_2$H$_4$.H$_2$O (11.6 g, 185.60 mmol), and the reaction mixture was stirred for 3 h at 95° C. in an oil bath. The resulting mixture was concentrated in vacuo to give a residue, which was purified by silica gel column chromatography with 2% to 10% methanol in dichloromethane to afford 5-amino-3-methyl-1H-pyrazole-4-carbonitrile as a white solid (8 g).

LC/MS (ES, m/z): [M+H]$^+$ 123.1.

Step 3: 5-(2H-1,3-benzodioxol-5-yl)-2-methyl-7-oxo-4H,7H-pyrazolo[1,5-a]pyrimidine-3-carbonitrile

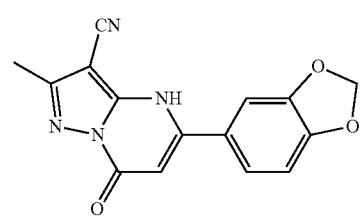 [SMILES: Cc1nn2c(=O)cc(-c3ccc4c(c3)OCO4)[nH]c2c1C#N]

To a solution of 5-amino-3-methyl-1H-pyrazole-4-carbonitrile (500 mg, 4.09 mmol) in n-BuOH (4 ml) was added 4-methylbenzene-1-sulfonic acid (27 mg, 0.16 mmol), ethyl 3-(2H-1,3-benzodioxol-5-yl)-3-oxopropanoate (1.1 g, 4.66 mmol), and the reaction mixture was stirred for 2 days at 130° C. in an oil bath. The solids were collected by filtration and washed with methanol (15 ml) to afford 5-(2H-1,3-benzodioxol-5-yl)-2-methyl-7-oxo-4H,7H-pyrazolo[1,5-a]pyrimidine-3-carbonitrile as a gray solid (900 mg, 75%).

LC/MS (ES, m/z): [M+H]$^+$ 295.1

$^1$H NMR (300 MHz, DMSO) δ 13.28 (s, 1H), 7.37-7.44 (m, 2H), 7.10 (d, J=8.1 Hz, 3H), 6.18 (s, 1H), 6.16 (s, 2H), 2.40 (s, 3H)

Step 4: 5-(2H-1,3-benzodioxol-5-yl)-2-methyl-7-oxo-4H,7H-pyrazolo[1,5-a]pyrimidine-3-carboxamide

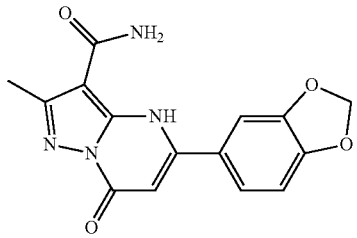 [SMILES: Cc1nn2c(=O)cc(-c3ccc4c(c3)OCO4)[nH]c2c1C(N)=O]

To a solution of 5-(2H-1,3-benzodioxol-5-yl)-2-methyl-7-oxo-4H,7H-pyrazolo[1,5-a]pyrimidine-3-carbonitrile (800 mg, 2.72 mmol) in DMSO (10 ml) was added NaOH (218 mg, 5.45 mmol) and water (1 ml), and the reaction mixture was stirred for 2 days at 90° C. in an oil bath. The reaction was quenched by the addition of water (25 ml) and adjusted to pH 7 with aqueous HCl (2 N). The solid was filtered and washed with water (20 ml) to afford 5-(2H-1,3-benzodioxol-5-yl)-2-methyl-7-oxo-4H,7H-pyrazolo[1,5-a]pyrimidine-3-carboxamide as a gray solid (680 mg, 80%).

LC/MS (ES, m/z): [M+H]$^+$ 313.1

$^1$H NMR (300 MHz, CD$_3$OD) δ 7.54-7.59 (m, 2H), 6.90 (d, J=8.4 Hz, 1H), 6.26 (s, 1H), 6.02 (s, 2H), 2.62 (s, 3H)

Step 5: 5-(2H-1,3-benzodioxol-5-yl)-2-methyl-3-(1,3-oxazol-2-yl)-4H,7H-pyrazolo[1,5-a]pyrimidin-7-one

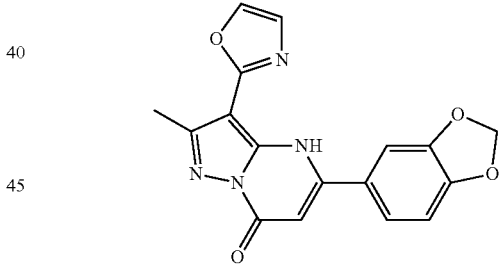

A solution of 5-(2H-1,3-benzodioxol-5-yl)-2-methyl-7-oxo-4H,7H-pyrazolo[1,5-a]pyrimidine-3-carboxamide (200 mg, 0.64 mmol) in 2-bromo-1,1-diethoxyethane (2 ml) was stirred for 4 h at 132° C. in an oil bath. The solids were collected by filtration and filter cake was dissolved in methanol (20 ml) and the solid was filtered off and the filtrate was concentrated in vacuo to afford a residue, which was purified by Prep-HPLC under the following conditions (IntelFlash-1: Column, C18 silica gel; mobile phase, CH$_3$CN=25 increasing to CH$_3$CN=55 within 0-10 min; Detector, UV 254 nm) to afford 5-(2H-1,3-benzodioxol-5-yl)-2-methyl-3-(1,3-oxazol-2-yl)-4H,7H-pyrazolo[1,5-a]pyrimidin-7-one as a white solid (32.3 mg, 15%).

LC/MS (ES, m/z): [M+H]$^+$ 337.0

$^1$H NMR (300 MHz, DMSO): δ 8.21 (s, 1H), 7.44 (s, 2H), 7.35 (d, J=8.1 Hz, 1H), 7.14 (d, J=8.1 Hz, 1H), 6.19 (s, 1H), 6.17 (s, 2H), 2.57 (s, 3H)

EXAMPLE 3

5-(2H-1,3-benzodioxol-5-yl)-3-(5-methyl-1,3-oxazol-2-yl)-4H,7H-pyrazolo[1,5-a]pyrimidin-7-one

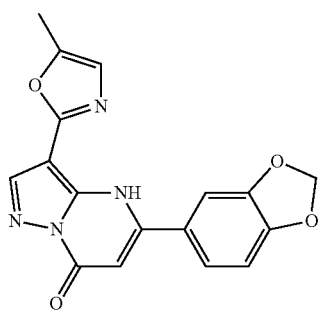 [SMILES: Cc1cnc(-c2cnn3c(=O)cc(-c4ccc5c(c4)OCO5)[nH]c23)o1]

Step 1: Ethyl 2-cyano-3-ethoxyprop-2-enoate

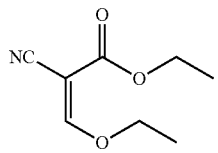

To a solution of ethyl 2-cyanoacetate (25 g, 0.22 mol) in acetic anhydride (36 g, 0.33 mol) was added triethoxymethane (26 g, 0.18 mol), and the reaction mixture was stirred for 24 h at 140° C. The reaction mixture was concentrated in vacuo to afford ethyl 2-cyano-3-ethoxyprop-2-enoate as a yellow solid (36 g, crude).

Step 2 Ethyl 5-amino-1H-pyrazole-4-carboxylate

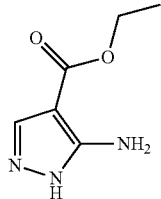

To a solution of ethyl (2Z)-2-cyano-3-ethoxyprop-2-enoate (36 g, crude) in ethanol (200 ml) was added $N_2H_4 \cdot H_2O$ (11.72 g, 0.23 mol) with stirring overnight at 95° C. The reaction mixture was concentrated in vacuo to give a residue, which was purified by a silica gel chromatography with 2% dichloromethane in methanol to afford ethyl 5-amino-1H-pyrazole-4-carboxylate as a light yellow solid (14 g, 40% 2 steps).

LC/MS (ES, m/z): [M+H]$^+$ 156.0

$^1$H NMR (300 MHz, CDCl$_3$) δ 7.77 (s, 1H), 5.65 (s, 3H), 4.27-4.34 (m, 2H), 1.34-1.39 (t, J=7.2 Hz, 3H)

Step 3: Ethyl 5-(2H-1,3-benzodioxol-5-yl)-7-oxo-4H,7H-pyrazolo[1,5-a]pyrimidine-3-carboxylate

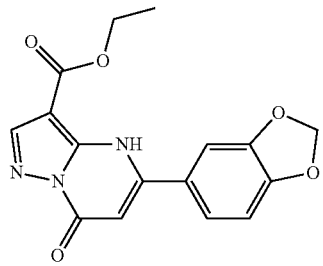 [SMILES: CCOC(=O)c1cnn2c(=O)cc(-c3ccc4c(c3)OCO4)[nH]c12]

To a solution of ethyl 5-amino-1H-pyrazole-4-carboxylate (1.0 g, 6.45 mmol) in n-BuOH (1 ml) was added to ethyl 3-(2H-1,3-benzodioxol-5-yl)-3-oxopropanoate (1.83 g, 7.75 mmol and TsOH (55 mg, 0.32 mmol), and the reaction mixture was stirred for 20 h at 130° C. The solid was collected by filtration and washed with methanol (3×10 ml) and dried in an oven under reduced pressure to afford ethyl 5-(2H-1,3-benzodioxol-5-yl)-7-oxo-4H,7H-pyrazolo[1,5-a]pyrimidine-3-carboxylate as a yellow solid (1.8 g, 85%).

LC/MS (ES, m/z): [M+H]$^+$ 328.0

$^1$H NMR (300 MHz, DMSO) δ 11.52 (s, 1H), 8.25 (s, 1H), 7.39 (d, J=1.8 Hz, 1H), 7.31-7.35 (m, 1H), 7.12 (d, J=8.1 Hz, 1H), 6.23 (s, 1H), 6.16 (s, 2H), 4.28-4.35 (m, 2H), 1.32-1.37 (t, J=7.2 Hz, 3H)

Step 4: 5-(2H-1,3-benzodioxol-5-yl)-7-oxo-4H,7H-pyrazolo[1,5-a]pyrimidine-3-carboxylic acid

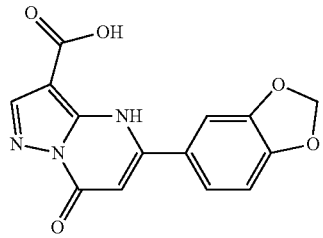

To a solution of ethyl 5-(2H-1,3-benzodioxol-5-yl)-7-oxo-4H,7H-pyrazolo[1,5-a]pyrimidine-3-carboxylate (1.8 g, 5.5 mmol) in DMSO (20 ml) and water (1.0 ml) was added sodium hydroxide (830 mg, 20.75 mmol), and the reaction mixture was stirred for 1 h at 70° C. The reaction mixture was then quenched by the addition of water (30 ml), adjusted to pH 4 with aq. HCl (2 N). The solids were collected by filtration and dried in an oven under reduced pressure to afford 5-(2H-1,3-benzodioxol-5-yl)-7-oxo-4H,7H-pyrazolo[1,5-a]pyrimidine-3-carboxylic acid as a yellow solid (1.3 g, 80%).

LC/MS (ES, m/z): [M+H]$^+$ 300.0

$^1$H NMR (300 MHz, DMSO) δ 11.37 (s, 1H), 8.21 (s, 1H), 7.33-7.40 (d, J=1.8 Hz, 1H), 7.30-7.32 (t, J=6.3 Hz, 1H), 7.12 (d, J=8.1 Hz, 1H), 6.21 (s, 1H), 6.16 (s, 2H)

Step 5: 5-(2H-1,3-benzodioxol-5-yl)-7-oxo-N-(prop-2-yn-1-yl)-4H,7H-pyrazolo[1,5-a]pyrimidine-3-carboxamide

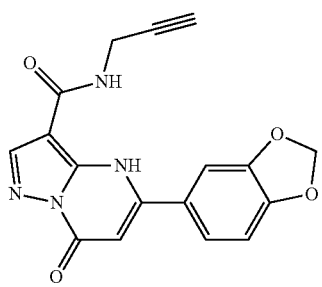 [SMILES: C#CCNC(=O)c1cnn2c(=O)cc(-c3ccc4c(c3)OCO4)[nH]c12]

To a solution of 5-(2H-1,3-benzodioxol-5-yl)-7-oxo-4H,7H-pyrazolo[1,5-a]pyrimidine-3-carboxylic acid (400 mg, 1.34 mmol) in DMF (10 ml) was added CDI (325 mg, 2.00 mmol), and the reaction mixture was stirred for 5 h at 50° C., then prop-2-yn-1-amine (95.7 mg, 1.74 mmol) was added drop wise to the reaction mixture and stirred for 15 h at 50° C. The reaction mixture was concentrated in vacuo, precipitated by the addition of water (10 ml), collected by filtration, dried in an oven under reduced pressure to afford 5-(2H-1,3-benzodioxol-5-yl)-7-oxo-N-(prop-2-yn-1-yl)-4H,7H-pyrazolo[1,5-a]pyrimidine-3-carboxamide as a light yellow solid (160 mg, 36%).

LC/MS (ES, m/z): [M+H]$^+$ 337.0

$^1$H NMR (300 MHz, DMSO): δ 8.89-8.93 (t, J=4.8 Hz, 1H), 8.07 (s, 1H), 7.54 (d, J=7.5 Hz, 2H), 7.01 (d, J=8.4 Hz, 1H), 6.10 (s, 3H), 4.13-4.15 (m, 2H)

Step 6: 5-(2H-1,3-benzodioxol-5-yl)-3-(5-methyl-1,3-oxazol-2-yl)-4H,7H-pyrazolo[1,5-a]pyrimidin-7-one

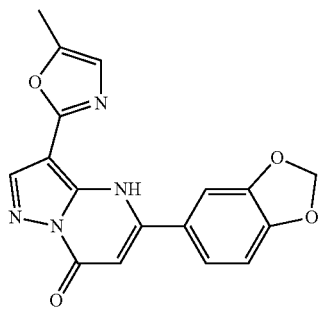 [SMILES: Cc1cnc(-c2cnn3c(=O)cc(-c4ccc5c(c4)OCO5)[nH]c23)o1]

A solution of sodium hydride (42.97 mg, 1.79 mmol) in DMSO (1 ml) was stirred until it became clear at 25° C. and then 5-(2H-1,3-benzodioxol-5-yl)-7-oxo-N-(prop-2-yn-1-yl)-4H,7H-pyrazolo[1,5-a]pyrimidine-3-carboxamide (130 mg, 0.38 mmol) was added, and the reaction mixture was stirred for 2 h at 25° C. The reaction mixture was then quenched by the addition of ice-water (10 ml) and the solids were collected by filtration to give the crude product (100 mg), which was purified by Prep-HPLC under the following conditions ((Xbridge): Column, 19*100 mm*5 um; mobile phase; B: CH$_3$CN A: H$_2$O+0.05% TFA 23%-43% in 10 min; flow rate: 10 mL/min; Detector, 254 nm) to afford of 5-(2H-1,3-benzodioxol-5-yl)-3-(5-methyl-1,3-oxazol-2-yl)-4H,7H-pyrazolo[1,5-a]pyrimidin-7-one as an off-white solid (20.9 mg, 17%).

LC/MS (ES, m/z): [M+H]$^+$ 337.0

$^1$H NMR (300 MHz, DMSO) δ 8.31 (s, 1H), 7.45 (s, 1H), 7.37 (d, J=8.1 Hz, 1H), 7.13 (d, J=8.1 Hz, 1H), 7.01 (s, 1H), 6.20 (s, 1H), 6.16 (s, 2H), 2.39 (s, 3H)

EXAMPLE 4

5-(2H-1,3-benzodioxol-5-yl)-3-(4-methyl-1,3-oxazol-2-yl)-4H,7H-pyrazolo[1,5-a]pyrimidin-7-one

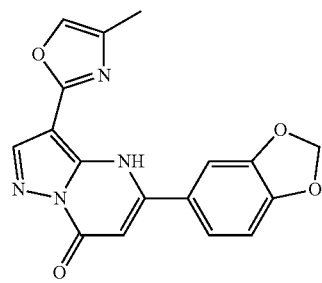 [SMILES: Cc1coc(-c2cnn3c(=O)cc(-c4ccc5c(c4)OCO5)[nH]c23)n1]

Step 1: Prop-2-yn-1-yl 5-(2H-1,3-benzodioxol-5-yl)-7-oxo-4H,7H-pyrazolo[1,5-a]pyrimidine-3-carboximidate hydrochloride

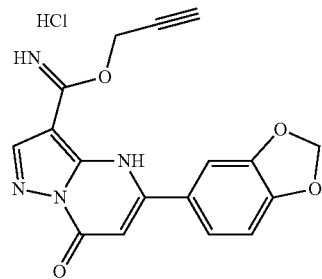 [SMILES: C#CCOC(=N)c1cnn2c(=O)cc(-c3ccc4c(c3)OCO4)[nH]c12 ; Cl]

To a solution of 5-(2H-1,3-benzodioxol-5-yl)-7-oxo-4H,7H-pyrazolo[1,5-a]pyrimidine-3-carbonitrile (600 mg, 2.14 mmol) in prop-2-yn-1-ol (15 ml) was introduced HCl (g), and the reaction mixture was stirred for 2 h at room temperature and then the reaction was concentrated in vacuo to afford the salt of prop-2-yn-1-yl 5-(2H-1,3-benzodioxol-5-yl)-7-oxo-4H,7H-pyrazolo[1,5-a]pyrimidine-3-carboximidate hydrochloride (520 mg, crude) as a yellow solid.

LC/MS (ES, m/z): [M+H]$^+$ 337.0

Step 2: 5-(2H-1,3-benzodioxol-5-yl)-3-(4-methyl-1,3-oxazol-2-yl)-4H,7H-pyrazolo[1,5-a]pyrimidin-7-one

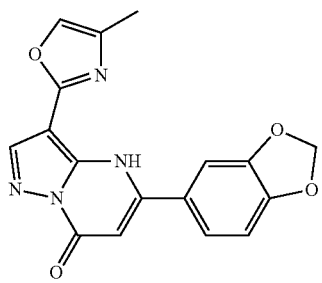 [SMILES: Cc1coc(-c2cnn3c(=O)cc(-c4ccc5c(c4)OCO5)[nH]c23)n1]

To a solution of prop-2-yn-1-yl 5-(2H-1,3-benzodioxol-5-yl)-7-oxo-4H,7H-pyrazolo[1,5-a]pyrimidine-3-carboximidate hydrochloride (500 mg, crude) in xylene (50 ml) was added DIEA (288 mg, 2.23 mmol) and TsOAg (20.78 mg, 0.07 mmol), and the reaction mixture was stirred for 3 h at 70° C. in an oil bath. The reaction mixture was concentrated in vacuo to give a residue, which was dissolved in DMSO (25 ml) and precipitated by the addition water (60 ml). The solids were collected by filtration and dried in an oven under reduced pressure to afford 5-(2H-1,3-benzodioxol-5-yl)-3-(4-methyl-1,3-oxazol-2-yl)-4H,7H-pyrazolo[1,5-a]pyrimidin-7-one (57.8 mg) as a gray solid.

LC/MS (ES, m/z): [M+H]$^+$ 337.0

$^1$H NMR (300 MHz, DMSO) δ 8.11 (s, 1H), 7.73 (s, 1H), 7.15-7.28 (m, 2H), 6.61 (s, 1H), 5.88 (s, 2H), 5.82 (s, 1H), 2.02 (s, 3H)

EXAMPLE 5

5-(1H-1,2,3-benzotriazol-5-yl)-3-(5-methyl-1,3-oxazol-2-yl)-4H,7H-pyrazolo[1,5-a]pyrimidin-7-one

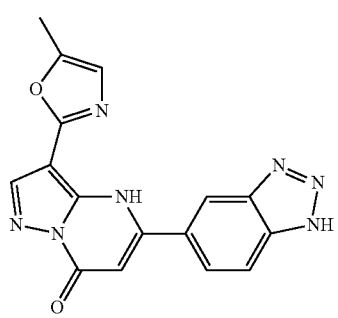 [SMILES: Cc1cnc(-c2cnn3c(=O)cc(-c4ccc5[nH]nnc5c4)[nH]c23)o1]

Step 1: Ethyl 5-(1H-1,2,3-benzotriazol-5-yl)-7-oxo-4H,7H-pyrazolo[1,5-a]pyrimidine-3-carboxylate

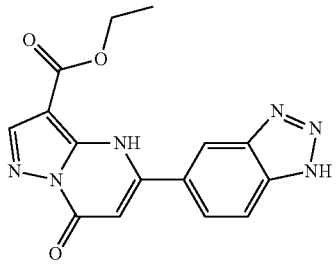 [SMILES: CCOC(=O)c1cnn2c(=O)cc(-c3ccc4[nH]nnc4c3)[nH]c12]

To a solution of (3-aminopyrazolidin-4-yl)(ethoxy)methanol (1 g, 6.20 mmol) in n-BuOH (10 ml) was added to ethyl 3-(1H-1,2,3-benzotriazol-5-yl)-3-oxopropanoate (1.85 g, 7.93 mmol) and TsOH (55 mg, 0.32 mmol) with stirring overnight at 130° C. The solids were collected by filtration and washed with methanol (30 ml) to afford ethyl 5-(1H-1,2,3-benzotriazol-5-yl)-7-oxo-4H,7H-pyrazolo[1,5-a]pyrimidine-3-carboxylate (1.75 g, 87%) as a light yellow solid.

(ES, m/z): [M+H]$^+$ 325.0

$^1$H NMR (300 MHz, DMSO) δ 16.07 (s, 1H), 12.07 (s, 1H), 8.58 (s, 1H), 8.28 (s, 1H), 7.86-7.92 (m, 2H), 6.37 (s, 1H), 4.29-4.36 (m, 2H), 1.33-1.38 (t, J=7.2 Hz, 3H)

Step 2: 5-(1H-1,2,3-benzotriazol-5-yl)-7-oxo-4H,7H-pyrazolo[1,5-a]pyrimidine-3-carboxylic acid

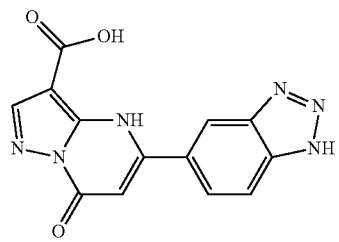

To a solution of ethyl 5-(1H-1,2,3-benzotriazol-5-yl)-7-oxo-4H,7H-pyrazolo[1,5-a]pyrimidine-3-carboxylate (1.75 g, 5.24 mmol) in DMSO (15 ml) was added sodium hydroxide (630 mg, 15.75 mmol) in water (2 ml), and the reaction mixture was stirred for overnight at 50° C. The reaction was then quenched with water (30 ml), adjusted pH to 3 with HCl (2 N). The solids were collected by filtration and dried in an oven under reduced pressure to afford 5-(1H-1,2,3-benzotriazol-5-yl)-7-oxo-4H,7H-pyrazolo[1,5-a]pyrimidine-3-carboxylic acid (1 g, 61%) as a yellow solid.

LC/MS (ES, m/z): [M+H]$^+$ 297.0

$^1$H NMR (300 MHz, DMSO) δ 15.98 (s, 1H), 8.58 (s, 1H), 8.18 (s, 1H), 7.94-7.96 (m, 2H), 6.34 (s, 1H).

Step 3: 5-(1H-1,2,3-benzotriazol-5-yl)-7-oxo-N-(prop-2-yn-1-yl)-4H,7H-pyrazolo[1,5-a]pyrimidine-3-carboxamide

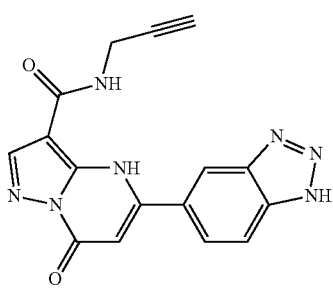 [SMILES: C#CCNC(=O)c1cnn2c(=O)cc(-c3ccc4[nH]nnc4c3)[nH]c12]

To a solution of 5-(1H-1,2,3-benzotriazol-5-yl)-7-oxo-4H,7H-pyrazolo[1,5-a]pyrimidine-3-carboxylic acid (1 g, 3.38 mmol) in DMF (6 ml) was added CDI (930 mg, 5.74 mmol) with stirring, and the reaction mixture was stirred overnight at 50° C. This was followed by the addition of prop-2-yn-1-amine (240 mg, 4.36 mmol), and the reaction mixture was stirred overnight at room temperature, concentrated in vacuo, and the product was precipitated by addition of water (10 ml) and the solid was collected by filtration, washed with methanol (10 ml) to afford 5-(1H-1,2,3-benzotriazol-5-yl)-7-oxo-N-(prop-2-yn-1-yl)-4H,7H-pyrazolo[1,5-a]pyrimidine-3-carboxamide as light yellow solid (400 mg, 36%).

LC/MS (ES, m/z): [M+H]+ 334.0

1H NMR (300 MHz, DMSO) δ 8.37 (s, 1H), 8.08 (s, 1H), 7.75-7.78 (m, 2H), 6.29 (s, 1H), 4.16-4.18 (m, 2H), 3.18 (s, 1H)

Step 4: 5-(1H-1,2,3-benzotriazol-5-yl)-3-(5-methyl-1,3-oxazol-2-yl)-4H,7H-pyrazolo[1,5-a]pyrimidin-7-one

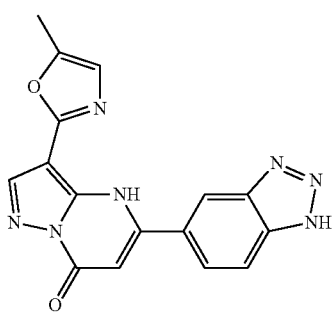 [SMILES: Cc1cnc(-c2cnn3c(=O)cc(-c4ccc5[nH]nnc5c4)[nH]c23)o1]

To a solution of sodium hydride (72 mg, 3.00 mmol) in DMSO (2 ml) was added 5-(1H-1,2,3-benzotriazol-5-yl)-7-oxo-N-(prop-2-yn-1-yl)-4H,7H-pyrazolo[1,5-a]pyrimidine-3-carboxamide (150 mg, 0.45 mmol), and the reaction mixture was stirred overnight at 30° C. The reaction was then quenched with water (3 ml) and adjusted pH to 3 with HCl (2 N). The solids were collected by filtration and purified by Prep-HPLC with the following conditions (Xbridge): Column, 19*100 mm*5 um; mobile phase; B: CH3CN A: H2O+0.05% TFA 23%-43% in 10 min; flow rate: 10 mL/min; Detector, 254 nm to afford 5-(1H-1,2,3-benzotriazol-5-yl)-3-(5-methyl-1,3-oxazol-2-yl)-4H,7H-pyrazolo[1,5-a]pyrimidin-7-one as a light yellow solid (20.6 mg, 14%).

LC/MS (ES, m/z): [M+H]+ 334.0

1H NMR (300 MHz, DMSO) δ 8.40 (s, 1H), 8.05 (s, 1H), 7.84 (d, J=8.7 Hz, 1H), 7.68 (d, J=8.1 Hz, 1H), 6.79 (s, 1H), 6.13 (s, 1H), 2.38 (s, 3H)

EXAMPLE 6

5-(1H-1,2,3-benzotriazol-5-yl)-3-(5-ethyl-1,3-oxazol-2-yl)-4H,7H-pyrazolo[1,5-a]pyrimidin-7-one

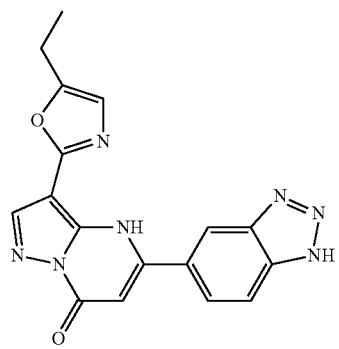 [SMILES: CCc1cnc(-c2cnn3c(=O)cc(-c4ccc5[nH]nnc5c4)[nH]c23)o1]

Step 1: 1-diazobutan-2-one

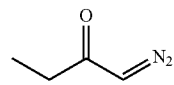

To a diazomethane ethyl ether solution (2 N, 500 ml) was added drop wise propanoyl chloride (10.0 g, 108.08 mmol), and the reaction mixture was stirred for 2 h at 0° C. in an ice-salt bath. The reaction mixture purged with argon to remove the excess diazomethane and then concentrated to (30 g, crude), which was used to the next step directly.

Step 2: 2-(chloromethyl)-5-ethyl-1,3-oxazole

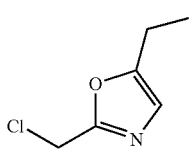

To a solution of boron trifluoride ethyl ether solution (60.0 ml, 47%) in chloroacetonitrile (80 ml) at 0° C. was added a solution of 1-diazo-3,3-dimethyl-2-butanone (30 g, crude) with stirring at 0° C. for 0.5 h and then poured onto saturated aqueous sodium bicarbonate solution to neutralize the acid. Product was extracted with dichloromethane (4×100 ml) and dried over anhydrous magnesium sulfate and concentrated in vacuo to afford 2-(chloromethyl)-5-ethyl-1,3-oxazole as a yellow liquid (1.8 g).

LC/MS (ES, m/z): [M+H]+ 146.0

Step 3: 2-(5-ethyl-1,3-oxazol-2-yl)acetonitrile

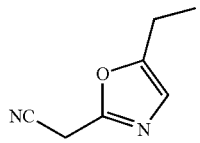

To a solution of 2-(chloromethyl)-5-ethyl-1,3-oxazole (1.6 g, 11.03 mmol) in CH$_3$CN (80 ml) and water (10 ml) was added KCN (2.69 g, 41.31 mmol), and the reaction mixture was stirred for overnight at 40° C. in an oil bath. The reaction mixture was diluted with water (250 ml) and extracted with ethyl acetate (3×80 ml) and the organic layers combined and dried over anhydrous magnesium sulfate, concentrated in vacuo to give a residue, which was purified by a silica gel column chromatography with 5% ethyl acetate in petroleum ether to afford 2-(5-ethyl-1,3-oxazol-2-yl)acetonitrile as yellow oil (500 mg, 30%).

LC/MS (ES, m/z): [M+H]$^+$ 137.0

$^1$H NMR (300 MHz, DMSO) δ 6.86 (s, 1H), 4.38 (s, 2H), 2.62-2.72 (m, 2H), 1.15-1.24 (m, 3H)

Step 4 3-(dimethylamino)-2-(5-ethyl-1,3-oxazol-2-yl)prop-2-enenitrile

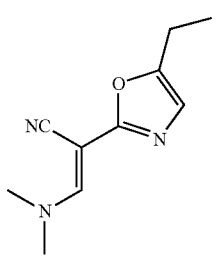

To a solution of 2-(5-ethyl-1,3-oxazol-2-yl)acetonitrile (500 mg, 3.67 mmol) in toluene (10 ml) was added DMF-DMA (656 mg, 5.51 mmol), and the reaction mixture was stirred for 1 h at 90° C. in an oil bath. The reaction mixture was concentrated in vacuo to afford 3-(dimethylamino)-2-(5-ethyl-1,3-oxazol-2-yl)prop-2-enenitrile as yellow oil (450 mg, crude).

LC/MS (ES, m/z): [M+H]$^+$ 192.0

Step 5: 4-(5-ethyl-1,3-oxazol-2-yl)-1H-pyrazol-5-amine

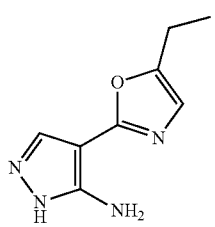

To a solution of 3-(dimethylamino)-2-(5-ethyl-1,3-oxazol-2-yl)prop-2-enenitrile (450 mg, crude) in C$_2$H$_5$OH (25 ml) was added NH$_2$NH$_2$·H$_2$O (345 mg, 6.90 mmol), and the reaction mixture was stirred for 2 h at 90° C. in an oil bath. The reaction mixture was concentrated in vacuo to give a residue, which was purified by a silica gel column chromatography with 2% dichloromethane in methanol to afford 4-(5-ethyl-1,3-oxazol-2-yl)-1H-pyrazol-5-amine as yellow oil (200 mg). LC/MS (ES, m/z): [M+H]$^+$ 179.0.

Step 6: 5-(1H-1,2,3-benzotriazol-5-yl)-3-(5-ethyl-1,3-oxazol-2-yl)-4H,7H-pyrazolo[1,5-a]pyrimidin-7-one

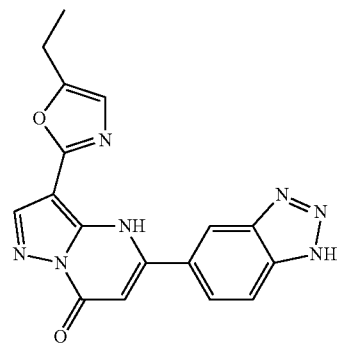 [SMILES: CCc1cnc(-c2cnn3c(=O)cc(-c4ccc5[nH]nnc5c4)[nH]c23)o1]

To a solution of 4-(5-ethyl-1,3-oxazol-2-yl)-1H-pyrazol-5-amine (100 mg, 0.56 mmol) in n-BuOH (5 ml) was added ethyl 3-(1H-1,2,3-benzotriazol-5-yl)-3-oxopropanoate (200 mg, 0.85 mmol) and TsOH (5 mg, 0.03 mmol), and the reaction mixture was stirred overnight at 130° C. in an oil bath. The solids were collected by filtration, washed with methanol (3×10 ml) to afford 5-(1H-1,2,3-benzotriazol-5-yl)-3-(5-ethyl-1,3-oxazol-2-yl)-4H,7H-pyrazolo[1,5-a]pyrimidin-7-one as an off-white solid (27.5 mg, 14%).

LC/MS (ES, m/z): [M+H]$^+$ 348.1

$^1$H NMR (300 MHz, DMSO) δ 8.50 (s, 1H), 8.10 (s, 1H), 7.91-7.98 (m, 1H), 7.75-7.86 (m, 1H), 6.82 (s, 1H), 6.20 (s, 1H), 2.75-2.82 (m, 2H), 1.27-1.32 (t, J=7.5 Hz, 3H)

EXAMPLE 7

5-(4-chlorophenyl)-3-(3-methyl-1,2,4-oxadiazol-5-yl)-4H,7H-pyrazolo[1,5-a]pyrimidin-7-one

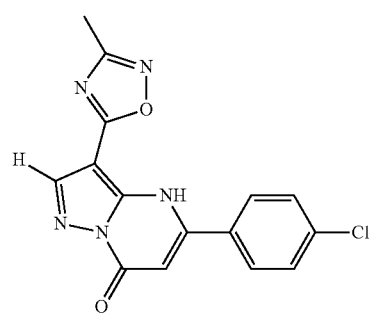 [SMILES: Cc1noc(-c2cnn3c(=O)cc(-c4ccc(Cl)cc4)[nH]c23)n1]

Step 1: 5-(4-chlorophenyl)-N-[(1E)-1-(dimethyl-amino)ethylidene]-7-oxo-4H,7H-pyrazolo[1,5-a]pyrimidine-3-carboxamide

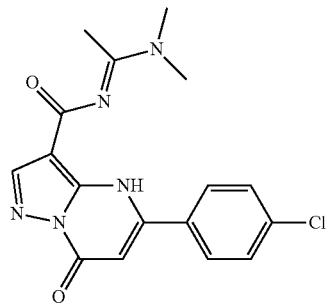 [SMILES: C/C(=N\C(=O)c1cnn2c(=O)cc(-c3ccc(Cl)cc3)[nH]c12)N(C)C]

To a solution of 5-(4-chlorophenyl)-7-oxo-4H,7H-pyrazolo[1,5-a]pyrimidine-3-carboxamide (300 mg, 1.04 mmol) in toluene (6 mL) was added N,N-dimethylformamide dimethyl acetal (DMF-DMA) (554 mg, 4.17 mmol), and the reaction mixture was stirred for 1.5 h at 130° C. The solids were collected by filtration and washed with Et$_2$O (3×15 mL) to afford of 5-(4-chlorophenyl)-N-[(1E)-1-(dimethyl-amino)ethylidene]-7-oxo-4H,7H-pyrazolo[1,5-a]pyrimidine-3-carboxamide as a light yellow solid (185 mg, 50%).

LC/MS (ES, m/z): [M+H]$^+$ 358.0

$^1$H NMR (300 MHz, DMSO) δ 8.08 (d, J=8.7 Hz, 2H), 8.00 (s, 1H), 7.48-7.51 (m, 2H), 6.12 (s, 1H), 3.06 (s, 6H), 1.95 (s, 3H)

Step 2: 5-(4-chlorophenyl)-3-(3-methyl-1,2,4-oxadiazol-5-yl)-4H,7H-pyrazolo[1,5-a]pyrimidin-7-one

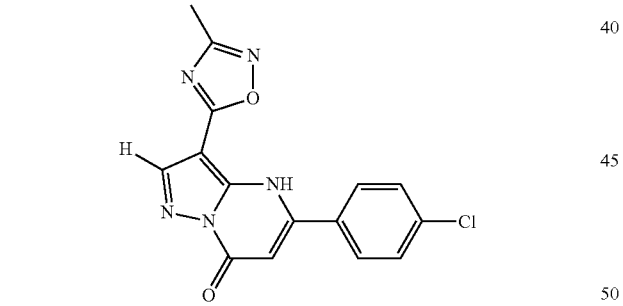

To a solution of 5-(4-chlorophenyl)-N-[(1E)-1-(dimethyl-amino)ethylidene]-7-oxo-4H,7H-pyrazolo[1,5-a]pyrimidine-3-carboxamide (160 mg, 0.45 mmol) in dioxane (3.0 mL) was added NH$_2$OH HCl (46.4 mg, 0.67 mmol), and the reaction mixture was stirred for 5 min. Then the mixture of AcOH (3.0 mL) and 10% NaOH (aq, 0.5 mL) was added dropwise to the reaction and stirred for 2.5 h at 100° C. The solid was removed by filtration and the mother liquid was concentrated in vacuo and washed with ether (3×10 mL) and MeOH (3×10 mL) to afford 5-(4-chlorophenyl)-3-(3-methyl-1,2,4-oxadiazol-5-yl)-4H,7H-pyrazolo[1,5-a]pyrimidin-7-one as an off-white solid (40 mg, 27%).

LC/MS (ES, m/z): [M+H]$^+$ 328.0

$^1$H NMR (300 MHz, DMSO) δ 8.25 (s, 1H), 8.09 (d, J=8.7 Hz, 2H), 7.50 (d, J=8.7 Hz, 2H), 6.24 (s, 1H), 2.32 (s, 3H)

EXAMPLE 8

5-(4-chlorophenyl)-2-methyl-3-(3-methyl-1,2,4-oxadiazol-5-yl)-4H,7H-pyrazolo[1,5-a]pyrimidin-7-one

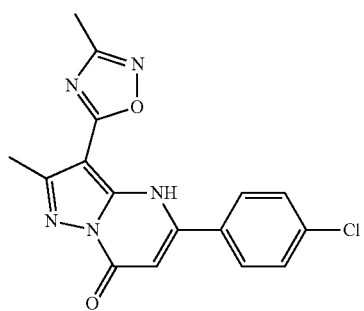 [SMILES: Cc1noc(-c2c(C)nn3c(=O)cc(-c4ccc(Cl)cc4)[nH]c23)n1]

Step 1: 5-(4-chlorophenyl)-N-[(1E)-1-(dimethyl-amino)ethylidene]-2-methyl-7-oxo-4H,7H-pyrazolo[1,5-a]pyrimidine-3-carboxamide

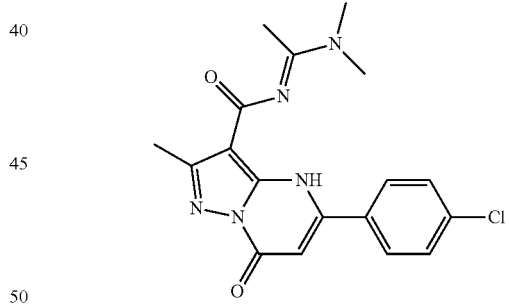

To a solution of 5-(4-chlorophenyl)-2-methyl-7-oxo-4H,7H-pyrazolo[1,5-a]pyrimidine-3-carboxamide (300 mg, 0.99 mmol) in DMF (3.0 mL) was added N,N-dimethylacetamide dimethyl acetal (DMA-DMA) (528 mg, 3.97 mmol), and the reaction mixture was stirred for 3.5 h at 130° C. The solids were collected by filtration, washed with Et$_2$O (3×15 mL) to afford 5-(4-chlorophenyl)-N-[(1E)-1-(dimethylamino)ethylidene]-2-methyl-7-oxo-4H,7H-pyrazolo[1,5-a]pyrimidine-3-carboxamide as a light yellow solid (200 mg, 54%).

LC/MS (ES, m/z): [M+H]$^+$ 372.0.

Step 2: 5-(4-chlorophenyl)-2-methyl-3-(3-methyl-1,2,4-oxadiazol-5-yl)-4H,7H-pyrazolo[1,5-a]pyrimidin-7-one

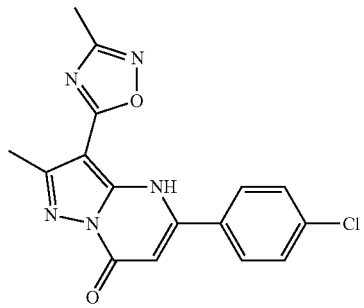 [SMILES: Cc1noc(-c2c(C)nn3c(=O)cc(-c4ccc(Cl)cc4)[nH]c23)n1]

To a solution of 5-(4-chlorophenyl)-N-[(1E)-1-(dimethylamino)ethylidene]-2-methyl-7-oxo-4H,7H-pyrazolo[1,5-a]pyrimidine-3-carboxamide (200 mg, 0.54 mmol) in dioxane (0.6 ml) was added NH$_2$OH.HCl (55.8 mg, 0.81 mmol), and the reaction mixture was stirred for 5 min. Then the mixture of AcOH (0.6 ml) and 10% NaOH (aq, 0.5 ml) was added drop wise to the reaction and stirred for 3 h at 100° C. The solid was removed by filtration and the mother liquid was concentrated in vacuo to give a residue, which was washed with methanol (30 ml) and ether (30 ml) to afford 5-(4-chlorophenyl)-2-methyl-3-(3-methyl-1,2,4-oxadiazol-5-yl)-4H,7H-pyrazolo[1,5-a]pyrimidin-7-one (66 mg, 36%) as an off-white solid.

LC/MS (ES, m/z): [M−H]$^-$ 342.0

$^1$H NMR (300 MHz, CD$_3$OD) δ 7.86 (d, J=8.7 Hz, 2H), 7.63 (d, J=8.4 Hz, 2H), 6.33 (s, 1H), 2.71 (s, 3H), 2.47 (s, 3H)

EXAMPLE 9

5-(4-chlorophenyl)-2-methoxy-3-(3-methyl-1,2,4-oxadiazol-5-yl)-4H,7H-pyrazolo[1,5-a]pyrimidin-7-one

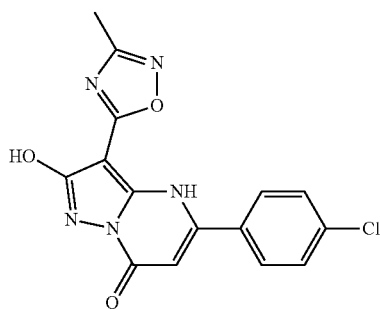 [SMILES: Cc1noc(-c2c(O)nn3c(=O)cc(-c4ccc(Cl)cc4)[nH]c23)n1]

Step 1: 2-(dimethoxymethylidene)propanedinitrile

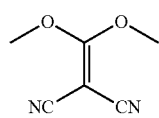

To a solution of ethene-1,1,2,2-tetracarbonitrile (10 g, 78.07 mmol) in methanol (25 ml) was added a solution of urea (1.6 g, 26.64 mmol), and the reaction mixture was stirred for 30 min at 35° C. and then ethyl ether (100 ml) was added at room temperature. The resulting solution was stirred for 4.5 hr at −78° C. The solids were collected by filtration and washed with cooled ether (3×50 ml) to afford 2-(dimethoxymethylidene)propanedinitrile as a white solid (6.5 g, 60%).

Step 2: 5-amino-3-methoxy-1H-pyrazole-4-carbonitrile

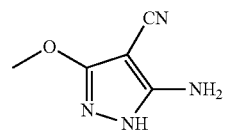

To a solution of 2-(dimethoxymethylidene)propanedinitrile (6.5 g, 47.1 mmol) in water (200 ml) was added N$_2$H$_4$.H$_2$O (10 ml). The resulting solution was stirred overnight at 25° C. The mixture was extracted with ethyl acetate (5×100 ml) and the organic layers combined and dried over anhydrous sodium sulfate. The solids were filtered out and the filtrate was concentrated in vacuo to afford 5-amino-3-methoxy-1H-pyrazole-4-carbonitrile as a light yellow solid (2.5 g, 38%).

LC/MS (ES, m/z): [M+H]$^+$ 139.0

$^1$H NMR (300 MHz, DMSO) δ 11.04 (s, 1H), 6.36 (s, 2H), 3.76 (s, 3H)

Step 3: 5-(4-chlorophenyl)-2-methoxy-7-oxo-4H,7H-pyrazolo[1,5-a]pyrimidine-3-carbonitrile

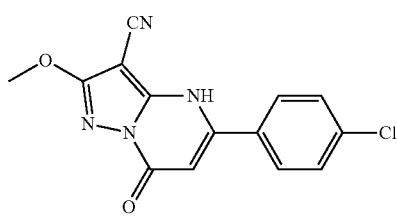 [SMILES: COc1nn2c(=O)cc(-c3ccc(Cl)cc3)[nH]c2c1C#N]

To a solution of 5-amino-3-methoxy-1H-pyrazole-4-carbonitrile (1 g, 7.24 mmol) in n-BuOH (8 ml) was added methyl 3-(4-chlorophenyl)-3-oxopropanoate (1.9 g, 8.96 mmol), TsOH (60 mg, 0.35 mmol), and the reaction mixture was stirred for 2 h at 130° C. The product were collected by filtration and washed with methanol (6 ml) to afford 5-(4-chlorophenyl)-2-methoxy-7-oxo-4H,7H-pyrazolo[1,5-a]pyrimidine-3-carbonitrile as a white solid (1.4 g, 64%).

LC/MS (ES, m/z): [M+H]$^+$ 301.0

$^1$H NMR (300 MHz, DMSO) δ 7.84 (d, J=8.4 Hz, 2H), 7.63 (d, J=8.7 Hz, 2H), 6.26 (s, 1H), 4.02 (s, 3H)

Step 4: 5-(4-chlorophenyl)-2-methoxy-7-oxo-4H,7H-pyrazolo[1,5-a]pyrimidine-3-carboxamide

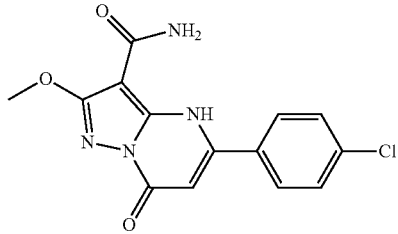 [SMILES: COc1nn2c(=O)cc(-c3ccc(Cl)cc3)[nH]c2c1C(N)=O]

To the solid 5-(4-chlorophenyl)-2-methoxy-7-oxo-4H,7H-pyrazolo[1,5-a]pyrimidine-3-carbonitrile (2 g, 6.67 mmol) was added sulfuric acid (con, 5 ml), and the reaction mixture was stirred for 2 h at 30° C. The reaction was then quenched by the addition of ice water (20 ml). The product was collected by filtration to afford 5-(4-chlorophenyl)-2-methoxy-7-oxo-4H,7H-pyrazolo[1,5-a]pyrimidine-3-carboxamide as a white solid (1.8 g, 85%).

LC/MS (ES, m/z): [M+H]$^+$ 319.0

Step 5: 5-(4-chlorophenyl)-N-[(1E)-1-(dimethylamino)ethylidene]-2-methoxy-7-oxo-4H,7H-pyrazolo[1,5-a]pyrimidine-3-carboxamide

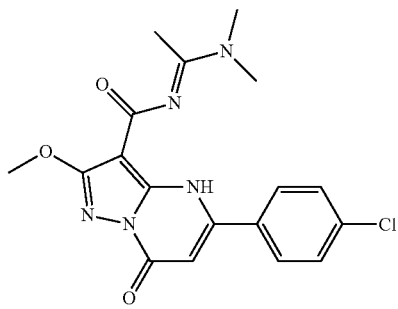 [SMILES: COc1nn2c(=O)cc(-c3ccc(Cl)cc3)[nH]c2c1C(=O)/N=C(\C)N(C)C]

To a solution of 5-(4-chlorophenyl)-2-methoxy-7-oxo-4H,7H-pyrazolo[1,5-a]pyrimidine-3-carboxamide (1 g, 3.14 mmol) in DMF (6 ml) was added DMA-DMA (6 g), and the reaction mixture was stirred for 8 h at 130° C. The resulting mixture was concentrated in vacuo to give a residue, which was re-crystallized from dichloromethane:ethyl ether (4:70). The solids were collected by filtration and washed with ethyl ether (3 ml) to afford 5-(4-chlorophenyl)-N-[(1E)-1-(dimethylamino)ethylidene]-2-methoxy-7-oxo-4H,7H-pyrazolo[1,5-a]pyrimidine-3-carboxamide as a light yellow solid (525 mg, 43%).

LC/MS (ES, m/z): [M+H]$^+$ 388.1

Step 6: 5-(4-chlorophenyl)-2-methoxy-3-(3-methyl-1,2,4-oxadiazol-5-yl)-4H,7H-pyrazolo[1,5-a]pyrimidin-7-one

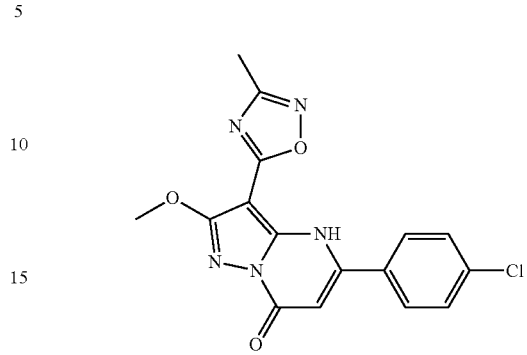

To a solution of 5-(4-chlorophenyl)-N-[(1E)-1-(dimethylamino)ethylidene]-2-methoxy-7-oxo-4H,7H-pyrazolo[1,5-a]pyrimidine-3-carboxamide (525 mg, 1.36 mmol) in dioxane (5 ml) was added NH$_2$OH.HCl (189 mg, 2.72 mmol). This was followed by the addition of a solution of sodium hydroxide (10%, 1.6 ml) in AcOH (8 ml) dropwise with stirring and then stirred for 1 h at 100° C. The reaction was then quenched by the addition of water (30 ml). The product were collected by filtration and washed with water (3 ml) to afford 5-(4-chlorophenyl)-2-methoxy-3-(3-methyl-1,2,4-oxadiazol-5-yl)-4H,7H-pyrazolo[1,5-a]pyrimidin-7-one as a light green solid (300 mg, crude).

LC/MS (ES, m/z): [M+H]$^+$ 358.0
$^1$H NMR (300 MHz, DMSO) δ 7.88 (d, J=8.4 Hz, 2H), 7.61 (d, J=8.4 Hz, 2H), 6.28 (s, 1H), 4.05 (s, 3H), 2.38 (s, 3H)

Step 7: 5-(4-chlorophenyl)-2-hydroxy-3-(3-methyl-1,2,4-oxadiazol-5-yl)-4H,7H-pyrazolo[1,5-a]pyrimidin-7-one

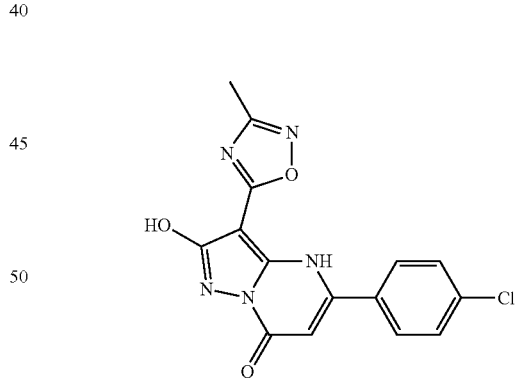

5-(4-chlorophenyl)-2-methoxy-3-(3-methyl-1,2,4-oxadiazol-5-yl)-4H,7H-pyrazolo[1,5-a]pyrimidin-7-one (300 mg, crude) in sulfuric acid (con, 4 ml) was stirred for 5 h at 90° C. The reaction was then quenched by the addition of ice water (20 ml). The product was collected by filtration and washed with water (3 ml) to give a crude product, which was purified by Prep-HPLC to afford 5-(4-chlorophenyl)-2-hydroxy-3-(3-methyl-1,2,4-oxadiazol-5-yl)-4H,7H-pyrazolo[1,5-a]pyrimidin-7-one as a gray solid (36.1 mg).

(ES, m/z): [M+H]$^+$ 344.0
$^1$H NMR (300 MHz, DMSO) δ 7.82 (d, J=8.4 Hz, 2H), 7.65 (d, J=8.4 Hz, 2H), 6.29 (s, 1H), 2.40 (s, 3H)

EXAMPLE 10

5-(4-chlorophenyl)-2-methoxy-3-(3-methyl-1,2,4-oxadiazol-5-yl)-4H,7H-pyrazolo[1,5-a]pyrimidin-7-one

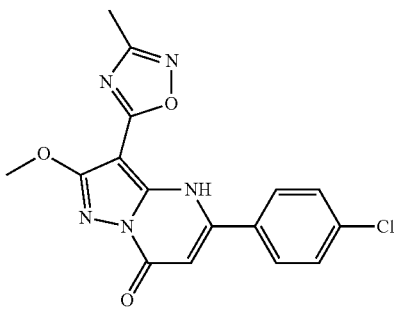 [SMILES: COc1nn2c(=O)cc(-c3ccc(Cl)cc3)[nH]c2c1-c1nc(C)no1]

Step 1: 5-(4-chlorophenyl)-N-[(1E)-1-(dimethylamino)ethylidene]-2-methoxy-7-oxo-4H,7H-pyrazolo[1,5-a]pyrimidine-3-carboxamide To a solution of 5-(4-chlorophenyl)-2-methoxy-7-oxo-4H,7H-pyrazolo[1,5-a]pyrimidine-3-carboxamide (600 mg, 1.88 mmol) in DMF (3 ml) was added DMA-DMA (3.51 g) with stirring overnight at 130° C. The resulting mixture was concentrated in vacuo to give a residue, which was washed with the mixture of dichloromethane (2 ml) and ethyl ether (60 ml). The product was collected by filtration and dried in an oven under reduced pressure to afford 5-(4-chlorophenyl)-N-[(1E)-1-(dimethylamino)ethylidene]-2-methoxy-7-oxo-4H,7H-pyrazolo[1,5-a]pyrimidine-3-carboxamide as a light yellow solid (350 mg, crude).

LC/MS (ES, m/z): [M+H]⁺ 388.0

Step 2: 5-(4-chlorophenyl)-2-methoxy-3-(3-methyl-1,2,4-oxadiazol-5-yl)-4H,7H-pyrazolo[1,5-a]pyrimidin-7-one

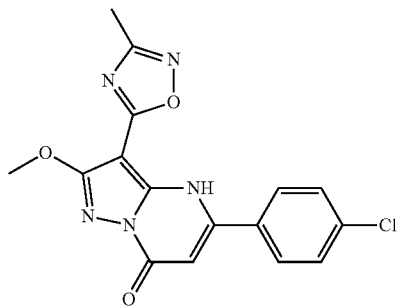

To a solution of 5-(4-chlorophenyl)-N-[(1E)-1-(dimethylamino)ethylidene]-2-methoxy-7-oxo-4H,7H-pyrazolo[1,5-a]pyrimidine-3-carboxamide (350 mg, crude) in dioxane (3 ml) was added NH$_2$OH.HCl (95 mg, 1.37 mmol), sodium hydroxide (10%, 0.8 ml), AcOH (4 ml), and the reaction mixture was stirred for 1 h at 100° C. The reaction mixture was then quenched by the addition of water (30 ml). The solids were collected by filtration and washed with water (5 ml) to afford crude product, which was purified by Prep-HPLC to afford 5-(4-chlorophenyl)-2-methoxy-3-(3-methyl-1,2,4-oxadiazol-5-yl)-4H,7H-pyrazolo[1,5-a]pyrimidin-7-one as an off-white solid (90.9 mg, 14% 2 steps).

LC/MS (ES, m/z): [M+H]⁺ 358.0

¹H NMR (300 MHz, DMSO) δ 7.83 (d, J=8.7 Hz, 2H), 7.65-7.67 (t, J=6.6 Hz, 2H), 6.30 (s, 1H), 4.07 (s, 3H), 2.40 (s, 3H)

EXAMPLE 11

5-(1H-1,2,3-benzotriazol-5-yl)-3-(4-methyl-1,3-oxazol-2-yl)-4H,7H-pyrazolo[1,5-a]pyrimidin-7-one

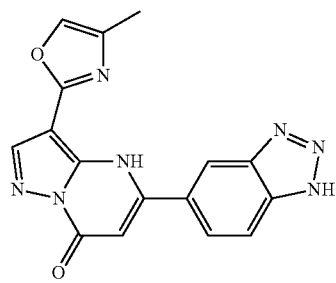 [SMILES: Cc1coc(-c2cnn3c(=O)cc(-c4ccc5[nH]nnc5c4)[nH]c23)n1]

Step 1: 5-(1H-1,2,3-benzotriazol-5-yl)-7-oxo-4H,7H-pyrazolo[1,5-a]pyrimidine-3-carbonitrile

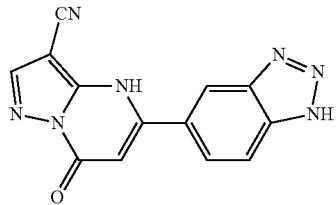 [SMILES: N#Cc1cnn2c(=O)cc(-c3ccc4[nH]nnc4c3)[nH]c12]

To a solution of 5-amino-1H-pyrazole-4-carbonitrile (1 g, 9.25 mmol) in n-BuOH (6 mL) was added ethyl 3-(1H-1,2,3-benzotriazol-5-yl)-3-oxopropanoate (2.3 g, 9.87 mmol) and TsOH (77 mg, 0.45 mmol), and the reaction mixture was stirred overnight at reflux. The solids were collected by filtration and washed with methanol (9 ml) to afford 5-(1H-1,2,3-benzotriazol-5-yl)-7-oxo-4H,7H-pyrazolo[1,5-a]pyrimidine-3-carbonitrile (2.1 g, 82%) as a wine solid.

LC/MS (ES, m/z): [M+H]$^+$ 278.0

$^1$H NMR (300 MHz, DMSO): δ 8.35 (s, 1H), 8.10 (s, 1H), 7.70-7.80 (m, 2H), 6.24 (s, 1H)

Step 2: Prop-2-ynyl 5-(1H-benzo[d][1,2,3]triazol-5-yl)-7-oxo-4,7-dihydropyrazolo[1,5-a]pyrimidine-3-carbimidate hydrochloride

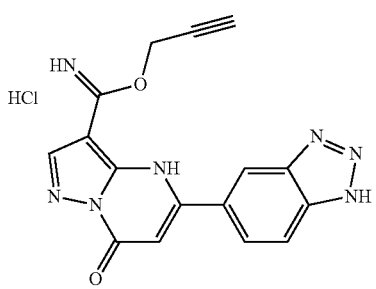 [SMILES: Cl ; C#CCOC(=N)c1cnn2c(=O)cc(-c3ccc4[nH]nnc4c3)[nH]c12]

HCl (gas) was transferred into the solution of 5-(1H-1,2,3-benzotriazol-5-yl)-7-oxo-4H,7H-pyrazolo[1,5-a]pyrimidine-3-carbonitrile (400 mg, 1.44 mmol) in prop-2-yn-1-ol (5 ml), and the reaction mixture was stirred for 2 h at room temperature. The resulting mixture was concentrated in vacuo to afford prop-2-ynyl 5-(1H-benzo[d][1,2,3]triazol-5-yl)-7-oxo-4,7-dihydropyrazolo[1,5-a]pyrimidine-3-carbimidate hydrochloride as a dark red solid (600 mg, crude).

LC/MS (ES, m/z): [M+H]$^+$ 334.0

Step 3: 5-(1H-1,2,3-benzotriazol-5-yl)-3-(4-methyl-1,3-oxazol-2-yl)-4H,7H-pyrazolo[1,5-a]pyrimidin-7-one

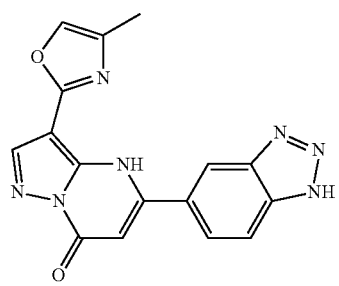 [SMILES: Cc1coc(-c2cnn3c(=O)cc(-c4ccc5[nH]nnc5c4)[nH]c23)n1]

To a solution of prop-2-yn-1-yl 5-(1H-1,2,3-benzotriazol-5-yl)-7-oxo-4H,7H-pyrazolo[1,5-a]pyrimidine-3-carboximidate hydrochloride (600 mg, crude) in xylene (8 ml) was added DIEA (319 mg, 2.47 mmol) and TsOAg (23 mg, 0.06 mmol), and the reaction mixture was stirred for 3 h at 70° C. To the reaction was then added methanol (5 ml) and ethyl ether (15 ml), and the solids were collected by filtration to give a crude product, which was purified by Flash-Prep-HPLC to afford 5-(1H-1,2,3-benzotriazol-5-yl)-3-(4-methyl-1,3-oxazol-2-yl)-4H,7H-pyrazolo[1,5-a]pyrimidin-7-one as a light yellow solid (77.6 mg, 13% 2 steps).

LC/MS (ES, m/z): [M+H]$^+$ 333.9

$^1$H NMR (300 MHz, DMSO): δ 8.45 (s, 1H), 8.15 (s, 1H), 7.70-7.90 (m, 3H), 6.19 (s, 1H), 2.13 (s, 3H)

EXAMPLE 12

5-(1-ethyl-1H-indazol-5-yl)-3-(5-methyl-1,3-oxazol-2-yl)-4H,7H-pyrazolo[1,5-a]pyrimidin-7-one

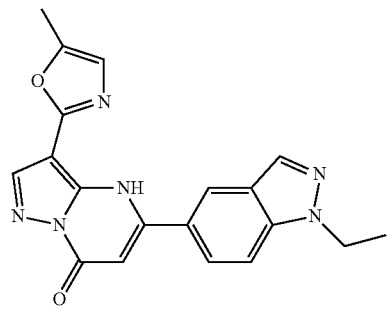 [SMILES: CCn1ncc2cc(-c3cc(=O)n4ncc(-c5ncc(C)o5)c4[nH]3)ccc21]

Step 1: Ethyl 5-(1-ethyl-1H-indazol-5-yl)-7-oxo-4H,7H-pyrazolo[1,5-a]pyrimidine-3-carboxylate

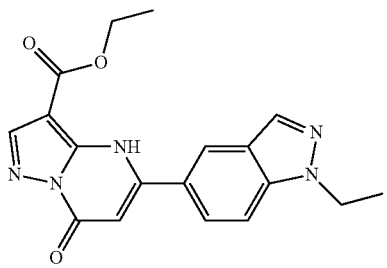 [SMILES: CCOC(=O)c1cnn2c(=O)cc(-c3ccc4c(cnn4CC)c3)[nH]c12]

To a solution of ethyl 5-amino-1H-pyrazole-4-carboxylate (1 g, 6.45 mmol) in n-BuOH (10 ml) was added TsOH (55 mg), ethyl 3-(1-ethyl-1H-indazol-5-yl)-3-oxopropanoate (2.01 g, 7.72 mmol), and the reaction mixture was stirred for 20 h at 130° C. The solids were collected by filtration and washed with methanol (10 ml) to afford ethyl 5-(1-ethyl-1H-indazol-5-yl)-7-oxo-4H,7H-pyrazolo[1,5-a]pyrimidine-3-carboxylate as a red solid (1.8 g, 79%).

LC/MS (ES, m/z): [M+H]$^+$ 352.0

Step 2: 5-(1-ethyl-1H-indazol-5-yl)-7-oxo-4H,7H-pyrazolo[1,5-a]pyrimidine-3-carboxylic acid

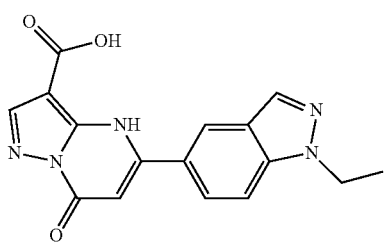 [SMILES: CCn1ncc2cc(-c3cc(=O)n4ncc(C(=O)O)c4[nH]3)ccc21]

To a solution of ethyl 5-(1-ethyl-1H-indazol-5-yl)-7-oxo-4H,7H-pyrazolo[1,5-a]pyrimidine-3-carboxylate (1 g, 2.85 mmol) in DMSO (10 ml) was added sodium hydroxide (500 mg, 12.50 mmol), water (1 ml), and the reaction mixture was stirred for 1 h at 70° C. The pH of the solution was adjusted to 4 with HCl (3N). The solids were collected by filtration and washed with water (10 ml) to afford 5-(1-ethyl-1H-indazol-5-yl)-7-oxo-4H,7H-pyrazolo[1,5-a]pyrimidine-3-carboxylic acid as a red solid (760 mg, 83%).

LC/MS (ES, m/z): [M+H]$^+$ 324.0

$^1$H NMR (300 MHz, DMSO) δ 8.22-8.27 (m, 3H), 7.77-7.89 (m, 2H), 6.29 (s, 1H), 4.48-4.55 (m, 2H), 1.39-1.44 (t, J=7.2 Hz, 3H)

Step 3: 5-(1-ethyl-1H-indazol-5-yl)-7-oxo-N-(prop-2-yn-1-yl)-4H,7H-pyrazolo[1,5-a]pyrimidine-3-carboxamide

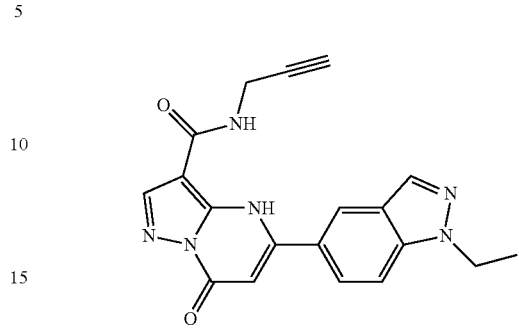

To a solution of 5-(1-ethyl-1H-indazol-5-yl)-7-oxo-4H,7H-pyrazolo[1,5-a]pyrimidine-3-carboxylic acid (400 mg, 1.24 mmol) in DMF (2 ml) was added CDI (400 mg) at 50° C. and then stirred overnight. Prop-2-yn-1-amine (500 mg, 9.08 mmol) was added, and the reaction mixture was stirred for 3 h at 50° C. The resulting mixture was concentrated in vacuo and washed with water (30 ml) to afford 5-(1-ethyl-1H-indazol-5-yl)-7-oxo-N-(prop-2-yn-1-yl)-4H,7H-pyrazolo[1,5-a]pyrimidine-3-carboxamide as a yellow solid (230 mg, crude).

LC/MS (ES, m/z): [M+H]$^+$ 361.0

Step 4: 5-(1-ethyl-1H-indazol-5-yl)-3-(5-methyl-1,3-oxazol-2-yl)-4H,7H-pyrazolo[1,5-a]pyrimidin-7-one

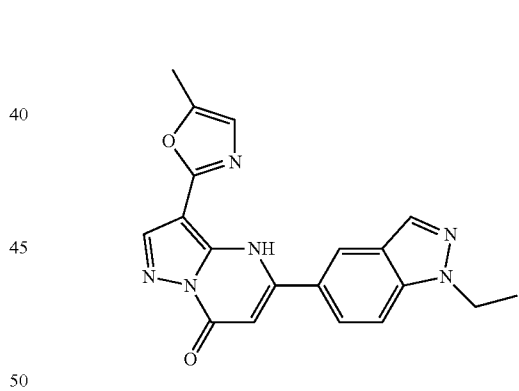

To a solution of 5-(1-ethyl-1H-indazol-5-yl)-7-oxo-N-(prop-2-yn-1-yl)-4H,7H-pyrazolo[1,5-a]pyrimidine-3-carboxamide (230 mg, crude) in DMSO (5 ml) was added sodium hydride (92 mg, 3.83 mmol), and the reaction mixture was stirred for 2 h at 25° C. The reaction was then quenched by the addition of water (15 ml) and adjusted pH to 3 with HCl (2N). The product was precipitated and collected by filtration to afford 5-(1-ethyl-1H-indazol-5-yl)-3-(5-methyl-1,3-oxazol-2-yl)-4H,7H-pyrazolo[1,5-a]pyrimidin-7-one as a light red solid (58 mg, 10% 2 steps).

LC/MS (ES, m/z): [M+H]$^+$ 361.0

$^1$H NMR (300 MHz, DMSO) δ 8.45 (s, 1H), 8.19 (s, 2H), 8.12 (d, J=8.7 Hz, 1H), 7.76 (d, J=8.7 Hz, 1H), 6.90 (s, 1H), 6.30 (s, 1H), 4.45-4.52 (m, 2H), 2.40 (s, 3H), 1.40-1.45 (t, J=7.2 Hz, 3H)

EXAMPLE 13

5-(1-Ethyl-1H-indazol-5-yl)-3-(4-methyl-1,3-oxazol-2-yl)-4H,7H-pyrazolo[1,5-a]pyrimidin-7-one

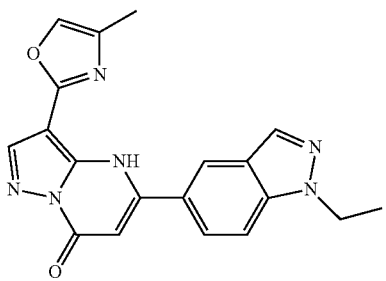 [SMILES: CCn1ncc2cc(-c3cc(=O)n4ncc(-c5nc(C)co5)c4[nH]3)ccc21]

Step 1: 5-(1-Ethyl-1H-indazol-5-yl)-7-oxo-4H,7H-pyrazolo[1,5-a]pyrimidine-3-carbonitrile

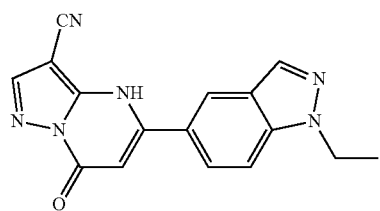 [SMILES: CCn1ncc2cc(-c3cc(=O)n4ncc(C#N)c4[nH]3)ccc21]

To a solution of ethyl 3-(1-ethyl-1H-indazol-5-yl)-3-oxo-propanoate (2.3 g, 8.84 mmol) in n-BuOH (15 ml) was added TsOH (70 mg, 0.41 mmol), 5-amino-1H-pyrazole-4-carbonitrile (800 mg, 7.59 mmol). The resulting solution was stirred overnight at reflux. The solids were collected by filtration and washed with ether (10 ml) and methanol (10 ml) to afford 5-(1-ethyl-1H-indazol-5-yl)-7-oxo-4H,7H-pyrazolo[1,5-a]pyrimidine-3-carbonitrile as a light red solid (1.2 g, 52%).
LC/MS (ES, m/z): [M+H]$^+$ 305.0
$^1$H NMR (300 MHz, DMSO)$^1$H NMR (300 MHz, DMSO) δ 8.44 (s, 1H), 8.27-8.33 (m, 2H), 7.81-7.89 (m, 2H), 6.31 (s, 1H), 4.48-4.55 (m, 2H), 1.39-1.44 (m, J=7.2 Hz, 3H)

Step 2: Prop-2-ynyl 5-(1-ethyl-1H-indazol-5-yl)-7-oxo-4,7-dihydropyrazolo[1,5-a]pyrimidine-3-carbimidate hydrochloride

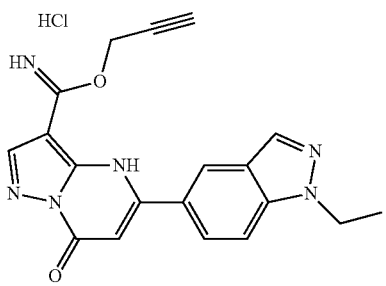 [SMILES: C#CCOC(=N)c1cnn2c(=O)cc(-c3ccc4c(cnn4CC)c3)[nH]c12 ; Cl]

HCl (g) was introduced into the solution of 5-(1-ethyl-1H-indazol-5-yl)-7-oxo-4H,7H-pyrazolo[1,5-a]pyrimidine-3-carbonitrile (450 mg, 1.48 mmol) in prop-2-yn-1-ol (10 ml) at 0° C. for 2 h and then stirred overnight at room temperature. The resulting mixture was concentrated in vacuo to afford prop-2-yn-1-yl5-(1-ethyl-1H-indazol-5-yl)-7-oxo-4H,7H-pyrazolo[1,5-a]pyrimidine-3-carboximidate hydrochloride as a black solid (600 g, crude).
LC/MS (ES, m/z): [M+H]$^+$. 361.0

Step 3: 5-(1-Ethyl-1H-indazol-5-yl)-3-(4-methyl-1,3-oxazol-2-yl)-4H,7H-pyrazolo[1,5-a]pyrimidin-7-one

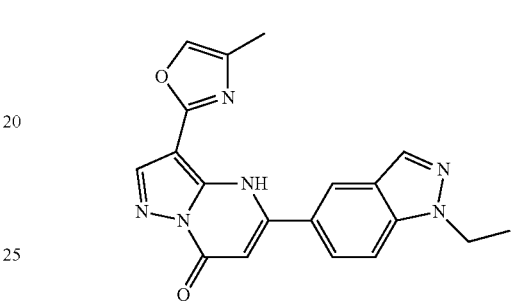

To a solution of prop-2-yn-1-yl 5-(1-ethyl-1H-indazol-5-yl)-7-oxo-4H,7H-pyrazolo[1,5-a]pyrimidine-3-carboximidate hydrochloride (600 mg, crude) in xylene (10 ml) was added DIEA (0.24 g, 1.50 mmol), TsOAg (17.6 mg, 0.05 mmol). The resulting solution was stirred for 3 h at 70° C. and then concentrated in vacuo. The crude product was precipitated from ethyl ether (10 ml) and purified by Flash-Prep-HPLC to afford 5-(1-ethyl-1H-indazol-5-yl)-3-(4-methyl-1,3-oxazol-2-yl)-4H,7H-pyrazolo[1,5-a]pyrimidin-7-one as a white solid (77.6 mg, 10% 2 steps).
LC/MS (ES, m/z): [M+H]$^+$ 361.0
$^1$H NMR (300 MHz, DMSO) δ 8.36 (s, 1H), 8.29 (s, 2H), 7.89-7.93 (t, J=8.7 Hz, 2H), 7.80-7.83 (m, 1H), 6.26 (s, 1H), 4.49-4.56 (m, 2H), 2.20 (s, 3H), 1.39-1.44 (t, J=7.2 Hz, 3H)

EXAMPLE 14

5-(2H-1,3-benzodioxol-5-yl)-3-(5-ethyl-1,3-oxazol-2-yl)-4H,7H-pyrazolo[1,5-a]pyrimidin-7-one

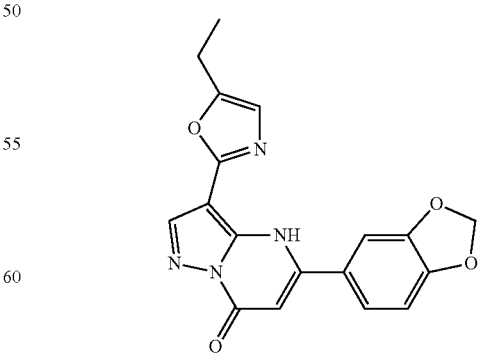

To a solution of 4-(5-ethyl-1,3-oxazol-2-yl)-1H-pyrazol-5-amine (100 mg, 0.56 mmol) in n-BuOH (5 ml) was added ethyl 3-(2H-1,3-benzodioxol-5-yl)-3-oxopropanoate (213 mg, 0.90 mmol) and TsOH (5.6 mg, 0.03 mmol) with stirring overnight at 130° C. in an oil bath. The product was precipitated by the addition of ethyl ether (20 ml) and collected by filtration, washed with methanol (3×10 ml) to afford 5-(2H-1,3-benzodioxol-5-yl)-3-(5-ethyl-1,3-oxazol-2-yl)-4H,7H-pyrazolo[1,5-a]pyrimidin-7-one as a light brown solid (44.3 mg, 22%).

LC/MS (ES, m/z): [M+H]+ 351.05

1H NMR (300 MHz, DMSO) δ 8.09 (s, 1H), 7.71 (s, 1H), 7.60-7.68 (m, 1H), 6.95-6.99 (m, 1H), 6.80 (s, 1H), 6.06 (s, 3H), 2.71-2.80 (m, 2H), 1.23-1.27 (m, 3H)

EXAMPLE 15

5-(1H-1,2,3-benzotriazol-5-yl)-3-(4-ethyl-1,3-oxazol-2-yl)-4H,7H-pyrazolo[1,5-a]pyrimidin-7-one

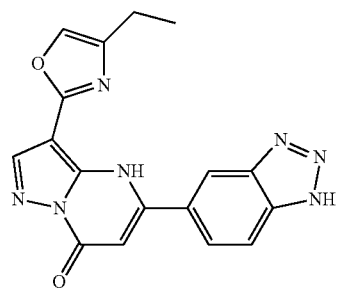 [SMILES: CCc1coc(-c2cnn3c(=O)cc(-c4ccc5[nH]nnc5c4)[nH]c23)n1]

Step 1: 2-chloro-N-(1-hydroxybutan-2-yl)acetamide

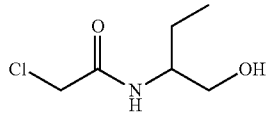

To a solution of 2-aminobutan-1-ol (20 g, 224.38 mmol) in dichloromethane (100 mL) was added TEA (60 mL). This was followed by the addition of 2-chloroacetyl chloride (18.4 mL, 247 mmol) dropwise with stirring at −70° C. over 15 min. The reaction mixture was stirred for 1 h at RT. The reaction was then quenched by the addition of water (100 mL), extracted with ethyl acetate (3×100 mL). The organic layers combined and concentrated in vacuo to afford 2-chloro-N-(1-hydroxybutan-2-yl)acetamide (28 g, 75%) as a brown solid.

Step 2: 2-chloro-N-(1-oxobutan-2-yl)acetamide

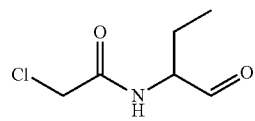

To a solution of (COCl)2 (25.8 g, 205 mmol) in dichloromethane (300 mL) was added DMSO (21.3 g, 272.62 mmol) dropwise with stirring at −78° C. over 10 min. To the mixture was added 2-chloro-N-(1-hydroxybutan-2-yl)acetamide (28 g, 169.06 mmol) dropwise with stirring at −78° C. over 40 min. Then TEA (48.4 g, 478.31 mmol) was added dropwise with stirring at −78° C. over 60 min. After stirring for 1 h at room temperature, ethyl acetate (200 mL) was added to the reaction mixture, filtered. The organic layer was washed with HCl (2×50 mL) and aqueous sodium bicarbonate (2×50 mL), dried over MgSO4. The resulting mixture was concentrated in vacuo to give the residue, which was applied on a silica gel column chromatography with 5% ethyl acetate in petroleum ether to afford 2-chloro-N-(1-oxobutan-2-yl)acetamide (17 g, 61%) as brown oil.

Step 3: 2-(chloromethyl)-4-ethyl-1,3-oxazole

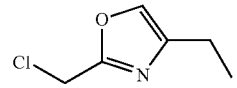

To a solution of 2-chloro-N-(1-oxobutan-2-yl)acetamide (8.0 g, 48.90) was added POCl3 (30 mL), and the reaction mixture was stirred for 2 h at 90° C. in an oil bath. The reaction was then quenched by the addition of ice water. The mixture was adjusted pH to 7 with potassium carbonate (aq.), extracted with dichloromethane (3×80 mL). The organic layer was combined, dried over anhydrous magnesium sulfate and concentrated in vacuo to give the residue, which was applied on a silica gel column chromatography with dichloromethane to afford 2-(chloromethyl)-4-ethyl-1,3-oxazole (2.0 g, 28%) as yellow oil.

LC/MS (ES, m/z): [M+H]+ 146

1H NMR (300 MHz, CDCl3): δ 7.38 (s, 1H), 4.78 (s, 2H), 2.57-2.60 (m, 2H), 1.21-1.28 (m, 3H)

Step 4: 2-(4-ethyl-1,3-oxazol-2-yl)acetonitrile

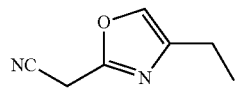

To a solution of 2-(chloromethyl)-4-ethyl-1,3-oxazole (2.0 g, 13.74 mmol) in CH3CN (50 mL) was added a solution of KCN (1.3 g, 19.96 mmol) in water (5.0 mL). The reaction mixture was stirred overnight at 40° C. in an oil bath. The resulting solution was diluted with H2O (200 mL), extracted with ethyl acetate (3×80 mL). The organic layer was combined, dried over anhydrous magnesium sulfate and concentrated in vacuo to give the residue, which was applied on a silica gel column chromatography with 5% ethyl acetate in petroleum to afford 2-(4-ethyl-1,3-oxazol-2-yl)acetonitrile (1.5 g, 80%) as yellow oil.

LC/MS (ES, m/z): [M+H]+ 137.0

1H NMR (300 MHz, CDCl3): δ 7.39 (s, 1H), 3.92 (s, 2H), 2.51-2.59 (m, 2H), 1.20-1.28 (m, 3H)

Step 5: (2Z)-3-(dimethylamino)-2-(4-ethyl-1,3-oxazol-2-yl)prop-2-enenitrile

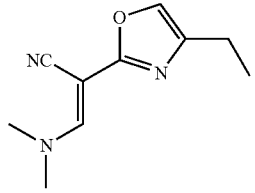

To a solution of 2-(4-ethyl-1,3-oxazol-2-yl)acetonitrile (1.5 g, 11.02 mmol) in toluene (30 mL) was added DMF-DMA (1.58 g, 13.28 mmol), and the reaction mixture was stirred for 1 h at 85° C. in an oil bath. The reaction mixture was concentrated in vacuo to afford (2Z)-3-(dimethylamino)-2-(4-ethyl-1,3-oxazol-2-yl)prop-2-enenitrile (1.8 g, crude) as a brown solid.
LC/MS (ES, m/z): [M+H]$^+$ 192.0

Step 6: 4-(4-ethyl-1,3-oxazol-2-yl)-1H-pyrazol-5-amine

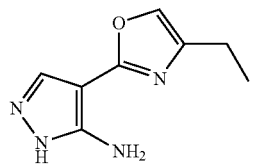

To a solution of (2Z)-3-(dimethylamino)-2-(4-ethyl-1,3-oxazol-2-yl)prop-2-enenitrile (1.8 g, 9.41 mmol) in C$_2$H$_5$OH (120 mL) was added NH$_2$NH$_2$H$_2$O (1.18 g, 23.60 mmol), and the reaction mixture was stirred overnight at 90° C. in an oil bath. The reaction mixture was concentrated in vacuo, and diluted with H$_2$O (50 mL). The resulting solution was extracted with dichloromethane (10×40 mL). The organic layer was combined, dried over magnesium sulfate and concentrated in vacuo to afford 4-(4-ethyl-1,3-oxazol-2-yl)-1H-pyrazol-5-amine (450 mg, crude) as a yellow solid.
LC/MS (ES, m/z): [M+H]$^+$ 179.0

Step 7: 5-(1H-1,2,3-benzotriazol-5-yl)-3-(4-ethyl-1,3-oxazol-2-yl)-4H,7H-pyrazolo[1,5-a]pyrimidin-7-one

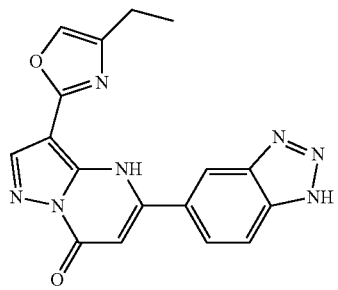 [SMILES: CCc1coc(-c2cnn3c(=O)cc(-c4ccc5[nH]nnc5c4)[nH]c23)n1]

To a solution of 4-(4-ethyl-1,3-oxazol-2-yl)-1H-pyrazol-5-amine (60 mg, 0.34 mmol) in n-BuOH (2 ml) was added ethyl 3-(1H-1,2,3-benzotriazol-5-yl)-3-oxopropanoate (102 mg, 0.44 mmol) and TsOH (2.9 mg, 0.02 mmol), and the reaction mixture was stirred for 8 h at 130° C. in an oil bath. The product was collected by filtration, washed with MeOH (3×10 ml) to afford 5-(1H-1,2,3-benzotriazol-5-yl)-3-(4-ethyl-1,3-oxazol-2-yl)-4H,7H-pyrazolo[1,5-a]pyrimidin-7-one (42.0 mg) as an off-white solid.
LC/MS (ES, m/z): [M+H]$^+$ 348.1
$^1$H NMR (300 MHz, DMSO): δ 8.41 (s, 1H), 8.09 (s, 1H), 7.85 (d, J=5.70 Hz, 1H), 7.70 (d, J=8.10 Hz, 2H), 6.14 (s, 1H), 2.51-2.55 (m, 2H), 1.20-1.24 (m, 3H)

EXAMPLE 16

5-(2H-1,3-benzodioxol-5-yl)-3-(4-ethyl-1,3-oxazol-2-yl)-4H,7H-pyrazolo[1,5-a]pyrimidin-7-one

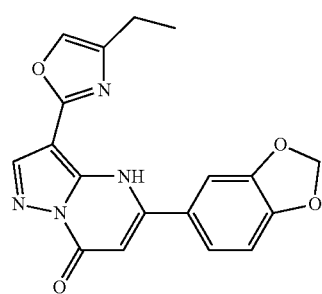 [SMILES: CCc1coc(-c2cnn3c(=O)cc(-c4ccc5c(c4)OCO5)[nH]c23)n1]

To a solution of 4-(4-ethyl-1,3-oxazol-2-yl)-1H-pyrazol-5-amine (100 mg, 0.56 mmol) in n-BuOH (2.0 mL) was added ethyl 3-(2H-1,3-benzodioxol-5-yl)-3-oxopropanoate (172 mg, 0.73 mmol) and TsOH (4.8 mg, 0.03 mmol), and the reaction mixture was stirred for 6 h at 130° C. in an oil bath. The product was collected by filtration, and washed with MeOH (3×10 mL) to afford 5-(2H-1,3-benzodioxol-5-yl)-3-(4-ethyl-1,3-oxazol-2-yl)-4H,7H-pyrazolo[1,5-a]pyrimidin-7-one (60 mg, 31%) as an off-white solid.
LC/MS (ES, m/z): [M+H]$^+$ 351.1
$^1$H NMR (300 MHz, DMSO): δ 8.33 (s, 1H), 7.59-7.64 (m, 3H), 6.90 (d, J=7.50 Hz, 1H), 6.26 (s, 1H), 6.02 (s, 2H), 6.14 (s, 1H), 2.58-2.66 (m, 2H), 1.28-1.33 (t, J$_1$=J$_2$=7.50 Hz, 3H)

EXAMPLE 17

5-(4-chloro-3-methoxyphenyl)-3-(5-methyl-1,3-oxazol-2-yl)-4H,7H-pyrazolo[1,5-a]pyrimidin-7-one

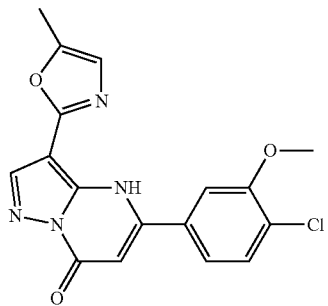 [SMILES: COc1cc(-c2cc(=O)n3ncc(-c4ncc(C)o4)c3[nH]2)ccc1Cl]

Step 1: Ethyl 5-(4-chloro-3-methoxyphenyl)-7-oxo-4H,7H-pyrazolo[1,5-a]pyrimidine-3-carboxylate

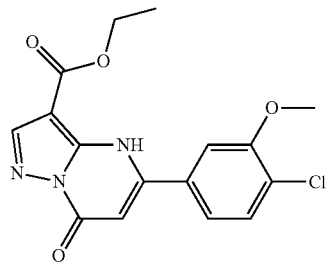 [SMILES: CCOC(=O)c1cnn2c(=O)cc(-c3ccc(Cl)c(OC)c3)[nH]c12]

To a solution of ethyl 5-amino-1H-pyrazole-4-carboxylate (1 g, 6.45 mmol) in n-BuOH (2 mL) was added ethyl 3-(4-chloro-3-methoxyphenyl)-3-oxopropanoate (2.5 g, 9.76 mmol), TsOH (55 mg, 0.32 mmol), and the reaction mixture was stirred overnight at 125° C. The solids were collected by filtration and washed with methanol (2×5 mL) to afford ethyl 5-(4-chloro-3-methoxyphenyl)-7-oxo-4H,7H-pyrazolo[1,5-a]pyrimidine-3-carboxylate as an off-white solid (1.5 g, 67%).

LC/MS (ES, m/z): [M+H]$^+$ 348.0.

Step 2: 5-(4-chloro-3-methoxyphenyl)-7-oxo-4H,7H-pyrazolo[1,5-a]pyrimidine-3-carboxylic acid

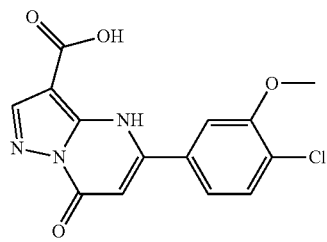 [SMILES: COc1cc(-c2cc(=O)n3ncc(C(=O)O)c3[nH]2)ccc1Cl]

To a solution of ethyl 5-(4-chloro-3-methoxyphenyl)-7-oxo-4H,7H-pyrazolo[1,5-a]pyrimidine-3-carboxylate (1 g, 2.88 mmol) in DMSO (25 mL) was added a solution of sodium hydroxide (350 mg, 8.75 mmol) in water (3 mL), and the reaction mixture was stirred for 2 h at 50° C. The reaction was then quenched by the addition of water (60 mL) and adjusted pH to 3 with HCl (2N). The solids were collected by filtration and dried in an oven under reduced pressure to afford 5-(4-chloro-3-methoxyphenyl)-7-oxo-4H,7H-pyrazolo[1,5-a]pyrimidine-3-carboxylic acid as a white solid (800 mg, 87%).

LC/MS (ES, m/z): [M+H]$^+$ 320.0

$^1$H NMR (300 MHz, DMSO): δ 8.23 (s, 1H), 7.62 (d, J=8.1 Hz, 1H), 7.52 (d, J=2.1 Hz, 1H), 7.32-7.35 (m, 1H), 6.36 (s, 1H), 3.98 (s, 3H)

Step 3: 5-(4-chloro-3-methoxyphenyl)-7-oxo-N-(prop-2-yn-1-yl)-4H,7H-pyrazolo[1,5-a]pyrimidine-3-carboxamide

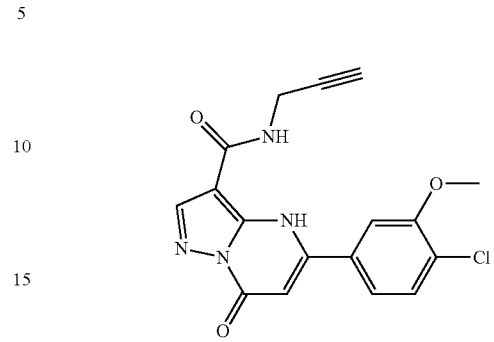

To a solution of 5-(4-chloro-3-methoxyphenyl)-7-oxo-4H,7H-pyrazolo[1,5-a]pyrimidine-3-carboxylic acid (400 mg, 1.25 mmol) in DMF (20 mL) was added CDI (400 mg, 2.80 mmol), and the reaction mixture was stirred for 15 h at 50° C. and then prop-2-yn-1-amine (100 mg, 1.82 mmol) was added at room temperature and stirred for 1 h. The resulting solution was diluted with ethyl ether (200 mL). The solids were collected by filtration to afford 5-(4-chloro-3-methoxyphenyl)-7-oxo-N-(prop-2-yn-1-yl)-4H,7H-pyrazolo[1,5-a]pyrimidine-3-carboxamide as a gray solid (310 mg, crude).

LC/MS (ES, m/z): [M+H]$^+$ 357.0

Step 4: 5-(4-chloro-3-methoxyphenyl)-3-(5-methyl-1,3-oxazol-2-yl)-4H,7H-pyrazolo[1,5-a]pyrimidin-7-one

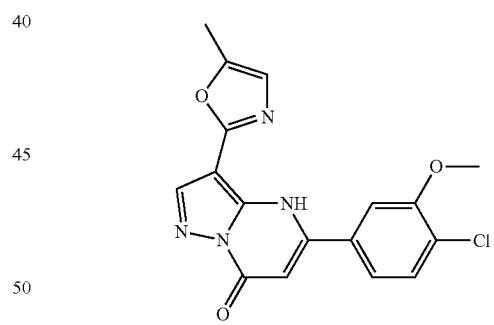

To a solution of 5-(4-chloro-3-methoxyphenyl)-7-oxo-N-(prop-2-yn-1-yl)-4H,7H-pyrazolo[1,5-a]pyrimidine-3-carboxamide (220 mg, crude) in DMSO (2.5 mL) was added sodium hydride (112 mg, 4.67 mmol), and the reaction mixture was stirred for 3 h at 25° C. The reaction was then quenched by the addition of water (10 mL) and the solids were collected by filtration to afford 5-(4-chloro-3-methoxyphenyl)-3-(5-methyl-1,3-oxazol-2-yl)-4H,7H-pyrazolo[1,5-a]pyrimidin-7-one as a light yellow solid (29.7 mg).

LC/MS (ES, m/z): [M+H]$^+$ 357.0

$^1$H NMR (300 MHz, DMSO): δ 8.35 (s, 1H), 7.66 (d, J=8.1 Hz, 1H), 7.57 (s, 1H), 7.39-7.41 (m, 1H), 7.01 (s, 1H), 6.37 (s, 1H), 4.00 (s, 3H), 2.31 (s, 3H)

EXAMPLE 18

5-(4-chloro-3-methoxyphenyl)-3-(4-methyl-1,3-oxazol-2-yl)-4H,7H-pyrazolo[1,5-a]pyrimidin-7-one

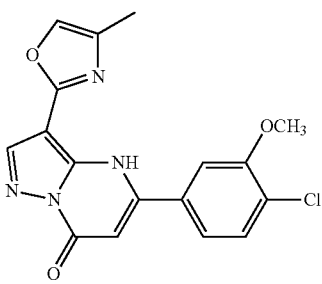 [SMILES: COc1cc(-c2cc(=O)n3ncc(-c4nc(C)co4)c3[nH]2)ccc1Cl]

Step 1: Prop-2-ynyl 5-amino-1H-pyrazole-4-carbimidate hydrochloride

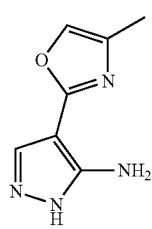

HCl (g) was introduced into the solution of 5-amino-1H-pyrazole-4-carbonitrile (280 g, 1.55 mmol) in prop-2-yn-1-ol (4 ml), and the reaction mixture was stirred for 2 h at room temperature. The product was precipitated by the addition of Et$_2$O (10 mL) to afford Prop-2-ynyl 5-amino-1H-pyrazole-4-carbimidate hydrochloride as a light brown solid (350 mg, crude).

Step 2: 4-(4-methyl-1,3-oxazol-2-yl)-1H-pyrazol-5-amine

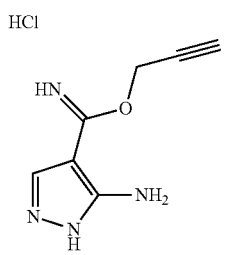

To a solution of Prop-2-ynyl 5-amino-1H-pyrazole-4-carbimidate hydrochloride (350 mg, crude) in xylene (3 ml) was added DIEA (350 mg, 2.72 mmol) and TsOAg (25 mg), and the reaction mixture was stirred for 3 h at 70° C. The reaction mixture was concentrated in vacuo to give a residue, which was purified by a silica gel column chromatography with 2% dichloromethane in methanol to afford 4-(4-methyl-1,3-oxazol-2-yl)-1H-pyrazol-5-amine as light red oil (200 mg, crude)

LC/MS (ES, m/z): [M+H]$^+$ 165.0 .

Step 3: 5-(4-chloro-3-methoxyphenyl)-3-(4-methyl-1,3-oxazol-2-yl)-4H,7H-pyrazolo[1,5-a]pyrimidin-7-one

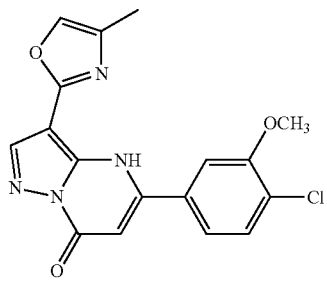 [SMILES: COc1cc(-c2cc(=O)n3ncc(-c4nc(C)co4)c3[nH]2)ccc1Cl]

To a solution of 4-(4-methyl-1,3-oxazol-2-yl)-1H-pyrazol-5-amine (200 mg, crude) in n-BuOH (1 ml) was added TsOH (7 mg, 0.04 mmol), ethyl 3-(4-chloro-3-methoxyphenyl)-3-oxopropanoate (320 mg, 1.25 mmol), and the reaction mixture was stirred overnight at 130° C. The solids were collected by filtration and washed with methanol (5×1 ml) to afford 5-(4-chloro-3-methoxyphenyl)-3-(4-methyl-1,3-oxazol-2-yl)-4H,7H-pyrazolo[1,5-a]pyrimidin-7-one as an off-white solid (33.4 mg).

LC/MS (ES, m/z): [M+H]$^+$ 357.0

$^1$H NMR (300 MHz, DMSO) δ 8.08 (s, 1H), 7.81 (d, J=1.8 Hz, 1H), 7.67-7.70 (m, 2H), 7.46 (d, J=8.4 Hz, 1H), 6.14 (s, 1H), 3.97 (s, 3H), 2.12 (d, J=0.9 Hz, 3H)

EXAMPLE 19

5-(4-chloro-3-methoxyphenyl)-3-(1,3-oxazol-2-yl)-4H,7H-pyrazolo[1,5-a]pyrimidin-7-one

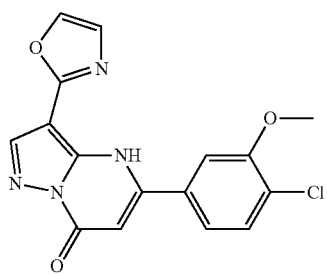 [SMILES: COc1cc(-c2cc(=O)n3ncc(-c4ncco4)c3[nH]2)ccc1Cl]

Step 1: 5-(4-chloro-3-methoxyphenyl)-7-oxo-4H,7H-pyrazolo[1,5-a]pyrimidine-3-carbonitrile

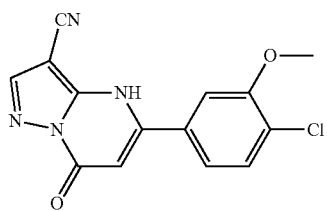 [SMILES: COc1cc(-c2cc(=O)n3ncc(C#N)c3[nH]2)ccc1Cl]

To a solution of 5-amino-1H-pyrazole-4-carbonitrile (1.5 g, 13.88 mmol) in n-BuOH (4 ml) was added ethyl 3-(4-chloro-3-methoxyphenyl)-3-oxopropanoate (5.3 g, 20.70 mmol), TsOH (20 mg, 0.12 mmol), and the reaction mixture was stirred overnight at 135° C. in an oil bath. The solids were collected by filtration and washed with methanol (20 ml), and dried over in an oven to afford 5-(4-chloro-3-methoxyphenyl)-7-oxo-4H,7H-pyrazolo[1,5-a]pyrimidine-3-carbonitrile as a gray solid (2.1 g, 53%).

LC/MS (ES, m/z): [M+H]+ 301.1

1H NMR (300 MHz, DMSO) δ 8.44 (s, 1H), 7.63 (d, J=8.4 Hz, 1H), 7.55-7.59 (m, 1H), 7.42-7.45 (m, 1H), 6.39 (s, 1H), 3.99 (s, 3H)

Step 2: 5-(4-chloro-3-methoxyphenyl)-7-oxo-4H, 7H-pyrazolo[1,5-a]pyrimidine-3-carboxamide

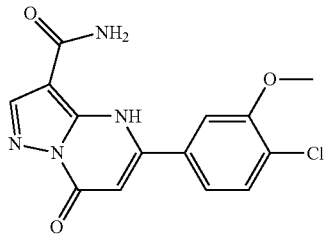 [SMILES: COc1cc(-c2cc(=O)n3ncc(C(N)=O)c3[nH]2)ccc1Cl]

5-(4-chloro-3-methoxyphenyl)-7-oxo-4H,7H-pyrazolo[1, 5-a]pyrimidine-3-carbonitrile (600 mg, 2 mmol) was added in sulfuric acid (conc.) (3 ml), and the reaction mixture was stirred for 2 h at 20° C. in an oil bath. The reaction was then quenched by the addition of ice water (10 ml). The solids were collected by filtration to afford 5-(4-chloro-3-methoxyphenyl)-7-oxo-4H,7H-pyrazolo[1,5-a]pyrimidine-3-carboxamide as an off-white solid (400 mg, 63%).

LC/MS (ES, m/z): [M+H]+ 319.1

Step 3: 5-(4-chloro-3-methoxyphenyl)-3-(1,3-oxazol-2-yl)-4H,7H-pyrazolo[1,5-a]pyrimidin-7-one

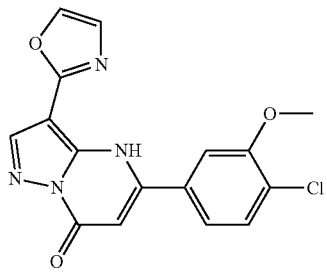 [SMILES: COc1cc(-c2cc(=O)n3ncc(-c4ncco4)c3[nH]2)ccc1Cl]

To a solution of 5-(4-chloro-3-methoxyphenyl)-7-oxo-4H,7H-pyrazolo[1,5-a]pyrimidine-3-carboxamide (200 mg, 0.63 mmol) in N-methyl-2-pyrrolidone (3 ml) was added 2-bromo-1,1-diethoxyethane (1 ml), TsOH (10 mg, 0.06 mmol), and the reaction mixture was stirred for 40 min at 100° C. in an oil bath. The reaction was then quenched with water (30 ml). The solids were collected by filtration and washed with water (20 ml). The filter cake was purified by Flash-Prep-HPLC to afford 5-(4-chloro-3-methoxyphenyl)-3-(1,3-oxazol-2-yl)-4H,7H-pyrazolo[1,5-a]pyrimidin-7-one as a gray solid (23.9 mg, 11%).

LC/MS (ES, m/z): [M+H]+ 343.1

1H NMR (300 MHz, DMSO) δ 8.13 (s, 1H), 8.01 (s, 1H), 7.72-7.81 (m, 2H), 7.50 (s, 1H), 7.20 (s, 1H), 6.18 (s, 1H), 3.97 (s, 3H)

EXAMPLE 20

5-(1-Ethyl-1H-indazol-5-yl)-3-(1,3-oxazol-2-yl)-4H, 7H-pyrazolo[1,5-a]pyrimidin-7-one

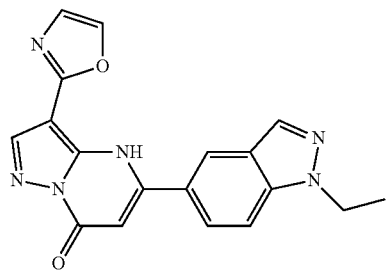 [SMILES: CCn1ncc2cc(-c3cc(=O)n4ncc(-c5ncco5)c4[nH]3)ccc21]

Step 1: 5-(1-Ethyl-1H-indazol-5-yl)-7-oxo-4H,7H-pyrazolo[1,5-a]pyrimidine-3-carbonitrile

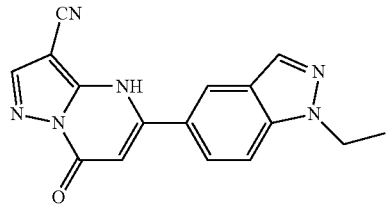 [SMILES: CCn1ncc2cc(-c3cc(=O)n4ncc(C#N)c4[nH]3)ccc21]

To a solution of ethyl 3-(1-ethyl-1H-indazol-5-yl)-3-oxopropanoate (1.2 g, 4.6 mmol) in n-BuOH (10 mL) was added TsOH (50 mg, 0.023 mmol), 5-amino-1H-pyrazole-4-carbonitrile (0.5 g, 4.6 mmol). The resulting solution was stirred for 8.5 h at 130° C. The solids were collected by filtration. The solid was washed with ether (50 mL). The solids were collected by filtration to afford 5-(1-ethyl-1H-indazol-5-yl)-7-oxo-4H,7H-pyrazolo[1,5-a]pyrimidine-3-carbonitrile as a light red solid (750 mg, 53%).

LC/MS (ES, m/z): [M+H]+ 305.0

1H NMR (300 MHz, DMSO) δ 8.44 (s, 1H), 8.27-8.33 (m, 2H), 7.81-7.89 (m, 2H), 6.31 (s, 1H), 4.48-4.55 (m, 2H), 1.39-1.44 (t, J=7.2 Hz, 3H)

Step 2: 5-(1-Ethyl-1H-indazol-5-yl)-7-oxo-4H,7H-pyrazolo[1,5-a]pyrimidine-3-carboxamide

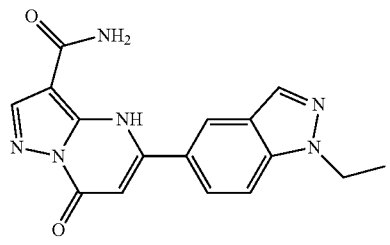

A solution of 5-(1-ethyl-1H-indazol-5-yl)-7-oxo-4H,7H-pyrazolo[1,5-a]pyrimidine-3-carbonitrile (500 mg, 1.64 mmol) in sulfuric acid (3 mL) was stirred for 1.5 h at 30° C. The reaction was then quenched by the addition water/ice (10 mL). The solids were collected by filtration to afford 5-(1-ethyl-1H-indazol-5-yl)-7-oxo-4H, 7H-pyrazolo[1,5-a]pyrimidine-3-carboxamide as a red solid (390 mg, 74%).

LC/MS (ES, m/z): [M+H]+ 323.0

¹H NMR (300 MHz, DMSO) δ 11.32 (s, 1H), 8.46 (s, 1H), 8.27 (d, J=3.3 Hz, 2H), 7.80-7.97 (m, 3H), 7.45 (s, 1H), 6.32 (s, 1H), 4.48-4.55 (m, 2H), 1.39 (t, J=7.2 Hz, 3H)

Step 3: 5-(1-Ethyl-1H-indazol-5-yl)-3-(1,3-oxazol-2-yl)-4H,7H-pyrazolo[1,5-a]pyrimidin-7-one

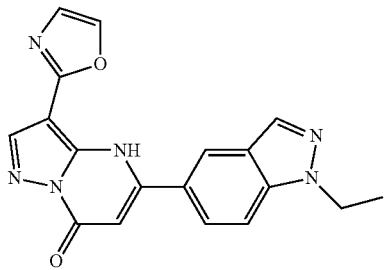 [SMILES: CCn1ncc2cc(-c3cc(=O)n4ncc(-c5ncco5)c4[nH]3)ccc21]

To a solution of 5-(1-ethyl-1H-indazol-5-yl)-7-oxo-4H, 7H-pyrazolo[1,5-a]pyrimidine-3-carboxamide (200 mg, 0.62 mmol), in N-methyl-2-pyrrolidone (NMP) (1 mL) was added 2-bromo-1,1-diethoxyethane (0.5 mL) and TsOH (5 mg). The resulting solution was stirred for 2 h at 80° C., then quenched with water (100 ml) and washed with ethyl ether (2×50 mL). The aqueous layers were extracted with dichloromethane (4×50 ml), which were then dried over anhydrous magnesium sulfate and concentrated in vacuo to give a residue, which was precipitated from ethyl ether (3 ml) and filtered to afford 5-(1-ethyl-1H-indazol-5-yl)-3-(1,3-oxazol-2-yl)-4H,7H-pyrazolo[1,5-a]pyrimidin-7-one as a brown solid (22.1 mg, 9%).

LC/MS (ES, m/z): [M+H]+ 347.1

¹H NMR (400 MHz, DMSO) δ 8.40 (s, 1H), 8.30 (d, J=3.6 Hz, 2H), 8.22 (s, 1H), 7.92 (d, J=8.8 Hz, 1H), 7.85 (d, J=8.4 Hz, 1H), 7.43 (s, 1H), 6.30 (s, 1H), 4.50-4.55 (m, 2H), 1.44 (t, J=7.2 Hz, 3H)

EXAMPLE 21

5-(4-chloro-3-ethoxyphenyl)-3-(4-methyl-1,3-oxazol-2-yl)-4H,7H-pyrazolo[1,5-a]pyrimidin-7-one

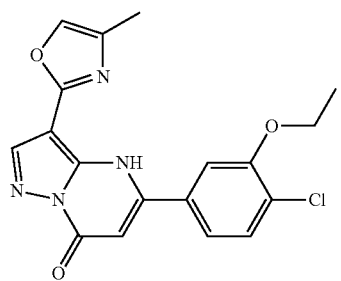 [SMILES: CCOc1cc(-c2cc(=O)n3ncc(-c4nc(C)co4)c3[nH]2)ccc1Cl]

To a solution of 4-(4-methyl-1,3-oxazol-2-yl)-1H-pyrazol-5-amine (100 mg, 0.61 mmol) in n-BuOH (1 mL) was added ethyl 3-(4-chloro-3-ethoxyphenyl)-3-oxopropanoate (247 mg, 0.96 mmol), TsOH (5.2 mg, 0.03 mmol), and the reaction mixture was stirred for 2 h at 130° C. The reaction progress was monitored by LCMS. The solids were collected by filtration to afford 5-(4-chloro-3-ethoxyphenyl)-3-(4-methyl-1,3-oxazol-2-yl)-4H,7H-pyrazolo[1,5-a]pyrimidin-7-one as a light yellow solid (88.4 mg, 41%).

LC/MS (ES, m/z): [M+H]+ 371.0

¹H NMR (300 MHz, DMSO) δ7.91 (m, 1H), 7.67 (d, J=1.20 Hz, 1H), 7.65 (d, J=2.10 Hz, 2H), 7.46 (m, 1H), 6.11 (s, 1H), 4.25 (s, 2H), 2.27 (m, 3H), 1.40 (m, 3H)

EXAMPLE 22

5-(1H-indazol-5-yl)-3-(4-methyl-1,3-oxazol-2-yl)-4H,7H-pyrazolo[1,5-a]pyrimidin-7-one

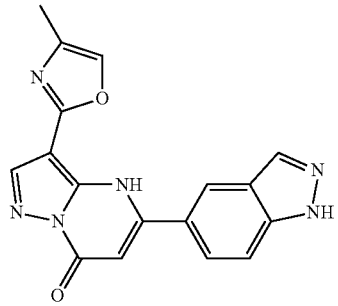 [SMILES: Cc1coc(-c2cnn3c(=O)cc(-c4ccc5[nH]ncc5c4)[nH]c23)n1]

To a solution of 4-(4-methyl-1,3-oxazol-2-yl)-1H-pyrazol-5-amine (100 mg, 0.61 mmol) in n-BuOH (1 mL) was added ethyl 3-(1-acetyl-1H-indazol-5-yl)-3-oxopropanoate (250 mg, 0.91 mmol), TsOH (5.16 mg, 0.03 mmol), and the reaction mixture was stirred for 2 h at 130° C. The solids were collected by filtration to afford 5-(1H-indazol-5-yl)-3-(4-methyl-1,3-oxazol-2-yl)-4H,7H-pyrazolo[1,5-a]pyrimidin-7-one as a light yellow solid (8.9 mg, 4%).

LC/MS (ES, m/z): [M+H]+ 375.0

¹H NMR (300 MHz, DMSO) δ8.44 (s, 1H), 8.15 (s, 1H), 8.06 (s, 1H), 7.69 (s, 1H), 7.58 (d, J=8.80 Hz, 1H), 6.11 (s, 1H), 2.14 (s, 3H)

EXAMPLE 23

5-(1H-indazol-5-yl)-3-(oxazol-2-yl)pyrazolo[1,5-a]pyrimidin-7(4H)-one

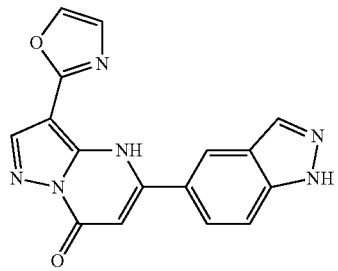 [SMILES: O=c1cc(-c2ccc3[nH]ncc3c2)[nH]c2c(-c3ncco3)cnn12]

To a solution of 5-(1H-indazol-5-yl)-7-oxo-4,7 dihydropyrazolo[1,5-a]pyrimidine-3-carboxamide (500 mg, 1.7 mmol) in NMP (5 mL) was added 2-bromo-1,1-diethoxyethane (402 mg, 2.1 mmol) and TsOH (15 mg, 0.034 mmol), and the reaction mixture was stirred for 30 mins at 110° C. in an oil bath. The reaction mixture was cooled to room temperature. The product was collected by filtration, washed with MeOH (3×10 ml) to afford 5-(1H-indazol-5-yl)-3-(oxazol-2-yl)pyrazolo[1,5-a]pyrimidin-7(4H)-one (29.7 mg) as an off-white solid.

LC/MS (ES, m/z): [M+H]+ 319.0

$^1$H NMR (300 MHz, DMSO): δ 8.21 (s, 1H), 8.18 (m, 3H), 8.04 (s, 1H), 7.59 (m, 1H), 7.22 (s, 1H), 6.25 (s, 1H)

EXAMPLE 24

5-(1H-indazol-5-yl)-7-oxo-N-(prop-2-yn-1-yl)-4H,7H-pyrazolo[1,5-a]pyrimidine-3-carboxamide

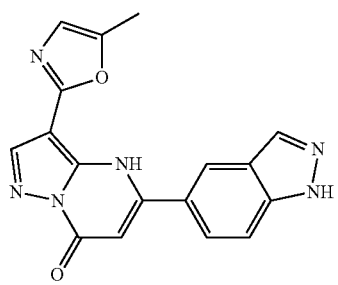 [SMILES: Cc1cnc(-c2cnn3c(=O)cc(-c4ccc5[nH]ncc5c4)[nH]c23)o1]

Step 1: Ethyl 5-(1H-indazol-5-yl)-7-oxo-4H,7H-pyrazolo[1,5-a]pyrimidine-3-carboxylate

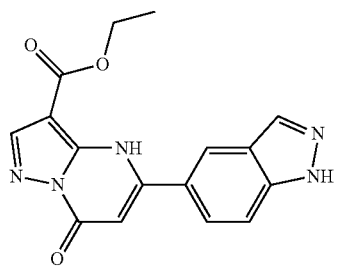 [SMILES: CCOC(=O)c1cnn2c(=O)cc(-c3ccc4[nH]ncc4c3)[nH]c12]

To a solution of ethyl 5-amino-1H-pyrazole-4-carboxylate (800 mg, 5.16 mmol) in n-BuOH (10 mL) was added ethyl 3-(1-acetyl-1H-indazol-5-yl)-3-oxopropanoate (1.8 g, 6.56 mmol), TsOH (44 mg, 0.26 mmol), and the reaction mixture was stirred overnight at 130° C. in an oil bath. The solids were collected by filtration and washed with MeOH (3×10 mL), and dried in an oven under reduced pressure to afford ethyl 5-(1H-indazol-5-yl)-7-oxo-4H,7H-pyrazolo[1,5-a]pyrimidine-3-carboxylate as a yellow solid (1.2 g, 72%).

LC/MS (ES, m/z): [M+H]+ 324.0

$^1$H NMR (300 MHz, DMSO) δ8.48 (s, 1H), 8.14-8.17 (m, 2H), 8.01-8.04 (m, 1H), 7.55-7.58 (d, J=8.70 Hz, 1H), 6.19 (s, 1H), 4.06-4.24 (m, 2H), 1.30-1.34 (m, 3H)

Step 2: 5-(1H-indazol-5-yl)-7-oxo-4H,7H-pyrazolo[1,5-a]pyrimidine-3-carboxylic acid

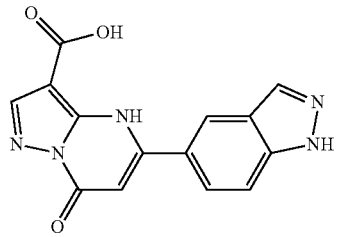 [SMILES: O=C(O)c1cnn2c(=O)cc(-c3ccc4[nH]ncc4c3)[nH]c12]

To a solution of ethyl 5-(1H-indazol-5-yl)-7-oxo-4H,7H-pyrazolo[1,5-a]pyrimidine-3-carboxylate (1.00 g, 3.09 mmol) in DMSO (30 mL) was added a solution of sodium hydroxide (123 mg, 3.08 mmol) in water (10 mL), and the reaction mixture was stirred overnight at 60° C. in an oil bath. The solution was adjusted to pH 4 with HCl (3N). The solids were collected by filtration and dried in an oven under reduced pressure to afford 5-(1H-indazol-5-yl)-7-oxo-4H,7H-pyrazolo[1,5-a]pyrimidine-3-carboxylic acid as a yellow solid (800 mg, 88%).

LC/MS (ES, m/z): [M+H]+ 296.0

$^1$H NMR (300 MHz, DMSO) δ8.41 (s, 1H), 8.19 (s, 1H), 7.99-8.05 (m, 2H), 7.61-7.64 (d, J=9.00 Hz, 1H), 6.21 (s, 1H), 2.51-2.55 (m, 2H) Step 3: 5-(1H-indazol-5-yl)-7-oxo-N-(prop-2-yn-1-yl)-4H,7H-pyrazolo[1,5-a]pyrimidine-3-carboxamide To a solution of 5-(1H-indazol-5-yl)-7-oxo-4H,7H-pyrazolo[1,5-a]pyrimidine-3-carboxylic acid (500 mg, 1.69 mmol) in DMF (8 mL) was added CDI (412 mg, 2.54 mmol), and the reaction mixture was stirred overnight at 55° C. To this was added prop-2-yn-1-amine (158 mg, 2.87 mmol). The resulting solution was stirred for 2 h at 25° C. The resulting mixture was concentrated in vacuo to afford 5-(1H-indazol-5-yl)-7-oxo-N-(prop-2-yn-1-yl)-4H,7H-pyrazolo[1,5-a]pyrimidine-3-carboxamide as a yellow solid (450 mg, 80%).

Step 4: 5-(1H-indazol-5-yl)-3-(5-methyloxazol-2-yl)pyrazolo[1,5-a]pyrimidin-7(4H)-one

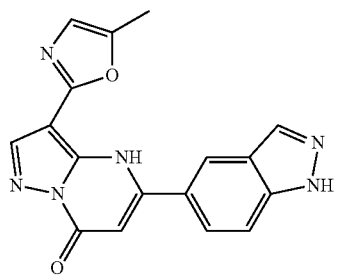 [SMILES: Cc1cnc(-c2cnn3c(=O)cc(-c4ccc5[nH]ncc5c4)[nH]c23)o1]

To a solution of 5-(1H-indazol-5-yl)-7-oxo-N-(prop-2-yn-1-yl)-4H,7H-pyrazolo[1,5-a]pyrimidine-3-carboxamide (20 mg, 0.06 mmol) in DMSO (0.5 mL) was added sodium hydride (9.6 mg, 0.40 mmol), and the reaction mixture was stirred for 2.5 h at 25° C. The result solution was poured into ice water (10 mL) and filtered to afford 5-(1H-indazol-5-yl)-3-(5-methyloxazol-2-yl)pyrazolo[1,5-a]pyrimidin-7(4H)-one as a light yellow solids (77.9 mg, 26%).

LC/MS (ES, m/z): [M+H]+ 333.0

$^1$H NMR (300 MHz, DMSO) δ8.47 (s, 1H), 8.16-8.20 (d, J=9.90 Hz, 2H), 8.06 (s, 1H), 7.58 (d, J=8.70 Hz, 1H), 6.81 (s, 1H), 6.15 (s, 1H), 2.52 (d, J=8.90 Hz, 1H), 2.38 (s, 3H)

EXAMPLE 25

5-(1-ethyl-1H-indazol-5-yl)-3-(4-methyl-1,3-thiazol-2-yl)-4H,7H-pyrazolo[1,5-a]pyrimidin-7-one

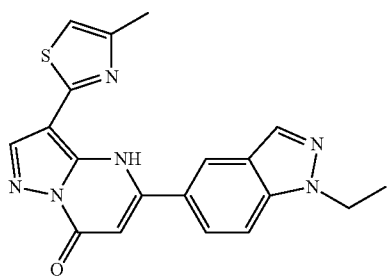 [SMILES: CCn1ncc2cc(-c3cc(=O)n4ncc(-c5nc(C)cs5)c4[nH]3)ccc21]

Step 1: 2-cyanoacetamide

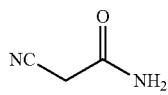

To a solution of ethyl 2-cyanoacetate (40 g, 353.62 mmol) in tetrahydrofuran (100 mL) was added ammonia (20 mL), and the reaction mixture was stirred for 1 h at room temperature. The resulting mixture was concentrated in vacuo. The solids were collected by filtration to afford 2-cyanoacetamide as a crude off-white solid (25 g, 84%).

Step 2: 2-cyanoethanethioamide

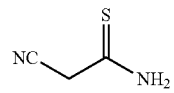

To a solution of 2-cyanoacetamide (20 g, 238 mmol) in THF (500 mL) was added Lawesson's Reagent (48 g, 119 mmol), and the reaction mixture was stirred for overnight at room temperature. The solids were collected by filtration to afford 2-cyanoethanethioamide as a crude yellow solid (12 g, 53%).

Step 3: 2-(4-methyl-1,3-thiazol-2-yl)acetonitrile

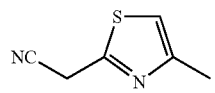

To a solution of 2-cyanoethanethioamide (5 g, 49.93 mmol) in ethanol (40 mL) was added 1-bromopropan-2-one (13.6 g, 99.29 mmol), triethylamine (20.2 g, 200.00 mmol), and the reaction mixture was stirred for 2 h at 50° C. in an oil bath. The reaction mixture was cooled. The resulting solution was extracted with 3×10 mL of dichloromethane. The organic layers combined and concentrated in vacuo to give the residue, which applied onto a silica gel column chromatography with 1% methanol in dichloromethane to afford of 2-(4-methyl-1,3-thiazol-2-yl)acetonitrile as a crude light brown solid (2.5 g, 70%).

Step 4: (E)-3-(dimethylamino)-2-(4-methylthiazol-2-yl)acrylonitrile

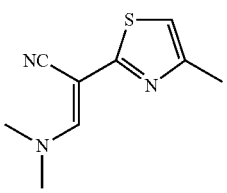

To a solution of 2-(4-methyl-1,3-thiazol-2-yl)acetonitrile (2.5 g, 18.09 mmol) in toluene (15 mL) was added of DMF-DMA (3.23 g, 27.14 mmol), and the reaction mixture was stirred for 1 h at 85° C. in an oil bath. The resulting mixture was concentrated in vacuo to give the residue, which was applied onto a silica gel column chromatography with 1% methanol in dichloromethane to afford (E)-3-(dimethylamino)-2-(4-methylthiazol-2-yl)acrylonitrile as a crude yellow oil (1.5 g, 70%).

Step 5:
4-(4-methylthiazol-2-yl)-1H-pyrazol-5-amine

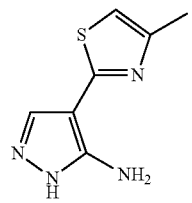

To a solution of (E)-3-(dimethylamino)-2-(4-methylthiazol-2-yl)acrylonitrile (1.5 g, 7.77 mmol) in ethanol (10 mL) was added N$_2$H$_4$.H$_2$O (1.17 g, 23.3 mmol), and the reaction mixture was stirred for 2 h at 90° C. in an oil bath. The resulting mixture was concentrated, diluted with water (25 mL) and extracted with 4×20 mL of dichloromethane. The organic layers were combined and dried over anhydrous sodium sulfate. The solids were filtered out. The resulting mixture was concentrated in vacuo to afford 4-(4-methylthiazol-2-yl)-1H-pyrazol-5-amine as yellow oil (500 mg, 6%).

LC/MS (ES, m/z): [M+H]$^+$ 181.0

$^1$H NMR (300 MHz, CD$_3$OD) δ7.64 (s, 1H), 6.69 (s, 1H), 2.29 (s, 3H)

Step 6: 5-(1-ethyl-1H-indazol-5-yl)-3-(4-methyl-1,3-thiazol-2-yl)-4H,7H-pyrazolo[1,5-a]pyrimidin-7-one

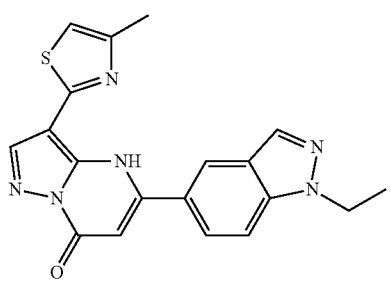 [SMILES: CCn1ncc2cc(-c3cc(=O)n4ncc(-c5nc(C)cs5)c4[nH]3)ccc21]

To a solution of 4-(4-methylthiazol-2-yl)-1H-pyrazol-5-amine (400 mg, 2.22 mmol) in n-BuOH (2 mL) was added ethyl 3-(1-ethyl-1H-indazol-5-yl)-3-oxopropanoate (865.8 mg, 3.33 mmol), TsOH (19.09 mg, 0.11 mmol), and the reaction mixture was stirred for 5 h at 130° C. in an oil bath. The solids were collected by filtration to afford 5-(1-ethyl-1H-indazol-5-yl)-3-(4-methyl-1,3-thiazol-2-yl)-4H,7H-pyrazolo[1,5-a]pyrimidin-7-one as a light yellow solid (77.8 mg 10%).

LC/MS (ES, m/z): [M+H]$^+$ 377.0

$^1$H NMR (300 MHz, CD$_3$OD) δ8.62 (s, 1H), 8.46 (s, 1H), 8.41-8.37 (m, 1H), 8.15 (s, 1H), 7.68-7.65 (d, J=9.00 Hz, 1H), 6.49 (s, 1H), 4.55-4.48 (q, J=7.20 Hz, 3H), 2.46 (s, 3H), 1.54-1.49 (t, J=7.20 Hz, 3H)

EXAMPLE 26

5-(1-ethyl-1H-indazol-5-yl)-3-(thiazol-2-yl)-4H,7H-pyrazolo[1,5-a]pyrimidin-7-one

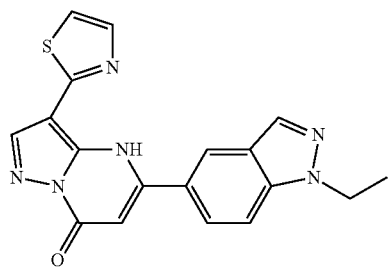 [SMILES: CCn1ncc2cc(-c3cc(=O)n4ncc(-c5nccs5)c4[nH]3)ccc21]

Step 1: 2-formylthiazole

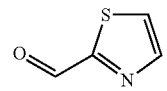

To a cooled solution (−78° C.) of n-butyllithium (1.7M in pentane, 323 mL, 550.8 mmol, 1.5 eq) in tetrahydrofuran (150 mL) under nitrogen was added 2-bromothiazole (60 g, 367.2 mmol). The resulting suspension was stirred below −78° C. for 45 min. The lithiated thiazole solution was transferred via cannula to a solution of dimethylformamide (25 mL) in tetrahydrofuran (200 mL) at −78° C. The reaction was allowed to warm to room temperature over 3 h and quenched by the addition of water (100 mL). The aqueous phase was extracted with ethyl acetate (3*100 mL). Combined organic extracts were dried over anhydrous magnesium sulfate, filtered and reduced to afford 2-formylthiazole as a crude oil.

Step 2: thiazol-2-ylmethanol

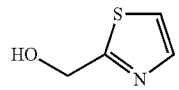

To a mixture of 2-formylthiazole (84.22 g, 0.75 mol) and methanol (100 mL) was added sodium borohydride (120 g, 1.5 mol) at 0° C., which was stirred for overnight at room temperature. Water was added to this reaction mixture, which was then extracted with ethyl acetate. The organic layer was separated, washed with saturated aqueous sodium chloride, dried over anhydrous magnesium sulfate, and filtered. The filtrate was concentrated under a reduced pressure, and the residue was purified by silica gel column chromatography with DCM/MeOH (100:1-50:1) to afford thiazol-2-ylmethanol as light yellow oil (12 g, 14%).

Step 3: 2-(chloromethyl)-1,3-thiazole

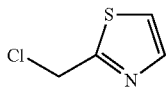

To a solution of thiazol-2-ylmethanol (7.0 g, 0.06 mol) in dichloromethane (10 mL) was added thionyl chloride (10.85 g, 0.09 mol). The resulting solution was stirred for 3 h at 25° C. in a water/ice bath. The reaction was then quenched by the addition of 50 mL of water/ice. The pH value of the solution was adjusted to 7-8 with sodium carbonate (19%). The resulting solution was extracted with 3×50 mL of ethyl acetate and the organic layers combined and dried over anhydrous sodium sulfate. The solids were filtered out. The resulting mixture was concentrated in vacuo to afford 2-(chloromethyl)-1,3-thiazole as a crude dark red oil (5 g, 61%).

Step 4: 2-(thiazol-2-yl)acetonitrile

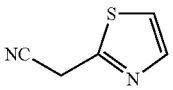

To a solution of 2-(chloromethyl)-1,3-thiazole (5 g, 0.04 mol) in water (8 mL) was added KCN (3.2 g, 0.05 mol) in acetonitrile (20 mL). The resulting solution was stirred overnight at 50° C. in an oil bath. The resulting solution was extracted with 4×50 mL of ethyl acetate and the organic layers combined. The reaction was then quenched by the addition of 50 mL of water. The solids were filtered out. The mixture was dried over anhydrous sodium sulfate and concentrated in vacuo. The residue was applied onto a silica gel column chromatography with ethyl acetate/petroleum ether (10:1-8:1) to afford 2-(thiazol-2-yl)acetonitrile as light yellow oil (2.0 g, 43%).

LC/MS (ES, m/z): [M+H]$^+$ 125.1

$^1$H NMR (300 MHz, CDCl$_3$) δ7.79 (d, J=3.3 Hz, 1H), 7.39 (d, J=3.3 Hz, 1H), 4.17-4.14 (m, 2H)

Step 5: (E)-3-(dimethylamino)-2-(thiazol-2-yl)acrylonitrile

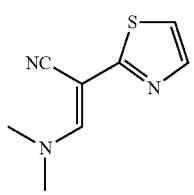

A solution of 2-(thiazol-2-yl)acetonitrile (2 g, 0.02 mol,) in toluene (2 mL) and DMF-DMA (2.88 g, 0.024 mol) was stirred for 1.5 h at 80° C. in an oil bath. The resulting mixture was concentrated in vacuo to afford (E)-3-(dimethylamino)-2-(thiazol-2-yl)acrylonitrile as a crude dark red oil.

Step 6: 3-(thiazol-2-yl)-1H-pyrrol-2-amine

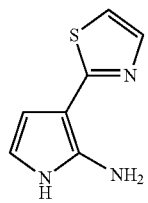 [SMILES: Nc1[nH]ccc1-c1nccs1]

To a solution of (E)-3-(dimethylamino)-2-(thiazol-2-yl) acrylonitrile (2.9 g, 0.016 mol) in AcOH (5 mL) was added N$_2$H$_4$.H$_2$O (4.05 g, 0.08 mol). The resulting solution was stirred for 4 h at 85° C. in an oil bath. The resulting mixture was concentrated in vacuo. The residue was applied onto a silica gel column with dichloromethane/methanol (100:1-80:1) to afford 3-(thiazol-2-yl)-1H-pyrrol-2-amine as an off-white solid (1 g, 37%).

LC/MS (ES, m/z): [M+H]$^+$ 177.0

$^1$H NMR (300 MHz, CD$_3$OD) δ7.79 (d, J=3.3 Hz, 1H), 7.39 (d, J=3.3 Hz, 1H), 4.17-4.14 (m, 2H)

Step 7: 5-(1-ethyl-1H-indazol-5-yl)-3-(thiazol-2-yl)-4H,7H-pyrazolo[1,5-a]pyrimidin-7-one

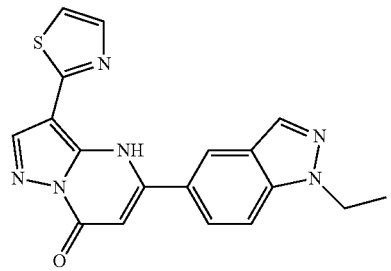

To a solution of 3-(thiazol-2-yl)-1H-pyrrol-2-amine (100 mg, 0.60 mmol) in n-BuOH (0.5 mL) was added ethyl 3-(1-ethyl-1H-indazol-5-yl)-3-oxopropanoate (234.9 mg, 0.90 mmol). The resulting solution was stirred for 3 h at 130° C. in an oil bath. The solids were collected by filtration to afford 5-(1-ethyl-1H-indazol-5-yl)-3-(thiazol-2-yl)-4H, 7H-pyrazolo[1,5-a]pyrimidin-7-one as a light yellow solid (32.0 mg, 15%).

LC/MS (ES, m/z): [M+H]$^+$ 362.0

$^1$H NMR (300 MHz, DMSO) δ 8.49 (s, 1H), 8.36 (s, 1H), 8.28 (s, 1H), 7.98-7.91 (m, 3H), 7.71 (d, J=3.6 Hz, 1H), 6.36 (s, 1H), 4.56-4.48 (q, J=7.2 Hz, 2H), 1.45-1.40 (t, J=7.2 Hz, 3H)

EXAMPLE 27

5-(1-ethyl-1H-indazol-5-yl)-3-(thiazol-2-yl)-4H,7H-pyrazolo[1,5-a]pyrimidin-7(4H)-one

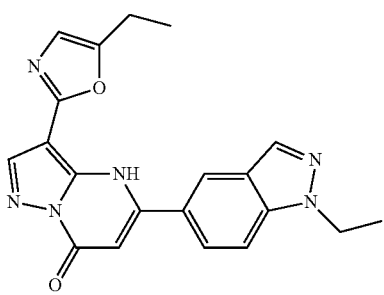 [SMILES: CCc1cnc(-c2cnn3c(=O)cc(-c4ccc5c(cnn5CC)c4)[nH]c23)o1]

To a solution of 4-(5-ethyloxazol-2-yl)-1H-pyrazol-5-amine (100 mg, 0.56 mmol) in n-BuOH (1 mL) was added ethyl 3-(1-ethyl-1H-indazol-5-yl)-3-oxopropanoate (219 mg, 0.84 mmol), TsOH (4.8 mg, 0.03 mmol), and the reaction mixture was stirred for 2 h at 130° C. The solids were collected by filtration to afford 5-(1-ethyl-1H-indazol-5-yl)-3-(5-ethyloxazol-2-yl)pyrazolo[1,5-a]pyrimidin-7(4H)-one as a light yellow solid (28.4 mg, 14%).

LC/MS (ES, m/z): [M+H]+ 333.0

$^1$H NMR (300 MHz, DMSO) δ 7.60 (d, J=12.30 Hz, 2H), 7.44 (s, 1H), 7.19 (m, 3H), 5.95 (s, 1H), 4.41 (m, 2H), 2.87 (m, 2H), 1.57 (m, 3H), 1.44 (m, 3H)

EXAMPLE 28

5-(1-ethyl-1H-indazol-5-yl)-3-(4-ethyloxazol-2-yl)pyrazolo[1,5-a]pyrimidin-7(4H)-one

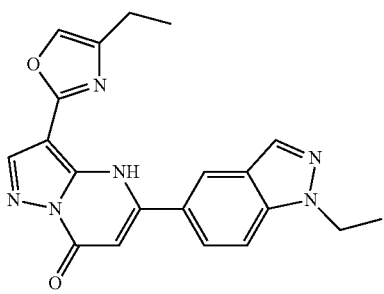 [SMILES: CCc1coc(-c2cnn3c(=O)cc(-c4ccc5c(cnn5CC)c4)[nH]c23)n1]

To a solution of 4-(4-ethyloxazol-2-yl)-1H-pyrazol-5-amine (80 mg, 0.45 mmol) in n-BuOH (1 mL) was added ethyl 3-(1-ethyl-1H-indazol-5-yl)-3-oxopropanoate (175 mg, 0.67 mmol), TsOH (3.87 mg, 0.02 mmol), and the reaction mixture was stirred for 2 h at 130° C. The solids were collected by filtration to afford 5-(1-ethyl-1H-indazol-5-yl)-3-(4-ethyloxazol-2-yl)pyrazolo[1,5-a]pyrimidin-7(4H)-one as a light yellow solid (81.8 mg, 51%).

LC/MS (ES, m/z): [M+H]+ 375.0

$^1$H NMR (300 MHz, DMSO) δ 8.36 (s, 1H), 8.29 (m, 2H), 7.92 (m, 2H), 7.80-7.84 (m, 1H), 6.29 (s, 2H), 4.28 (m, 2H), 2.58 (m, 2H), 1.43 (m, 3H), 1.18 (m, 3H)

EXAMPLE 29

5-(1-ethyl-1H-indazol-5-yl)-2-methyl-3-(oxazol-2-yl)-4H,7H-pyrazolo[1,5-a]pyrimidin-7-one

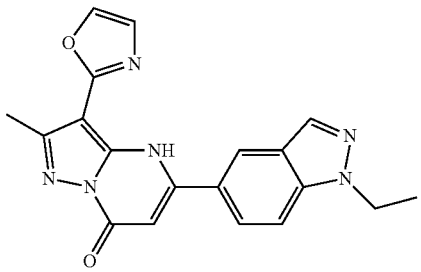 [SMILES: CCn1ncc2cc(-c3cc(=O)n4nc(C)c(-c5ncco5)c4[nH]3)ccc21]

Step 1: 5-(1-ethyl-1H-indazol-5-yl)-2-methyl-7-oxo-4,7-dihydropyrazolo[1,5-a]pyrimidine-3-carboxamide

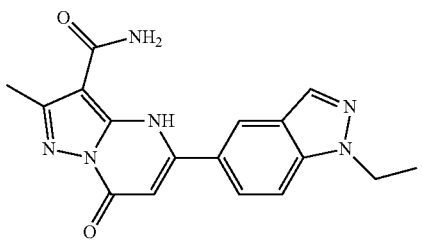 [SMILES: CCn1ncc2cc(-c3cc(=O)n4nc(C)c(C(N)=O)c4[nH]3)ccc21]

A solution of 5-(1-ethyl-1H-indazol-5-yl)-7-oxo-4,7-dihydropyrazolo[1,5-a]pyrimidine-3-carbonitrile (500 mg, 1.6 mmol) in H$_2$SO$_4$ (2 mL) was stirred for 2 h at RT. The reaction was then quenched by the addition of ice water (10 mL). The product was collected by filtration, washed with MeOH (3×10 ml) to afford 5-(1-ethyl-1H-indazol-5-yl)-2-methyl-7-oxo-4,7-dihydropyrazolo[1,5-a]pyrimidine-3-carboxamide (400 mg) as an orange solid.

LC/MS (ES, m/z): [M+H]+ 337.1

$^1$H NMR (300 MHz, DMSO): δ 8.47 (m, 1H), 8.36 (s, 1H), 8.05 (m, 1H), 8.03 (m, 1H), 6.10 (s, 1H), 4.45 (q, J=14.4 Hz, 6.9 Hz, 2H), 2.51 (s, 3H), 1.41 (t, J=14.4 Hz, 7.2 Hz, 3H)

Step 2: 5-(1-ethyl-1H-indazol-5-yl)-2-methyl-3-(oxazol-2-yl)-4H,7H-pyrazolo[1,5-a]pyrimidin-7-one

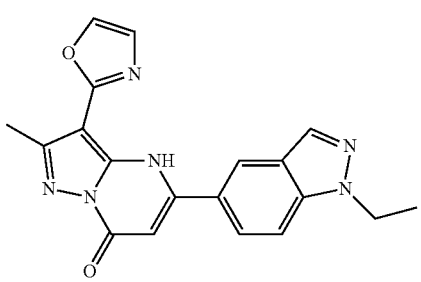 [SMILES: CCn1ncc2cc(-c3cc(=O)n4nc(C)c(-c5ncco5)c4[nH]3)ccc21]

2-Bromo-1,1-diethoxyethane (190 mg, 0.75 mmol) was added to a solution of 5-(1-ethyl-1H-indazol-5-yl)-2-methyl-7-oxo-4,7-dihydropyrazolo[1,5-a]pyrimidine-3-carboxamide (210 mg, 0.63 mmol) and TsOH (5 mg) in NMP (5 mL), and the reaction was stirred for 1 h at 80° C. in an oil bath. The reaction mixture was cooled to room temperature. The reaction was then quenched by the addition of 2 mL of water, extracted with 4×10 mL of dichloromethane. The organic layers were combined and dried over anhydrous sodium sulfate and concentrated in vacuo. The residue was purified by silica gel column chromatography with dichloromethane/methanol (100:1-80:1) to afford 5-(1-ethyl-1H-indazol-5-yl)-2-methyl-3-(oxazol-2-yl)-4H,7H-pyrazolo[1,5-a]pyrimidin-7-one as a yellow solid.

LC/MS (ES, m/z): [M+H]$^+$ 361.1

$^1$H NMR (300 MHz, CD$_3$OD): δ 8.52 (s, 1H), 8.18 (d, J=9.0 Hz, 1H), 8.13 (s, 1H), 7.93 (s, 1H), 7.62 (d, J=9.0 Hz, 1H), 7.26 (s, 1H), 6.37 (s, 1H), 4.45 (q, J=14.4 Hz, 6.9 Hz, 2H), 2.67 (s, 3H), 1.19 (t, J=14.1 Hz, 7.2 Hz, 3H)

EXAMPLE 30

5-(1-ethyl-1H-indazol-4-yl)-2-methyl-3-(5-methyl-oxazol-2-yl)-4H,7H-pyrazolo[1,5-a]pyrimidin-7-one

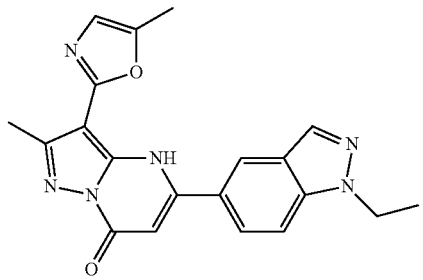 [SMILES: CCn1ncc2cc(-c3cc(=O)n4nc(C)c(-c5ncc(C)o5)c4[nH]3)ccc21]

Step 1: Ethyl(2E)-2-cyano-3-methoxybut-2-enoate

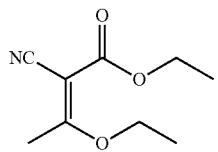

To a solution of ethyl 2-cyanoacetate (30 g, 270 mmol) in AcOH (500 ml) was added 1,1,1-trimethoxyethane (65.6 g, 405 mmol) and the reaction was stirred overnight at 100° C. The resulting solution was concentrated in vacuo to afford ethyl(2E)-2-cyano-3-methoxybut-2-enoate as light yellow solid (18.5 g).

Step 2: Ethyl 5-amino-3-methyl-1H-pyrazole-4-carboxylate

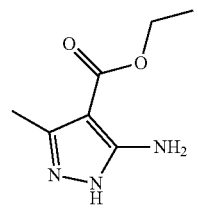

To a solution of ethyl(2E)-2-cyano-3-methoxybut-2-enoate (18.5 g, 106.40 mmol) in ethanol (150 mL) was added N$_2$H$_4$.H$_2$O (10.7 g) dropwise at 0° C. The reaction was stirred overnight at 80° C. Then the resulting solution was concentrated in vacuo. The residue was purified by silica gel column chromatography with dichloromethane/methanol (80:1) to afford ethyl 5-amino-3-methyl-1H-pyrazole-4-carboxylate as a light yellow oil (4 g, 20%).

LC/MS (ES, m/z): [M+H]$^+$ 170.0

$^1$H NMR (300 MHz, DMSO) δ4.25-4.30 (m, 2H), 3.32-3.37 (m, 1H), 2.35 (s, 3H), 1.30-1.38 (m, 3H)

Step 3: Ethyl 5-(1-ethyl-1H-indazol-5-yl)-2-methyl-7-oxo-4H,7H-pyrazolo[1,5-a]pyrimidine-3-carboxylate

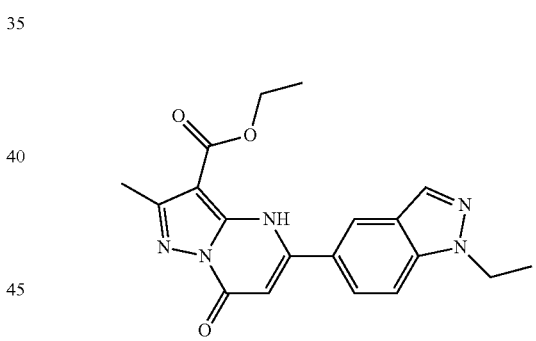

Ethyl 3-(1-ethyl-1H-indazol-5-yl)-3-oxopropanoate (2.3 g, 8.84 mmol) was added to a solution of ethyl 5-amino-3-methyl-1H-pyrazole-4-carboxylate (1 g, 5.91 mmol) in n-BuOH (5 mL) and TsOH (50 mg, 0.29 mmol), and the reaction mixture was stirred for 2 h at 130° C. The solids were collected by filtration to afford ethyl 5-(1-ethyl-1H-indazol-5-yl)-2-methyl-7-oxo-4H,7H-pyrazolo[1,5-a]pyrimidine-3-carboxylate as a light yellow solid (500 mg, 23%).

LC/MS (ES, m/z): [M+H]$^+$ 366.0

$^1$H NMR (300 MHz, DMSO) δ8.26 (d, J=3.30 Hz, 2H), 7.80-7.90 (m, 2H), 6.28 (s, 1H), 4.50-4.55 (m, 2H), 4.28-4.36 (m, 2H), 1.33-1.44 (m, 9H) Step 4: 5-(1-ethyl-1H-indazol-5-yl)-2-methyl-7-oxo-4H,7H-pyrazolo[1,5-a]pyrimidine-3-carboxylic acid

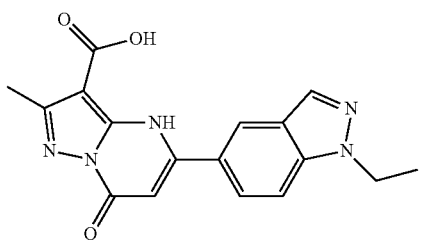

Sodium hydroxide (175 mg, 4.38 mmol) in water (0.5 mL) was added to a solution of ethyl 5-(1-ethyl-1H-indazol-5-yl)-2-methyl-7-oxo-4H,7H-pyrazolo[1,5-a]pyrimidine-3-carboxylate (400 mg, 1.09 mmol) in DMSO (5 mL) and the reaction was stirred for 3 h at 50° C. Then the reaction was quenched by the addition of water (10 mL). The solution was adjusted to pH 4 with aqueous HCl (4N). The solids were collected by filtration to afford 5-(1-ethyl-1H-indazol-5-yl)-2-methyl-7-oxo-4H,7H-pyrazolo[1,5-a]pyrimidine-3-carboxylic acid as a light yellow solid (250 mg, 68%).

Step 5: 5-(1-ethyl-1H-indazol-5-yl)-2-methyl-7-oxo-N-(prop-2-yn-1-yl)-4H,7H-pyrazolo[1,5-a]pyrimidine-3-carboxamide

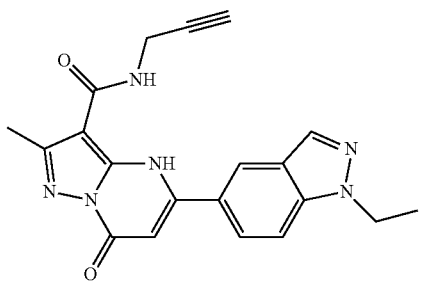 [SMILES: C#CCNC(=O)c1c(C)nn2c(=O)cc(-c3ccc4c(cnn4CC)c3)[nH]c12]

To a solution of 5-(1-ethyl-1H-indazol-5-yl)-2-methyl-7-oxo-4H,7H-pyrazolo[1,5-a]pyrimidine-3-carboxylic acid (250 mg, 0.74 mmol) in DMF (1 mL) was added CDI (156 mg, 0.96 mmol), followed by prop-2-yn-1-amine (62 mg, 1.13 mmol). The reaction was stirred for 2 h at room temperature. The resulting mixture was concentrated in vacuo. Then it was diluted with H₂O (10 mL). The solids were collected by filtration. The solid was dried in an oven under reduced pressure to afford 5-(1-ethyl-1H-indazol-5-yl)-2-methyl-7-oxo-N-(prop-2-yn-1-yl)-4H,7H-pyrazolo[1,5-a]pyrimidine-3-carboxamide as a orange solid (150 mg, 54%).

LC/MS (ES, m/z): [M+H]⁺ 375.0

¹H NMR (300 MHz, DMSO) δ 8.36 (s, 1H), 8.17 (s, 1H), 7.97-8.01 (m, 1H), 7.74 (d, J=9.00 Hz, 1H), 6.16 (s, 1H), 4.43-4.50 (m, 2H), 2.50-2.54 (m, 3H), 1.40-1.44 (m, 3H)

Step 6: 5-(1-ethyl-1H-indazol-4-yl)-2-methyl-3-(5-methyloxazol-2-yl)-4H,7H-pyrazolo[1,5-a]pyrimidin-7-one

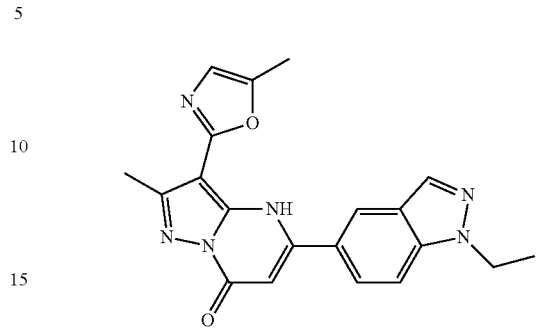

Sodium hydride (48 mg, 2.00 mmol) was added to a solution of 5-(1-ethyl-1H-indazol-4-yl)-2-methyl-7-oxo-N-(prop-2-yn-1-yl)-4H,7H-pyrazolo[1,5-a]pyrimidine-3-carboxamide (150 mg, 0.40 mmol) in DMSO (0.5 mL), and the reaction was stirred for 2 h at room temperature. Then it was quenched by the addition of water/ice (10 mL). The solution was adjusted to pH 7 with aqueous HCl (4N). The solids were collected by filtration to afford 5-(1-ethyl-1H-indazol-4-yl)-2-methyl-3-(5-methyloxazol-2-yl)-4H,7H-pyrazolo[1,5-a]pyrimidin-7-one as a light yellow solid (48.4 mg, 32%).

LC/MS (ES, m/z): [M+H]⁺ 375.0

¹H NMR (300 MHz, DMSO) δ 7.60 (s, 1H), 7.40 (s, 1H), 7.15-7.30 (m, 3H), 5.90 (s, 1H), 4.39-4.55 (m, 2H), 2.58 (s, 3H), 2.31 (s, 3H), 1.52-1.58 (t, J=5.70 Hz, 3H)

EXAMPLE 31

5-(1-ethyl-1H-indazol-5-yl)-3-(5-methyl-1,3,4-oxadiazol-2-yl)-4H,7H-pyrazolo[1,5-a]pyrimidin-7-one

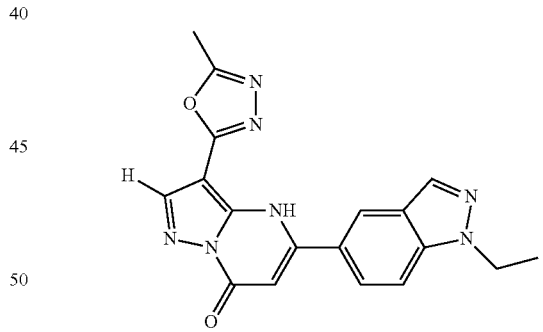

Step 1: 2-cyanoacetohydrazide

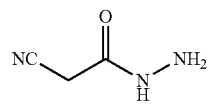

N₂H₄·H₂O (4.42 g, 885.0 mmol) was added dropwise to a solution of ethyl 2-cyanoacetate (10.0 g, 885.0 mmol) in ethanol (100 mL) at 0° C. The reaction was stirred for 2 h at 0-5° C. in an ice/salt bath. The solids were collected by filtration, washed with 100 mL of EtOH and dried in an oven under reduced pressure to afford 2-cyanoacetohydrazide as a white powder (6.0 g, 68%).

Step 2: N-acetyl-2-cyanoacetohydrazide

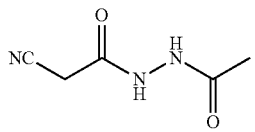

2-Cyanoacetohydrazide (6.0 g, 60.6 mmol) was dissolved in (AcO)$_2$O (200 mL) and stirred 12 h at 60° C. in an oil bath. The reaction mixture was cooled with a water/ice bath. The solids were collected by filtration, washed with 100 mL of Et$_2$O and dried in an oven under reduced pressure to afford N-acetyl-2-cyanoacetohydrazide as a light yellow solid (4.0 g, 35%).

LC/MS (ES, m/z): [M+H]$^+$ 142.0

$^1$H NMR (300 MHz, DMSO) δ 10.16 (s, 1H), 9.96 (s, 1H), 3.73 (s, 2H), 1.87 (d, J=4.50 Hz, 3H)

Step 3: 2-(5-methyl-1,3,4-oxadiazol-2-yl)acetonitrile

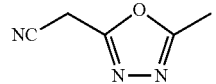

POCl$_3$ (6.5 g, 42.6 mmol) was added in several batches to a solution of N-acetyl-2-cyanoacetohydrazide (4.0 g, 28.4 mmol) in toluene (150 mL). Then the reaction was stirred for 4 h at 80° C. in an oil bath. The resulting mixture was concentrated in vacuo and quenched by the addition of 100 mL of water. The pH value of the solution was adjusted to 7 with sodium carbonate (19%) and extracted with 3×100 mL of ethyl acetate. The organic layers were combined and dried over anhydrous sodium sulfate. The solids were filtered off. The resulting solution was concentrated in vacuo to afford 2-(5-methyl-1,3,4-oxadiazol-2-yl) acetonitrile as orange oil (2.5 g, 70%).

Step 4: (E)-3-(dimethylamino)-2-(5-methyl-1,3,4-oxadiazol-2-yl)acrylonitrile

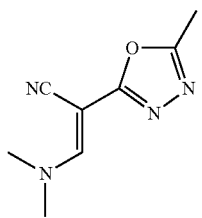

To a solution of 2-(5-methyl-1,3,4-oxadiazol-2-yl)acetonitrile (2.5 g, 20.3 mmol) in toluene (10 mL) was added DMF-DMA (3.6 g, 30.5 mmol), and the reaction mixture was stirred for 3 h at 85° C. in an oil bath. The resulting mixture was concentrated in vacuo to afford (E)-3-(dimethylamino)-2-(5-methyl-1,3,4-oxadiazol-2-yl)acrylonitrile as a crude orange red oil.

Step 5: 4-(5-methyl-1,3,4-oxadiazol-2-yl)-1H-pyrazol-5-amine

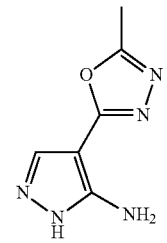

To a solution of (E)-3-(dimethylamino)-2-(5-methyl-1,3,4-oxadiazol-2-yl)acrylonitrile (5.0 g, 28.1 mmol) in ethanol (100 mL) was added the N$_2$H$_4$.H$_2$O (4.2 g, 84.3 mmol), and the reaction mixture was stirred for 1 h at 90° C. in an oil bath. The resulting mixture was concentrated in vacuo to give the residue, which was purified by silica gel column chromatography with dichloromethane/methanol (80:1-30:1) to afford 4-(5-methyl-1,3,4-oxadiazol-2-yl)-1H-pyrazol-5-amine as a golden powder (3 g, 39%).

LC/MS (ES, m/z): [M+H]+ 166.0

$^1$H NMR (300 MHz, DMSO) δ7.86-7.81 (m, 1H), 2.56 (s, 3H)

Step 6: 5-(1-ethyl-1H-indazol-5-yl)-3-(5-methyl-1,3,4-oxadiazol-2-yl)-4H,7H-pyrazolo[1,5-a]pyrimidin-7-one

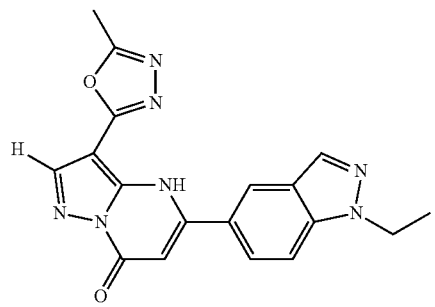 [SMILES: CCn1ncc2cc(-c3cc(=O)n4ncc(-c5nnc(C)o5)c4[nH]3)ccc21]

p-TsOH (10.35 mg, 0.06 mmol) and ethyl 3-(1-ethyl-1H-indazol-5-yl)-3-oxopropanoate (473 mg, 1.82 mmol) were added to a solution of 4-(5-methyl-1,3,4-oxadiazol-2-yl)-1H-pyrazol-5-amine (200 mg, 1.21 mmol) in n-BuOH (1 mL). The reaction was stirred for 5 h at 130° C. After concentrating, the residue was purified by silica gel column chromatography with dichloromethane/methanol (25:1) to afford 5-(1-ethyl-1H-indazol-5-yl)-3-(5-methyl-1,3,4-oxadiazol-2-yl)-4H,7H-pyrazolo[1,5-a]pyrimidin-7-one as a white solid (80 mg, 18%).

LC/MS (ES, m/z): [M+H]+ 362.1

$^1$H NMR (300 MHz, DMSO) δ 8.40 (s, 1H), 8.29 (s, 2H), 7.90 (d, J=8.70 Hz, 1H), 7.82 (dd, J=9.00 Hz, 1.5 Hz, 1H), 6.31 (s, 1H), 4.52 (q, J=7.20 Hz, 2H), 2.6 (s, 3H), 1.42 (t, J=7.20 Hz, 3H)

EXAMPLE 32

5-(1-ethyl-1H-indazol-5-yl)-3-(1-methyl-1H-pyrazol-3-yl)-4H,7H-pyrazolo[1,5-a]pyrimidin-7-one

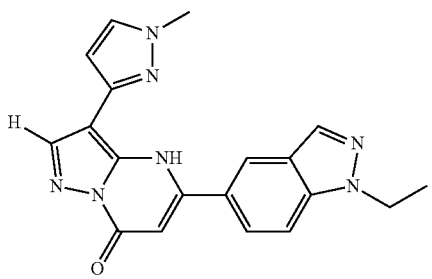 [SMILES: CCn1ncc2cc(-c3cc(=O)n4ncc(-c5ccn(C)n5)c4[nH]3)ccc21]

Step 1: Methyl 1-methyl-1H-pyrazole-3-carboxylate

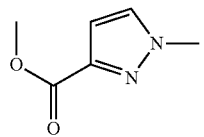

To a solution of 1H-pyrazole-3-carboxylic acid (25.0 g, 223.04 mmol) in DMF (250 mL) was added potassium carbonate (61.6 g, 445.70 mmol) and CH₃I (69.7 g, 491.05 mmol) dropwise at 0° C. and the reaction was stirred for 2 h at room temperature. The resulting mixture was concentrated in vacuo. The residue was dissolved in 150 mL of H₂O, and the pH was adjusted to 7 with HCl (36%). The resulting solution was extracted with 5×100 mL of ethyl acetate and the organic layers combined and dried over anhydrous sodium sulfate. The solids were filtered out. The resulting mixture was concentrated in vacuo to afford the residue, which was purified by silica gel column chromatography with ethyl acetate/petroleum ether (1:5) to afford methyl 1-methyl-1H-pyrazole-3-carboxylate as a light yellow solid (22.0 g, 75%).

Step 2: (1-methyl-1H-pyrazol-3-yl)methanol

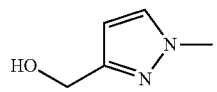

To a solution of methyl 1-methyl-1H-pyrazole-3-carboxylate (22.0 g, 157.14 mmol) in tetrahydrofuran (150 mL) was added lithium aluminum hydride (11.9 g, 314.29 mmol) in portions at 0-5° C. Then the reaction was stirred for 18 h at room temperature. The reaction mixture was cooled to 0° C. with a water/ice bath, quenched by the addition of 15 mL of water. The resulting solution was diluted with 200 mL of DCM and dried over anhydrous sodium sulfate. The solids were filtered out. The resulting mixture was concentrated in vacuo to afford (1-methyl-1H-pyrazol-3-yl)methanol as light yellow liquid (6.0 g, 35%).

Step 3: 3-(chloromethyl)-1-methyl-1H-pyrazole

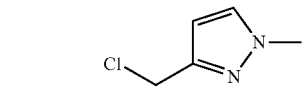

To a solution of (1-methyl-1H-pyrazol-3-yl)methanol (6.0 g, 53.57 mmol) in dichloromethane (20 mL) was added thionyl chloride (9.56 g, 80.36 mmol) dropwise at 0-5° C. Then the reaction was stirred for 2 h at room temperature. The reaction mixture was cooled to 5° C. with a water/ice bath. The reaction was quenched by water (25 mL), adjusted to pH=7-8 with sodium carbonate. The resulting solution was extracted with 3×50 mL of dichloromethane and the organic layers were combined and dried over anhydrous sodium sulfate. The solids were filtered off. The resulting mixture was concentrated in vacuo to afford 3-(chloromethyl)-1-methyl-1H-pyrazole as a crude yellow oil.

Step 4: 2-(1-methyl-1H-pyrazol-3-yl)acetonitrile

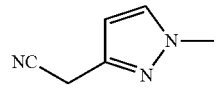

To a solution of 3-(chloromethyl)-1-methyl-1H-pyrazole (6.0 g, 45.26 mmol) in CH₃CN/H₂O (25 mL) was added potassium cyanide (4.8 g, 73.72 mmol). The reaction was stirred for 24 h at 50° C. in an oil bath. The resulting solution was extracted with 5×50 mL of ethyl acetate and the organic layers were combined and dried over anhydrous sodium sulfate. The solids were filtered off. The resulting mixture was concentrated in vacuo to afford the residue, which was purified by silica gel column chromatography with ethyl acetate/petroleum ether (1:50) to afford 2-(1-methyl-1H-pyrazol-3-yl)acetonitrile as a light yellow solid (2.0 g, 31%).

Step 5: (Z)-3-(dimethylamino)-2-(1-methyl-1H-pyrazol-3-yl)acrylonitrile

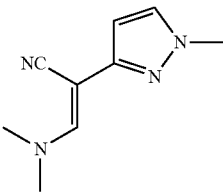

To a solution of 2-(1-methyl-1H-pyrazol-3-yl)acetonitrile (2.0 g, 16.53 mmol,) in toluene (2.0 mL) was added DMF-DMA (2.95 g, 24.79 mmol, 1.50 equiv), and the reaction mixture was stirred for 3 h at 85° C. in an oil bath. The resulting mixture was concentrated in vacuo to afford (Z)-3-(dimethylamino)-2-(1-methyl-1H-pyrazol-3-yl)acrylonitrile which was used crude in the next step.

Step 6: 1-methyl-1H,1'H-3,4'-bipyrazol-5'-amine

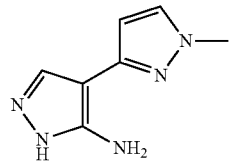

N$_2$H$_4$.H$_2$O (5.68 g, 113.60 mmol) was added to a solution of (Z)-3-(dimethylamino)-2-(1-methyl-1H-pyrazol-3-yl)acrylonitrile (4.0 g, 22.70 mmol) in AcOH (3 mL). The reaction was stirred for 4 h at 90° C. in an oil bath. The resulting mixture was concentrated in vacuo to give a residue, which was purified by silica gel column chromatography with dichloromethane/methanol (100:1-50:1) to afford 1-methyl-1H,1'H-3,4'-bipyrazol-5'-amine as a yellow solid (800 mg, 31%).

LC/MS (ES, m/z): [M+H]$^+$ 164.0

$^1$H NMR (300 MHz, DMSO) δ7.63-7.61 (m, 2H), 6.31 (d, J=2.4 Hz, 1H), 3.81 (s, 3H)

Step 7: 5-(1-ethyl-1H-indazol-5-yl)-3-(1-methyl-1H-pyrazol-3-yl)-4H,7H-pyrazolo[1,5-a]pyrimidin-7-one

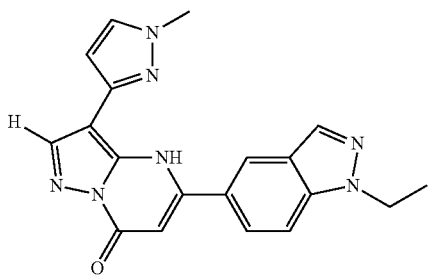 [SMILES: CCn1ncc2cc(-c3cc(=O)n4ncc(-c5ccn(C)n5)c4[nH]3)ccc21]

Ethyl 3-(1-ethyl-1H-indazol-5-yl)-3-oxopropanoate (478.6 mg, 1.84 mmol) and p-TsOH (5.28 mg, 0.03 mmol) were added to a solution of 1-methyl-1H,1'H-3,4'-bipyrazol-5'-amine (200 mg, 1.22 mmol) in n-BuOH (0.4 mL). The reaction was stirred for 3 h at 130° C. in an oil bath. The solids were collected by filtration to afford 5-(1-ethyl-1H-indazol-5-yl)-3-(1-methyl-1H-pyrazol-3-yl)-4H,7H-pyrazolo[1,5-a]pyrimidin-7-one as a white solid (42.2 mg, 19%).

LC/MS (ES, m/z): [M+H]$^+$ 360.0

$^1$H NMR (300 MHz, DMSO) δ11.26 (s, 1H), 8.30 (m, 3H), 7.90 (m, 3H), 6.69 (d, J=1.8 Hz, 1H), 6.21 (s, 1H), 4.52 (q, J=7.2 Hz, 2H), 3.94 (s, 3H), 1.43 (t, J=7.2 Hz 3H)

EXAMPLE 33

3-(benzo[d]oxazol-2-yl)-5-(1-ethyl-1H-indazol-5-yl)pyrazolo[1,5-a]pyrimidin-7(4H)-one

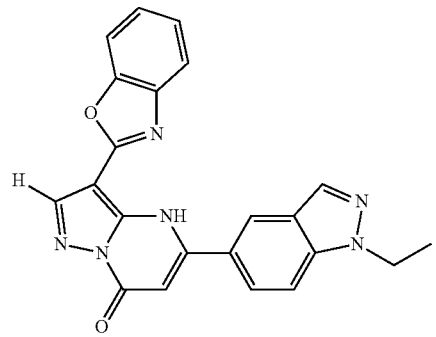 [SMILES: CCn1ncc2cc(-c3cc(=O)n4ncc(-c5nc6ccccc6o5)c4[nH]3)ccc21]

Step 1: 2-(benzo[d]oxazol-2-yl)acetonitrile

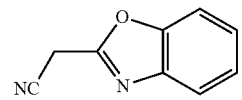 [SMILES: N#CCc1nc2ccccc2o1]

Propanedinitrile (16.65 g, 252.04 mmol) and AcOH (300 mg, 5.00 mmol) were added to a solution of 2-aminophenol (11 g, 100.80 mmol) in ethanol (200 mL). The reaction was stirred overnight at 70° C. The resulting mixture was concentrated in vacuo and then diluted with H$_2$O (300 mL). The resulting solution was extracted with ethyl acetate (3×50 mL) and the organic layers were combined and concentrated in vacuo. The residue was purified by silica gel column chromatography with dichloromethane/methanol (80:1) to afford 2-(benzo[d]oxazol-2-yl)acetonitrile as a red solid (5 g, 31%).

LC/MS (ES, m/z): [M+H]+ 159.0

$^1$H NMR (300 MHz, DMSO) δ7.75 (d, J=7.50 Hz, 1H), 7.56 (d, J=7.20 Hz, 1H), 7.36-7.41 (m, 2H), 4.11 (s, 2H)

Step 2: (E)-2-(benzo[d]oxazol-2-yl)-3-(dimethylamino)acrylonitrile

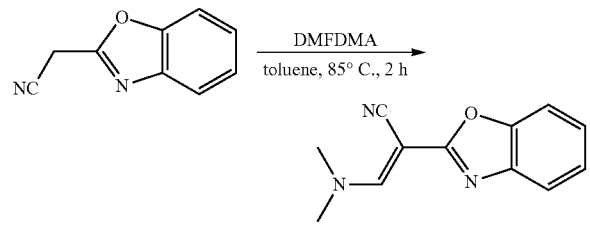

DMFDMA (7.2 g, 1.50 equiv) was added to a solution of 2-(benzo[d]oxazol-2-yl)acetonitrile (6.4 g, 40.47 mmol) in toluene (30 mL), and the reaction was stirred for 2 h at 85° C. The resulting mixture was concentrated in vacuo and diluted with H$_2$O (200 mL). The reaction was extracted with ethyl acetate (3×50 mL) and the organic layers were combined and concentrated in vacuo to afford (E)-2-(benzo[d]oxazol-2-yl)-3-(dimethylamino)acrylonitrile as dark red crude oil (7 g, 81%).

Step 3: 4-(benzo[d]oxazol-2-yl)-1H-pyrazol-5-amine

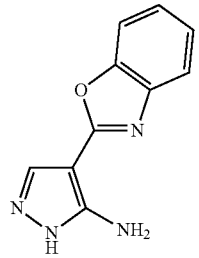 [SMILES: Nc1[nH]ncc1-c1nc2ccccc2o1]

N₂H₄·H₂O (6.0 g) was added to a solution of (E)-2-(benzo[d]oxazol-2-yl)-3-(dimethylamino)acrylonitrile (6.5 g, 30.48 mmol) in ethanol (100 mL), The reaction was stirred for 2 h at 90° C. Then it was concentrated in vacuo, and diluted with H₂O (200 mL). The resulting solution was extracted with ethyl acetate (3×50 mL) and the organic layers were combined and concentrated in vacuo. The residue was purified by silica gel column chromatography eluting with dichloromethane/methanol (80:1) to afford 4-(benzo[d]oxazol-2-yl)-1H-pyrazol-5-amine as a white solid (1 g, 16%).

LC/MS (ES, m/z): [M+H]+ 201.0

¹H NMR (300 MHz, DMSO) δ7.78 (d, J=10.50 Hz, 1H), 7.64 (d, J=8.70 Hz, 2H), 7.27-7.34 (m, 2H)

Step 4: 3-(benzo[d]oxazol-2-yl)-5-(1-ethyl-1H-indazol-5-yl)pyrazolo[1,5-a]pyrimidin-7(4H)-one

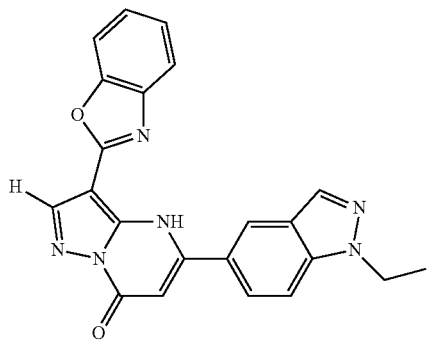 [SMILES: CCn1ncc2cc(-c3cc(=O)n4ncc(-c5nc6ccccc6o5)c4[nH]3)ccc21]

Ethyl 3-(1-ethyl-1H-indazol-5-yl)-3-oxopropanoate (224 mg, 0.86 mmol) and TsOH (30 mg, 0.17 mmol) were added to a solution of 4-(benzo[d]oxazol-2-yl)-1H-pyrazol-5-amine (100 mg, 0.50 mmol) in diphenyl ether (1 mL) and the reaction was stirred for 2 h at 170° C. The solids were collected by filtration and washed with MeOH (1 mL×3) to afford 3-(benzo[d]oxazol-2-yl)-5-(1-ethyl-1H-indazol-5-yl)pyrazolo[1,5-a]pyrimidin-7(4H)-one as a light yellow solid (52.7 mg, 27%).

LC/MS (ES, m/z): [M+H]+ 397.0

¹H NMR (300 MHz, DMSO) δ 8.53 (s, 1H), 8.17-8.31 (m, 3H), 7.62-7.75 (m, 3H), 7.22-7.32 (m, 2H), 6.22 (s, 1H), 4.43-4.51 (q, J=7.20 Hz, 2H), 1.40-1.45 (t, J=7.20 Hz, 3H)

EXAMPLE 34

5-(4-chloro-3-ethoxyphenyl)-3-(oxazol-2-yl)-4H,7H-pyrazolo[1,5-a]pyrimidin-7-one

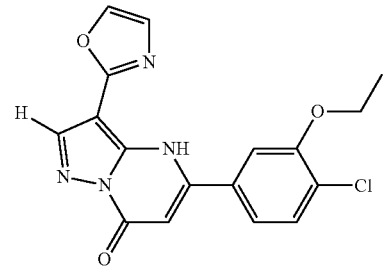 [SMILES: CCOc1cc(-c2cc(=O)n3ncc(-c4ncco4)c3[nH]2)ccc1Cl]

Step 1: 5-(4-chloro-3-ethoxyphenyl)-7-oxo-4H,7H-pyrazolo[1,5-a]pyrimidine-3-carbonitrile

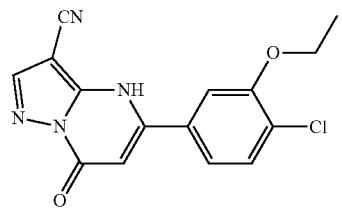 [SMILES: CCOc1cc(-c2cc(=O)n3ncc(C#N)c3[nH]2)ccc1Cl]

To a solution of 5-amino-1H-pyrazole-4-carbonitrile (400 mg, 3.70 mmol) in n-BuOH (1 mL) was added ethyl 3-(4-chloro-3-methoxyphenyl)-3-oxopropanoate (982 mg, 3.83 mmol), TsOH (21 mg, 0.12 mmol) and the reaction was stirred for 2 h at 130° C. The solids were collected by filtration to afford 5-(4-chloro-3-ethoxyphenyl)-7-oxo-4H,7H-pyrazolo[1,5-a]pyrimidine-3-carbonitrile as a crude light yellow solid (500 mg, 45%).

Step 2: 5-(4-chloro-3-ethoxyphenyl)-7-oxo-4H,7H-pyrazolo[1,5-a]pyrimidine-3-carboxamide

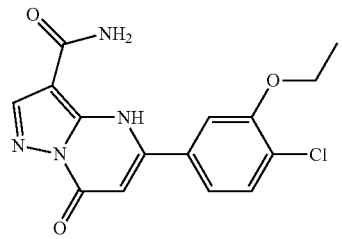 [SMILES: CCOc1cc(-c2cc(=O)n3ncc(C(N)=O)c3[nH]2)ccc1Cl]

5-(4-chloro-3-ethoxyphenyl)-7-oxo-4H,7H-pyrazolo[1,5-a]pyrimidine-3-carbonitrile (500 mg, 1.66 mmol) was dissolved in sulfuric acid (2 mL) and stirred for 30 min at room temperature. Then the reaction was quenched by the addition of water/ice (30 mL). The solids were collected by filtration to afford 5-(4-chloro-3-ethoxyphenyl)-7-oxo-4H,7H-pyrazolo[1,5-a]pyrimidine-3-carboxamide as a crude light yellow solid (200 mg, 38%).

Step 3: 5-(4-chloro-3-ethoxyphenyl)-3-(oxazol-2-yl)-4H,7H-pyrazolo[1,5-a]pyrimidin-7-one

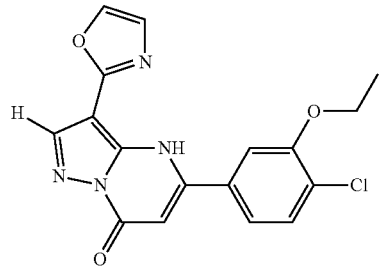 [SMILES: CCOc1cc(-c2cc(=O)n3ncc(-c4ncco4)c3[nH]2)ccc1Cl]

TsOH (5.16 mg, 0.03 mmol) and 2-bromo-1,1-diethoxyethane (177 mg, 0.90 mmol) were added to a solution of 5-(4-chloro-3-ethoxyphenyl)-7-oxo-4H,7H-pyrazolo[1,5-a]pyrimidine-3-carboxamide (200 mg, 0.63 mmol) in NMP (1 mL). The reaction was stirred for 40 min at 80° C. The solids were collected by filtration to afford 5-(4-chloro-3-ethoxyphenyl)-3-(oxazol-2-yl)-4H,7H-pyrazolo[1,5-a]pyrimidin-7-one as a light yellow solid (24.5 mg, 11%).

LC/MS (ES, m/z): [M+H]+ 357.0

$^1$H NMR (300 MHz, DMSO) δ8.10 (s, 1H), 8.00 (s, 1H), 7.78 (d, J=1.80 Hz, 1H), 7.69 (m, 1H), 7.47 (d, J=8.10 Hz, 1H), 7.19 (s, 1H), 6.13 (s, 1H), 4.25 (m, 2H), 1.42 (d, J=9.90 Hz, 3H)

EXAMPLE 35

5-(4-chloro-3-ethoxyphenyl)-3-(5-ethyloxazol-2-yl)-4H,7H-pyrazolo[1,5-a]pyrimidin-7-one

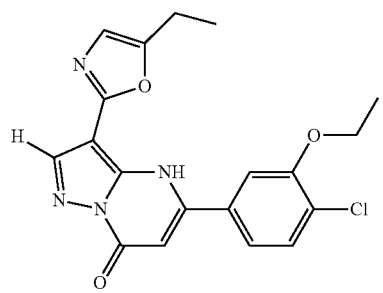 [SMILES: CCOc1cc(-c2cc(=O)n3ncc(-c4ncc(CC)o4)c3[nH]2)ccc1Cl]

Ethyl 3-(4-chloro-3-ethoxyphenyl)-3-oxopropanoate (216 mg, 0.84 mmol) and TsOH (4.8 mg, 0.03 mmol) were added to a solution of 4-(5-ethyloxazol-2-yl)-1H-pyrazol-5-amine (100 mg, 0.56 mmol) in n-BuOH (1 mL). The reaction was stirred for 2 h at 130° C. Then the solids were collected by filtration to afford 5-(4-chloro-3-ethoxyphenyl)-3-(5-ethyl-oxazol-2-yl)-4H,7H-pyrazolo[1,5-a]pyrimidin-7-one as a light yellow solid (69.9 mg, 34%).

LC/MS (ES, m/z): [M+H]+ 385.0

$^1$H NMR (300 MHz, DMSO) δ 8.32 (s, 1H), 7.90 (s, 1H), 7.57 (m, 1H), 7.40 (d, J=8.10 Hz, 1H), 6.84 (s, 1H), 6.30 (s, 1H), 4.28 (m, 2H), 2.77 (m, 2H), 1.46 (m, 3H), 1.33 (m, 3H)

EXAMPLE 36

5-(3-ethoxy-4-fluorophenyl)-3-(5-methyloxazol-2-yl)-4H,7H-pyrazolo[1,5-a]pyrimidin-7-one

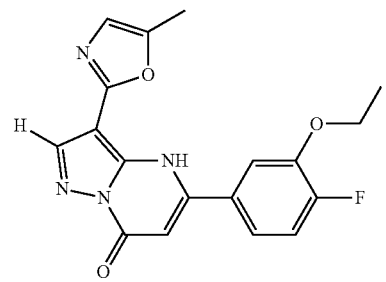 [SMILES: CCOc1cc(-c2cc(=O)n3ncc(-c4ncc(C)o4)c3[nH]2)ccc1F]

Step 1: Ethyl 3-ethoxy-4-fluorobenzoate

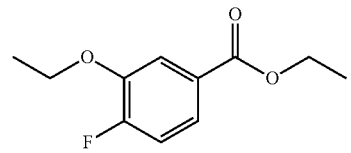

Potassium carbonate (8.3 g, 60.05 mmol) and EtI (10 g) were added to a solution of 4-fluoro-3-hydroxybenzoic acid (5 g, 32.03 mmol) in DMF (20 mL) and the reaction was stirred for 4 h at room temperature. The resulting mixture was concentrated in vacuo and then diluted with H$_2$O (200 mL). The resulting solution was extracted with ethyl acetate (3×50 mL) and the organic layers combined. The residue was purified by silica gel column chromatography with ethyl acetate/petroleum ether (1:50) to afford ethyl 3-ethoxy-4-fluorobenzoate as a white solid (5 g, 74%).

LC/MS (ES, m/z): [M+H]+ 213.0

$^1$H NMR (300 MHz, DMSO) δ 7.60-7.66 (m, 2H), 7.07-7.14 (m, 1H), 4.33-4.40 (m, 2H), 4.13-4.20 (m, 2H), 1.45-1.50 (m, 3H), 1.37-1.43 (m, 3H)

Step 2: 3-ethoxy-4-fluorobenzoic acid

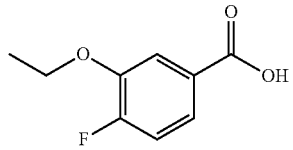

To a solution of ethyl 3-ethoxy-4-fluorobenzoate (5 g, 23.56 mmol) in methanol (30 mL) was added a solution of sodium hydroxide (3.8 g, 95.00 mmol) in water (10 mL) and the reaction was stirred for 2 h at 55° C. The resulting mixture was concentrated in vacuo and then diluted with H$_2$O (100 mL). The solution was adjusted to pH 4 with HCl (4N). The solids were collected by filtration to afford 3-ethoxy-4-fluorobenzoic acid as a white solid (4 g, 92%).

LC/MS (ES, m/z): [M+H]+ 185.0

$^1$H NMR (300 MHz, DMSO) δ7.69-7.74 (m, 2H), 7.13-7.19 (m, 1H), 4.15-4.22 (m, 2H), 1.47-1.52 (m, 3H)

Step 3: Ethyl 3-(3-ethoxy-4-fluorophenyl)-3-oxopropanoate

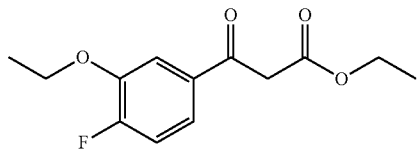 [SMILES: CCOC(=O)CC(=O)c1ccc(F)c(OCC)c1]

CDI (5.28 g) was added to a solution of 3-ethoxy-4-fluorobenzoic acid (4 g, 21.72 mmol) in tetrahydrofuran (100 mL) and the resulting solution was stirred for 3 h at room temperature. To a solution of potassium 3-ethoxy-3-oxopropanoate (11.2 g) in CH$_3$CN (150 mL) was added triethylamine (6.56 g, 64.83 mmol), and MgCl$_2$ (9.36 g) in ice water bath, the resulting solution was stirred for 3 h at room temperature. Then the two above reaction mixtures were combined and stirred for 2 h at room temperature. The resulting mixture was concentrated in vacuo and diluted with H$_2$O (500 mL), adjusted to pH 4 with HCl (4M), extracted with ethyl acetate (5×100 mL) and the organic layers were combined and dried over anhydrous sodium sulfate. The solids were filtered off. The residue was purified by silica gel column chromatography with ethyl acetate/petroleum ether (1:20) to afford ethyl 3-(3-ethoxy-4-fluorophenyl)-3-oxopropanoate as red oil (4 g, 72%).

LC/MS (ES, m/z): [M+H]+ 255.0

$^1$H NMR (300 MHz, DMSO) δ7.58-7.66 (m, 2H), 7.35-7.43 (m, 1H), 4.02-4.25 (m, 6H), 1.35-1.40 (m, 3H), 1.19-1.30 (m, 3H)

Step 4: 5-(3-ethoxy-4-fluorophenyl)-3-(5-methyloxazol-2-yl)-4H,7H-pyrazolo[1,5-a]pyrimidin-7-one

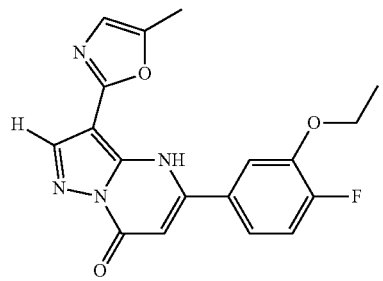 [SMILES: CCOc1cc(-c2cc(=O)n3ncc(-c4ncc(C)o4)c3[nH]2)ccc1F]

Ethyl 3-(3-ethoxy-4-fluorophenyl)-3-oxopropanoate (159 mg, 0.63 mmol) and TsOH (30 mg, 0.17 mmol) were added to a solution of 4-(5-methyloxazol-2-yl)-1H-pyrazol-5-amine (100 mg, 0.61 mmol) in n-BuOH (1 mL). The reaction was stirred for 4 h at 130° C. The solids were collected by filtration to afford 5-(3-ethoxy-4-fluorophenyl)-3-(5-methyloxazol-2-yl)-4H,7H-pyrazolo[1,5-a]pyrimidin-7-one as a off-white solid (51.9 mg, 24%).

LC/MS (ES, m/z): [M+H]+ 355.0

$^1$H NMR (300 MHz, DMSO) δ 8.31 (s, 1H), 7.95-7.97 (m, 1H), 7.60-7.63 (m, 1H), 7.16-7.21 (m, 1H), 6.83 (s, 1H), 6.32 (s, 1H), 4.27-4.33 (q, J=7.20 Hz, 2H), 2.44 (s, 3H), 1.48-1.52 (t, J=7.20 Hz, 3H)

EXAMPLE 37

5-[4-chloro-3-(2,2,2-trifluoroethoxy)phenyl]-3-(5-methyloxazol-2-yl)-4H,7H-pyrazolo[1,5-a]pyrimidin-7-one

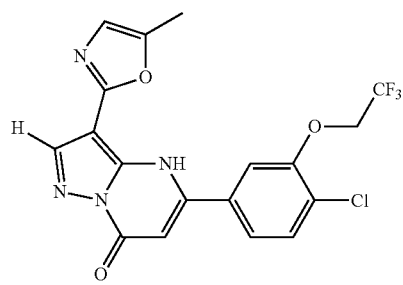 [SMILES: Cc1cnc(-c2cnn3c(=O)cc(-c4ccc(Cl)c(OCC(F)(F)F)c4)[nH]c23)o1]

Step 1: Methyl 4-chloro-3-hydroxybenzoate

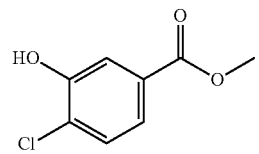

Thionyl chloride (6 g) was added to a solution of 4-chloro-3-hydroxybenzoic acid (4.4 g, 25.50 mmol) in methanol (100 mL) and the reaction was stirred for 2 h at 70° C. Then the reaction was concentrated in vacuo. The resulting solution was diluted with n-hexane (50 mL). The solids were collected by filtration, dried in an oven under reduced pressure to afford methyl 4-chloro-3-hydroxybenzoate as a light yellow solid (4 g, 84%).

LC/MS (ES, m/z): [M+H]$^+$ 187.0

$^1$H NMR (300 MHz, DMSO) δ 10.69 (s, 1H), 7.55 (d, J=2.10 Hz, 1H), 7.49 (d, J=8.40 Hz, 1H), 7.36-7.40 (m, 1H), 3.83-3.85 (d, J=8.40 Hz, 3H)

Step 2: Methyl 4-chloro-3-(2,2,2-trifluoroethoxy)benzoate

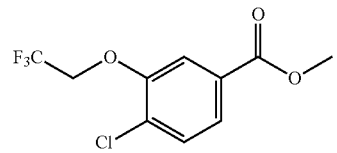 [SMILES: COC(=O)c1ccc(Cl)c(OCC(F)(F)F)c1]

KHCO$_3$ (1 g) was added to a solution of methyl 4-chloro-3-hydroxybenzoate (1 g, 5.36 mmol) in acetone (10 mL) and the reaction was stirred for 30 mins at 70° C. Then 2,2,2-trifluoroethyl trifluoromethanesulfonate (3.4 g) was added dropwise and the reaction was stirred overnight at 70° C. The resulting mixture was concentrated in vacuo. The resulting solution was diluted with H$_2$O (20 mL) and extracted with ether (3×10 mL) and the organic layers were combined to afford methyl 4-chloro-3-(2,2,2-trifluoroethoxy)benzoate as a white solid (1.3 g, 90%).

LC/MS (ES, m/z): [M+H]+ 269.0

$^1$H NMR (300 MHz, DMSO) δ7.76 (s, 1H), 7.64 (d, J=8.40 Hz, 2H), 4.97-5.05 (m, 2H), 3.88 (s, 3H)

Step 3: 4-chloro-3-(2,2,2-trifluoroethoxy)benzoic acid

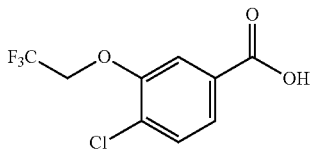

A solution of sodium hydroxide (700 mg, 17.50 mmol) in water (1 mL) was added to a solution of methyl 4-chloro-3-(2,2,2-trifluoroethoxy)benzoate (1.2 g, 4.47 mmol) in methanol (10 mL) and the reaction was stirred for 3 h at room temperature. The resulting mixture was concentrated in vacuo and diluted with H$_2$O (50 mL). The solution was adjusted to pH 4 with HCl (3N). The solids were collected by filtration to afford 4-chloro-3-(2,2,2-trifluoroethoxy)benzoic acid as a white solid (1.09 g, 96%).

LC/MS (ES, m/z): [M+H]+ 255.0

$^1$H NMR (300 MHz, DMSO) δ13.33 (s, 1H), 7.74 (s, 1H), 7.63 (s, 2H), 4.95-5.04 (m, 2H)

Step 4: Ethyl 3-[4-chloro-3-(2,2,2-trifluoroethoxy)phenyl]-3-oxopropanoate

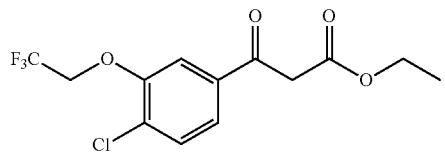 [SMILES: CCOC(=O)CC(=O)c1ccc(Cl)c(OCC(F)(F)F)c1]

To a solution of 4-chloro-3-(2,2,2-trifluoroethoxy)benzoic acid (1.09 g, 4.28 mmol) in tetrahydrofuran (30 mL) was added CDI (1.04 g), and the reaction mixture was stirred for 2 h at room temperature. To a solution of potassium 3-ethoxy-3-oxopropanoate (2.2 g) in CH$_3$CN (100 mL) was added triethylamine (1.3 g, 12.85 mmol), MgCl$_2$ (1.81 g, 4.50 equiv), and the reaction mixture was stirred for 2 h at room temperature. The two above reaction mixtures were combined and stirred for 2 h at room temperature. The resulting mixture was concentrated in vacuo, diluted with H$_2$O (100 mL). The pH was adjusted to pH 4 with HCl (3N), extracted with ethyl acetate (3×50 mL), and the organic layers combined and dried over anhydrous sodium sulfate. The solids were filtered off. The residue was purified by silica gel column chromatography with ethyl acetate/petroleum ether (1:80) to afford ethyl 3-[4-chloro-3-(2,2,2-trifluoroethoxy)phenyl]-3-oxopropanoate as light yellow oil (1.3 g, 94%).

LC/MS (ES, m/z): [M+H]+ 325.0

$^1$H NMR (300 MHz, DMSO) δ7.53-7.77 (m, 3H), 4.95-5.06 (m, 2H), 4.22-4.29 (m, 2H), 4.09-4.17 (m, 2H), 1.16-1.23 (m, 3H)

Step 5: 5-[4-chloro-3-(2,2,2-trifluoroethoxy)phenyl]-3-(5-methyloxazol-2-yl)-4H,7H-pyrazolo[1,5-a]pyrimidin-7-one

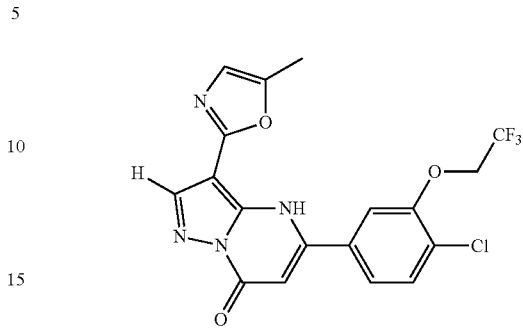

To a solution of 4-(5-methyloxazol-2-yl)-1H-pyrazol-5-amine (100 mg, 0.61 mmol) in n-BuOH (1 M) was added ethyl 3-[4-chloro-3-(2,2,2-trifluoroethoxy)phenyl]-3-oxopropanoate (294 mg, 0.91 mmol) and TsOH (5.16 mg, 0.03 mmol), and the reaction mixture was stirred for 2 h at 130° C. The solids were collected by filtration to afford 5-[4-chloro-3-(2,2,2-trifluoroethoxy)phenyl]-3-(5-methyloxazol-2-yl)-4H,7H-pyrazolo[1,5-a]pyrimidin-7-one as a light yellow solid (25 mg, 10%).

LC/MS (ES, m/z): [M+H]+ 425.0

$^1$H NMR (300 MHz, DMSO) δ7.98-8.05 (m, 2H), 7.82-7.85 (m, 1H), 7.52 (d, J=8.40 Hz, 1H), 6.77 (s, 1H), 6.22 (s, 1H), 4.97-5.06 (m, 2H), 2.35 (s, 3H)

EXAMPLE 38

5-[4-chloro-3-(trifluoromethoxy)phenyl]-3-(5-methyloxazol-2-yl)-4H,7H-pyrazolo[1,5-a]pyrimidin-7-one

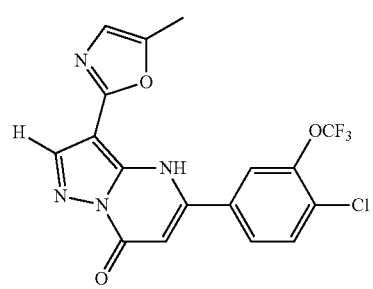 [SMILES: Cc1cnc(-c2cnn3c(=O)cc(-c4ccc(Cl)c(OC(F)(F)F)c4)[nH]c23)o1]

Step 1: Methyl 4-amino-3-(trifluoromethoxy)benzoate

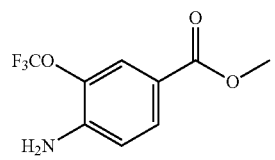

To a solution of 4-bromo-2-(trifluoromethoxy)aniline (10 g, 50.21 mmol) in methanol (150 mL) in a pressure tank reactor was added TEA (11.84 g, 117.01 mmol), Pd(dppf)Cl$_2$ $^-$CH$_2$Cl$_2$(2.4 g, 2.94 mmol). Then the reactor was charged with CO (g) (20 atm). The resulting reaction was stirred for 1.5 days at 100° C. Then it was diluted with water (200 mL), extracted with ethyl acetate (3×100 mL) and the organic layers combined and dried in an oven under reduced pressure. The resulting mixture was concentrated in vacuo. The residue was purified by silica gel column chromatography with ethyl acetate/petroleum ether (1:50) to afford methyl 4-amino-3-(trifluoromethoxy)benzoate as yellow solid (5 g, 54%).

Step 2: Methyl 4-chloro-3-(trifluoromethoxy)benzoate

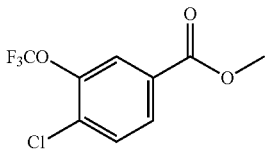

To a solution of methyl 4-amino-3-(trifluoromethoxy) benzoate (5 g, 25.33 mmol) in CH$_3$CN (100 mL) was added concentrated HCl (20 mL) in an ice/water bath. This was followed by the addition of a solution of NaNO$_2$ (5.9 g, 85.51 mmol) in water (20 mL) dropwise at 0-5° C. The reaction was stirred for 40 min at 0° C. in an ice/water bath. To this was added copper chloride (5.9 g, 59.60 mmol) in portions at 0° C. The resulting solution was stirred for 1.5 min at 0° C. in a water/ice bath maintained under an inert atmosphere of nitrogen. The resulting solution was extracted with ethyl acetate (3×100 mL) and the organic layers combined and dried in an oven under reduced pressure. The resulting mixture was concentrated in vacuo. The residue was purified by silica gel column chromatography with ethyl acetate/petroleum ether (1:100) to afford methyl 4-chloro-3-(trifluoromethoxy)benzoate as yellow oil (3 g, 55%).

LC/MS (ES, m/z): [M+H]$^+$ 255.0
$^1$H NMR (300 MHz, DMSO) δ7.91-7.99 (m, 2H), 7.56 (d, J=8.70 Hz, 1H), 3.94 (s, 3H)

Step 3: 4-chloro-3-(trifluoromethoxy)benzoic acid

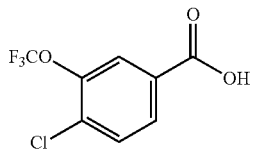 [SMILES: O=C(O)c1ccc(Cl)c(OC(F)(F)F)c1]

To a solution of methyl 4-chloro-3-(trifluoromethoxy) benzoate (3.1 g, 12.18 mmol) in methanol (30 mL) was added a solution of sodium hydroxide (1.46 g, 36.50 mmol) in water (10 mL) at room temperature, and the reaction mixture was stirred for 1.5 h at room temperature. The solution was adjusted to pH 4 with HCl (36%). The resulting solution was extracted with ethyl acetate (3×100 mL) and the organic layers combined and dried over anhydrous sodium sulfate. The solids were filtered out. The resulting mixture was concentrated in vacuo to afford 4-chloro-3-(trifluoromethoxy)benzoic acid as a light yellow solid (2.10 g, 74%).

LC/MS (ES, m/z): [M+H]$^+$ 241.0
$^1$H NMR (300 MHz, DMSO) δ 7.92-7.99 (m, 2H), 7.40-7.47 (m, 1H)

Step 4: Ethyl 3-[4-chloro-3-(trifluoromethoxy)phenyl]-3-oxopropanoate

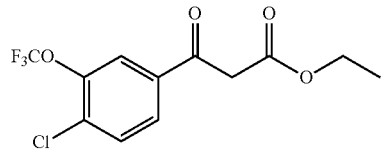 [SMILES: CCOC(=O)CC(=O)c1ccc(Cl)c(OC(F)(F)F)c1]

To a solution of 4-chloro-3-(trifluoromethoxy)benzoic acid (2.10 g, 7.51) in tetrahydrofuran (40 mL) was added CDI (3.11 g, 19.18 mmol) with stirring 2 h at r.t. To a solution of potassium 3-ethoxy-3-oxopropanoate (6.53 g, 38.37 mmol) in CH$_3$CN (80 mL) was added triethylamine (3.88 g, 38.34 mmol) dropwise, MgCl$_2$ (5.47 g, 57.58 mmol) with stirring at 0° C. The reaction was stirred for 2 h at RT. The two above reaction mixtures were combined and stirred for 2.5 h at room temperature and the resulting mixture was concentrated in vacuo. The resulting solution was diluted with H$_2$O (100 mL). The solution was adjusted to pH 7 with HCl (4N), extracted with ethyl acetate (3×100 mL) and the organic layers combined and dried over anhydrous sodium sulfate and concentrated in vacuo. The residue was purified by silica gel column chromatography with ethyl acetate/ petroleum ether (1:80) to afford ethyl 3-[4-chloro-3-(trifluoromethoxy)phenyl]-3-oxopropanoate as brown oil (1.63 g, 54%).

LC/MS (ES, m/z): [M+H]$^+$ 311.0
$^1$H NMR (300 MHz, DMSO) δ 7.50-7.66 (m, 3H), 4.18-4.32 (m, 2H), 3.96-4.03 (m, 2H), 1.24-1.36 (m, 3H)

Step 5: 5-[4-chloro-3-(trifluoromethoxy)phenyl]-3-(5-methyloxazol-2-yl)-4H,7H-pyrazolo[1,5-a]pyrimidin-7-one

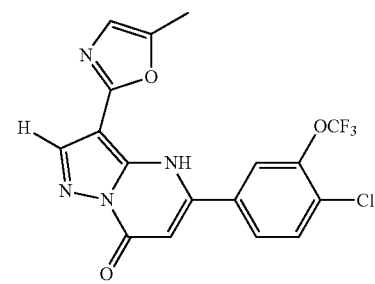 [SMILES: Cc1cnc(-c2cnn3c(=O)cc(-c4ccc(Cl)c(OC(F)(F)F)c4)[nH]c23)o1]

To a solution of ethyl 3-[4-chloro-3-(trifluoromethoxy) phenyl]-3-oxopropanoate (280 mg, 0.90 mmol) in n-BuOH (1 mL) was added 4-(5-methyloxazol-2-yl)-1H-pyrazol-5-amine (100 mg, 0.60 mmol) and TsOH (20 mg, 0.12 mmol), and the reaction mixture was stirred for 3 h at 120° C. The reaction mixture was cooled to room temperature and the solids were collected by filtration. Then the solids were washed with MeOH (3×1 mL) and dried in an oven under reduced pressure to afford 5-[4-chloro-3-(trifluoromethoxy) phenyl]-3-(5-methyl-1,3-oxazol-2-yl)-4H,7H-pyrazolo[1,5-a]pyrimidin-7-one as a light yellow solid (120 mg, 49%).

LC/MS (ES, m/z): [M+H]+ 411.0

¹H NMR (300 MHz, DMSO) δ8.32 (m, 2H), 8.10 (d, J=8.10 Hz, 1H), 7.66 (d, J=8.70 Hz, 1H), 6.84 (s, 1H), 6.36 (s, 1H), 2.44 (s, 3H)

EXAMPLE 39

5-(4-chloro-3-methoxyphenyl)-3-(thiazol-2-yl)-4H,7H-pyrazolo[1,5-a]pyrimidin-7-one

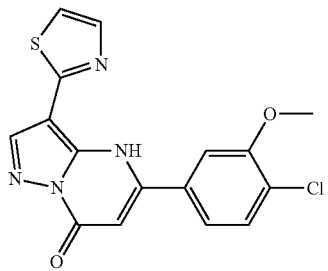 [SMILES: COc1cc(-c2cc(=O)n3ncc(-c4nccs4)c3[nH]2)ccc1Cl]

To a solution of 4-(thiazol-2-yl)-1H-pyrazol-5-amine (100 mg, 0.60 mmol) in n-BuOH (0.5 mL) was added p-TsOH (8.6 mg, 0.05 mmol) and ethyl 3-(4-chloro-3-methoxyphenyl)-3-oxopropanoate (230 mg, 0.90 mmol), and the reaction mixture was stirred for 1 h at 130° C. in an oil bath. The solids were collected by filtration and washed with MeOH (1 mL×3) to afford 5-(4-chloro-3-methoxyphenyl)-3-(thiazol-2-yl)-4H,7H-pyrazolo[1,5-a]pyrimidin-7-one as a light yellow solid (73.4 mg, 35%).

LC/MS (ES, m/z): [M+H]+ 359.0

¹H NMR (300 MHz, CD₃OD) δ 8.50 (s, 1H), 8.11 (m, 1H), 7.75 (m, 2H), 7.46 (m, 2H), 6.45 (s, 1H), 4.10 (s, 3H)

EXAMPLE 40

3-(benzo[d]thiazol-2-yl)-5-(1-ethyl-1H-indazol-5-yl)pyrazolo[1,5-a]pyrimidin-7(4H)-one

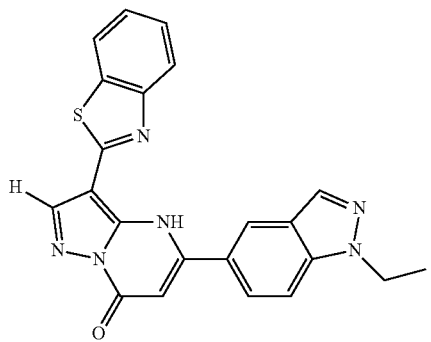

Step 1: 2-(benzo[d]thiazol-2-yl)acetonitrile

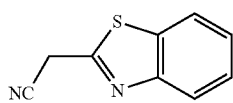 [SMILES: N#CCc1nc2ccccc2s1]

To a solution of 2-aminobenzenethiol (10 g, 80 mmol) in ethanol (200 mL) was added propanedinitrile (16.65 g, 200 mmol), AcOH (200 mL) and the reaction was stirred overnight at RT. The resulting mixture was concentrated in vacuo and then diluted with H₂O (300 mL), and extracted with ethyl acetate (3×50 mL) and the organic layers were combined. The residue was purified by silica gel column chromatography with dichloromethane/methanol (80:1) to afford 2-(benzo[d]thiazol-2-yl)acetonitrile as a yellow solid (5 g, 36%).

LC/MS (ES, m/z): [M+H]+ 159.0

¹H NMR (300 MHz, CDCl₃) δ 8.05 (d, J=8.21 Hz, 1H), 7.90 (d, J=8.21 Hz, 1H), 7.56-7.43 (m, 2H), 4.25 (s, 2H)

Step 2: (E)-2-(benzo[d]thiazol-2-yl)-3-(dimethylamino)acrylonitrile

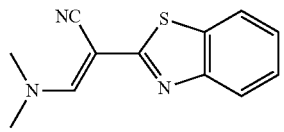 [SMILES: CN(C)/C=C(\C#N)c1nc2ccccc2s1]

To a solution 2-(benzo[d]thiazol-2-yl)acetonitrile (5 g, 28.7 mmol) in toluene (30 mL) was added DMFDMA (5.2 g, 43.1 mmol), and the reaction mixture was stirred for 2 h at 85° C. The resulting mixture was concentrated in vacuo to afford (E)-2-(benzo[d]thiazol-2-yl)-3-(dimethylamino)acrylonitrile as dark red crude solid.

Step 3: 4-(benzo[d]thiazol-2-yl)-1H-pyrazol-5-amine

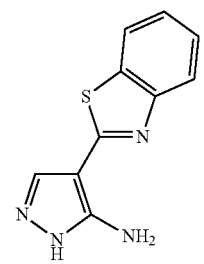

N₂H₄·H₂O (14.0 g) was added to a solution of (E)-2-(benzo[d]thiazol-2-yl)-3-(dimethylamino)acrylonitrile (10 g, 43.6 mmol) in AcOH (50 mL). The reaction was stirred for 2 h at 90° C. Then it was concentrated in vacuo, diluted with H₂O (200 mL), and extracted with ethyl acetate (3×50 mL). The organic layers were combined and the residue was purified by silica gel column chromatography with dichloromethane/methanol (80:1) to afford 4-(benzo[d]thiazol-2-yl)-1H-pyrazol-5-amine as a yellow solid (2.3 g, 16%).

LC/MS (ES, m/z): [M+H]+ 201.0

¹H NMR (300 MHz, DMSO) δ12.21 (s, 1H), 7.98 (d, J=8.21 Hz, 1H), 7.85 (d, J=8.21 Hz, 1H), 7.57-7.49 (m, 1H), 7.48-7.43 (m, 1H), 6.56-5.64 (m, 2H)

Step 4: 3-(benzo[d]thiazol-2-yl)-5-(1-ethyl-1H-indazol-5-yl)pyrazolo[1,5-a]pyrimidin-7(4H)-one

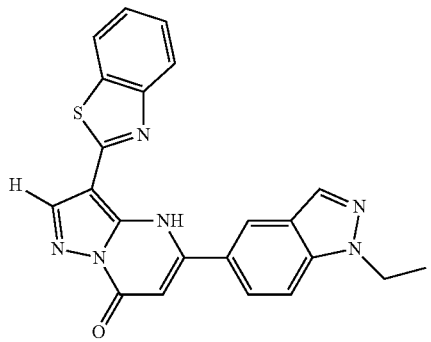

TsOH (10 mg, 0.15 mmol) was added to a solution of 4-(benzo[d]thiazol-2-yl)-1H-pyrazol-5-amine (100 mg, 0.40 mmol) in n-BuOH (1 mL) followed by the addition of ethyl 3-(1-ethyl-1H-indazol-5-yl)-3-oxopropanoate (180 mg, 0.60 mmol). The reaction was stirred for 2 h at 130° C. The solids were collected by filtration and washed with MeOH (1 mL×3) to afford 3-(benzo[d]thiazol-2-yl)-5-(1-ethyl-1H-indazol-5-yl)pyrazolo[1,5-a]pyrimidin-7(4H)-one as a light yellow solid (23.6 mg, 13%).

LC/MS (ES, m/z): [M+H]+ 413.2

$^1$H NMR (400 MHz, DMSO) δ 8.61 (s, 1H), 8.38-8.36 (m, 2H), 8.20 (s, 1H), 8.05 (d, J=8.00 Hz, 1H), 7.84 (d, J=8.00 Hz, 1H), 7.78 (d, J=8.80 Hz, 1H), 7.43 (t, J=7.20 Hz, 1H), 7.28 (t, J=7.20 Hz, 1H), 6.28 (s, 1H), 4.51-4.46 (q, J=7.20 Hz, 2H), 1.46-1.42 (t, J=7.20 Hz, 3H)

EXAMPLE 41

3-(benzo[d]thiazol-2-yl)-5-(4-chloro-3-methoxyphenyl)pyrazolo[1,5-a]pyrimidin-7(4H)-one

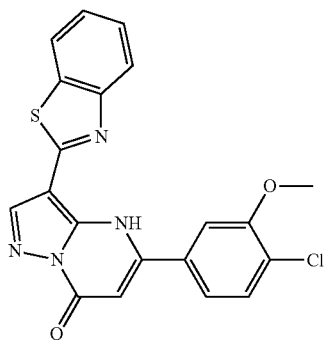 [SMILES: COc1cc(-c2cc(=O)n3ncc(-c4nc5ccccc5s4)c3[nH]2)ccc1Cl]

TsOH (10 mg, 0.15 mmol) was added to a solution of 4-(benzo[d]thiazol-2-yl)-1H-pyrazol-5-amine (100 mg, 0.40 mmol) in n-BuOH (1 mL) followed by the addition of ethyl 3-(4-chloro-3-methoxyphenyl)-3-oxopropanoate (180 mg, 0.60 mmol). The reaction was stirred for 2 h at 130° C., then the solids were collected by filtration and washed with MeOH (1 mL×3) to afford 3-(benzo[d]thiazol-2-yl)-5-(4-chloro-3-methoxyphenyl)pyrazolo[1,5-a]pyrimidin-7(4H)-one as a light yellow solid (28.6 mg, 15%).

LC/MS (ES, m/z): [M+H]+ 408.9

$^1$H NMR (300 MHz, DMSO) δ 8.35 (s, 1H), 8.04-8.01 (m, 2H), 7.85-7.82 (m, 2H), 7.55-7.52 (m, 1H), 7.44-7.39 (m, 1H), 7.29-7.24 (m, 1H), 6.29 (s, 1H), 4.05 (s, 3H)

EXAMPLE 42

5-(1-ethyl-1H-indazol-5-yl)-2-methyl-3-(4-methyloxazol-2-yl)-4H,7H-pyrazolo[1,5-a]pyrimidin-7-one

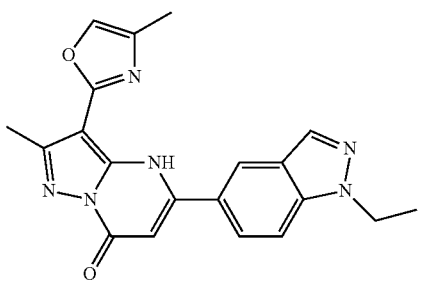

Step 1:
2-chloro-N-(1-hydroxypropan-2-yl)acetamide

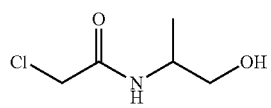

Under an inert atmosphere of nitrogen was added a solution of 2-aminopropan-1-ol (25 g, 333.5 mmol) and Et$_3$N (67 g, 666.7 mmol) in dichloromethane (800 mL). The resulting solution was cooled to −70° C., followed by the addition of a solution of 2-chloroacetyl chloride (41 g, 363.7 mmol) in dichloromethane (200 mL). Then the reaction was stirred for 16 hours at room temperature and quenched by water (200 mL). The organic layer was separated and the aqueous layer was extracted with dichloromethane (3×300 mL). The combined organic layers were dried over anhydrous sodium sulfate and concentrated in vacuo to afford a residue, which was purified by a silica gel column chromatography by eluting with 1%-2% methanol in dichloromethane to give 2-chloro-N-(1-hydroxypropan-2-yl)acetamide as a light yellow oil (15.0 g, 50%).

LC/MS (ES, m/z): [M+H]+ 152.1

$^1$H NMR (400 MHz, CDCl$_3$) δ 6.75 (bs, 1H), 4.16-4.04 (m, 3H), 3.74-3.71 (m, 1H), 3.62-3.59 (m, 1H), 1.28-1.22 (m, 3H)

Step 2: 2-chloro-N-(1-oxopropan-2-yl)acetamide

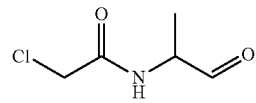

A solution of DMSO (29.5 g, 397.3 mmol) in dry dichloromethane (500 mL) was treated with oxalyl chloride (35.8 g, 298 mmol) at −70° C. for 1 hour under nitrogen atmosphere, followed by the addition of 2-chloro-N-(1-hydroxy-propan-2-yl)acetamide (15 g, 99.3 mmol). After an additional 2 hours at −30° C., triethylamine (57.4 g, 596 mmol) was added at −70° C. and the resulting mixture stirred for another 3 hours at −30° C. The reaction was then quenched by the addition of water (500 mL) and extracted with dichloromethane (3×500 mL). The combined organic layer was washed with brine (2×200 mL), dried over anhydrous sodium sulfate and concentrated in vacuo to give a residue, which was purified by silica gel column chromatography by eluting with 1% methanol in dichloromethane to afford 2-chloro-N-(1-oxopropan-2-yl) acetamide as light yellow oil (6.5 g, 41%).

LC/MS (ES, m/z): [M+H]+ 150.1

$^1$H NMR (300 MHz, CDCl$_3$) δ 9.56 (s, 1H), 7.22 (bs, 1H), 4.60-4.50 (m, 1H), 4.06 (s, 2H), 1.45-1.43 (m, 3H)

Step 3: 2-(chloromethyl)-4-methyloxazole

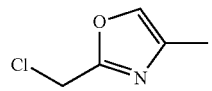

A solution of 2-chloro-N-(1-oxopropan-2-yl)acetamide (6.5 g, 43.6 mmol) in POCl$_3$ (20 mL) was kept for 4 hours at 90° C., then the reaction was quenched by water/ice (500 mL) cautiously and the pH value was adjusted to pH 7 with sodium bicarbonate. The resulting solution was extracted with dichloromethane (3×100 mL) and the combined organic layers were washed with brine (50 mL), dried over anhydrous sodium sulfate and concentrated in vacuo at low temperature to afford 2-(chloromethyl)-4-methyloxazole as a crude light yellow oil (5 g), which was used in the next step without further purification.

Step 4: 2-(4-methyloxazol-2-yl)acetonitrile

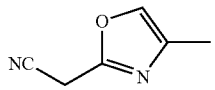

To a solution of the above crude 2-(chloromethyl)-4-methyloxazole (5.0 g) in CH$_3$CN (100 mL) and water (3 mL) was added KCN (3.0 g, 46 mmol). The resulting mixture was stirred 10 hours at 50° C. then diluted with water (300 mL) and extracted with ethyl acetate (3×100 mL). The combined organic layers were washed with brine (2×50 mL), dried over anhydrous sodium sulfate and concentrated in vacuo to give a residue, which was purified by silica gel column chromatography and eluted with 0.5%-1% methanol in dichloromethane to afford 2-(4-methyloxazol-2-yl)acetonitrile as a light yellow oil (1.0 g, 20%).

LC/MS (ES, m/z): [M+H]+ 123.1

$^1$H NMR (300 MHz, CDCl$_3$) δ 7.40 (s, 1H), 3.90 (s, 2H), 2.18 (s, 3H)

Step 5: 3-(dimethylamino)-2-(4-methyloxazol-2-yl)but-2-enenitrile

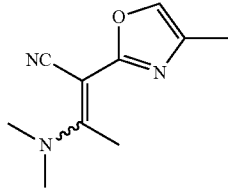

A solution of 2-(4-methyloxazol-2-yl)acetonitrile (1.0 g, 8.2 mmol) in toluene (2 mL) was treated with N,N-dimethylacetamide dimethyl acetal (1.46 g, 12 mmol) for 2 hours at 85° C., then the resulting mixture was concentrated in vacuo to afford crude 3-(dimethylamino)-2-(4-methyloxazol-2-yl)but-2-enenitrile as a dark red oil (1 g), which was used in the next step without further purification.

Step 6: 3-methyl-4-(4-methyloxazol-2-yl)-1H-pyrazol-5-amine

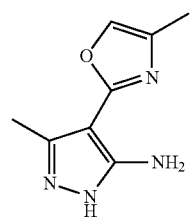

To a solution of the above crude 3-(dimethylamino)-2-(4-methyloxazol-2-yl)but-2-enenitrile (1.0 g, 5.6 mmol) in AcOH (2 mL) was added N$_2$H$_4$.H$_2$O (2.34 g, 46.8 mmol). The resulting solution was kept for 4 hours at 90° C., then solvent was removed in vacuo to afford a residue, which was dissolved in methanol (10 mL) and neutralized with NH$_4$OH (27% aqueous solution). After concentration, the crude product was purified by silica gel column chromatography, eluted with 2%-10% methanol in dichloromethane to afford 3-methyl-4-(4-methyloxazol-2-yl)-1H-pyrazol-5-amine as a yellow solid (200 mg, 12%).

LC/MS (ES, m/z): [M+H]+ 179.0

$^1$H NMR (300 MHz, DMSO) δ 11.69 (bs, 1H), 7.65 (s, 1H), 5.63 (bs, 2H), 2.32 (s, 3H), 2.10 (s, 3H)

Step 7: 5-(1-ethyl-1H-indazol-5-yl)-2-methyl-3-(4-methyloxazol-2-yl)-4H,7H-pyrazolo[1,5-a]pyrimidin-7-one

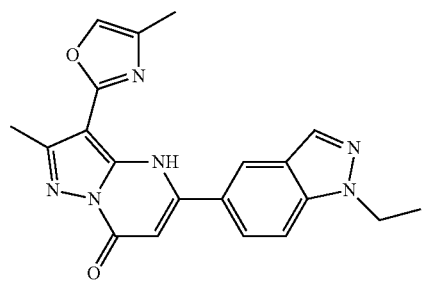

To a solution of 3-methyl-4-(4-methyloxazol-2-yl)-1H-pyrazol-5-amine (100 mg, 0.56 mmol) in n-BuOH (0.4 mL) was added ethyl 3-(1-ethyl-1H-indazol-5-yl)-3-oxopropanoate (197 mg, 0.76 mmol) and p-TsOH (4 mg, 0.03 mmol). After heating to reflux for 2 hours, the resulting mixture was diluted with ether (10 mL) and filtered. The filter cake was washed with ether (3×10 mL) and water (3×10 mL). The solids were collected to afford the crude product, which was purified by Prep-HPLC with the following conditions: Column, Sun fire prep. C18; mobile phase, water with 0.05% trifluoroacetic acid and acetonitrile from 30% up to 60% in 10 mins to afford 5-(1-ethyl-1H-indazol-5-yl)-2-methyl-3-(4-methyloxazol-2-yl)-4H,7H-pyrazolo[1,5-a]pyrimidin-7-one as a light yellow solid (17.2 mg, 8%).

LC/MS (ES, m/z): [M+H]+ 376.0

$^1$H NMR (300 MHz, DMSO+NH$_3$ (saturated D$_2$O solution, 1 drop)) δ 8.28 (d, J=6.0 Hz, 2H), 7.90 (m, 3H), 6.25 (s, 1H), 4.45-4.53 (q, J=7.2 Hz, 2H), 2.56 (s, 3H), 2.20 (s, 3H), 1.44-1.39 (t, J=7.2 Hz, 3H)

EXAMPLE 43

5-(1-ethyl-1H-indazol-5-yl)-3-(3-methyl-1,2,4-oxadiazol-5-yl)-4H,7H-pyrazolo[1,5-a]pyrimidin-7-one

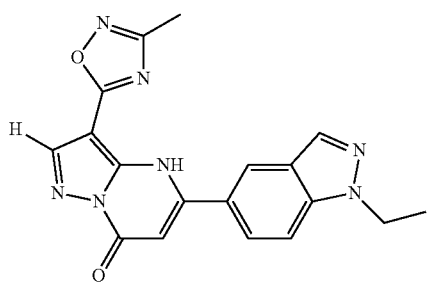 [SMILES: CCn1ncc2cc(-c3cc(=O)n4ncc(-c5nc(C)no5)c4[nH]3)ccc21]

Step 1: 5-(1-ethyl-1H-indazol-5-yl)-7-oxo-4,7-dihydropyrazolo[1,5-a]pyrimidine-3-carbonitrile

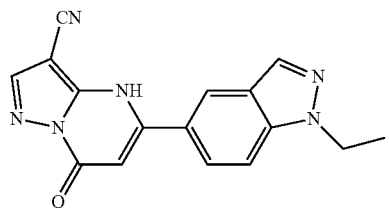 [SMILES: CCn1ncc2cc(-c3cc(=O)n4ncc(C#N)c4[nH]3)ccc21]

To a solution of 5-amino-1H-pyrazole-4-carbonitrile (500 mg, 4.6 mmol) in n-BuOH (1 mL) was added ethyl 3-(1-ethyl-1H-indazol-5-yl)-3-oxopropanoate (1.8 g, 6.9 mmol) and p-TsOH (45 mg, 0.3 mmol) at room temperature. After 4 hours at reflux, the solids were collected by filtration and washed with methanol (3×5 mL) to afford 5-(1-ethyl-1H-indazol-5-yl)-7-oxo-4,7-dihydropyrazolo[1,5-a]pyrimidine-3-carbonitrile as a yellow solid (750 mg, 53%).

LC/MS (ES, m/z): [M+H]$^+$ 305.1

$^1$H NMR (400 MHz, DMSO+NH$_3$ (saturated D$_2$O solution)) δ 13.52 (s, 1H), 8.44 (s, 1H), 8.34 (s, 1H), 8.28 (s, 1H), 7.89-7.83 (m, 2H), 6.31 (s, 1H), 4.55-4.41 (m, 2H), 1.49-1.41 (t, J=7.2 Hz, 3H)

Step 2: 5-(1-ethyl-1H-indazol-5-yl)-7-oxo-4,7-dihydropyrazolo[1,5-a]pyrimidine-3-carboxamide

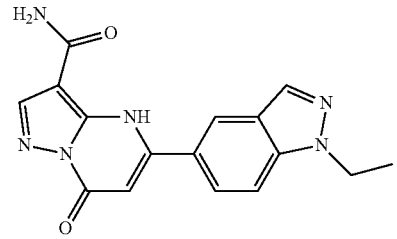 [SMILES: CCn1ncc2cc(-c3cc(=O)n4ncc(C(N)=O)c4[nH]3)ccc21]

5-(1-ethyl-1H-indazol-5-yl)-7-oxo-4,7-dihydropyrazolo[1,5-a]pyrimidine-3-carbonitrile (750 mg, 2.9 mmol) was dissolved in concentrated sulfuric acid (5 mL, 98%) at room temperature. After 2 hours, the reaction was quenched cautiously by water/ice (30 mL). The solids were collected by filtration, washed with water (3×10 mL) and dried to afford 5-(1-ethyl-1H-indazol-5-yl)-7-oxo-4,7-dihydropyrazolo[1,5-a]pyrimidine-3-carboxamide as a yellow solid (500 mg, 63%).

LC/MS (ES, m/z): [M+H]$^+$ 323.1

$^1$H NMR (400 MHz, DMSO+NH$_3$ (saturated D$_2$O solution)) δ 11.25 (bs, 1H), 8.51 (s, 1H), 8.28-8.27 (d, J=5.2 Hz, 1H), 7.97 (bs, 1H), 7.90-7.88 (d, J=8.8 Hz, 2H), 7.82-7.80 (d, J=8.8 Hz, 2H), 7.44 (bs, 1H), 6.32 (s, 1H), 4.54-4.49 (q, J=7.2 Hz, 2H), 1.44-1.38 (t, J=7.2 Hz, 3H)

Step 3: N-(1-(dimethylamino)ethylidene)-5-(1-ethyl-1H-indazol-5-yl)-7-oxo-4,7-dihydropyrazolo[1,5-a]pyrimidine-3-carboxamide

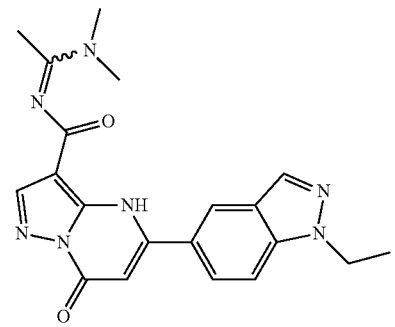 [SMILES: CCn1ncc2cc(-c3cc(=O)n4ncc(C(=O)N=C(C)N(C)C)c4[nH]3)ccc21]

To a solution of 5-(1-ethyl-1H-indazol-5-yl)-7-oxo-4,7-dihydropyrazolo[1,5-a]pyrimidine-3-carboxamide (200 mg, 0.6 mmol) in N, N-dimethylformamide (1 mL) was added N,N-dimethylacetamide dimethyl acetal (826 mg, 6.2 mmol) at room temperature. Then the reaction was heated to 130° C. for 4 hrs. The resulting mixture was diluted with ether (20 mL) and a filtration was performed. The filter cake was washed with ether (3×20 mL) to afford crude N-(1-(dimethylamino)ethylidene)-5-(1-ethyl-1H-indazol-5-yl)-7-oxo-4,7-dihydropyrazolo[1,5-a]pyrimidine-3-carboxamide as a yellow solid (300 mg), which was used in the next step without further purification.

Step 4: 5-(1-ethyl-1H-indazol-5-yl)-3-(3-methyl-1,2,
4-oxadiazol-5-yl)-4H,7H-pyrazolo[1,5-a]pyrimidin-
7-one

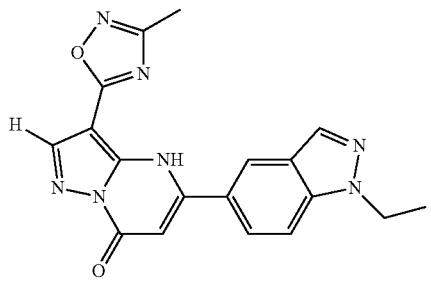 [SMILES: CCn1ncc2cc(-c3cc(=O)n4ncc(-c5nc(C)no5)c4[nH]3)ccc21]

To a solution of N-(1-(dimethylamino)ethylidene)-5-(1-ethyl-1H-indazol-5-yl)-7-oxo-4,7-dihydropyrazolo[1,5-a]pyrimidine-3-carboxamide (150 mg, 0.4 mmol) in 1,4-dioxane (2 mL) was added hydroxylamine hydrochloride (40 mg, 0.6 mmol) and sodium hydroxide (0.6 mL, 10% aq.) at room temperature. After 4 hours, acetic acid (1.2 mL) was added and the mixture was heated to 100° C. for 2 hours. The reaction mixture was cooled, diluted with H$_2$O (50 mL) and extracted with ethyl acetate (4×20 mL). The organic layer was combined, dried over anhydrous magnesium sulfate and concentrated under vacuum to give a residue, which was purified by Prep-HPLC with the following conditions: Column, Sun fire prep. C18; mobile phase, water with 0.05% trifluoroacetic acid and acetonitrile from 30% up to 60% in 10 mins to afford 5-(1-ethyl-1H-indazol-5-yl)-3-(3-methyl-1,2,4-oxadiazol-5-yl)-4H,7H-pyrazolo[1,5-a]pyrimidin-7-one as an off-white solid (28.1 mg, 20%).

LC/MS (ES, m/z): [M+H]$^+$ 362.0

$^1$H NMR (300 MHz, DMSO+NH$_3$ (saturated D$_2$O solution)) δ 8.50 (s, 1H), 8.19-8.17 (d, J=7.5 Hz, 3H), 7.74-7.71 (d, J=9.0 Hz, 1H), 6.24 (s, 1H), 4.51-4.43 (q, J=7.2 Hz, 2H), 2.40 (s, 3H), 1.45-1.41 (t, J=7.2 Hz, 3H)

EXAMPLE 44

5-(benzofuran-5-yl)-3-(thiazol-2-yl)pyrazolo[1,5-a]
pyrimidin-7(4H)-one

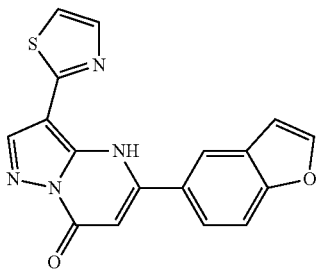 [SMILES: O=c1cc(-c2ccc3occc3c2)[nH]c2c(-c3nccs3)cnn12]

Step 1: ethyl 3-(benzofuran-5-yl)-3-oxopropanoate

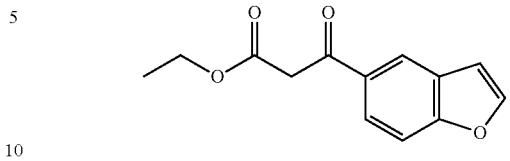

To a solution of benzofuran-5-carboxylic acid (5 g, 30.8 mmol) in tetrahydrofuran (50 mL) was added CDI (7.3 g, 45 mmol) at room temperature. The resulting solution was kept for 2 hours at 40° C., then added a solution of the magnesium salt of malonic acid monoethyl ester (prepared via the following procedure: to a solution of potassium monoethylonate (16.1 g, 93 mmol) in acetonitrile (100 mL) was added Et$_3$N (9.5 g, 93 mmol) and MgCl$_2$ (13.5 g, 130 mmol) at room temperature and stirred for 2 hours) at 0° C. The reaction mixture was stirred for additional 2 hours at 70° C. and quenched by the addition of water (300 mL). The pH value was adjusted to pH 4 with HCl (3N) and the mixture was extracted with ethyl acetate (3×150 mL). The combined organic layer was washed with brine (200 mL), dried over anhydrous magnesium sulfate, and concentrated under vacuum to give a residue, which was purified by a silica gel column chromatography, eluted with 10%-30% ethyl acetate in petroleum ether to afford ethyl 3-(benzofuran-5-yl)-3-oxopropanoate as a yellow solid (4 g, 56%).

LC/MS (ES, m/z): [M+H]$^+$ 233.0

Step 2: 5-(benzofuran-5-yl)-3-(thiazol-2-yl)pyrazolo
[1,5-a]pyrimidin-7(4H)-one

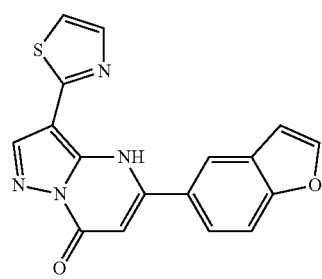 [SMILES: O=c1cc(-c2ccc3occc3c2)[nH]c2c(-c3nccs3)cnn12]

To a solution of 4-(thiazol-2-yl)-1H-pyrazol-5-amine (100 mg, 0.6 mmol) in n-BuOH (0.5 mL) was added ethyl 3-(1-benzofuran-5-yl)-3-oxopropanoate (209.6 mg, 0.9 mmol) and p-TsOH (5.16 mg, 0.03 mmol) at room temperature. After refluxing 2 hours, the solids were collected by filtration and washed with methanol (3×5 mL) to afford 5-(benzofuran-5-yl)-3-(thiazol-2-yl)pyrazolo[1,5-a]pyrimidin-7(4H)-one as a light yellow solid (69.7 mg, 35%).

LC/MS (ES, m/z): [M+H]$^+$ 335.0

$^1$H NMR (300 MHz, DMSO+NH$_3$ (saturated D$_2$O solution, 1 drop)): δ 8.49 (s, 1H), 8.24-8.20 (m, 1H), 8.16-8.15 (d, J=3.3 Hz, 1H), 7.97-7.96 (d, J=3.6 Hz, 1H), 7.88-7.81 (m, 2H), 7.71-7.70 (m, 1H), 7.15-7.14 (m, 1H), 6.33 (s, 1H)

EXAMPLE 45

3-(benzo[d]oxazol-2-yl)-5-(4-chloro-3-methoxyphenyl)pyrazolo[1,5-a]pyrimidin-7(4H)-one

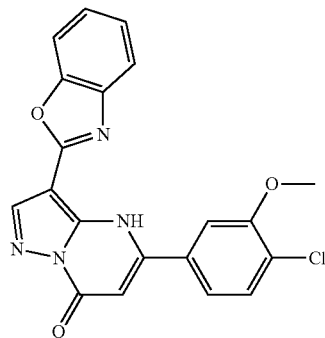 [SMILES: COc1cc(-c2cc(=O)n3ncc(-c4nc5ccccc5o4)c3[nH]2)ccc1Cl]

To a solution of 4-(benzo[d]oxazol-2-yl)-1H-pyrazol-5-amine (100 mg, 0.5 mmol) in diphenyl ether (1 mL) was added ethyl 3-(4-chloro-3-methoxyphenyl)-3-oxopropanoate (192 mg, 0.7 mmol) and p-TsOH (4.3 mg, 0.02 mmol) at room temperature. After 2 hours at 170° C., the resulting mixture was diluted with ether (20 mL) and a filtration was performed, the filter cake was washed with ether (3×20 mL). The solids were collected to give the crude product, which was purified by Prep-HPLC under the following conditions: [(Agilent 1200 prep HPLC): Column, Sun Fire Prep C18*50 mm 5um; mobile phase, water with 0.05% trifluoroacetic acid and acetonitrile from 30% up to 60% in 10 min to afford 3-(benzo[d]oxazol-2-yl)-5-(4-chloro-3-methoxyphenyl)pyrazolo[1,5-a]pyrimidin-7(4H)-one as a light yellow solid (63.7 mg, 32%).

LC/MS (ES, m/z): [M+H]+ 393.0

$^1$H NMR (300 MHz, DMSO+NH$_3$ (saturated D$_2$O solution)) δ 8.31 (s, 1H), 7.95 (d, J=1.50 Hz, 1H), 7.76-7.73 (m, 1H), 7.65-7.61 (m, 2H), 7.52-7.49 (d, J=8.10 Hz, 1H), 7.32-7.25 (m, 2H), 6.25 (s, 1H), 3.98 (s, 3H)

EXAMPLE 46

5-(4-chloro-3-ethoxyphenyl)-3-(5-methyloxazol-2-yl)pyrazolo[1,5-a]pyrimidin-7(4H)-one

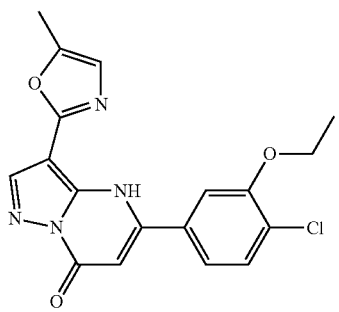 [SMILES: CCOc1cc(-c2cc(=O)n3ncc(-c4ncc(C)o4)c3[nH]2)ccc1Cl]

Step 1: Ethyl 4-chloro-3-ethoxybenzoate

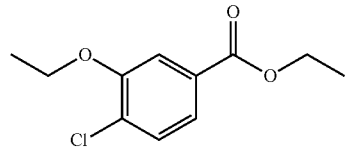

To a solution of 4-chloro-3-hydroxybenzoic acid (10 g, 57.9 mmol) in DMF (200 mL) was added iodoethane (20 g, 128.2 mmol) and potassium carbonate (16 g, 115.8 mmol) at room temperature. After 3 hours, the volume was reduced in vacuo to afford a residue, which was dissolved in ethyl acetate (100 mL), washed with brine (4×100 mL) and dried over anhydrous sodium sulfate. After filtration, the filtrate was concentrated in vacuo to afford crude ethyl 4-chloro-3-ethoxybenzoate as a white solid (12 g), which was carried on crude to the next step.

Step 2: 4-chloro-3-ethoxybenzoic acid

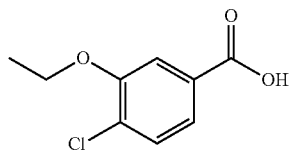

A solution of the above crude ethyl 4-chloro-3-ethoxybenzoate (12 g) in methanol (200 mL) was treated with sodium hydroxide (8.4 g, 210 mmol) in water (10 mL) and stirred overnight at room temperature. The solvent was removed in vacuo to afford a residue, which was dissolved in water (200 mL). The pH was adjusted to pH 4 with aq. HCl (3N). The solids were collected by filtration, washed with water (3×50 mL) and dried to afford 4-chloro-3-ethoxybenzoic acid as a white solid (9 g, 81%, two steps).

LC/MS (ES, m/z): [M+H]+ 201.0

$^1$H NMR (300 MHz, DMSO) δ 7.65-7.61 (m, 2H), 7.47-7.44 (d, J=8.1 Hz, 1H), 4.22-4.18 (q, J=6.9 Hz, 2H), 1.53-1.48 (t, J=6.9 Hz, 3H)

Step 3: Ethyl 3-(4-chloro-3-ethoxyphenyl)-3-oxopropanoate

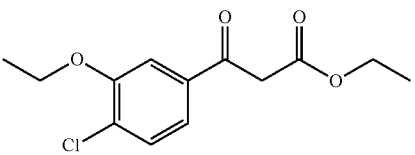 [SMILES: CCOC(=O)CC(=O)c1ccc(Cl)c(OCC)c1]

A solution of 4-chloro-3-ethoxybenzoic acid (9 g, 45 mmol) in tetrahydrofuran (100 mL) was treated with CDI (18.5 g, 114.1 mmol) for 2 hours at 40° C. Then a solution of the magnesium salt of malonic acid monoethyl ester (prepared via the following procedure: to a solution of potassium monoethylonate (29 g, 170.4 mmol) in acetonitrile (200 mL) was added Et$_3$N (17.3 g, 170.9 mmol) and MgCl$_2$ (24 g, 270 mmol) at room temperature and kept for 2 hours) was added at 0° C. The reaction mixture was heated for 2 hours at 70° C., then quenched by the addition of water (300 mL). The pH value was adjusted to pH 4 with aq. HCl (3N) and the mixture was extracted with ethyl acetate (3×150 mL). The combined organic layers were washed with brine (200 mL), dried over anhydrous magnesium sulfate, and concentrated in vacuo to provide a residue, which was purified by a silica gel column chromatography eluting with 1%-5% ethyl acetate in petroleum ether to afford ethyl 3-(4-chloro-3-ethoxyphenyl)-3-oxopropanoate as a light yellow oil (9 g, 60%).

LC/MS (ES, m/z): [M+H]$^+$ 271.0

$^1$H NMR (300 MHz, DMSO) δ 7.71-7.46 (m, 3H), 4.28-4.09 (m, 6H), 1.41-1.34 (t, J=7.8 Hz, 3H), 1.30-1.16 (t, J=6.9 Hz, 3H)

Step 4: 5-(4-chloro-3-ethoxyphenyl)-3-(5-methyloxazol-2-yl)pyrazolo[1,5-a]pyrimidin-7(4H)-one

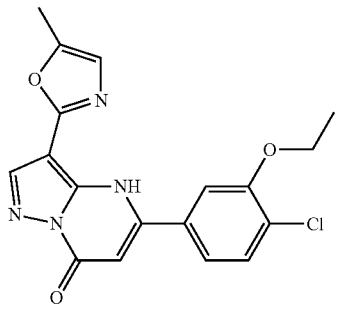 [SMILES: CCOc1cc(-c2cc(=O)n3ncc(-c4ncc(C)o4)c3[nH]2)ccc1Cl]

To a solution of 4-(5-methyloxazol-2-yl)-1H-pyrazol-5-amine (100 mg, 0.6 mmol) in n-BuOH (1 mL) was added ethyl 3-(4-chloro-3-ethoxyphenyl)-3-oxopropanoate (245 mg, 0.9 mmol) and p-TsOH (5 mg, 0.03 mmol) at room temperature. After refluxing 2 hours, the solids were collected by filtration and washed with methanol (3×5 mL) to afford 5-(4-chloro-3-ethoxyphenyl)-3-(5-methyloxazol-2-yl)pyrazolo[1,5-a]pyrimidin-7(4H)-one as a light yellow solid (43.8 mg, 19%).

LC/MS (ES, m/z): [M+H]$^+$ 371.0

$^1$H NMR (300 MHz, DMSO+NH$_3$ (saturated D$_2$O solution)) δ 8.04 (s, 1H), 7.94-7.93 (d, J=1.5 Hz, 1H), 7.66-7.63 (dd, J=1.5 Hz, 8.1 Hz, 1H), 7.47-7.44 (d, J=8.1 Hz, 1H), 6.77 (s, 1H), 6.11 (s, 1H), 4.29-4.22 (q, J=6.9 Hz, 2H), 2.35 (s, 3H), 1.44-1.40 (t, J=6.9 Hz, 3H)

EXAMPLE 47

5-(4-chlorophenyl)-3-(5-methyloxazol-2-yl)pyrazolo[1,5-a]pyrimidin-7(4H)-one

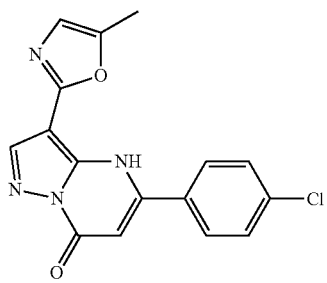 [SMILES: Cc1cnc(-c2cnn3c(=O)cc(-c4ccc(Cl)cc4)[nH]c23)o1]

To a solution of 4-(5-methyloxazol-2-yl)-1H-pyrazol-5-amine (100 mg, 0.6 mmol) in n-BuOH (1 mL) was added ethyl 3-(4-chlorophenyl)-3-oxopropanoate (210 mg, 0.9 mmol) and p-TsOH (10 mg, 0.1 mmol) at room temperature. After refluxing 2 hours, the solids were collected by filtration and washed with methanol (3×5 mL) to afford 5-(4-chlorophenyl)-3-(5-methyloxazol-2-yl)pyrazolo[1,5-a]pyrimidin-7(4H)-one as a light yellow solid (32.3 mg, 33%).

LC/MS (ES, m/z): [M+H]$^+$ 327.0

$^1$H NMR (300 MHz, DMSO+NH$_3$ (saturated D$_2$O solution)) δ 8.13-8.06 (m, 3H), 7.48-7.51 (d, J=8.4 Hz, 2H), 6.80 (s, 1H), 6.01 (s, 1H), 2.28 (s, 3H)

EXAMPLE 48

5-(4-chlorophenyl)-3-(oxazol-2-yl)pyrazolo[1,5-a]pyrimidin-7(4H)-one

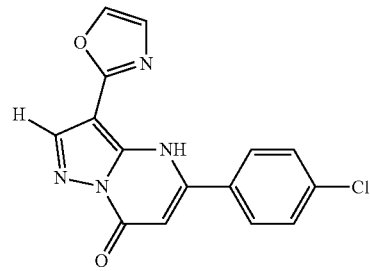 [SMILES: O=c1cc(-c2ccc(Cl)cc2)[nH]c2c(-c3ncco3)cnn12]

Step 1: 5-(4-chlorophenyl)-7-oxo-4,7-dihydropyrazolo[1,5-a]pyrimidine-3-carbonitrile

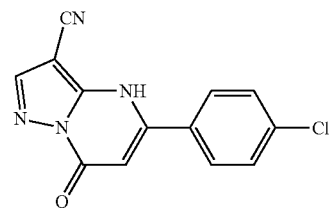 [SMILES: N#Cc1cnn2c(=O)cc(-c3ccc(Cl)cc3)[nH]c12]

To a solution of 5-amino-1H-pyrazole-4-carbonitrile (500 mg, 4.6 mmol) in n-BuOH (1 mL) was added ethyl 3-(4-chlorophenyl)-3-oxopropanoate (1.6 g, 6.9 mmol) and p-TsOH (21 mg, 0.12 mmol) at room temperature. After refluxing 2 hours, the solids were collected by filtration and washed with methanol (3×5 mL) to afford 5-(4-chlorophenyl)-7-oxo-4,7-dihydropyrazolo[1,5-a]pyrimidine-3-carbonitrile as a light yellow solid (600 mg, 48%).

LC/MS (ES, m/z): [M+H]$^+$ 271.0

$^1$H NMR (300 MHz, DMSO+NH$_3$ (saturated D$_2$O solution)) δ 8.43 (s, 1H), 7.86-7.89 (d, J=8.4 Hz, 2H), 7.64-7.67 (d, J=8.7 Hz, 2H), 6.30 (s, 1H)

Step 2: 5-(4-chlorophenyl)-7-oxo-4,7-dihydropyrazolo[1,5-a]pyrimidine-3-carboxamide

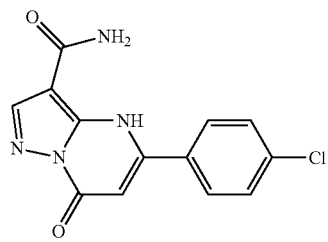 [SMILES: NC(=O)c1cnn2c(=O)cc(-c3ccc(Cl)cc3)[nH]c12]

5-(4-chlorophenyl)-7-oxo-4,7-dihydropyrazolo[1,5-a]pyrimidine-3-carbonitrile (600 mg, 2.2 mmol) was dissolved into concentrated sulfuric acid (5 mL, 98%) at room temperature. After 1 hr, the reaction was quenched cautiously by the addition of water/ice (50 mL). The solids were collected by filtration, washed with water (3×10 mL) and dried to afford 5-(4-chlorophenyl)-7-oxo-4,7-dihydropyrazolo[1,5-a]pyrimidine-3-carboxamide as a light yellow solid (500 mg, 78%).

LC/MS (ES, m/z): [M+H]+ 289.0

1H NMR (300 MHz, DMSO+NH3 (saturated D2O solution)) δ 11.35 (bs, 1H), 8.38 (s, 1H), 7.94 (bs, 1H), 7.94-7.82 (d, J=8.4 Hz, 2H), 7.64-7.67 (d, J=8.4 Hz, 2H), 7.42 (bs, 1H), 6.28 (s, 1H)

Step 3: 5-(4-chlorophenyl)-3-(oxazol-2-yl)pyrazolo[1,5-a]pyrimidin-7(4H)-one

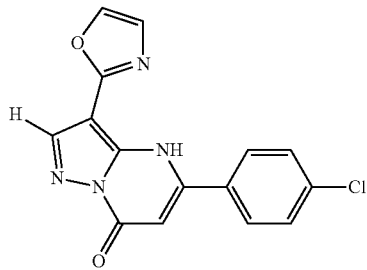 [SMILES: O=c1cc(-c2ccc(Cl)cc2)[nH]c2c(-c3ncco3)cnn12]

To a solution of 5-(4-chlorophenyl)-7-oxo-4,7-dihydropyrazolo[1,5-a]pyrimidine-3-carboxamide (100 mg, 0.3 mmol) in NMP (1 mL) was added p-TsOH (5.1 mg, 0.03 mmol) and 2-bromo-1,1-diethoxyethane (103 mg, 0.5 mmol) at room temperature. After stirring 20 mins at 110° C., the resulting mixture was diluted with ether (20 mL) and filtered; the filter cake was washed with ether (3×20 mL) and water (3×10 mL). The solids were collected to give the crude product, which was purified by Prep-HPLC under the following conditions: [(Agilent 1200 prep HPLC): Column, Sun Fire Prep C18*50 mm 5um; mobile phase, water with 0.05% trifluoroacetic acid and acetonitrile from 30% up to 60% in 10 min to afford 5-(4-chlorophenyl)-3-(oxazol-2-yl)pyrazolo[1,5-a]pyrimidin-7(4H)-one as a light yellow solid (29.0 mg, 27%).

LC/MS (ES, m/z): [M+H]+ 313.1

1H NMR (300 MHz, DMSO+NH3 (saturated D2O solution)) δ 8.12-8.10 (m, 3H), 8.00 (s, 1H), 7.51-7.48 (d, J=8.4 Hz, 2H), 7.19 (s, 1H), 6.09 (s, 1H)

EXAMPLE 49

5-(1-ethyl-1H-benzo[d][1,2,3]triazol-5-yl)-3-(oxazol-2-yl)pyrazolo[1,5-a]pyrimidin-7(4H)-one

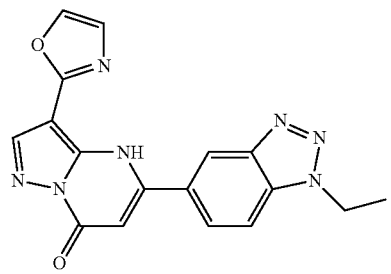 [SMILES: CCn1nnc2cc(-c3cc(=O)n4ncc(-c5ncco5)c4[nH]3)ccc21]

Step 1: 4-(ethylamino)-3-nitrobenzoic acid

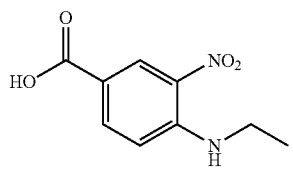

To a solution of 4-fluoro-3-nitrobenzoic acid (6 g, 27 mmol) in EtNH2 (20 mL, 70% in water) was added sodium bicarbonate (4.5 g, 53.6 mmol). The resulting solution was stirred 2 hours at 50° C. then quenched by the addition of water (200 mL) and the pH value was adjusted to pH 4 with aq. HCl (3N). The solids were collected by filtration, washed with water (20 mL) and dried to afford 4-(ethylamino)-3-nitrobenzoic acid as a light yellow solid (5.3 g, 77%).

LC/MS (ES, m/z): [M+H]+ 211.0

1H NMR (300 MHz, DMSO) δ 8.61-8.60 (d, J=2.1 Hz, 1H), 8.50-8.46 (t, J=5.4 Hz, 1H), 7.99-7.95 (dd, J=1.8 Hz, 9.0 Hz, 1H), 7.14-7.10 (d, J=9.3 Hz, 1H), 3.50-3.43 (q, J=7.2 Hz, 2H), 1.26-1.21 (t, J=7.2 Hz, 3H)

Step 2: 3-amino-4-(ethylamino)benzoic acid

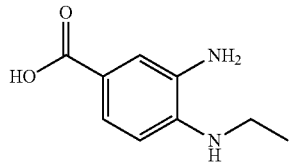

To a solution of 4-(ethylamino)-3-nitrobenzoic acid (5.3 g, 25 mmol) in methanol (200 mL) was added Pd/C (50 mg, 10% w/w) then H2 (g) was introduced and the reaction was stirred for 10 hours at room temperature. The solids were filtered off and the filtrate was concentrated in vacuo to afford 3-amino-4-(ethylamino)benzoic acid as a light yellow solid (4.3 g, 95%).

LC/MS (ES, m/z): [M+H]+ 181.0

¹H NMR (300 MHz, DMSO) δ 7.22-7.17 (m, 2H), 6.43-6.40 (d, J=8.4 Hz, 1H), 5.12 (bs, 2H), 3.17-3.09 (q, J=6.6 Hz, 2H), 1.29-1.14 (t, J=6.6 Hz, 3H)

Step 3: 1-ethyl-1H-benzo[d][1,2,3]triazole-5-carboxylic acid

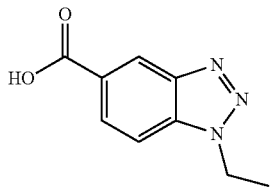

To a solution of 3-amino-4-(ethylamino)benzoic acid (4.3 g, 29.4 mmol) in AcOH (200 mL) was added a solution of NaNO₂ (8.1 g, 117.4 mmol) in water (2 mL) at 0-5° C. Then the mixture was warmed to room temperature, and after 3 hrs of stirring, the solution was concentrated in vacuo to a minimum volume then diluted with H₂O (200 mL). The solids were collected by filtration, washed with water (3×50 mL) and dried to afford 1-ethyl-1H-benzo[d][1,2,3]triazole-5-carboxylic acid as a dark red solid (2.5 g, 73%).

LC/MS (ES, m/z): [M+H]+ 192.0

¹H NMR (300 MHz, DMSO) δ 13.12 (s, 1H), 8.61 (s, 1H), 8.11-8.09 (d, J=8.7 Hz, 1H), 8.01-7.98 (d, J=8.7 Hz, 1H), 4.80-4.78 (q, J=7.2 Hz, 2H), 1.55-1.53 (t, J=7.2 Hz, 3H)

Step 4: ethyl 3-(1-ethyl-1H-benzo[d][1,2,3]triazol-5-yl)-3-oxopropanoate

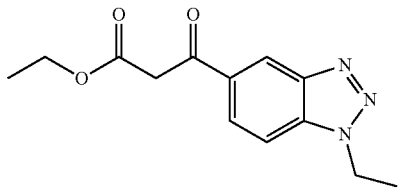 [SMILES: CCOC(=O)CC(=O)c1ccc2c(c1)nnn2CC]

To a solution of 1-ethyl-1H-benzo[d][1,2,3]triazole-5-carboxylic acid (2.5 g, 22.5 mmol) in tetrahydrofuran (50 mL) was added CDI (7.3 g, 45 mmol) at room temperature. After 2 hours of stirring at 40° C. a solution of the magnesium salt of malonic acid monoethyl ester was added at 0° C. (prepared via the following procedure: to a solution of potassium monoethylonate (10.2 g, 60 mmol) in acetonitrile (100 mL) was added Et₃N (6 g, 60 mmol) and MgCl₂ (8.55 g, 90 mmol) at room temperature and stirred for 2 hrs). The reaction mixture was stirred for 2 hours at 70° C. and quenched by the addition of water (300 mL). The pH value was adjusted to 4 with HCl (3N), and the mixture was extracted with ethyl acetate (3×150 mL). The combined organic layer was washed with brine (200 mL), dried over anhydrous magnesium sulfate, and concentrated in vacuo to afford a residue, which was purified by silica gel column chromatography, eluting with 10%-30% ethyl acetate in petroleum ether to afford ethyl 3-(1-ethyl-1H-benzo[d][1,2,3]triazol-5-yl)-3-oxopropanoate as a red solid (2.5 g, 73%).

LC/MS (ES, m/z): [M+H]+ 262.0

¹H NMR (300 MHz, DMSO) δ 8.80 (s, 1H), 8.11-8.02 (m, 2H), 4.83-4.76 (q, J=7.2 Hz, 2H), 4.35 (s, 2H), 4.18-4.07 (q, J=7.2 Hz, 2H), 1.56-1.52 (t, J=7.2 Hz, 3H), 1.22-1.17 (t, J=7.2 Hz, 3H)

Step 5: 5-(1-ethyl-1H-benzo[d][1,2,3]triazol-5-yl)-7-oxo-4,7-dihydropyrazolo[1,5-a]pyrimidine-3-carbonitrile

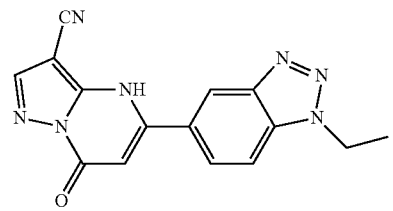 [SMILES: CCn1nnc2cc(-c3cc(=O)n4ncc(C#N)c4[nH]3)ccc21]

To a solution of 5-amino-1H-pyrazole-4-carbonitrile (500 mg, 4.6 mmol) in n-BuOH (1 mL) was added ethyl 3-(1-ethyl-1H-benzo[d][1,2,3]triazol-5-yl)-3-oxopropanoate (1.5 g, 5.7 mmol) and p-TsOH (34 mg, 0.2 mmol) at room temperature. After refluxing 2 hrs, the solids were collected by filtration and washed with methanol (3×5 mL) to afford 5-(1-ethyl-1H-benzo[d][1,2,3]triazol-5-yl)-7-oxo-4,7-dihydropyrazolo[1,5-a]pyrimidine-3-carbonitrile as a light yellow solid (900 mg, 63%).

LC/MS (ES, m/z): [M+H]+ 306.0

Step 6: 5-(1-ethyl-1H-benzo[d][1,2,3]triazol-5-yl)-7-oxo-4,7-dihydropyrazolo[1,5-a]pyrimidine-3-carboxamide

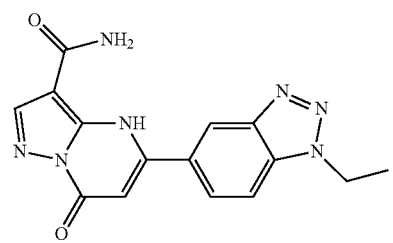 [SMILES: CCn1nnc2cc(-c3cc(=O)n4ncc(C(N)=O)c4[nH]3)ccc21]

5-(1-Ethyl-1H-benzo[d][1,2,3]triazol-5-yl)-7-oxo-4,7-dihydropyrazolo[1,5-a]pyrimidine-3-carbonitrile (900 mg, 2.95 mmol) was dissolved in concentrated sulfuric acid (5 mL, 98%) with stirring at room temperature. After 2 hours, the reaction was then quenched by cautiously adding water/ice (30 mL). The solids were collected by filtration, washed with water (3×10 mL) and dried to afford 5-(1-ethyl-1H-benzo[d][1,2,3]triazol-5-yl)-7-oxo-4,7-dihydropyrazolo[1,5-a]pyrimidine-3-carboxamide as a light yellow solid (600 mg, 63%).

LC/MS (ES, m/z): [M+H]+ 324.0

¹H NMR (300 MHz, DMSO) δ 8.62 (s, 1H), 8.46 (s, 1H), 8.13-8.10 (d, J=9.0 Hz, 1H), 8.02-7.99 (d, J=8.7 Hz, 1H), 6.42 (s, 1H), 4.79-4.85 (q, J=7.2 Hz, 2H), 1.52-1.57 (t, J=7.2 Hz, 3H)

Step 7: 5-(1-ethyl-1H-benzo[d][1,2,3]triazol-5-yl)-3-(oxazol-2-yl)pyrazolo[1,5-a]pyrimidin-7(4H)-one

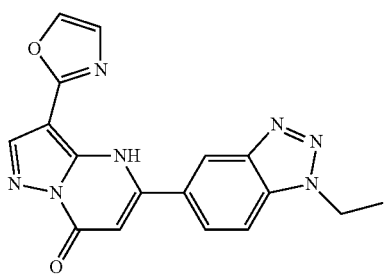 [SMILES: CCn1nnc2cc(-c3cc(=O)n4ncc(-c5ncco5)c4[nH]3)ccc21]

To a solution of 5-(1-ethyl-1H-benzo[d][1,2,3]triazol-5-yl)-7-oxo-4,7-dihydropyrazolo[1,5-a]pyrimidine-3-carboxamide (100 mg, 0.3 mmol) in NMP (1 mL) was added 2-bromo-1,1-diethoxyethane (91 mg, 0.5 mmol) and p-TsOH (5 mg, 0.03 mmol) at room temperature. After stirring for 20 min at 110° C., the resulting mixture was diluted with ether (20 mL) and filtered. The filter cake was washed with ether (3×20 mL) and water (3×10 mL). The solids were collected to give the crude product, which was purified by Prep-HPLC with the following conditions: [(Agilent 1200 prep HPLC): Column, Sun Fire Prep C18*50 mm 5 um; mobile phase, water with 0.05% trifluoroacetic acid and acetonitrile from 30% up to 60% in 10 mins to afford 5-(1-ethyl-1H-benzo[d][1,2,3]triazol-5-yl)-3-(oxazol-2-yl)pyrazolo[1,5-a]pyrimidin-7(4H)-one as a light yellow solid (23.7 mg, 22%).

LC/MS (ES, m/z): [M+H]$^+$ 348.0

$^1$H NMR (300 MHz, DMSO+NH$_3$ (saturated D$_2$O solution, 1d)) δ 8.71 (s, 1H), 8.38-8.35 (d, J=9.0 Hz, 1H), 8.13 (s, 1H), 8.04 (s, 1H), 7.95-7.92 (d, J=9.0 Hz, 1H), 7.21 (s, 1H), 6.24 (s, 1H), 4.79-4.75 (q, J=7.2 Hz, 2H), 1.61-1.57 (t, J=7.2 Hz, 3H)

EXAMPLE 50

3-(benzo[d]isoxazol-3-yl)-5-(4-chloro-3-methoxyphenyl)pyrazolo[1,5-a]pyrimidin-7(4H)-one

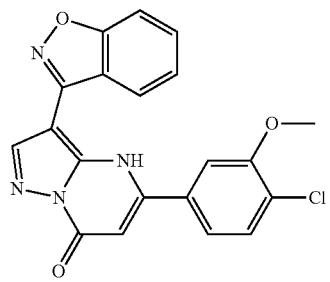 [SMILES: COc1cc(-c2cc(=O)n3ncc(-c4noc5ccccc45)c3[nH]2)ccc1Cl]

Step 1: 2-(1-iminoethyl)phenol

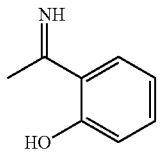

1-(2-Hydroxyphenyl)ethanone (15 g, 110 mmol) was treated with saturated NH$_3$ (g) in methanol (200 mL) for 12 hrs at room temperature. Then the solution was concentrated in vacuo to afford 2-(1-iminoethyl)phenol as a yellow green solid (14.7 g, 99%).

LC/MS (ES, m/z): [M+H]$^+$ 136.0

$^1$H NMR (300 MHz, DMSO) δ 15.1 (bs, 1H), 9.26 (bs, 1H), 7.53-7.50 (d, J=7.80 Hz, 1H), 7.38-7.33 (m, 1H), 7.00-6.98 (d, J=8.40 Hz, 1H), 6.85-6.80 (m, 1H), 2.52 (s, 3H)

Step 2: 3-methylbenzo[d]isoxazole

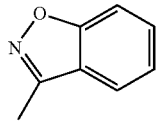

A mixture of 2-(1-iminoethyl)phenol (14.7 g, 108.7 mmol) and potassium carbonate (30 g, 217 mmol) in tetrahydrofuran (150 mL) was treated with N-chlorosuccinimide (NCS) (22 g, 164.7 mmol) for 10 hours at room temperature. The resulting mixture was quenched with water (300 mL) and extracted with ethyl acetate (4×100 mL). The combined organic layers were washed with brine (2×100 mL), dried over anhydrous sodium sulfate and concentrated in vacuo to afford a residue, which was purified by a silica gel column chromatography eluting with 1% ethyl acetate in petroleum ether to afford 3-methylbenzo[d]isoxazole as a light green liquid (8.8 g, 61%).

LC/MS (ES, m/z): [M+H]$^+$ 134.0

$^1$H NMR (300 MHz, DMSO) δ 7.65-7.62 (d, J=7.80 Hz, 1H), 7.57-7.51 (m, 2H), 7.34-7.26 (m, 1H), 2.60 (s, 3H)

Step 3: 3-(bromomethyl)benzo[d]isoxazole

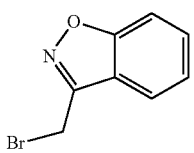 [SMILES: BrCc1noc2ccccc12]

To a solution of 3-methylbenzo[d]isoxazole (10.3 g, 77 mmol) in CCl$_4$ (200 mL) was added N-bromosuccinimide (NBS) (16.5 g, 93 mmol) and benzoyl peroxide (BPO) (5.6 g, 22 mmol). The resulting solution was heated to reflux for 10 hours. The solids were filtered off and the filtrate was concentrated in vacuo to afford crude 3-(bromomethyl)benzo[d]isoxazole as a green oil (15.3 g).

Step 4: 2-(benzo[d]isoxazol-3-yl)acetonitrile

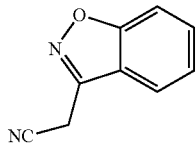 [SMILES: N#CCc1noc2ccccc12]

To a solution of the above crude 3-(bromomethyl)benzo[d]isoxazole (15.3 g) in CH$_3$CN (100 mL) was added a solution of KCN (4 g, 61 mmol) in water (19 mL). The resulting solution was stirred overnight at 40° C., and then quenched with water (200 mL) and extracted with ethyl acetate (4×200 mL). The combined organic layers were washed with brine (2×100 mL), dried over anhydrous sodium sulfate and concentrated in vacuo to afford a residue, which was purified by a silica gel column chromatography eluting with 1%-2% ethyl acetate in petroleum ether to afford 2-(benzo[d]isoxazol-3-yl)acetonitrile as a yellow solid (1.15 g, 15%).

LC/MS (ES, m/z): [M+H]$^+$ 159.0

$^1$H NMR (300 MHz, DMSO) δ 7.87-7.84 (d, J=8.10 Hz, 1H), 7.66-7.61 (m, 2H), 7.47-7.40 (m, 1H), 4.13 (s, 2H)

Step 5: 2-(benzo[d]isoxazol-3-yl)-3-(dimethylamino)acrylonitrile

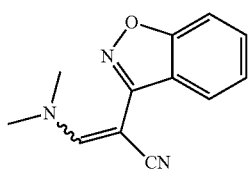 [SMILES: CN(C)C=C(C#N)c1noc2ccccc12]

To a solution of 2-(benzo[d]isoxazol-3-yl)acetonitrile (350 mg, 2.2 mmol) in toluene (1.5 mL) was added DMF-DMA (395 mg, 3.3 mmol). The resulting solution was heated to 85° C. for 2 hrs, then concentrated in vacuo to afford crude 2-(benzo[d]isoxazol-3-yl)-3-(dimethylamino) acrylonitrile as a green solid (470 mg), which was used in the next step without further purification.

Step 6: 4-(benzo[d]isoxazol-3-yl)-1H-pyrazol-5-amine

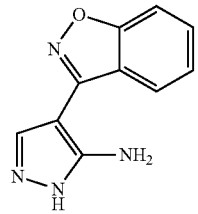 [SMILES: Nc1[nH]ncc1-c1noc2ccccc12]

To a solution of the above crude 2-(benzo[d]isoxazol-3-yl)-3-(dimethylamino)acrylonitrile (470 mg) in AcOH (3 mL) was added N$_2$H$_4$·H$_2$O (554 mg, 11 mmol). The resulting solution was heated to reflux for 4 hrs, then quenched with water (30 ml) and filtered. The filter cake was washed with ether (3×10 mL) and water (3×10 mL), dried in a vacuum oven to afford 4-(benzo[d]isoxazol-3-yl)-1H-pyrazol-5-amine as a light yellow solid (180 mg, 41%).

LC/MS (ES, m/z): [M+H]$^+$ 201.0

$^1$H NMR (300 MHz, DMSO) δ 12.17 (bs, 1H), 8.36 (bs, 2H), 7.69-7.75 (d, J=6.30 Hz, 1H), 7.70-7.66 (m, 1H), 7.45-7.41 (m, 1H), 5.58 (s, 2H)

Step 7: 3-(benzo[d]isoxazol-3-yl)-5-(4-chloro-3-methoxyphenyl)pyrazolo[1,5-a]pyrimidin-7(4H)-one

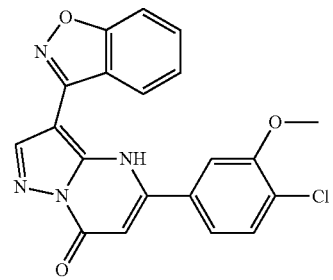 [SMILES: COc1cc(-c2cc(=O)n3ncc(-c4noc5ccccc45)c3[nH]2)ccc1Cl]

To a solution of 4-(benzo[d]isoxazol-3-yl)-1H-pyrazol-5-amine (50 mg, 0.25 mmol) in n-BuOH (1 mL) was added ethyl 3-(4-chloro-3-methoxyphenyl)-3-oxopropanoate (96 mg, 0.37 mmol) and p-TsOH (2 mg, 0.01 mmol). The resulting solution was heated to reflux for 2 hrs, then solids were collected by filtration and washed with methanol (3×10 mL) to afford 3-(benzo[d]isoxazol-3-yl)-5-(4-chloro-3-methoxyphenyl)pyrazolo[1,5-a]pyrimidin-7(4H)-one as a light yellow solid (39.6 mg, 40%).

LC/MS (ES, m/z): [M+H]$^+$ 393.0

$^1$H NMR (300 MHz, DMSO+NH$_3$ (saturated D$_2$O solution)) δ 9.18 (d, J=8.10 Hz, 1H), 8.25 (s, 1H), 7.92 (s, 1H), 7.72-7.62 (m, 3H), 7.42-7.49 (m, 1H), 7.42-7.37 (m, 1H), 6.20 (s, 1H), 3.96 (s, 3H)

EXAMPLE 51

5-(4-chloro-3-methoxyphenyl)-3-(1-methyl-1H-pyrazol-5-yl)pyrazolo[1,5-a]pyrimidin-7(4H)-one

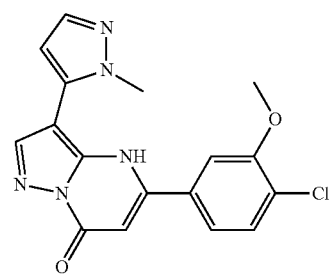 [SMILES: COc1cc(-c2cc(=O)n3ncc(-c4ccnn4C)c3[nH]2)ccc1Cl]

To a solution of 4-(1-methyl-1H-pyrazol-5-yl)-1H-pyrazol-5-amine (50 mg, 0.31 mmol) in n-BuOH (0.5 mL) was added p-TsOH (10 mg, 0.06 mmol) and ethyl 3-(4-chloro-3-methoxyphenyl)-3-oxopropanoate (118 mg, 0.46 mmol). The resulting solution was stirred for 2 h at reflux, then cooled to room temperature and diluted with methanol (1 mL). The solids were collected by filtration and washed with MeOH (3×1 mL) to afford 5-(4-chloro-3-methoxyphenyl)-

3-(1-methyl-1H-pyrazol-5-yl)pyrazolo[1,5-a]pyrimidin-7(4H)-one as a white solid (49 mg 45%).

(ES, m/z): [M+H]⁺: 355.9

¹H NMR (300 MHz, DMSO+NH₃ (saturated D2O solution, 1d)) δ 7.92 (s, 1H), 7.79 (d, J=1.8 Hz, 1H), 7.64 (dd, J=1.8 Hz, 8.4 Hz, 1H), 7.45 (d, J=8.4 Hz, 1H), 7.38 (d, J=1.8 Hz, 1H), 6.58 (d, J=1.8 Hz, 1H), 6.09 (s, 1H), 4.01 (s, 3H), 3.95 (s, 3H)

EXAMPLE 52

5-(4-chloro-3-methoxyphenyl)-3-(3-methylisoxazol-5-yl)pyrazolo[1,5-a]pyrimidin-7(4H)-one

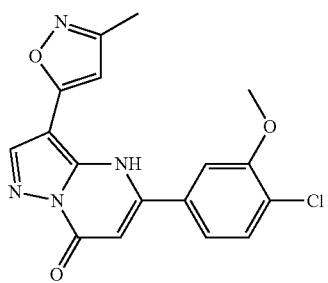 [SMILES: COc1cc(-c2cc(=O)n3ncc(-c4cc(C)no4)c3[nH]2)ccc1Cl]

Step 1: (3-methylisoxazol-5-yl)methanol

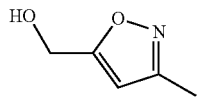

To a solution of 3-methylisoxazole-5-carboxylic acid (3 g, 23.6 mmol) in tetrahydrofuran (20 mL) was added LiAlH₄ (1.8 g, 47.37 mmol) in portions at 0° C. under nitrogen atmosphere. After additional 2 hours at room temperature, the reaction was then quenched by water (2 mL). The mixture was dried over anhydrous sodium sulfate, filtered and concentrated under reduced pressure to give a residue, which was purified by a silica gel column, eluted with 10%-30% ethyl acetate in petroleum ether to afford (3-methylisoxazol-5-yl)methanol as colorless oil (1.5 g, 56%); (ES, m/z): [M+H]+ 114.1; ¹H NMR (300 MHz, CDCl₃) δ 6.09 (s, 1H), 4.74 (s, 2H), 2.30 (s, 3H), 2.10 (brs, 1H).

Step 2: (3-methylisoxazol-5-yl)methyl methanesulfonate

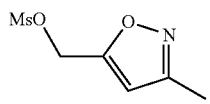

To a solution of (3-methylisoxazol-5-yl)methanol (1.5 g, 13.26 mmol) in dichloromethane (20 mL) was added triethylamine (2 g, 19.8 mmol) and methanesulfonyl chloride (1.8 g, 15.79 mmol) at room temperature. After additional 2 hours, the reaction was then quenched by water (10 mL), extracted with dichloromethane (4×20 mL). The combined organic layer was dried over anhydrous sodium sulfate and concentrated under vacuum to give the residue, which was purified by a silica gel column, eluted with 1%-10% ethyl acetate in petroleum ether to afford (3-methylisoxazol-5-yl) methyl methanesulfonate as light yellow oil (1.2 g, 47%).

(ES, m/z): [M+H]+ 192.1

¹H NMR (300 MHz, CDCl₃) δ 6.29 (s, 1H), 5.27 (s, 2H), 3.05 (s, 3H), 2.34 (s, 3H)

Step 3: 2-(3-methylisoxazol-5-yl)acetonitrile

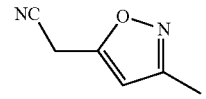

To a solution of (3-methylisoxazol-5-yl)methyl methanesulfonate (1.2 g, 6.28 mmol) in DMF (20 mL) was added KCN (1.2 g, 18.46 mmol) at room temperature. After 3 hours at 65° C., the reaction was then quenched by the addition water (100 mL), extracted with ethyl acetate (4×50 mL). The combined organic layer was washed with brine (3×10 mL), dried over anhydrous sodium sulfate and concentrated under reduced pressure to give a residue, which was purified by a silica gel column, eluted with 1%-20% ethyl acetate in petroleum ether to afford 2-(3-methylisoxazol-5-yl)acetonitrile as red oil (0.4 g, 52%).

(ES, m/z): [M+H]+ 123.0

¹H NMR (300 MHz, DMSO) δ 6.39 (s, 1H), 4.38 (s, 2H), 2.23 (s, 3H)

Step 4: 3-(dimethylamino)-2-(3-methylisoxazol-5-yl)acrylonitrile

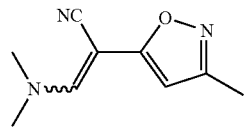

To a solution of 2-(3-methylisoxazol-5-yl)acetonitrile (400 mg, 3.28 mmol) in toluene (10 mL) was added DMF-DMA (2 g, 16.81 mmol). The resulting solution was heated to 85° C. for 8 hours, then concentrated in vacuo to afford crude 3-(dimethylamino)-2-(3-methylisoxazol-5-yl)acrylonitrile as a yellow solid (800 mg), which was used in the next step without further purification.

Step 5: 4-(3-methylisoxazol-5-yl)-1H-pyrazol-5-amine

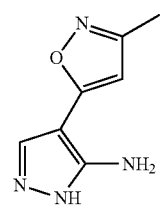

To a solution of the above crude 3-(dimethylamino)-2-(3-methylisoxazol-5-yl)acrylonitrile (800 mg) in AcOH (10 mL) was added N₂H₄·H₂O (10 mL). The resulting solution was heated to 80° C. for 8 hours then quenched with water (50 ml). Solids were collected by filtration, washed with water (3×10 mL) and ether (3×10 mL) successively, dried in a vacuum oven to afford 4-(3-methylisoxazol-5-yl)-1H-pyrazol-5-amine as a yellow solid (150 mg, 20%).

(ES, m/z): [M+H]⁺ 164.0

¹H NMR (300 MHz, CDCl₃) δ 7.67 (s, 1H), 6.02 (s, 1H), 2.32 (s, 3H)

Step 6: 5-(4-chloro-3-methoxyphenyl)-3-(3-methyl-isoxazol-5-yl)pyrazolo[1,5-a]pyrimidin-7(4H)-one

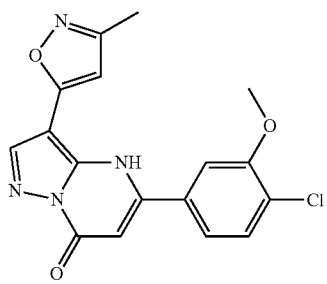 [SMILES: COc1cc(-c2cc(=O)n3ncc(-c4cc(C)no4)c3[nH]2)ccc1Cl]

To a solution of 4-(3-methylisoxazol-5-yl)-1H-pyrazol-5-amine (50 mg, 0.30 mmol) in n-BuOH (1 mL) was added ethyl 3-(4-chloro-3-methoxyphenyl)-3-oxopropanoate (120 mg, 0.47 mmol) and p-TsOH (2 mg, 0.012 mmol). The resulting solution was heated to reflux for 1 hour, then solids were collected by filtration and washed with methanol (3×10 mL) to afford 5-(4-chloro-3-methoxyphenyl)-3-(3-methyl-isoxazol-5-yl)pyrazolo[1,5-a]pyrimidin-7(4H)-one as a yellow solid (24.4 mg, 25%).

(ES, m/z): [M+H]⁺ 356.9

¹H NMR (300 MHz, DMSO+NH₃ (saturated D₂O solution)) δ 8.06 (s, 1H), 7.82 (d, J=1.8 Hz, 1H), 7.73 (dd, J=1.8 Hz, 8.1 Hz, 1H), 7.48 (d, J=8.4 Hz, 1H), 6.60 (s, 1H), 6.18 (s, 1H), 3.94 (s, 3H), 2.22 (s, 3H)

EXAMPLE 53

5-(1-ethyl-1H-indazol-5-yl)-3-(1-methyl-1H-pyra-zol-5-yl)pyrazolo[1,5-a]pyrimidin-7(4H)-one

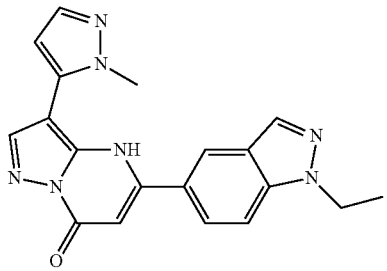 [SMILES: CCn1ncc2cc(-c3cc(=O)n4ncc(-c5ccnn5C)c4[nH]3)ccc21]

Step 1: (1-methyl-1H-pyrazol-5-yl)methanol

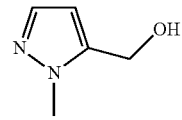

To a solution of 1-methyl-1H-pyrazole-5-carboxylic acid (2 g, 15.86 mmol) in tetrahydrofuran (50 mL) was added LiAlH₄ (720 mg, 18.97 mmol) in portions at 0° C. under an inert atmosphere of nitrogen. The reaction was stirred for 2 hours at room temperature then quenched by the addition of water (2 mL). The mixture was dried over by anhydrous sodium sulfate and the solids were filtered out. The filtrates were concentrated under reduced pressure to afford (1-methyl-1H-pyrazol-5-yl)methanol as colorless oil (1.2 g, 67%).

(ES, m/z): [M+H]⁺ 113.0

¹H NMR (300 MHz, CDCl₃) δ 7.36 (d, J=1.8 Hz, 1H), 6.18 (d, J=1.8 Hz, 1H), 4.66 (s, 2H), 3.88 (s, 3H)

Step 2: 5-(chloromethyl)-1-methyl-1H-pyrazole

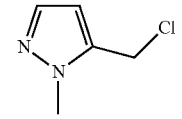

A solution of (1-methyl-1H-pyrazol-5-yl)methanol (1.2 g, 10.71 mmol) in dichloromethane (25 mL) was treated with thionyl chloride (1.9 mL) at room temperature for 2 hours. Then the reaction was quenched by the addition of water (20 mL) and neutralized with saturated aqueous sodium carbonate. The organic layer was separated and the aqueous layer extracted with dichloromethane (3×20 mL). The combined organic layer was dried over by anhydrous sodium sulfate. The solids were filtered out and the filtrates were concentrated under reduced pressure to afford 5-(chloromethyl)-1-methyl-1H-pyrazole as light yellow oil (800 mg, 57%).

(ES, m/z): [M+H]⁺ 131.0

¹H NMR (300 MHz, CDCl₃) δ 7.41 (d, J=1.8 Hz, 1H), 6.27 (d, J=1.8 Hz, 1H), 4.61 (s, 2H), 3.93 (s, 3H)

Step 3

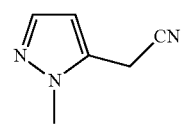

2-(1-methyl-1H-pyrazol-5-yl)acetonitrile

To a solution of 5-(chloromethyl)-1-methyl-1H-pyrazole (800 mg, 6.15 mmol) in CH₃CN (25 mL) and water (10 mL) was added KCN at room temperature. The resulting solution was stirred for 10 hours at 50° C. After cooling to room temperature, the resulting solution was diluted with water (100 mL) and extracted with ethyl acetate (3×50 mL). The combined organic layer was washed with brine (2×30 mL), dried over by anhydrous sodium sulfate. The solids were filtered out and the filtration was concentrated under reduced pressure to give the residue, which was purified by a silica gel column with 1% methanol in dichloromethane to afford 2-(1-methyl-1H-pyrazol-5-yl)acetonitrile as light yellow oil (500 mg, 67%).

(ES, m/z): [M+H]⁺ 122.0

¹H NMR (300 MHz, CDCl₃) δ 7.44 (d, J=1.8 Hz, 1H), 6.29 (d, J=1.8 Hz, 1H), 3.88 (s, 3H), 3.76 (s, 2H)

Step 4: 3-(dimethylamino)-2-(1-methyl-1H-pyrazol-5-yl)acrylonitrile

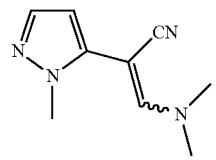

To a solution of 2-(1-methyl-1H-pyrazol-5-yl)acetonitrile (500 mg, 4.13 mmol) in toluene (10 mL) was added DMF-DMA (1.97 g, 16.5 mmol) at room temperature. The resulting solution was stirred for 4 hours at 85° C., then concentrated in vacuo to afford crude 3-(dimethylamino)-2-(1-methyl-1H-pyrazol-5-yl)acrylonitrile as brown crude oil, which was used in the next step without further purification.

(ES, m/z): [M+H]⁺ 177.0

Step 5: 2-methyl-1'H,2H-3,4'-bipyrazol-5'-amine

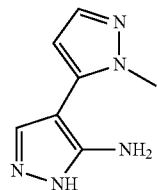

To a solution of the above crude 3-(dimethylamino)-2-(1-methyl-1H-pyrazol-5-yl)acrylonitrile in acetic acid (5 mL) was added hydrazine hydrate (3.23 g, 64.6 mmol) at room temperature. The resulting solution was stirred for 4 hours at 80° C., then concentrated in vacuo to give a residue, which was purified by a silica gel column, eluted with 1%-5% methanol in dichloromethane to afford 2-methyl-1'H,2H-3,4'-bipyrazol-5'-amine as a off-white solid (250 mg, 37% of two steps).

(ES, m/z): [M+H]⁺ 164.0

¹H NMR (300 MHz, DMSO) δ 11.87 (brs, 1H), 7.52 (brs, 1H), 7.38 (d, J=1.8 Hz, 1H), 6.27 (s, 1H), 4.62 (brs, 2H), 3.77 (s, 3H)

Step 6: 5-(1-ethyl-1H-indazol-5-yl)-3-(1-methyl-1H-pyrazol-5-yl)pyrazolo[1,5-a]pyrimidin-7(4H)-one

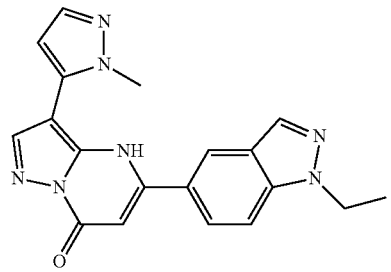 [SMILES: CCn1ncc2cc(-c3cc(=O)n4ncc(-c5ccnn5C)c4[nH]3)ccc21]

To a solution of 2-methyl-1'H,2H-3,4'-bipyrazol-5'-amine (50 mg, 0.31 mmol) in n-BuOH (1 mL) was added ethyl 3-(1-ethyl-1H-indazol-5-yl)-3-oxopropanoate (120 mg, 0.46 mmol) and p-TsOH (5 mg, 0.03 mmol). The resulting solution was heated to reflux for 1 hour, then solids were collected by filtration and washed with methanol (3×10 mL) to afford 5-(1-ethyl-1H-indazol-5-yl)-3-(1-methyl-1H-pyrazol-5-yl)pyrazolo[1,5-a]pyrimidin-7(4H)-one as a white solid (28.0 mg, 25%).

(ES, m/z): [M+H]⁺ 360.1

¹H NMR (300 MHz, DMSO+NH₃ (saturated D₂O solution)) δ 8.41 (s, 1H), 8.16-8.13 (m, 2H), 7.91 (s, 1H), 7.68 (d, J=9.0 Hz, 1H), 7.40 (d, J=1.8 Hz, 1H), 6.60 (d, J=2.1 Hz, 1H), 6.09 (s, 1H), 4.47 (q, J=7.2 Hz, 2H), 4.02 (s, 3H), 1.41 (t, J=7.2 Hz, 3H)

EXAMPLE 54

5-(4-chloro-3-methoxyphenyl)-3-(1-methyl-1H-pyrazol-3-yl)pyrazolo[1,5-a]pyrimidin-7(4H)-one

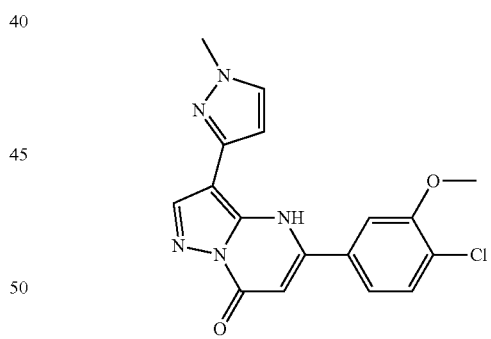

To a solution of 1-methyl-1H,1'H-3,4'-bipyrazol-5'-amine (50 mg, 0.3 mmol) in n-BuOH (1 mL) was added ethyl 3-(4-chloro-3-methoxyphenyl)-3-oxopropanoate (120 mg, 0.45 mmol) and p-TsOH (5 mg, 0.05 mmol) at room temperature. After refluxing 2 hours, the solids were collected by filtration and washed with methanol (3×2 mL) to afford 5-(4-chloro-3-methoxyphenyl)-3-(1-methyl-1H-pyrazol-3-yl)pyrazolo[1,5-a]pyrimidin-7(4H)-one as a light yellow solid (27.7 mg, 25%).

LCMS (ES, m/z): [M+H]⁺ 355.8

¹H NMR (300 MHz, DMSO+NH₃ (saturated D₂O solution)) δ 8.26 (s, 1H), 7.78 (s, 1H), 7.67-7.58 (m, 2H), 7.47-7.45 (m, 1H), 6.67 (s, 1H), 6.29 (s, 1H), 4.00 (s, 3H), 3.91 (s, 3H)

EXAMPLE 55

5-(1-ethyl-1H-indazol-5-yl)-3-(1H-pyrazol-3-yl) pyrazolo[1,5-a]pyrimidin-7(4H)-one

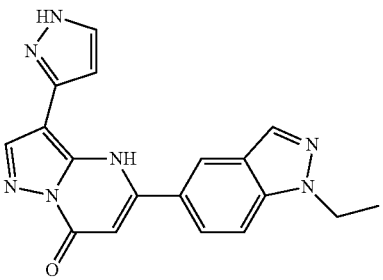 [SMILES: CCn1ncc2cc(-c3cc(=O)n4ncc(-c5cc[nH]n5)c4[nH]3)ccc21]

Step 1: (1H-pyrazol-3-yl)methanol

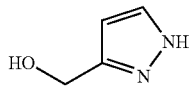

To a solution of 1H-pyrazole-3-carboxylic acid (10 g, 89.22 mmol) in tetrahydrofuran (200 mL) was added LiAlH$_4$ (6.79 g, 178.92 mmol) at 0-5° C. in an ice/salt bath. Then the mixture was warmed to room temperature and after an additional 2 hours, the reaction was quenched with ice/water (10 mL) and extracted with dichloromethane (3×50 mL). The combined organic layers were dried over anhydrous sodium sulfate and concentrated n vacuo at low temperature to afford (1H-pyrazol-3-yl)methanol as a crude light yellow oil (4.0 g, 46%).

Step 2: 3-(chloromethyl)-1H-pyrazole

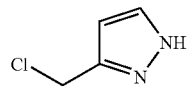

To a solution of (1H-pyrazol-3-yl)methanol (4.0 g, 40.77 mmol) in dichloromethane (20 mL) was added thionyl chloride (12.1 g, 101.68 mmol) at 0-5° C. in an ice/salt bath. Then the mixture was warmed to room temperature and after an additional 2 hours, the reaction was cautiously quenched with ice/water (250 mL) and the pH was adjusted to pH 7 with sodium bicarbonate. The resulting solution was extracted with dichloromethane (3×100 mL) and the combined organic layers were washed with brine (50 mL), dried over anhydrous sodium sulfate and concentrated in vacuo at low temperature to afford 3-(chloromethyl)-1H-pyrazole as crude yellow oil (2.5 g, 53%).

Step 3: 2-(1H-pyrazol-3-yl)acetonitrile

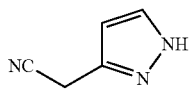

To a solution of 3-(chloromethyl)-1H-pyrazole (2.5 g, 21.45 mmol) in CH$_3$CN (50 mL) and water (2 mL) was added KCN (1.8 g, 28.15 mmol) at room temperature. The resulting mixture was stirred 10 hours at 50° C. then diluted with water (300 mL) and extracted with ethyl acetate (3×100 mL). The combined organic layers were washed with brine (2×50 mL), dried over anhydrous sodium sulfate and concentrated in vacuo to afford a residue, which was purified by a silica gel column chromatography by eluting with 2%-10% methanol in dichloromethane to afford 2-(1H-pyrazol-3-yl)acetonitrile as a dark red oil (1.5 g, 64%).

LCMS (ES, m/z): [M+H]$^+$ 108.1

$^1$H NMR (300 MHz, DMSO) δ 12.83 (s, 1H), 7.71 (s, 1H), 6.26-6.22 (m, 1H), 3.95 (s, 2H)

Step 4: (Z)-3-(dimethylamino)-2-(1H-pyrazol-3-yl) acrylonitrile

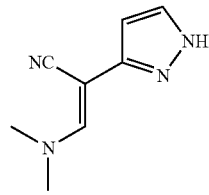

A solution of 2-(1H-pyrazol-3-yl)acetonitrile (1.5 g, 14.1 mmol) in toluene (20 mL) was reacted with DMF-DMA (2.19 g, 18 mmol) for 4 hours at 85° C. Then the resulting mixture was concentrated in vacuo to afford crude (Z)-3-(dimethylamino)-2-(1H-pyrazol-3-yl)acrylonitrile as a dark red oil (2 g), which was used in the next step without further purification.

Step 5: 1H,1'H-3,4'-bipyrazol-5'-amine

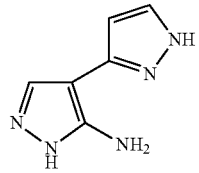 [SMILES: Nc1[nH]ncc1-c1cc[nH]n1]

To a solution of the above crude (Z)-3-(dimethylamino)-2-(1H-pyrazol-3-yl)acrylonitrile (2.0 g, 12.33 mmol) in AcOH (2 mL) was added N$_2$H$_4$.H$_2$O (3.1 g, 62.00 mmol) at room temperature. The resulting solution stirred at 90° C. for 2 hours. Then solvent was removed in vacuo to provide a residue, which was dissolved in methanol (10 mL). After concentration in vacuo, the crude product was purified by silica gel column chromatography, eluting with 2%-10% methanol in dichloromethane to afford 1H,1'H-3,4'-bipyrazol-5'-amine as yellow oil (800 mg, 43%).

LCMS (ES, m/z): [M+H]$^+$ 150.0

$^1$H NMR (300 MHz, MeOD) δ 7.98 (s, 1H), 7.60 (d, J=2.1 Hz, 1H), 6.42 (d, J=2.1 Hz, 1H), 4.62 (s, 1H), 3.36 (s, 1H)

Step 6: 5-(1-ethyl-1H-indazol-5-yl)-3-(1H-pyrazol-3-yl)pyrazolo[1,5-a]pyrimidin-7(4H)-one

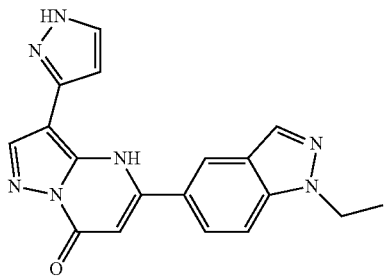 [SMILES: CCn1ncc2cc(-c3cc(=O)n4ncc(-c5cc[nH]n5)c4[nH]3)ccc21]

To a solution of 1H,1'H-3,4'-bipyrazol-5'-amine (100 mg, 0.67 mmol) in n-BuOH (0.3 mL) was added ethyl 3-(1-ethyl-1H-indazol-5-yl)-3-oxopropanoate (261.7 mg, 1.01 mmol) and p-TsOH (5.76 mg, 0.03 mmol) at room temperature. After refluxing 2 hours, the solids were collected by filtration and washed with methanol (3×5 mL) to afford 5-(1-ethyl-1H-indazol-5-yl)-3-(1H-pyrazol-3-yl)pyrazolo[1,5-a]pyrimidin-7(4H)-one as a light yellow solid (42.3 mg, 18%).

LCMS (ES, m/z): [M+H]$^+$ 346.1

$^1$H NMR (300 MHz, CD$_3$OD) δ 13.06 (s, 1H), 8.34 (m, 3H), 7.87 (q, J=9 Hz, 3H), 6.71 (d, J=2.1 Hz, 1H), 6.25 (d, J=1.5 Hz, 1H), 4.53 (q, J=7.2 Hz, 2H), 1.45-1.34 (m, 3H)

EXAMPLE 56

5-(4-chloro-3-methoxyphenyl)-3-(5-methylthiazol-2-yl)pyrazolo[1,5-a]pyrimidin-7(4H)-one

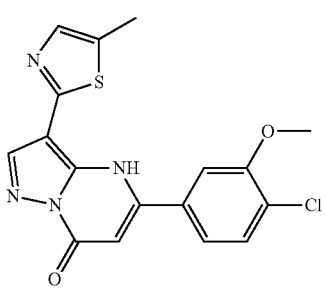 [SMILES: COc1cc(-c2cc(=O)n3ncc(-c4ncc(C)s4)c3[nH]2)ccc1Cl]

To a solution of 4-(5-methylthiazol-2-yl)-1H-pyrazol-5-amine (90 mg, 0.50 mmol) in n-BuOH (1 mL) was added ethyl 3-(4-chloro-3-methoxyphenyl)-3-oxopropanoate (190 mg, 0.74 mmol) and p-TsOH (5 mg) at room temperature. After refluxing 2 hours, the solids were collected by filtration and washed with methanol (3×2 mL) to afford 5-(4-chloro-3-methoxyphenyl)-3-(5-methylthiazol-2-yl)pyrazolo[1,5-a]pyrimidin-7(4H)-one as a yellow solid (32.3 mg, 18%). LCMS (ES, m/z): [M+H]+ 372.9

$^1$H NMR (400 MHz, DMSO+NH$_3$ (saturated D$_2$O solution)) δ 8.16 (s, 1H), 8.01 (s, 1H), 7.79-7.77 (d, J=8.4 Hz, 1H), 7.52-7.50 (d, J=8.4 Hz, 1H), 7.33 (s, 1H), 6.22 (s, 1H), 4.00 (s, 3H), 2.29 (s, 3H)

EXAMPLE 57

5-(4-chlorophenyl)-3-(thiazol-2-yl)pyrazolo[1,5-a]pyrimidin-7(4H)-one

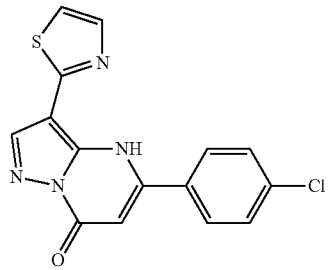 [SMILES: O=c1cc(-c2ccc(Cl)cc2)[nH]c2c(-c3nccs3)cnn12]

To a solution of 4-(thiazol-2-yl)-1H-pyrazol-5-amine (50 mg, 0.3 mmol) in n-BuOH (0.2 mL) was added ethyl 3-(4-chlorophenyl)-3-oxopropanoate (100 mg, 0.45 mmol) and p-TsOH (5 mg) at room temperature. After refluxing 1 hour, the solids were collected by filtration and washed with methanol (3×2 mL) to afford 5-(4-chlorophenyl)-3-(thiazol-2-yl)pyrazolo[1,5-a]pyrimidin-7(4H)-one as a yellow solid (28.0 mg, 28%).

LCMS (ES, m/z): [M+H]$^+$ 329.0

$^1$H NMR (300 MHz, DMSO+NH$_3$ (saturated D$_2$O solution)) δ 8.25-8.20 (m, 3H), 7.69-7.67 (d, J=3.6 Hz, 1H), 7.55-7.52 (d, J=8.7 Hz, 2H), 7.45-7.43 (d, J=3.3 Hz, 1H), 6.18 (s, 1H)

EXAMPLE 58

5-(4-chlorophenyl)-3-(4-methylthiazol-2-yl)pyrazolo[1,5-a]pyrimidin-7(4H)-one

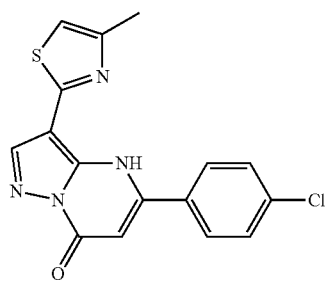 [SMILES: Cc1csc(-c2cnn3c(=O)cc(-c4ccc(Cl)cc4)[nH]c23)n1]

Step 1: 2-(4-methylthiazol-2-yl)acetonitrile

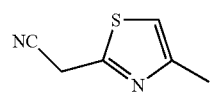

To a solution of 2-cyanoethanethioamide (10 g, 99.9 mmol,) in ethanol (150 mL) was added 1-bromopropan-2-one (27.2 g, 198.6 mmol) and triethylamine (40.4 g, 400.1 mmol) at room temperature. After stirring 2 hours at 50° C., the reaction was concentrated in vacuo and diluted with water (100 mL). The mixture was extracted with dichloromethane (3×100 mL). The combined organic layers were washed with brine (200 mL), dried over anhydrous magnesium sulfate and concentrated in vacuo to afford a residue, which was purified by silica gel column chromatography, by eluting with 5%-12.5% ethyl acetate in petroleum ether to afford 2-(4-methylthiazol-2-yl)acetonitrile as a black oil (2.5 g, 21%).

LCMS (ES, m/z): [M+H]+ 139.0

$^1$H NMR (300 MHz, DMSO) δ 7.28 (d, J=1.2 Hz, 1H), 4.56-4.48 (m, 2H), 2.38-2.2.33 (m, 3H)

Step 2: (E)-3-(dimethylamino)-2-(4-methylthiazol-2-yl)acrylonitrile

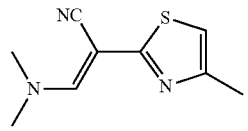

A solution of 2-(4-methylthiazol-2-yl)acetonitrile (2.5 g, 18.1 mmol) in toluene (2 mL) was treated with DMF-DMA (7.5 g, 63.1 mmol) overnight at 85° C., then the resulting mixture was concentrated in vacuo to afford crude (E)-3-(dimethylamino)-2-(4-methylthiazol-2-yl)acrylonitrile as a black solid (4.4 g), which was used in the next step without further purification.

Step 3: 4-(4-methylthiazol-2-yl)-1H-pyrazol-5-amine

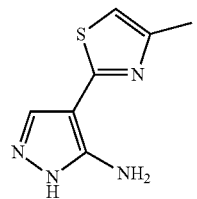

To a solution of the above crude (E)-3-(dimethylamino)-2-(4-methylthiazol-2-yl)acrylonitrile (4.4 g, 22.8 mmol) in AcOH (8 mL) was added N$_2$H$_4$.H$_2$O (4.6 g, 92.1 mmol) at room temperature. After stirring 2 hours at 90° C., the solvent was removed in vacuo to afford a residue, which was dissolved in methanol (10 mL) and neutralized with NH$_4$OH (27% aqueous solution). After concentration, the crude product was purified by silica gel column chromatograph by eluting with 2%-10% methanol in dichloromethane to afford 4-(4-methylthiazol-2-yl)-1H-pyrazol-5-amine as a light brown solid (1.0 g, 24%).

LCMS (ES, m/z): [M+H]+ 181.0

$^1$H NMR (300 MHz, DMSO-D6) δ 11.90 (brs, 1H), 7.77 (s, 1H), 6.92 (brs, 1H), 5.52 (d, J=6.0 Hz, 2H), 2.33 (s, 3H)

Step 4: 5-(4-chlorophenyl)-3-(4-methylthiazol-2-yl)pyrazolo[1,5-a]pyrimidin-7(4H)-one

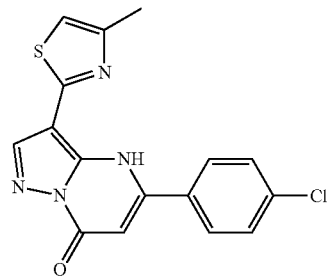 [SMILES: Cc1csc(-c2cnn3c(=O)cc(-c4ccc(Cl)cc4)[nH]c23)n1]

To a solution of 4-(4-methylthiazol-2-yl)-1H-pyrazol-5-amine (50 mg, 0.28 mmol) in n-BuOH (1 mL) was added ethyl 3-(4-chlorophenyl)-3-oxopropanoate (94.17 mg, 0.42 mmol) and p-TsOH (2.39 mg, 0.01 mmol) at room temperature. After refluxing 2 hours, the solids were collected by filtration and washed with methanol (3×5 mL) to afford 5-(4-chlorophenyl)-3-(4-methylthiazol-2-yl)pyrazolo[1,5-a]pyrimidin-7(4H)-one as a yellow solid (40 mg, 42%).

LCMS (ES, m/z): [M+H]$^+$ 343.0

$^1$H NMR (300 MHz, DMSO+NH$_3$ (saturated D$_2$O solution)) δ 8.49 (s, 1H), 8.06 (d, J=8.4 Hz, 2H), 7.61 (d, J=8.4 Hz, 2H), 7.28 (s, 1H), 6.38 (s, 1H), 2.45 (s, 3H)

EXAMPLE 59

3-(benzo[d]isoxazol-3-yl)-5-(1-ethyl-1H-indazol-5-yl)pyrazolo[1,5-a]pyrimidin-7(4H)-one

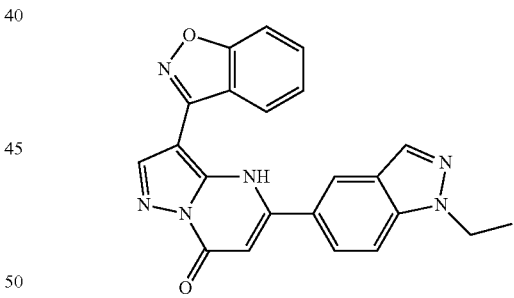

To a solution of 4-(benzo[d]isoxazol-3-yl)-1H-pyrazol-5-amine (50 mg, 0.25 mmol) in n-BuOH (0.2 mL) was added ethyl 3-(1-ethyl-1H-indazol-5-yl)-3-oxopropanoate (100 mg, 0.37 mmol) and p-TsOH (5 mg) at room temperature. After refluxing 1 hour, the solids were collected by filtration and washed with methanol (3×2 mL) to afford 3-(benzo[d]isoxazol-3-yl)-5-(1-ethyl-1H-indazol-5-yl)pyrazolo[1,5-a]pyrimidin-7(4H)-one as a light yellow solid (39.9 mg, 40%).

LCMS (ES, m/z): [M+H]+ 397.0

$^1$H NMR (300 MHz, DMSO+NH$_3$ (saturated D$_2$O solution)) δ 11.9 (s, 1H), 8.72 (s, 1H), 8.30-8.28 (m, 3H), 7.92-7.73 (m, 4H), 7.55-7.50 (m, 1H), 6.32 (s, 1H), 4.55-4.48 (q, J=7.2 Hz, 2H), 1.44-1.39 (t, J=7.2 Hz, 3H)

EXAMPLE 60

3-(benzo[d]isoxazol-3-yl)-5-(3,4-dichlorophenyl)pyrazolo[1,5-a]pyrimidin-7(4H)-one

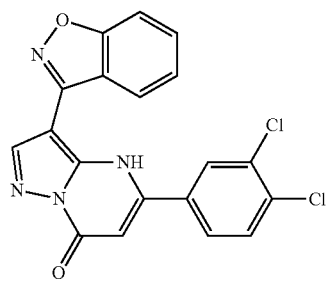 [SMILES: O=c1cc(-c2ccc(Cl)c(Cl)c2)[nH]c2c(-c3noc4ccccc34)cnn12]

To a solution of 4-(benzo[d]isoxazol-3-yl)-1H-pyrazol-5-amine (50 mg, 0.25 mmol) in n-BuOH (0.2 mL) was added ethyl 3-(3,4-dichlorophenyl)-3-oxopropanoate (100 mg, 0.37 mmol) and p-TsOH (5 mg) at room temperature. After refluxing 1 hour, the solids were collected by filtration and washed with methanol (3×2 mL) to afford 3-(benzo[d]isoxazol-3-yl)-5-(3,4-dichlorophenyl)pyrazolo[1,5-a]pyrimidin-7(4H)-one as a yellow solid (42.5 mg, 43%).

LCMS (ES, m/z): [M+H]+ 396.9

$^1$H NMR (400 MHz, DMSO+NH$_3$ (saturated D$_2$O solution)) δ 12.3 (brs, 1H), 8.72 (s, 1H), 8.30-8.28 (m, 1H), 8.11 (s, 1H), 7.88-7.74 (m, 4H), 7.53-7.49 (m, 1H), 6.34 (s, 1H)

EXAMPLE 61

3-(benzo[d]isoxazol-3-yl)-5-(4-chloro-3-ethoxyphenyl)pyrazolo[1,5-a]pyrimidin-7(4H)-one

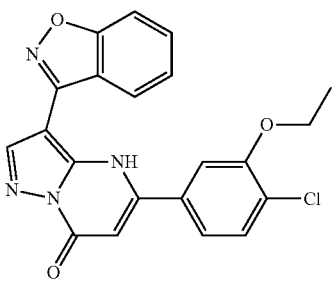 [SMILES: CCOc1cc(-c2cc(=O)n3ncc(-c4noc5ccccc45)c3[nH]2)ccc1Cl]

To a solution of 4-(benzo[d]isoxazol-3-yl)-1H-pyrazol-5-amine (50 mg, 0.25 mmol) in n-BuOH (0.2 mL) was added ethyl 3-(4-chloro-3-ethoxyphenyl)-3-oxopropanoate (110 mg, 0.37 mmol) and p-TsOH (5 mg) at room temperature. After refluxing 1 hour, the solids were collected by filtration and washed with methanol (3×2 mL) to afford 3-(benzo[d]isoxazol-3-yl)-5-(4-chloro-3-ethoxyphenyl)pyrazolo[1,5-a]pyrimidin-7(4H)-one as a white solid (47.1 mg, 46%).

LCMS (ES, m/z): [M+H]+ 407.1

$^1$H NMR (300 MHz, DMSO+NH$_3$ (saturated D$_2$O solution)) δ 9.17-9.17 (d, J=8.1 Hz, 1H), 8.24 (s, 1H), 7.90 (d, J=1.5 Hz, 1H), 7.71-760 (m, 3H), 7.50-7.47 (d, J=8.4 Hz, 1H), 7.39-7.34 (m, 1H), 6.17 (s, 1H), 4.26-4.19 (q, J=6.9 Hz, 2H), 1.42-1.38 (t, J=6.9 Hz, 3H)

EXAMPLE 62

5-(benzofuran-5-yl)-3-(3-methyl-1,2,4-oxadiazol-5-yl)-4H,7H-pyrazolo[1,5-a]pyrimidin-7-one

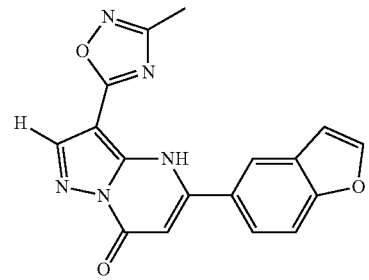 [SMILES: Cc1noc(-c2cnn3c(=O)cc(-c4ccc5occc5c4)[nH]c23)n1]

Step 1: 5-(benzofuran-5-yl)-7-oxo-4H,7H-pyrazolo[1,5-a]pyrimidine-3-carbonitrile

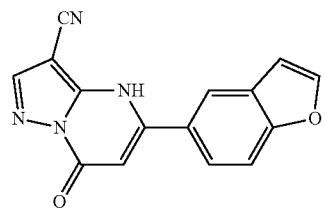 [SMILES: N#Cc1cnn2c(=O)cc(-c3ccc4occc4c3)[nH]c12]

To a solution of 5-amino-1H-pyrazole-4-carbonitrile (500 mg, 4.63 mmol) in n-BuOH (1 mL) was added ethyl 3-(benzofuran-5-yl)-3-oxopropanoate (1.4 g, 6.03 mmol), and p-TsOH (10 mg) and the reaction was stirred for 2 hours at 125° C. The solids were collected by filtration to afford 5-(benzofuran-5-yl)-7-oxo-4H,7H-pyrazolo[1,5-a]pyrimidine-3-carbonitrile as a light brown solid (900 mg, 70%).

LCMS (ES, m/z): [M+H]$^+$ 277.0

$^1$H NMR (300 MHz, DMSO) δ8.45 (s, 1H), 8.16-8.19 (m, 2H), 7.77-7.83 (m, 2H), 7.14 (s, 1H), 6.29 (s, 1H)

Step 2: 5-(benzofuran-5-yl)-7-oxo-4H,7H-pyrazolo[1,5-a]pyrimidine-3-carboxamide

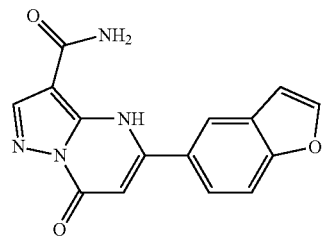 [SMILES: NC(=O)c1cnn2c(=O)cc(-c3ccc4occc4c3)[nH]c12]

Potassium carbonate (3M) (15 mL) was added to a solution of 5-(benzofuran-5-yl)-7-oxo-4H,7H-pyrazolo[1,5-a]pyrimidine-3-carbonitrile (900 mg, 3.26 mmol) in DMSO (12 mL) and methanol (18 mL) and the reaction was stirred for 5 minutes at room temperature. Then H$_2$O$_2$ (30%, 15 mL) was added and the reaction was stirred for 30 minutes at room temperature. Then the reaction was warmed up to 60° C. for 2 hours. Then it was concentrated in vacuo and diluted with water (50 mL). The solution was adjusted to pH 5 with aqueous HCl (3M). The solids were collected by filtration to afford 5-(benzofuran-5-yl)-7-oxo-4H,7H-pyrazolo[1,5-a]pyrimidine-3-carboxamide as a light yellow solid (650 mg, 76%).

LCMS (ES, m/z): [M+H]$^+$ 295.0
$^1$H NMR (300 MHz, DMSO) δ 11.25 (s, 1H), 7.47-8.38 (m, 6H), 7.14 (s, 1H)

Step 3: 5-(benzofuran-5-yl)-N-[1-(dimethylamino)ethylidene]-7-oxo-4H,7H-pyrazolo[1,5-a]pyrimidine-3-carboxamide

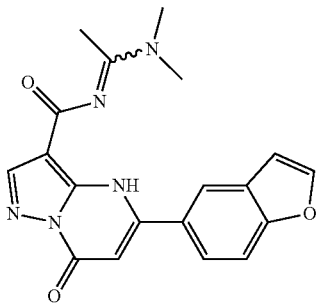 [SMILES: CC(=NC(=O)c1cnn2c(=O)cc(-c3ccc4occc4c3)[nH]c12)N(C)C]

To a solution of 5-(benzofuran-5-yl)-7-oxo-4H,7H-pyrazolo[1,5-a]pyrimidine-3-carboxamide (300 mg, 1.02 mmol) in N,N-dimethylformamide (1 mL) was added DMA-DMA (1 mL) and the reaction was stirred for 1 h at 130° C. The resulting mixture was washed with ether (3×100 mL) to afford 5-(benzofuran-5-yl)-N-[1-(dimethylamino)ethylidene]-7-oxo-4H,7H-pyrazolo[1,5-a]pyrimidine-3-carboxamide as brown crude oil (450 mg).

Step 4: 5-(benzofuran-5-yl)-3-(3-methyl-1,2,4-oxadiazol-5-yl)-4H,7H-pyrazolo[1,5-a]pyrimidin-7-one

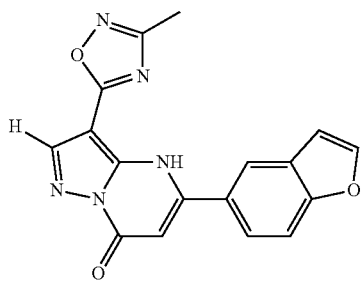 [SMILES: Cc1noc(-c2cnn3c(=O)cc(-c4ccc5occc5c4)[nH]c23)n1]

To a solution of 5-(benzofuran-5-yl)-N-[1-(dimethylamino)ethylidene]-7-oxo-4H,7H-pyrazolo[1,5-a]pyrimidine-3-carboxamide (450 mg, 1.24 mmol) in dioxane (10 mL) was added NH$_2$OH.HCl (130 mg) and the reaction was stirred for 5 minutes at room temperature. Then a solution of sodium hydroxide (10% aqueous, 2 mL) in AcOH (16 mL) was added at RT. The resulting solution was stirred for 2 hours at 100° C. The resulting mixture was concentrated in vacuo. The residue was purified by silica gel column chromatography with dichloromethane/methanol (150:1) to afford 5-(benzofuran-5-yl)-3-(3-methyl-1,2,4-oxadiazol-5-yl)-4H,7H-pyrazolo[1,5-a]pyrimidin-7-one as a light yellow solid (27.7 mg, 9%).

LCMS (ES, m/z): [M+H]$^+$ 333.9
$^1$H NMR (300 MHz, DMSO) δ8.39 (s, 1H), 8.21 (s, 1H), 8.12 (d, J=8.4 Hz, 1H), 8.03 (s, 1H), 7.67 (d, J=8.4 Hz, 1H), 7.08 (s, 1H), 6.23 (s, 1H), 2.34 (s, 3H)

EXAMPLE 63

5-(4-chloro-3-methoxyphenyl)-3-(5-phenyloxazol-2-yl)-4H,7H-pyrazolo[1,5-a]pyrimidin-7-one

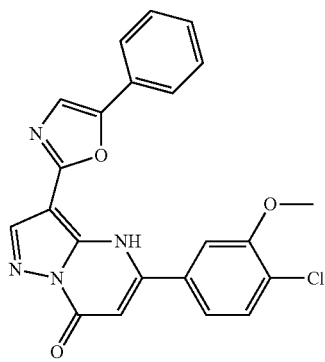 [SMILES: COc1cc(-c2cc(=O)n3ncc(-c4ncc(-c5ccccc5)o4)c3[nH]2)ccc1Cl]

Step 1: 2-cyano-N-(2-oxo-2-phenylethyl)acetamide

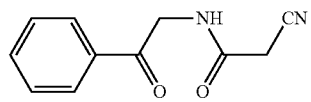

To a solution of 2-amino-1-phenylethanone hydrochloride (5 g, 29.13 mmol, 1.00 equiv) in dichloromethane (100 mL) was added 2-cyanoacetic acid (2.5 g, 29.39 mmol, 1.00 equiv), hydroxybenzotriazole (HOBT) (5 g, 37.00 mmol, 1.20 equiv) and EDCI (7 g, 36.46 mmol, 1.20 equiv) at room temperature. This was followed by the dropwise addition of TEA (16 mL, 4.00 equiv) with stirring at 0-5° C. in 30 min. The reaction was stirred overnight at room temperature. The reaction progress was monitored by TLC (PE/EA=1/1). The residue was dissolved in 200 mL of water, extracted with 3×200 mL of dichloromethane and the organic layers combined and dried over anhydrous sodium sulfate and concentrated in vacuo to afford a residue which was purified by silica gel column chromatography with ethyl acetate/petroleum ether (1:15) to afford 2-cyano-N-(2-oxo-2-phenylethyl)acetamide (2.5 g, 43%) as a yellow solid.

LC-MS: (ES, m/z): [M+H]$^+$ 203.0
$^1$H NMR (300 MHz, DMSO): δ 8.65-8.61 (t, J=5.1 Hz, 1H), 8.01-7.98 (m, 2H), 7.71-7.66 (m, 1H), 7.58-7.53 (m, 2H), 4.71-4.69 (d, J=5.4 Hz, 2H), 3.80 (s, 2H)

Step 2: 2-(5-phenyloxazol-2-yl)acetonitrile

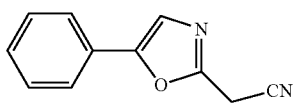 [SMILES: N#CCc1ncc(-c2ccccc2)o1]

To a solution of 2-cyano-N-(2-oxo-2-phenylethyl)acetamide (2.5 g, 12.38 mmol, 1.00 equiv) in POCl₃ (30 mL) at room temperature. The resulting solution was stirred for 3 h at 100° C. in an oil bath. The reaction progress was monitored by TLC (PE/EA=1/1). The resulting mixture was concentrated under vacuum. The residue was dissolved in 100 mL of water, extracted with 3×100 mL of ethyl acetate and the organic layers combined and dried over anhydrous sodium sulfate. The solids were filtered out. The resulting mixture was concentrated in vacuo to afford a residue, which was purified by silica gel column chromatography with ethyl acetate/petroleum ether (1:40-1:20) to afford 2-(5-phenyl-1, 3-oxazol-2-yl)acetonitrile (1.8 g, 79%) as a brown solid.

LC-MS (ES, m/z): [M+H]+ 185.0
¹H NMR (400 MHz, DMSO): δ 7.71-7.69 (m, 3H), 7.51-7.47 (m, 2H), 7.41-7.38 (m, 1H), 4.53 (s, 2H)

Step 3: 3-(dimethylamino)-2-(5-phenyloxazol-2-yl) acrylonitrile

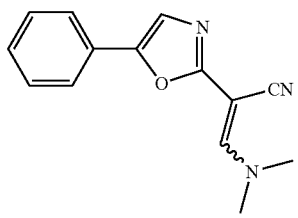 [SMILES: CN(C)C=C(C#N)c1ncc(-c2ccccc2)o1]

To a solution of 2-(5-phenyloxazol-2-yl)acetonitrile (1.8 g, 9.78 mmol, 1.00 equiv) in toluene (1.5 mL) was added DMF-DMA (1.7 g, 14.29 mmol, 1.50 equiv.) at room temperature. The reaction was stirred for 2 h at 80° C. in an oil bath and monitored by TLC (ethyl acetate/petroleum ether=1:1). The resulting mixture was concentrated in vacuo to afford 3-(dimethylamino)-2-(5-phenyloxazol-2-yl)acrylonitrile (2 g, crude) as a brown solid.

LC-MS (ES, m/z): [M+H]+ 240.0

Step 4: 4-(5-phenyloxazol-2-yl)-1H-pyrazol-5-amine

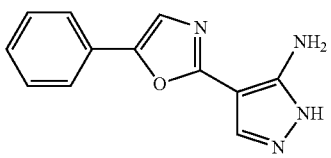 [SMILES: Nc1[nH]ncc1-c1ncc(-c2ccccc2)o1]

To a solution of 3-(dimethylamino)-2-(5-phenyloxazol-2-yl)acrylonitrile (2 g, crude) in acetic acid (4 mL) was added N₂H₄·H₂O (2.1 g, 42.00 mmol, 5.00 equiv) dropwise at 0° C. After stirring for 4 h at 90° C. in an oil bath, the reaction was concentrated in vacuo. The residue was dissolved in 100 mL of water, extracted with 3×100 mL of ethyl acetate and the organic layers were combined and dried over anhydrous sodium sulfate and concentrated in vacuo to afford a residue. Purification by silica gel column chromatography with dichloromethane/methanol (100:1) afforded 4-(5-phenyloxazol-2-yl)-1H-pyrazol-5-amine (800 mg, 42%) as an orange solid.

LC-MS (ES, m/z): [1\4+H]+ 227.0. ¹H NMR (300 MHz, DMSO): δ 7.90 (s, 1H), 7.76-7.74 (m, 2H), 7.58 (s, 1H), 7.49-7.44 (m, 2H), 7.35-7.30 (m, 1H), 5.69 (brs, 1H)

Step 5: 5-(4-chloro-3-methoxyphenyl)-3-(5-phenyloxazol-2-yl)-4H,7H-pyrazolo[1,5-a]pyrimidin-7-one

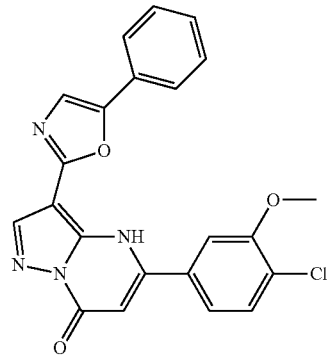 [SMILES: COc1cc(-c2cc(=O)n3ncc(-c4ncc(-c5ccccc5)o4)c3[nH]2)ccc1Cl]

To a solution of 4-(5-phenyloxazol-2-yl)-1H-pyrazol-5-amine (50 mg, 0.22 mmol, 1.00 equiv) in n-BuOH (0.2 mL) was added ethyl 3-(4-chloro-3-methoxyphenyl)-3-oxopropanoate (85 mg, 0.33 mmol, 1.50 equiv) and p-TsOH (2 mg, 0.01 mmol, 0.05 equiv) at room temperature. After refluxing for 2 h, the mixture was dissolved in 2 mL of methanol. The solids were collected by filtration and washed with MeOH (4×1 mL) to afford 5-(4-chloro-3-methoxyphenyl)-3-(5-phenyloxazol-2-yl)-4H,7H-pyrazolo[1,5-a]pyrimidin-7-one (45.9 mg, 50%) as an off-white solid.

LC-MS (ES, m/z): [M+H]+ 419.0
¹H NMR (300 MHz, DMSO): δ 8.19 (s, 1H), 8.07-8.06 (d, J=2.1 Hz, 1H), 7.83-7.80 (m, 2H), 7.76-7.73 (m, 1H), 7.70 (s, 1H), 7.53-7.45 (m, 3H), 7.35-7.33 (m, 1H), 6.21 (s, 1H), 4.04 (s, 3H)

EXAMPLE 64

5-(1-ethyl-1H-indazol-5-yl)-3-(5-phenyloxazol-2-yl)pyrazolo[1,5-a]pyrimidin-7(4H)-one

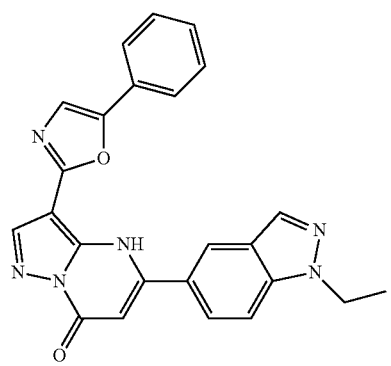 [SMILES: CCn1ncc2cc(-c3cc(=O)n4ncc(-c5ncc(-c6ccccc6)o5)c4[nH]3)ccc21]

To a solution of 4-(5-phenyloxazol-2-yl)-1H-pyrazol-5-amine (50 mg, 0.22 mmol) in n-BuOH (0.2 mL) was added ethyl 3-(1-ethyl-1H-indazol-5-yl)-3-oxopropanoate (90 mg, 0.33 mmol) and p-TsOH (5 mg) at room temperature. After refluxing 1 hour, the solids were collected by filtration and washed with methanol (3×2 mL) to afford 5-(1-ethyl-1H-indazol-5-yl)-3-(5-phenyloxazol-2-yl)pyrazolo[1,5-a]pyrimidin-7(4H)-one as a off-white solid (57.2 mg, 61%).

LCMS (ES, m/z): [M+H]$^+$ 422.9

$^1$H NMR (300 MHz, DMSO+NH$_3$ (saturated D$_2$O solution)) δ 8.63 (s, 1H), 8.55 (s, 1H), 8.35 (s, 1H), 8.24-8.11 (m, 1H), 7.89-7.78 (m, 4H), 7.70-7.51 (m, 2H), 7.40-7.30 (m, 1H), 6.28 (s, 1H), 4.55-4.82 (q, J=7.2 Hz, 2H), 1.46-1.35 (t, J=7.2 Hz, 3H)

EXAMPLE 65

5-(4-chloro-3-methoxyphenyl)-3-(1-ethyl-1H-pyrazol-5-yl)pyrazolo[1,5-a]pyrimidin-7(4H)-one

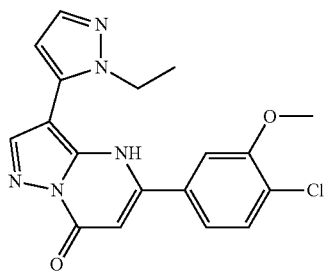 [SMILES: CCn1nccc1-c1cnn2c(=O)cc(-c3ccc(Cl)c(OC)c3)[nH]c12]

Step 1: (1-ethyl-1H-pyrazol-5-yl)methanol

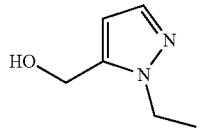

1-ethyl-1H-pyrazole-5-carboxylic acid (6 g, 42.84 mmol) was dissolved in tetrahydrofuran (20 mL) under an inert atmosphere of nitrogen. Then LiAlH$_4$ (1.95 g, 113.8 mmol) was added in portions at 0-5° C. The reaction was stirred for 2 h at room temperature. Then the reaction was quenched by the addition of water (2 mL). The mixture was dried over anhydrous sodium sulfate and concentrated in vacuo to afford (1-ethyl-1H-pyrazol-5-yl)methanol as a crude colorless oil (4 g, 74%).

LCMS (ES, m/z): [M+H]$^+$ 127.0

$^1$H NMR (300 MHz, CDCl$_3$) δ 7.42 (d, J=1.5 Hz, 1H), 6.19 (d, J=1.5 Hz, 1H), 4.68 (s, 2H), 4.22 (q, J=7.2 Hz, 2H), 1.46 (t, J=7.2 Hz, 3H)

Step 2: 5-(chloromethyl)-1-ethyl-1H-pyrazole

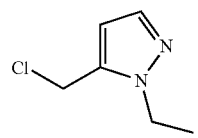

(1-ethyl-1H-pyrazol-5-yl)methanol (4 g, 31.72 mmol) was dissolved in 40 mL of dichloromethane. Then thionyl chloride (6 g) was added dropwise at 0-5° C. The resulting solution was warmed to RT and stirred for 4 h. Then the reaction was cooled to 0° C. and quenched by the addition of water (40 mL). The pH value of the solution was adjusted to pH 7-8 with sodium carbonate. Then the reaction was extracted with dichloromethane (3×50 mL), and the organic layers were combined and dried over anhydrous sodium sulfate and concentrated in vacuo to afford 5-(chloromethyl)-1-ethyl-1H-pyrazole as a crude colorless oil.

LCMS (ES, m/z): [M+H]$^+$ 145.0

$^1$H NMR (300 MHz, CDCl$_3$) δ 7.45 (d, J=1.5 Hz, 1H), 6.27 (d, J=1.5 Hz, 1H), 4.62 (s, 2H), 4.22 (q, J=7.2 Hz, 2H), 1.50 (t, J=7.2 Hz, 3H)

Step 3: 2-(1-ethyl-1H-pyrazol-5-yl)acetonitrile

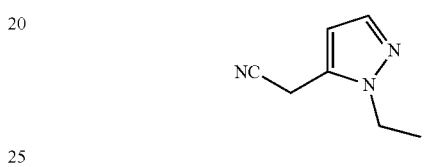

5-(Chloromethyl)-1-ethyl-1H-pyrazole (4.8 g, 33.20 mmol), KCN (2.6 g) were dissolved in a mixture of water (10 mL) and CH$_3$CN (40 mL). The reaction was stirred for 10 h at 60° C. Then the reaction was extracted with ethyl acetate (3×50 mL) and the organic layers were combined and dried over by anhydrous sodium sulfate. The organics were concentrated in vacuo to afford a residue which was purified by silica gel column chromatography with dichloromethane/methanol (400:1-200:1) to afford 2-(1-ethyl-1H-pyrazol-5-yl)acetonitrile as a yellow oil (2.5 g, 57%).

LCMS (ES, m/z): [M+H]$^+$ 136.0

$^1$H NMR (300 MHz, CDCl$_3$) δ 7.48 (d, J=1.5 Hz, 1H), 6.29 (s, 1H), 4.15 (q, J=7.5 Hz, 2H), 3.76 (s, 2H), 1.48 (t, J=7.5 Hz, 3H)

Step 4: 3-(dimethylamino)-2-(1-ethyl-1H-pyrazol-5-yl)acrylonitrile

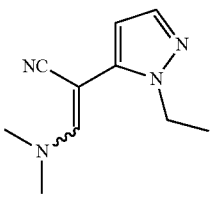

2-(1-Ethyl-1H-pyrazol-5-yl)acetonitrile (2.5 g, 18.5 mmol) was dissolved in a mixture of DMF-DMA (8.8 g, 74 mmol) and toluene (10 mL). The reaction was stirred 4 h at 85° C. Then the reaction was concentrated in vacuo to afford 3-(dimethylamino)-2-(1-ethyl-1H-pyrazol-5-yl)acrylonitrile as a crude brown oil.

LCMS (ES, m/z): [M+H]$^+$ 191.0

Step 5: 2-ethyl-1'H,2H-3,4'-bipyrazol-5'-amine

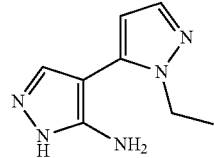

N$_2$H$_4$·H$_2$O (9.9 g) was added to a solution of 3-(dimethylamino)-2-(1-ethyl-1H-pyrazol-5-yl)acrylonitrile (crude) in AcOH (10 mL). The reaction was stirred for 2 h at 90° C. in an oil bath. After cooling to RT, the resulting mixture was concentrated in vacuo and the residue was purified by silica gel column chromatography with dichloromethane/methanol (50:1) to afford 2-ethyl-1'H,2H-3,4'-bipyrazol-5'-amine as an off-white solid (1.4 g, 43% of two steps)

LCMS (ES, m/z): [M+H]$^+$ 178.0

$^1$H NMR (300 MHz, DMSO) δ 7.51 (s, 1H), 7.42 (d, J=1.8 Hz, 1H), 6.22 (d, J=1.8 Hz, 1H), 4.68 (brs, 1H), 4.06 (q, J=7.2 Hz, 2H), 1.27 (t, J=7.2 Hz, 3H)

Step 6: 5-(4-chloro-3-methoxyphenyl)-3-(1-ethyl-1H-pyrazol-5-yl)pyrazolo[1,5-a]pyrimidin-7(4H)-one

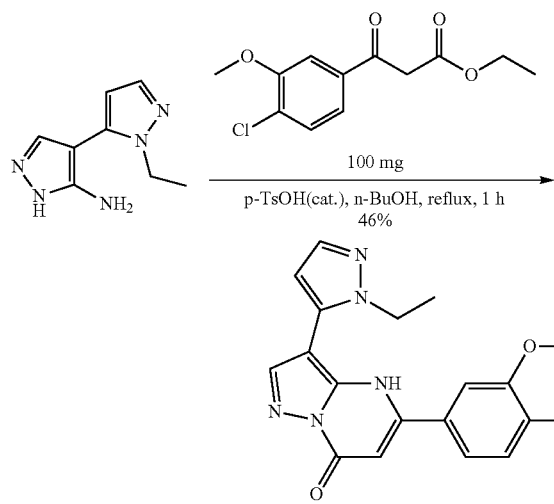

To a solution of 2-ethyl-1'H,2H-3,4'-bipyrazol-5'-amine (50 mg, 0.28 mmol) in n-BuOH (1 mL) was added ethyl 3-(4-chloro-3-methoxy-phenyl)-3-oxopropanoate (100 mg, 0.42 mg) and p-TsOH (9.7 mg) at room temperature. After refluxing 1 hour, the solids were collected by filtration and washed with methanol (3×2 mL) to afford 5-(4-chloro-3-methoxyphenyl)-3-(1-ethyl-1H-pyrazol-5-yl)pyrazolo[1,5-a]pyrimidin-7(4H)-one as a white solid (47.7 mg, 46%).

LCMS (ES, m/z): [M+H]$^+$ 370.0

$^1$H NMR (300 MHz, DMSO+NH$_3$ (saturated D$_2$O solution)) 7.85 (s, 1H), 7.70 (d, J=1.8 Hz), 7.61 (dd, J$_1$=2.1 Hz, J$_2$=8.4 Hz, 1H), 7.45 (s, 1H), 7.42 (t, J=2.1 Hz, 2H), 6.49 (d, J=1.8 Hz, 1H), 6.07 (s, 1H), 4.40 (q, J=7.2 Hz), 1.34 (t, J=7.2 Hz)

EXAMPLE 66

5-(4-chlorophenyl)-3-(1-ethyl-1H-pyrazol-5-yl)pyrazolo[1,5-a]pyrimidin-7(4H)-one

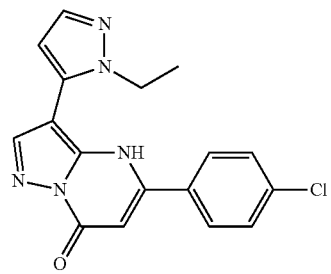 [SMILES: CCn1nccc1-c1cnn2c(=O)cc(-c3ccc(Cl)cc3)[nH]c12]

To a solution of 2-ethyl-1'H,2H-3,4'-bipyrazol-5'-amine (50 mg, 0.28 mmol) in n-BuOH (0.2 mL) was added ethyl 3-(4-chlorophenyl)-3-oxopropanoate (95 mg, 0.42 mmol) and p-TsOH (5 mg) at room temperature. After refluxing 1 hour, the solids were collected by filtration and washed with methanol (3×2 mL) to afford 5-(4-chlorophenyl)-3-(1-ethyl-1H-pyrazol-5-yl)pyrazolo[1,5-a]pyrimidin-7(4H)-one as a white solid (50.6 mg, 53%).

LCMS (ES, m/z): [M+H]$^+$ 340.0

$^1$H NMR (300 MHz, DMSO+NH$_3$ (saturated D$_2$O solution)) δ 8.06-8.04 (m, 2H), 7.85 (s, 1H), 7.48-7.42 (m, 3H), 6.51-6.50 (d, J=1.8 Hz, 1H), 6.02 (s, 1H), 4.40-4.33 (q, J=7.2 Hz, 2H), 1.34-1.30 (t, J=7.2 Hz, 3H)

EXAMPLE 67

5-(1-ethyl-1H-indazol-5-yl)-3-(1-ethyl-1H-pyrazol-5-yl)pyrazolo[1,5-a]pyrimidin-7(4H)-one

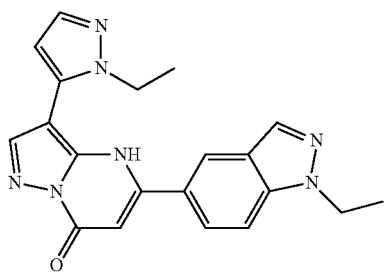 [SMILES: CCn1nccc1-c1cnn2c(=O)cc(-c3ccc4c(cnn4CC)c3)[nH]c12]

To a solution of 2-ethyl-1'H,2H-3,4'-bipyrazol-5'-amine (50 mg, 0.28 mmol) in n-BuOH (0.2 mL) was added ethyl 3-(1-ethyl-1H-indazol-5-yl)-3-oxopropanoate (100 mg, 0.42 mmol) and p-TsOH (5 mg) at room temperature. After refluxing 1 hour, the solids were collected by filtration and washed with methanol (3×2 mL) to afford 5-(1-ethyl-1H-indazol-5-yl)-3-(1-ethyl-1H-pyrazol-5-yl)pyrazolo[1,5-a]pyrimidin-7(4H)-one as a white solid (49.5 mg, 47%).

LCMS (ES, m/z): [M+H]$^+$ 374.1.0

$^1$H NMR (300 MHz, DMSO+NH$_3$ (saturated D$_2$O solution)) δ 8.40 (s, 1H), 8.16-8.12 (m, 2H), 7.87 (s, 1H), 7.70-7.67 (d, J=8.7 Hz, 1H), 7.45 (d, J=1.5 Hz, 1H), 6.54 (d, J=1.8 Hz, 1H), 6.11 (s, 1H), 4.49-4.38 (m, 4H), 1.44-1.32 (m, 6H)

EXAMPLE 68

5-(1-ethyl-1H-indazol-5-yl)-3-(3-methyl-1H-pyrazol-5-yl)pyrazolo[1,5-a]pyrimidin-7(4H)-one

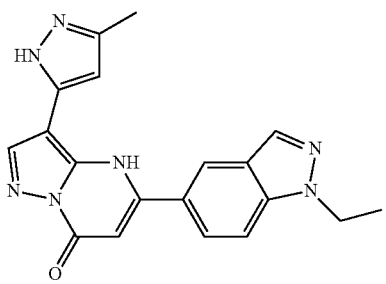

Step 1: (3-methyl-1H-pyrazol-5-yl)methanol

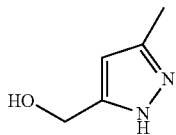

LiAlH$_4$ (900 mg, 23.70 mmol) was added in portions to a solution of ethyl 3-methyl-1H-pyrazole-5-carboxylate (3 g, 19.48 mmol) in tetrahydrofuran (50 mL) at 0-5° C. under an inert atmosphere of nitrogen. The reaction was stirred for 2 h at room temperature. Then the reaction was quenched by the dropwise addition of water (1 mL). The mixture was dried over anhydrous sodium sulfate and the solids were filtered off. The resulting solution was concentrated in vacuo to afford (3-methyl-1H-pyrazol-5-yl) methanol as white solid (1.5 g, 69%).

$^1$H NMR (300 MHz, DMSO): δ 12.20 (brs, 1H), 5.91 (s, 1H), 4.37 (s, 1H), 2.17 (s, 3H)

Step 2: 5-(chloromethyl)-3-methyl-1H-pyrazole

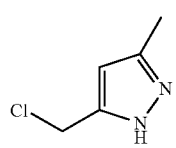

(3-methyl-1H-pyrazol-5-yl) methanol (1.5 g, 13.39 mmol) was dissolved in dichloromethane (30 mL) and cooled to 0° C. Then thionyl chloride (2.4 g, 20.34 mmol) was added dropwise. The resulting reaction was stirred for 5 h at room temperature. Then the reaction was quenched by the addition of water (20 mL). The pH value of the solution was adjusted to pH 7-8 with sodium carbonate. Then it was extracted with dichloromethane (3×50 mL). Then the organic layers were combined and dried over anhydrous sodium sulfate, and concentrated in vacuo to afford 5-(chloromethyl)-3-methyl-1H-pyrazole as colorless oil (1.2 g, crude).

Step 3: 2-(3-methyl-1H-pyrazol-5-yl)acetonitrile

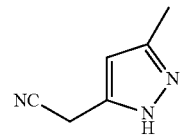

KCN (0.72 g, 11.1 mmol) was added to a solution of 5-(chloromethyl)-3-methyl-1H-pyrazole (1.2 g, 9.20 mmol, crude) in water (10 mL) and CH$_3$CN (25 mL) at room temperature. The resulting reaction was stirred for 10 hours at 60° C. Then it was extracted with ethyl acetate (4×40 mL) and the organic layers were combined and dried over anhydrous sodium sulfate. Then the reaction was concentrated in vacuo to afford a residue which was purified by a silica gel column chromatography with 1% methanol in dichloromethane to afford 2-(3-methyl-1H-pyrazol-5-yl)acetonitrile as yellow solid (600 mg, yield of step 2 and step 3: 37%).

LCMS: (ES, m/z): [M+H]$^+$ 122.0

Step 4: 3-(dimethylamino)-2-(3-methyl-1H-pyrazol-5-yl)acrylonitrile

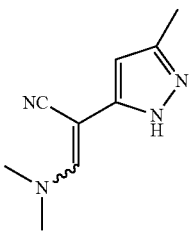

To a solution of 2-(3-methyl-1H-pyrazol-5-yl)acetonitrile (600 mg, 4.95 mmol) in toluene (1 mL) was added dimethoxy-N,N-dimethylmethanamine (885 mg, 7.44 mmol) at room temperature. The resulting solution was stirred for 4 hours at 85° C., then volatiles were distilled out to afford crude 3-(dimethylamino)-2-(3-methyl-1H-pyrazol-5-yl)acrylonitrile as a brown crude oil, which was used in the next step without further purification.

LCMS (ES, m/z): [M+H]$^+$ 177.0

Step 5: 5-methyl-1'H,2H-3,4'-bipyrazol-5'-amine

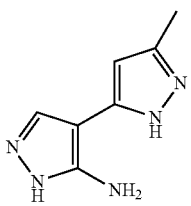

N$_2$H$_4$H$_2$O (994 mg, 19.88 mmol) was added to a solution of 3-(dimethylamino)-2-(3-methyl-1H-pyrazol-5-yl)acrylonitrile (crude as above) in acetic acid (5 mL). The resulting solution was stirred for 4 hours at 80° C. in an oil bath. The resulting mixture was concentrated in vacuo and the residue was purified by silica gel column chromatography with 10% methanol in dichloromethane to afford 5-methyl-1'H,2H-3,4'-bipyrazol-5'-amine as a brown solid (300 mg, 37% of two steps).

LCMS (ES, m/z): [M+H]+ 164.0
¹H NMR (300 MHz, DMSO): δ 7.58 (s, 1H), 6.09 (s, 1H), 2.20 (s, 3H)

Step 6: 5-(1-ethyl-1H-indazol-5-yl)-3-(3-methyl-1H-pyrazol-5-yl)pyrazolo[1,5-a]pyrimidin-7(4H)-one

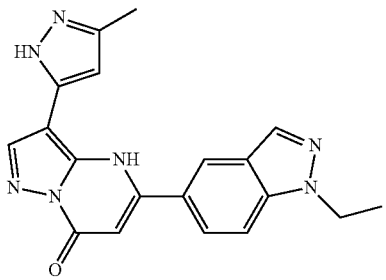 [SMILES: CCn1ncc2cc(-c3cc(=O)n4ncc(-c5cc(C)n[nH]5)c4[nH]3)ccc21]

To a solution of 5-methyl-1'H,2H-3,4'-bipyrazol-5'-amine (50 mg, 0.31 mmol) in n-BuOH (1 mL) was added ethyl 3-(1-ethyl-1H-indazol-5-yl)-3-oxopropanoate (120 mg, 0.46 mmol) and p-TsOH (5 mg). The resulting solution was heated to reflux for 1 hour, then the solids were collected by filtration and washed with methanol (3×10 mL) to afford 5-(1-ethyl-1H-indazol-5-yl)-3-(3-methyl-1H-pyrazol-5-yl)pyrazolo[1,5-a]pyrimidin-7(4H)-one as an off-white solid (48.2 mg, 44%).

LCMS (ES, m/z): [M+H]⁺ 360.1
¹H NMR (300 MHz, CD₃OD+NH₃ (saturated D₂O solution)) δ 8.48 (s, 1H), 8.15-8.24 (m, 3H), 7.67 (d, J=9.0 Hz, 1H), 6.59 (s, 1H), 6.36 (s, 1H), 4.51 (q, J=7.2 Hz, 2H), 2.34 (s, 1H), 1.51 (t, J=7.2 Hz, 3H)

EXAMPLE 69

5-(4-chloro-3-methoxyphenyl)-3-(3-methyl-1H-pyrazol-5-yl)pyrazolo[1,5-a]pyrimidin-7(4H)-one

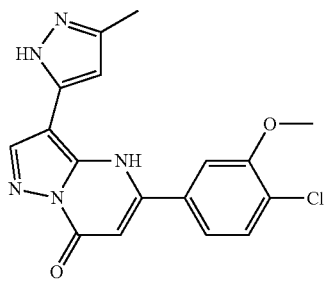 [SMILES: COc1cc(-c2cc(=O)n3ncc(-c4cc(C)n[nH]4)c3[nH]2)ccc1Cl]

To a solution of 5-methyl-1'H,2H-3,4'-bipyrazol-5'-amine (50 mg, 0.3 mmol) in n-BuOH (0.2 mL) was added ethyl 3-(4-chloro-3-methoxyphenyl)-3-oxopropanoate (110 mg, 0.45 mmol) and p-TsOH (5 mg) at room temperature. After refluxing 1 hour, the solids were collected by filtration and washed with methanol (3×2 mL) to afford 5-(4-chloro-3-methoxyphenyl)-3-(3-methyl-1H-pyrazol-5-yl)pyrazolo[1,5-a]pyrimidin-7(4H)-one as a white solid (57.2 mg, 61%).

LCMS (ES, m/z): [M+H]⁺ 356.0
¹H NMR (300 MHz, DMSO) δ 12.71-12.67 (brs, 1H), 8.23 (s, 1H), 7.68-7.58 (m, 2H), 7.43-7.40 (d, J=8.1 Hz, 1H), 6.44 (s, 1H), 6.27 (s, 1H), 4.00 (s, 3H), 2.28 (s, 3H)

EXAMPLE 70

5-(3,4-dichlorophenyl)-3-(1H-pyrazol-3-yl)pyrazolo[1,5-a]pyrimidin-7(4H)-one

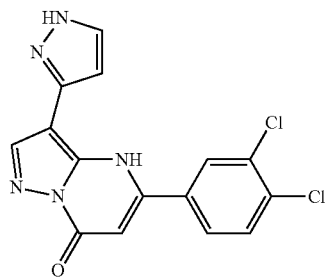 [SMILES: O=c1cc(-c2ccc(Cl)c(Cl)c2)[nH]c2c(-c3cc[nH]n3)cnn12]

To a solution of 1'H,2H-3,4'-bipyrazol-5'-amine (50 mg, 0.33 mmol) in n-BuOH (0.2 mL) was added ethyl 3-(3,4-dichlorophenyl)-3-oxopropanoate (130 mg, 0.50 mmol) and p-TsOH (5 mg) at room temperature. After refluxing 1 hour, the solids were collected by filtration and washed with methanol (3×2 mL) to afford 5-(3,4-dichlorophenyl)-3-(1H-pyrazol-3-yl)pyrazolo[1,5-a]pyrimidin-7(4H)-one as a white solid (93 mg, 80%).

LCMS (ES, m/z): [M+H]⁺ 345.9
¹H NMR (300 MHz, DMSO) δ 8.32-8.28 (d, J=11.7 Hz, 1H), 8.17 (s, 1H), 7.88-7.80 (m, 3H), 6.71-6.70 (d, J=2.1 Hz, 1H), 6.21 (s, 1H)

EXAMPLE 71

5-(1-methyl-1H-indazol-5-yl)-3-(1H-pyrazol-3-yl)-4H,7H-pyrazolo[1,5-a]pyrimidin-7-one

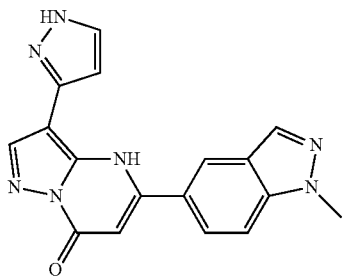 [SMILES: Cn1ncc2cc(-c3cc(=O)n4ncc(-c5cc[nH]n5)c4[nH]3)ccc21]

Step 1: Methyl 4-amino-3-methylbenzoate

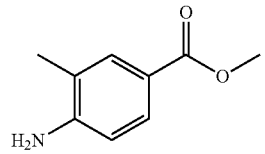

To a solution of methyl 3-methyl-4-nitrobenzoate (50 g, 256.2 mmol) in methanol (1.5 L) was added palladium on carbon (2.5 g). Then H$_2$ (g) was introduced and the reaction was stirred overnight at room temperature. The solids were filtered off and the resulting solution was concentrated in vacuo to afford methyl 4-amino-3-methylbenzoate as a light yellow solid (38 g, 90%).

LCMS (ES, m/z): [M+H]$^+$ 166.1

Step 2: Methyl 1H-indazole-5-carboxylate

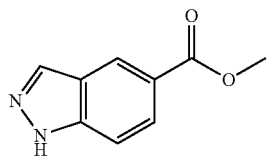

NaNO$_2$ (20 g, 0.29 mol) was added portion wise to a solution of methyl 4-amino-3-methylbenzoate (38 g, 0.23 mol) in aqueous HBF$_4$ (48% wt, 200 mL) at 0° C. The reaction was allowed to stir for 4 h at room temperature. The solids were collected by filtration and washed with 3×200 mL of ether. The solids were dried in an oven under reduced pressure. Under an inert atmosphere of nitrogen, was placed CH$_3$COOK (45 g, 0.46 mol), 18-crown-6 (3 g, 0.012 mol), and chloroform (200 mL). This was followed by the portion wise addition of the dried solid at 0° C. The reaction was stirred for 3 h at room temperature. Then 1 L of H$_2$O was added and the resulting solution was extracted with 5×100 mL of DCM. The organic layers were dried over anhydrous sodium sulfate and the filtrate was concentrated in vacuo to afford a residue which was purified by silica gel column chromatography with 1% methanol in CH$_2$Cl$_2$ to afford of methyl 1H-indazole-5-carboxylate as a yellow solid (22 g, 55%).

LCMS (ES, m/z): [M+H]$^+$ 177.1
$^1$H NMR (300 MHz, DMSO) δ 13.41 (s, 1H), 8.50 (s, 1H), 8.26 (s, 1H), 7.94-7.90 (dd, J=1.50, 8.70 Hz, 1H), 7.64 (d, J=8.70 Hz, 1H), 3.90 (s, 3H)

Step 3: Methyl 1-methyl-1H-indazole-5-carboxylate

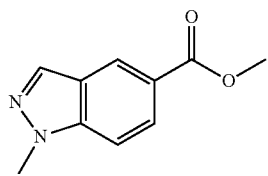

Potassium carbonate (60 g, 0.0.44 mol) was added to a solution of methyl 1H-indazole-5-carboxylate (22 g, 0.13 mol) in N,N-dimethylformamide (200 mL) followed by the dropwise addition of CH$_3$I (62 g, 0.44 mol). Then the reaction was stirred for 5 h at room temperature. The reaction was then quenched by the addition of 200 mL of water, extracted with 4×200 mL of ethyl acetate and the organic layers were combined, dried over anhydrous sodium sulfate, and concentrated in vacuo to give a residue. Purification by silica gel column chromatography with 2% ethyl acetate in petroleum ether afforded methyl 1-methyl-1H-indazole-5-carboxylate as an orange solid (13 g, 55%).

LCMS (ES, m/z): [M+H]+ 191.0
$^1$H NMR (300 MHz, DMSO) δ 8.48 (s, 1H), 8.24 (s, 1H), 7.97-7.94 (dd, J=1.50, 8.70 Hz, 1H), 7.77-7.72 (m, 1H), 4.09 (s, 3H), 3.88 (s, 3H)

Step 4: 1-methyl-1H-indazole-5-carboxylic acid

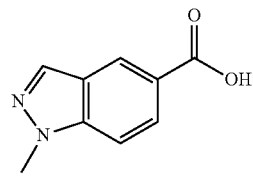

A solution of sodium hydroxide (11 g, 275.00 mmol) in water (30 mL) was added to a solution of methyl 1-methyl-1H-indazole-5-carboxylate (13 g, 68.35 mmol) in methanol (100 mL) and the reaction was stirred overnight at room temperature. The resulting mixture was concentrated in vacuo and dissolved in water (100 ml), adjusted to pH 6 with HCl (3N). The product was precipitated from water and collected by filtration to afford 1-methyl-1H-indazole-5-carboxylic acid as a yellow solid (10 g, 83%).

LCMS (ES, m/z): [M+H]+ 177.0
$^1$H NMR (300 MHz, DMSO) δ12.79 (s, 1H), 8.44 (s, 1H), 8.22 (d, J=0.60 Hz, 1H), 7.97-7.93 (dd, J=1.50, 9.00 Hz, 1H), 7.76-7.73 (dd, J=1.50, 9.00 Hz, 1H), 4.08 (s, 3H)

Step 5: Ethyl 3-(1-methyl-1H-indazol-5-yl)-3-oxopropanoate

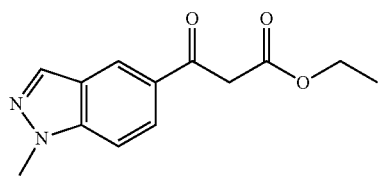 [SMILES: CCOC(=O)CC(=O)c1ccc2c(cnn2C)c1]

To a solution 1-methyl-1H-indazole-5-carboxylic acid (10 g, 61.67 mmol) in THF (200 ml) was added CDI (41 g, 252.85 mmol) with stirring at room temperature for 2 hours followed by the dropwise addition of a solution of the magnesium salt of malonic acid monoethyl ester (prepared via the addition of Et$_3$N (26 g, 185.43 mmol) and MgCl$_2$ (36 g, 278.1 mmol) to a solution of potassium monoethylonate (43 g, 252.64 mmol) in acetonitrile (200 ml) followed by stirring at room temperature for 2 h) at 0° C. The reaction mixture was stirred overnight at RT, quenched by the addition of water (500 ml), and adjusted to pH 4 with HCl (4N). The mixture was extracted with ethyl acetate (5×100 ml) and the organic layers were combined, dried over anhydrous magnesium sulfate and concentrated in vacuo to give a residue which was purified by a silica gel column chromatography by eluting with 2% ethyl acetate in petroleum ether to afford ethyl 3-(1-methyl-1H-indazol-5-yl)-3-oxopropanoate as a red solid (10 g, 72%).

LCMS (ES, m/z): [M+H]$^+$ 247.0
$^1$H NMR (300 MHz, DMSO) δ 8.53 (s, 1H), 8.28 (s, 1H), 7.97-7.94 (dd, J=1.20, 8.70 Hz, 1H), 7.76-7.69 (m, 1H), 4.24 (s, 2H), 4.17-4.08 (m, 5H), 1.22-1.16 (m, 3H)

Step 6: 5-(1-methyl-1H-indazol-5-yl)-3-(1H-pyrazol-3-yl)-4H,7H-pyrazolo[1,5-a]pyrimidin-7-one

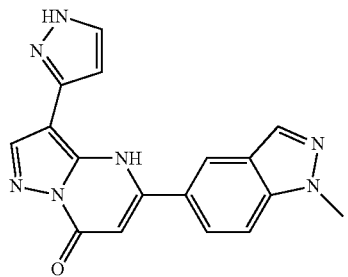 [SMILES: Cn1ncc2cc(-c3cc(=O)n4ncc(-c5cc[nH]n5)c4[nH]3)ccc21]

To a solution of 1'H,2H-3,4'-bipyrazol-5'-amine (50 mg, 0.34 mmol) in n-BuOH (0.5 mL) was added ethyl 3-(1-methyl-1H-indazol-5-yl)-3-oxopropanoate (107 mg, 0.43 mmol) and p-TsOH (3 mg, 0.02 mmol) with stirring for 1 h at 130° C. The solids were collected by filtration and washed with methanol (3×1 mL) to afford 5-(1-methyl-1H-indazol-5-yl)-3-(1H-pyrazol-3-yl)-4H,7H-pyrazolo[1,5-a]pyrimidin-7-one as a light yellow solid (86.6 mg, 75%).

LCMS (ES, m/z): [M+H]$^+$ 331.0

$^1$H NMR (300 MHz, DMSO) δ 8.50 (s, 1H), 8.26-8.22 (dd, J=1.50, 9.00 Hz, 1H), 8.15 (d, J=0.60 Hz, 1H), 8.06 (s, 1H), 7.69 (d, J=8.70 Hz, 1H), 7.52 (s, 1H), 6.79 (s, 1H), 4.08 (s, 3H)

EXAMPLE 72

5-(1-methyl-1H-indazol-5-yl)-3-(4-methylthiazol-2-yl)pyrazolo[1,5-a]pyrimidin-7(4H)-one

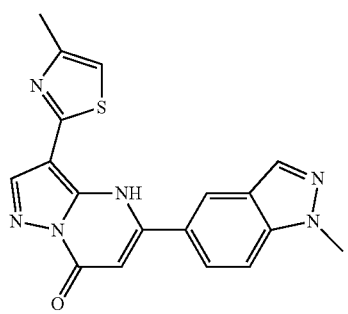 [SMILES: Cc1csc(-c2cnn3c(=O)cc(-c4ccc5c(cnn5C)c4)[nH]c23)n1]

To a solution of 4-(4-methylthiazol-2-yl)-1H-pyrazol-5-amine (50 mg, 0.27 mmol) in n-BuOH (0.2 mL) was added ethyl 3-(1-methyl-1H-indazol-5-yl)-3-oxopropanoate (100 mg, 0.41 mmol) and p-TsOH (5 mg) at room temperature. After refluxing 1 hour, the solids were collected by filtration and washed with methanol (3×2 mL) to afford 5-(1-methyl-1H-indazol-5-yl)-3-(4-methylthiazol-2-yl)pyrazolo[1,5-a]pyrimidin-7(4H)-one as a white solid (86.3 mg, 86%).

LCMS (ES, m/z): [M+H]$^+$ 363.0

$^1$H NMR (300 MHz, DMSO+NH$_3$ (saturated D$_2$O solution)) δ 8.56 (s, 1H), 8.34-8.31 (m, 1H), 8.15-8.14 (m, 2H), 7.71-7.68 (d, J=9.0 Hz, 1H), 6.96 (s, 1H), 6.17 (s, 1H), 4.08 (s, 3H), 2.37 (s, 3H)

EXAMPLE 73

5-(1-methyl-1H-indazol-5-yl)-3-(oxazol-2-yl)-4H,7H-pyrazolo[1,5-a]pyrimidin-7-one

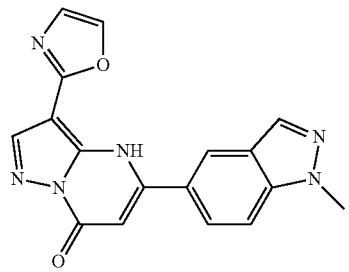 [SMILES: Cn1ncc2cc(-c3cc(=O)n4ncc(-c5ncco5)c4[nH]3)ccc21]

Step 1: 2-(ethoxymethylene)malononitrile

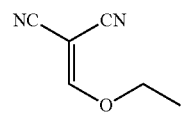

To a solution of malononitrile (20 g, 302.75 mmol) in methanol (75 mL) was added a solution of trimethoxyorthoformate (67 g, 452.09 mmol) in acetic acid (75 mL) and the reaction was stirred overnight at 100° C. The resulting mixture was concentrated in vacuo to afford 2-(ethoxymethylene)malononitrile as a crude red oil (20 g, crude) which was used without purification in the next step.

Step 2: 5-amino-1H-pyrazole-4-carbonitrile

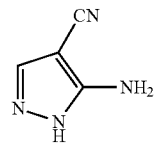

N$_2$H$_4$.H$_2$O (33 g, 640 mmol) was added to a solution of 2-(ethoxymethylene)malononitrile (20 g, 163.77 mmol) in acetic acid (200 mL) and the reaction was stirred overnight at 85° C. The resulting mixture was concentrated in vacuo and the residue was diluted with H$_2$O (100 mL) and extracted with ethyl acetate (20×500 mL) and the organic layers were combined, dried over anhydrous sodium sulfate and concentrated in vacuo to afford a residue which was purified by silica gel column chromatograpy with 50% ethyl acetate in petroleum ether to afford 5-amino-1H-pyrazole-4-carbonitrile as a light yellow solid (8 g, 45%).

Step 3: 5-(1-methyl-1H-indazol-5-yl)-7-oxo-4H,7H-pyrazolo[1,5-a]pyrimidine-3-carbonitrile

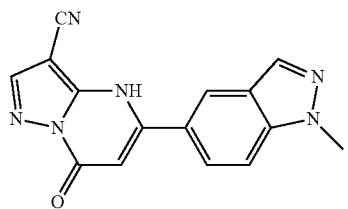 [SMILES: Cn1ncc2cc(-c3cc(=O)n4ncc(C#N)c4[nH]3)ccc21]

To a solution of 5-amino-1H-pyrazole-4-carbonitrile (500 mg, 4.63 mmol) in n-BuOH (1 mL) was added ethyl 3-(1-methyl-1H-indazol-5-yl)-3-oxopropanoate (1.7 g, 6.90 mmol), p-TsOH (40 mg, 0.23 mmol) with stirring for 1 h at 130° C. The product was collected by filtration and washed with methanol (3×5 ml) to afford 5-(1-methyl-1H-indazol-5-yl)-7-oxo-4H,7H-pyrazolo[1,5-a]pyrimidine-3-carbonitrile as a light yellow solid (1 g, 74%).

LCMS (ES, m/z): [M+H]+ 291.0; $^1$H NMR (300 MHz, DMSO) δ 8.40 (s, 1H), 8.25 (s, 1H), 8.20 (s, 1H), 8.01 (d, J=9.00 Hz, 1H), 7.76 (d, J=9.00 Hz, 1H), 6.28 (s, 1H), 4.12 (s, 3H)

Step 4: 5-(1-methyl-1H-indazol-5-yl)-7-oxo-4H,7H-pyrazolo[1,5-a]pyrimidine-3-carboxamide

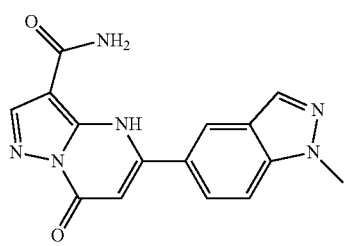 [SMILES: Cn1ncc2cc(-c3cc(=O)n4ncc(C(N)=O)c4[nH]3)ccc21]

Concentrated sulfuric acid (5 mL) was added to 5-(1-methyl-1H-indazol-5-yl)-7-oxo-4H,7H-pyrazolo[1,5-a]pyrimidine-3-carbonitrile (1 g, 3.44 mmol) and the reaction was stirred for 1 h at room temperature. The reaction was then quenched by the addition of ice/water (50 mL). The solids were collected by filtration, washed with water (3×1 mL) and dried in a vacuum oven to afford 5-(1-methyl-1H-indazol-5-yl)-7-oxo-4H,7H-pyrazolo[1,5-a]pyrimidine-3-carboxamide as a light yellow solid (900 mg, 85%).

LCMS (ES, m/z): [M+H]+ 309.0

$^1$H NMR (300 MHz, DMSO) δ 8.40 (d, J=0.90 Hz, 1H), 8.22 (s, 1H), 8.13 (d, J=0.90 Hz, 1H), 8.09-8.06 (dd, J=1.50, 8.70 Hz, 1H), 7.95 (s, 1H), 7.69 (d, J=8.70 Hz, 1H), 6.12 (s, 1H), 4.07 (s, 3H)

Step 5: 5-(1-methyl-1H-indazol-5-yl)-3-(oxazol-2-yl)-4H,7H-pyrazolo[1,5-a]pyrimidin-7-one

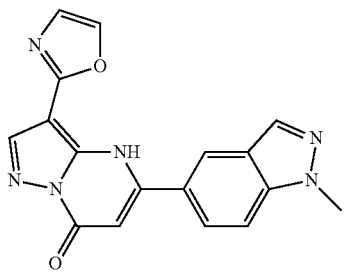 [SMILES: Cn1ncc2cc(-c3cc(=O)n4ncc(-c5ncco5)c4[nH]3)ccc21]

To a solution of 5-(1-methyl-1H-indazol-5-yl)-7-oxo-4H,7H-pyrazolo[1,5-a]pyrimidine-3-carboxamide (200 mg, 0.65 mmol) in NMP (1 mL) was added p-TsOH (6 mg, 0.03 mmol), 2-bromo-1,1-diethoxyethane (19.5 mg, 1.13 mmol) and the reaction was stirred for 20 min at 100° C. The reaction was quenched by the addition of methanol (1 mL). The solids were collected by filtration and washed with methanol (3×1 mL), concentrated and purified by silica gel column chromatography with 10% methanol in dichloromethane to afford 5-(1-methyl-1H-indazol-5-yl)-3-(1,3-oxazol-2-yl)-4H,7H-pyrazolo[1,5-a]pyrimidin-7-one as a light yellow solid (43.2 mg, 20%).

LCMS (ES, m/z): [M+H]+ 333.0

$^1$H NMR (300 MHz, DMSO) δ8.46 (s, 1H), 8.22-8.19 (dd, J=0.90, 9.00 Hz, 1H), 8.14 (d, J=9.00 Hz, 2H), 8.01 (s, 1H), 7.68 (d, J=9.00 Hz, 1H), 6.15 (s, 1H), 4.08 (s, 3H)

EXAMPLE 74

3-(3-methyl-1,2,4-oxadiazol-5-yl)-5-(1-methyl-1H-indazol-5-yl)-4H,7H-pyrazolo[1,5-a]pyrimidin-7-one

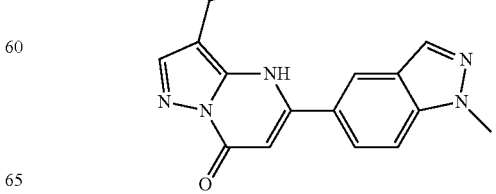

Step 1: N-(1-(dimethylamino)ethylidene)-5-(1-methyl-1H-indazol-5-yl)-7-oxo-4,7-dihydropyrazolo[1,5-a]pyrimidine-3-carboxamide

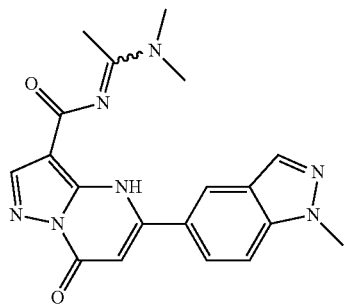 [SMILES: CC(=NC(=O)c1cnn2c(=O)cc(-c3ccc4c(cnn4C)c3)[nH]c12)N(C)C]

To a solution of 5-(1-methyl-1H-indazol-5-yl)-7-oxo-4H,7H-pyrazolo[1,5-a]pyrimidine-3-carboxamide (400 mg, 1.30 mmol) in N,N-dimethylformamide (0.8 mL) was added DMA-DMA (0.8 mL) with stirring for 4 h at 130° C. The resulting mixture was concentrated in vacuo to afford N-(1-(dimethylamino)ethylidene)-5-(1-methyl-1H-indazol-5-yl)-7-oxo-4,7-dihydropyrazolo[1,5-a]pyrimidine-3-carboxamide as a dark red oil (500 mg, crude).

Step 2: 3-(3-methyl-1,2,4-oxadiazol-5-yl)-5-(1-methyl-1H-indazol-5-yl)-4H,7H-pyrazolo[1,5-a]pyrimidin-7-one

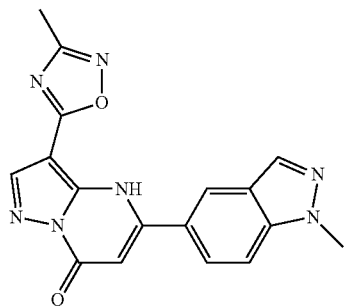 [SMILES: Cc1noc(-c2cnn3c(=O)cc(-c4ccc5c(cnn5C)c4)[nH]c23)n1]

$NH_2OH \cdot HCl$ (139 mg, 2.01 mmol) was added to a solution of N-(1-(dimethylamino)ethylidene)-5-(1-methyl-1H-indazol-5-yl)-7-oxo-4,7-dihydropyrazolo[1,5-a]pyrimidine-3-carboxamide (500 mg, 1.32 mmol) in 1,4-dioxane (3 mL) and the reaction was stirred for 5 mins at room temperature. Then a solution of 10% aqueous sodium hydroxide (1 mL) in AcOH (5 mL) was added at room temperature. After stirring 1 hour at 100° C., the resulting mixture was concentrated in vacuo. The residue was diluted with water (50 mL). The solids were collected by filtration and purified by silica gel column chromatography eluting with 10% methanol in dichloromethane to afford 3-(3-methyl-1,2,4-oxadiazol-5-yl)-5-(1-methyl-1H-indazol-5-yl)-4H,7H-pyrazolo[1,5-a]pyrimidin-7-one as an off-white solid (57.3 mg, 12%).

LCMS (ES, m/z): $[M+H]^+$ 348.0

$^1$H NMR (300 MHz, DMSO) δ 8.50 (s, 1H), 8.22-8.16 (dd, J=1.50, 8.70 Hz, 3H), 7.70 (d, J=9.00 Hz, 1H), 6.24 (s, 1H), 4.08 (s, 3H), 2.34 (s, 3H)

EXAMPLE 75

2-hydroxy-5-(3-(oxazol-2-yl)-7-oxo-4,7-dihydropyrazolo[1,5-a]pyrimidin-5-yl)benzonitrile

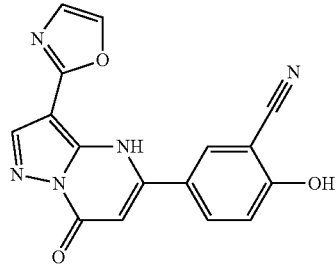 [SMILES: N#Cc1cc(-c2cc(=O)n3ncc(-c4ncco4)c3[nH]2)ccc1O]

Step 1: ethyl 3-(benzo[d]isoxazol-5-yl)-3-oxopropanoate

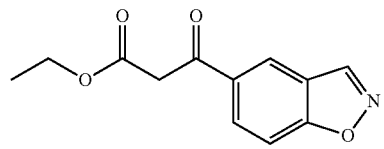 [SMILES: CCOC(=O)CC(=O)c1ccc2oncc2c1]

To a solution benzo[d]isoxazole-5-carboxylic acid (1.4 g, 8.58 mmol, 1.00 equiv) in THF (20 ml) was added CDI (2.1 g, 12.95 mmol, 1.50 equiv) with stirring at room temperature for 2 hours and then a solution of the magnesium salt of malonic acid monoethyl ester [prepared via the addition of $Et_3N$ (2.6 g, 25.69 mmol, 3.00 equiv) and $MgCl_2$ (3.7 g, 38.95 mmol, 4.50 equiv) to a solution of potassium monoethylonate (4.4 g, 25.88 mmol, 3.00 equiv) in acetonitrile (70 ml)] was added dropwise. The reaction mixture was then stirred overnight at RT, quenched by the addition of water (70 ml) and adjusted to pH 4 with aq. HCl (4N). The mixture was extracted with ethyl acetate (4×30 ml) and the organic layers were combined, dried over anhydrous magnesium sulfate and concentrated in vacuo to afford a residue, which was purified by silica gel column chromatography with 1.25% methanol in dichloromethane to afford ethyl 3-(benzo[d]isoxazol-5-yl)-3-oxopropanoate as a yellow solid (1.5 g, 75%).

LC-MS: (ES, m/z): $[M+H]^+$ 234

$^1$H NMR (300 MHz, DMSO): δ 7.85-7.84 (d, J=2.4 Hz, 1H), 7.58-7.55 (dd, J=9.3 Hz, 1.5 Hz, 1H), 6.20-6.16 (dd, J=9.3 Hz, 1.5 Hz, 1H), 4.11-4.04 (q, J=7.2 Hz, 2H), 3.83 (s, 2H), 1.22-1.17 (t, J=7.2 Hz, 3H)

Step 2: 5-(3-cyano-4-hydroxyphenyl)-7-oxo-4,7-dihydropyrazolo[1,5-a]pyrimidine-3-carbonitrile

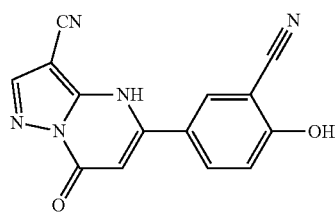 [SMILES: N#Cc1cc(-c2cc(=O)n3ncc(C#N)c3[nH]2)ccc1O]

To a solution of 5-amino-1H-pyrazole-4-carbonitrile (1.1 g, 10.18 mmol, 1.00 equiv) in n-BuOH (1 mL) was added ethyl 3-(benzo[d]isoxazol-5-yl)-3-oxopropanoate (2.8 g, 12.01 mmol, 1.20 equiv) and p-TsOH (87 mg, 0.51 mmol, 0.05 equiv) at room temperature. The resulting solution was stirred for 2 h at 120° C. in an oil bath. The reaction progress was monitored by LCMS. The mixture was poured into 2 mL of methanol. The solids were collected by filtration. The solid was washed with 4×1 mL of methanol. This resulted in 900 mg (32%) of 5-(3-cyano-4-hydroxyphenyl)-7-oxo-4,7-dihydropyrazolo[1,5-a]pyrimidine-3-carbonitrile as a yellow solid.

LC-MS: (ES, m/z): [M+H]$^+$ 278

$^1$H NMR (300 MHz, DMSO): δ 11.90 (s, 1H), 8.43 (s, 1H), 8.20-8.19 (d, J=2.4 Hz, 1H), 8.00-7.96 (dd, J=9.0 Hz, 2.4 Hz, 1H), 7.14-7.08 (m, 1H), 6.28 (s, 1H)

Step 3: 5-(3-cyano-4-hydroxyphenyl)-7-oxo-4,7-dihydropyrazolo[1,5-a]pyrimidine-3-carboxamide

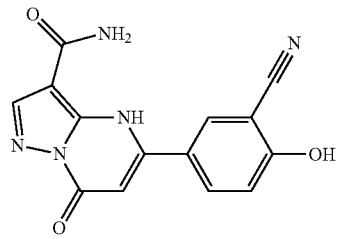 [SMILES: N#Cc1cc(-c2cc(=O)n3ncc(C(N)=O)c3[nH]2)ccc1O]

To a solution of 5-(3-cyano-4-hydroxyphenyl)-7-oxo-4,7-dihydropyrazolo[1,5-a]pyrimidine-3-carbonitrile (800 mg, 2.89 mmol, 1.00 equiv) in methanol (14.4 mL)/DMSO (9 mL) was added potassium carbonate (24 mL). This was followed by the dropwise addition of H$_2$O$_2$ (24 mL) over 20 min. The reaction was stirred for 3 h at 50° C. in an oil bath. The reaction progress was monitored by LCMS. The resulting mixture was concentrated in vacuo. The residue was diluted with 20 mL of water. The pH value of the solution was adjusted to pH 3 with HCl (4N). The solids were collected by filtration. The solid was washed with 4×2 mL of methanol. This resulted in 800 mg (94%) of 5-(3-cyano-4-hydroxyphenyl)-7-oxo-4,7-dihydropyrazolo[1,5-a]pyrimidine-3-carboxamide as a brown solid.

LC-MS (ES, m/z): [M+H]$^+$ 296

$^1$H NMR (300 MHz, DMSO): δ 11.64-11.51 (m, 2H), 8.24-7.94 (m, 4H), 7.26-7.06 (m, 2H), 6.22 (s, 1H)

Step 4: 2-hydroxy-5-(3-(oxazol-2-yl)-7-oxo-4,7-dihydropyrazolo[1,5-a]pyrimidin-5-yl)benzonitrile

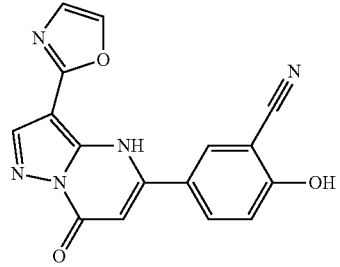 [SMILES: N#Cc1cc(-c2cc(=O)n3ncc(-c4ncco4)c3[nH]2)ccc1O]

To a solution of 5-(3-cyano-4-hydroxyphenyl)-7-oxo-4,7-dihydropyrazolo[1,5-a]pyrimidine-3-carboxamide (250 mg, 0.85 mmol, 1.00 equiv) in NMP (0.3 mL) was added 2-bromo-1,1-diethoxyethane (250 mg, 1.27 mmol, 1.50 equiv) and p-TsOH (7 mg, 0.05 equiv). The resulting solution was stirred for 0.5 h at 110° C. in an oil bath. The reaction progress was monitored by LCMS. The resulting solution was diluted with 3 mL of water and the solids were collected by filtration. The crude product was purified by Prep-HPLC under the following conditions: Column: 5 um, 19*150 mm; mobile phase: water with 0.05% TFA and MeCN (15.0% MeCN up to 28.0% in 9 min, up to 97.0% in 1 min, down to 15.0% in 1 min) This resulted in 22.3 mg (8%) of 2-hydroxy-5-(3-(oxazol-2-yl)-7-oxo-4,7-dihydropyrazolo[1,5-a]pyrimidin-5-yl)benzonitrile as a light yellow solid.

LC-MS (ES, m/z): [M+H]$^+$ 320

$^1$H NMR (300 MHz, DMSO): δ 11.91 (s, 1H), 8.38 (s, 1H), 8.21 (s, 1H), 8.14-8.13 (d, J=2.1 Hz, 1H), 7.96-7.93 (dd, J=8.7 Hz, 2.1 Hz, 1H), 7.42 (s, 1H), 7.20-7.10 (m, 1H), 6.24 (s, 1H)

EXAMPLE 76

5-(4-chloro-3-isopropoxyphenyl)-3-(1-methyl-1H-pyrazol-5-yl)pyrazolo[1,5-a]pyrimidin-7(4H)-one

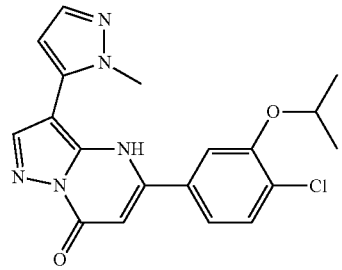 [SMILES: CC(C)Oc1cc(-c2cc(=O)n3ncc(-c4ccnn4C)c3[nH]2)ccc1Cl]

Step 1: isopropyl 4-chloro-3-isopropoxybenzoate

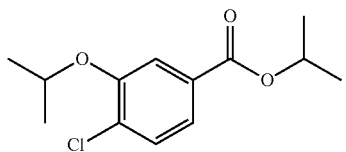 [SMILES: CC(C)OC(=O)c1ccc(Cl)c(OC(C)C)c1]

To a solution of 4-chloro-3-hydroxybenzoic acid (12 g, 69.54 mmol) in N,N-dimethylformamide (200 mL) was added potassium carbonate (30 g, 217.06 mmol) and 2-iodopropane (42 g, 247.07 mmol) at 0° C. and the reaction was stirred overnight at room temperature. The resulting mixture was concentrated in vacuo. The residue was diluted with H$_2$O (500 mL), extracted with ethyl acetate (3×100 mL). The organic layers were combined, dried over anhydrous sodium sulfate and concentrated in vacuo to give a residue which was purified by a silica gel column chromatography eluting with 5% ethyl acetate in petroleum ether to afford isopropyl 4-chloro-3-isopropoxybenzoate as a white solid (14 g, 80%).

LCMS (ES, m/z): [M+H]+ 257.0

¹H NMR (300 MHz, DMSO) δ7.59-7.56 (m, 2H), 7.52-7.49 (m, 1H), 5.19-5.19 (m, 1H), 4.79-4.71 (m, 1H), 1.33-1.31 (m, 12H)

Step 2: 4-chloro-3-isopropoxybenzoic acid

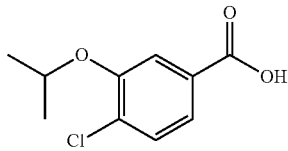

To a solution of isopropyl 4-chloro-3-isopropoxybenzoate (14 g, 54.53 mmol) in methanol (200 mL) was added a solution of sodium hydroxide (8.75 g, 218.75 mmol) in water (20 mL) and the reaction was stirred for 10 h at 55° C. The resulting mixture was concentrated in vacuo. The residue was dissolved in water (100 ml), adjusted to pH 4 with aq. HCl (3N). The product was precipitated from water and collected by filtration to afford 4-chloro-3-isopropoxybenzoic acid as a white solid (10 g, 85%).

LCMS (ES, m/z): [M+H]+ 215.0

¹H NMR (300 MHz, DMSO) δ13.19 (s, 1H), 7.59-7.49 (m, 3H), 4.78-4.70 (m, 1H), 1.33 (d, J=6.00 Hz, 6H)

Step 3: ethyl 3-(4-chloro-3-isopropoxyphenyl)-3-oxopropanoate

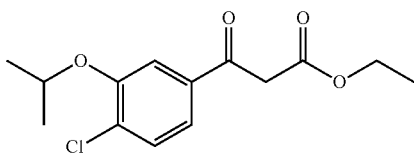 [SMILES: CCOC(=O)CC(=O)c1ccc(Cl)c(OC(C)C)c1]

To a solution 4-chloro-3-isopropoxybenzoic acid (10 g, 46.59 mmol) in tetrahydrofuran (200 mL) was added CDI (23 g, 141.84 mmol) and the reaction was stirred at room temperature for 3 hours. Then a solution of the magnesium salt of malonic acid monoethyl ester [prepared via the addition of Et₃N (14 g, 138.35 mmol) and MgCl₂ (21 g) to a solution of potassium monoethylonate (74 g, 434.77 mmol) in acetonitrile (300 ml) followed by stirring at room temperature for 2 h] was added dropwise at 0° C. The reaction mixture was then stirred overnight at RT, quenched by the addition of water (250 ml) and adjusted to pH 2 with aq. HCl (3N). The mixture was extracted with ethyl acetate with (4×200 ml) and the organic layers were combined, dried over anhydrous magnesium sulfate and concentrated in vacuo to give a residue, which was purified by silica gel column chromatography with 20% ethyl acetate in petroleum ether to afford ethyl 3-(4-chloro-3-isopropoxyphenyl)-3-oxopropanoate as a white solid (11 g, 83%).

LCMS (ES, m/z): [M+H]+ 285.0

¹H NMR (300 MHz, DMSO) δ 7.55 (d, J=1.50 Hz, 1H), 7.47-7.42 (m, 2H), 4.71-4.61 (m, 1H), 4.31-4.18 (m, 2H), 3.95 (s, 2H), 1.64 (d, J=5.40 Hz, 6H), 1.26 (t, J=7.20 Hz, 3H)

Step 4: 5-(4-chloro-3-isopropoxyphenyl)-3-(1-methyl-1H-pyrazol-5-yl)pyrazolo[1,5-a]pyrimidin-7(4H)-one

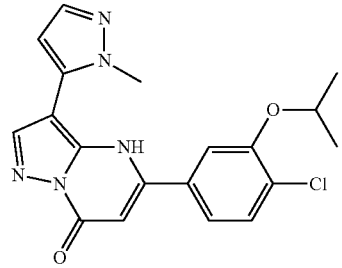 [SMILES: CC(C)Oc1cc(-c2cc(=O)n3ncc(-c4ccnn4C)c3[nH]2)ccc1Cl]

To a solution of 2-methyl-1'H,2H-3,4'-bipyrazol-5'-amine (50 mg, 0.31 mmol) in n-BuOH (1 mL) was added ethyl 3-(4-chloro-3-isopropoxyphenyl)-3-oxopropanoate (130 mg, 0.46 mmol) and p-TsOH (2.63 mg, 0.02 mmol) at room temperature. After refluxing 1 hour, the solids were collected by filtration and washed with methanol (3×2 mL) to afford 5-(4-chloro-3-isopropoxyphenyl)-3-(1-methyl-1H-pyrazol-5-yl)pyrazolo[1,5-a]pyrimidin-7(4H)-one as a white solid (69.4 mg, 59%).

LCMS (ES, m/z): [M+H]+ 384.0

¹H NMR (300 MHz, DMSO) δ 7.95 (s, 1H), 7.80 (s, 1H), 7.60 (d, J=7.80 Hz, 1H), 7.47 (d, J=8.10 Hz, 1H), 7.39 (s, 1H), 7.21 (s, 1H), 6.58 (s, 1H), 6.07 (s, 1H), 4.81-4.73 (m, 1H), 4.31-4.18 (m, 2H), 4.00 (s, 3H), 1.37 (d, J=6.00 Hz, 6H)

EXAMPLE 77

5-(4-chloro-3-isopropoxyphenyl)-3-(3-methyl-1,2,4-oxadiazol-5-yl)pyrazolo[1,5-a]pyrimidin-7(4H)-one

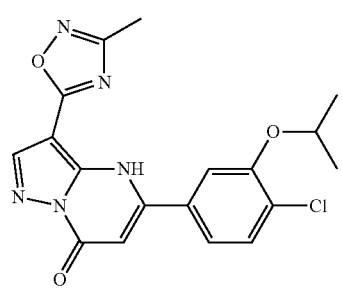 [SMILES: Cc1noc(-c2cnn3c(=O)cc(-c4ccc(Cl)c(OC(C)C)c4)[nH]c23)n1]

Step 1: 5-(4-chloro-3-isopropoxyphenyl)-7-oxo-4,7-dihydropyrazolo[1,5-a]pyrimidine-3-carbonitrile

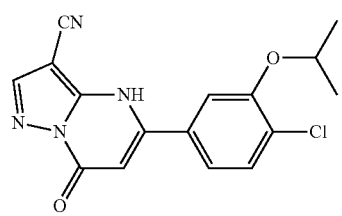 [SMILES: CC(C)Oc1cc(-c2cc(=O)n3ncc(C#N)c3[nH]2)ccc1Cl]

To a solution of 5-amino-1H-pyrazole-4-carbonitrile (400 mg, 3.70 mmol) in n-BuOH (1 mL) was added ethyl 3-(4-chloro-3-isopropoxyphenyl)-3-oxopropanoate (1.5 g, 5.27 mmol) and p-TsOH (32 mg, 0.1 mmol) and the reaction was stirred for 1 h at 130° C. The solids were collected by filtration and washed with methanol (3×1 mL) to afford 5-(4-chloro-3-isopropoxyphenyl)-7-oxo-4,7-dihydropyrazolo[1,5-a]pyrimidine-3-carbonitrile as a light yellow solid (880 mg, 72%).

LCMS (ES, m/z): [M+H]$^+$ 329.0

$^1$H NMR (300 MHz, DMSO) δ 8.44 (s, 1H), 7.65 (d, J=8.40 Hz, 1H), 7.57 (d, J=1.80 Hz, 1H), 7.42-7.39 (m, 1H), 6.34 (s, 1H), 4.92-4.84 (m, 1H), 1.35 (d, J=6.00 Hz, 6H)

Step 2: 5-(4-chloro-3-isopropoxyphenyl)-7-oxo-4,7-dihydropyrazolo[1,5-a]pyrimidine-3-carboxamide

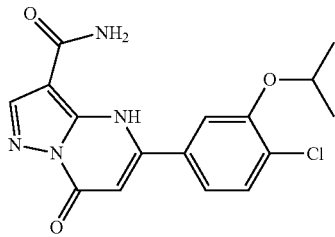 [SMILES: CC(C)Oc1cc(-c2cc(=O)n3ncc(C(N)=O)c3[nH]2)ccc1Cl]

To a solution of 5-(4-chloro-3-isopropoxyphenyl)-7-oxo-4,7-dihydropyrazolo[1,5-a]pyrimidine-3-carbonitrile (880 mg, 2.68 mmol) in DMSO/MeOH (10 mL/16 mL) was added a solution of potassium carbonate (3 M) (25 mL) at room temperature. Then the H$_2$O$_2$ (30% aq., 25 mL) was added dropwise at 60° C. The resulting solution was stirred for 3 h at 60° C. The resulting mixture was concentrated in vacuo. The residue was diluted with 100 mL of H$_2$O and adjusted to pH 4 with aq. HCl (4N). The solids were collected by filtration, washed with water (3×10 mL) and dried in an oven under reduced pressure to afford 5-(4-chloro-3-isopropoxyphenyl)-7-oxo-4,7-dihydropyrazolo[1,5-a]pyrimidine-3-carboxamide as a light yellow solid (880 mg, 95%).

LCMS (ES, m/z): [M+H]+ 347.0

$^1$H NMR (300 MHz, DMSO) δ7.98 (s, 1H), 7.72 (d, J=1.20 Hz, 1H), 7.59-7.56 (m, 1H), 7.49 (d, J=6.00 Hz, 1H), 6.13 (s, 1H), 4.81-4.79 (m, 1H), 1.35 (d, J=4.50 Hz, 6H)

Step 3: (E)-5-(4-chloro-3-isopropoxyphenyl)-N-(1-(dimethylamino)ethylidene)-7-oxo-4,7-dihydropyrazolo[1,5-a]pyrimidine-3-carboxamide

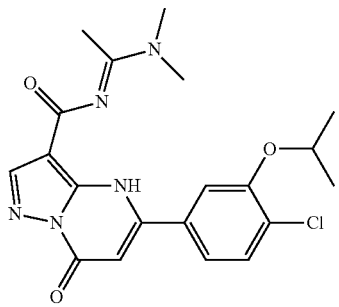 [SMILES: C/C(=N\C(=O)c1cnn2c(=O)cc(-c3ccc(Cl)c(OC(C)C)c3)[nH]c12)N(C)C]

To a solution of 5-(4-chloro-3-isopropoxyphenyl)-7-oxo-4,7-dihydropyrazolo[1,5-a]pyrimidine-3-carboxamide (400 mg, 1.15 mmol) in N,N-dimethylformamide (1 mL) was added DMA-DMA (1 mL) and the reaction was stirred for 2 h at 130° C. The resulting mixture was concentrated in vacuo to afford (E)-5-(4-chloro-3-isopropoxyphenyl)-N-(1-(dimethylamino)ethylidene)-7-oxo-4,7-dihydropyrazolo[1,5-a]pyrimidine-3-carboxamide as black oil (400 mg, crude).

Step 4: 5-(4-chloro-3-isopropoxyphenyl)-3-(3-methyl-1,2,4-oxadiazol-5-yl)pyrazolo[1,5-a]pyrimidin-7(4H)-one

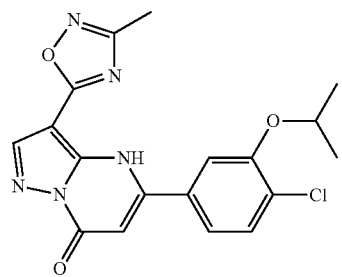 [SMILES: Cc1noc(-c2cnn3c(=O)cc(-c4ccc(Cl)c(OC(C)C)c4)[nH]c23)n1]

NH$_2$OH.HCl (131 mg) was added to a solution of (E)-5-(4-chloro-3-isopropoxyphenyl)-N-(1-(dimethylamino)ethylidene)-7-oxo-4,7-dihydropyrazolo[1,5-a]pyrimidine-3-carboxamide (400 mg, 0.96 mmol) in 1,4-dioxane (5 mL) and the reaction was stirred for 5 min at room temperature. Then a solution of sodium hydroxide (10% aqueous, 2 mL) in AcOH (10 mL) was added at room temperature. After stirring 1 hr at 100° C., the resulting mixture was concentrated in vacuo. The residue was diluted with water (50 mL) and the solids were collected by filtration, Further purification by silica gel column chromatography with 10% methanol in dichloromethane afforded 5-(4-chloro-3-isopropoxyphenyl)-3-(3-methyl-1,2,4-oxadiazol-5-yl)pyrazolo[1,5-a]pyrimidin-7(4H)-one as a white solid (59.8 mg, 16%).

LCMS (ES, m/z): [M+H]$^+$ 386.0

$^1$H NMR (300 MHz, DMSO) δ 8.21 (s, 1H), 7.88 (d, J=1.80 Hz, 1H), 7.70-7.67 (dd, J=2.10, 8.40 Hz, 1H), 7.50 (d, J=8.40 Hz, 1H), 6.23 (s, 1H), 4.81-4.78 (m, 1H), 2.32 (s, 3H), 1.38 (d, J=6.00 Hz, 6H)

EXAMPLE 78

5-(3-ethoxy-4-fluorophenyl)-3-(1-methyl-1H-pyrazol-5-yl)pyrazolo[1,5-a]pyrimidin-7(4H)-one

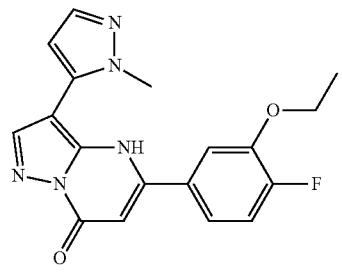 [SMILES: CCOc1cc(-c2cc(=O)n3ncc(-c4ccnn4C)c3[nH]2)ccc1F]

To a solution of 2-methyl-1'H,2H-3,4'-bipyrazol-5'-amine (50 mg, 0.3 mmol) in n-BuOH (0.2 mL) was added ethyl 3-(3-ethoxy-4-fluorophenyl)-3-oxopropanoate (118 mg, 0.45 mmol) and p-TsOH (5 mg) at room temperature. After refluxing 1 hour, the solids were collected by filtration and washed with methanol (3×2 mL) to afford 5-(3-ethoxy-4-fluorophenyl)-3-(1-methyl-1H-pyrazol-5-yl)pyrazolo[1,5-a]pyrimidin-7(4H)-one as a white solid (69.6 mg, 64%).

LCMS (ES, m/z): [M+H]$^+$ 354.0

$^1$H NMR (300 MHz, DMSO) δ 7.95 (s, 1H), 7.76-7.73 (m, 1H), 7.56 (brs, 1H), 7.40 (d, J=1.5 Hz, 1H), 7.28 (s, 1H), 7.29-7.22 (m, 1H), 6.55 (d, J=1.5 Hz, 1H), 6.07 (s, 1H), 4.24-4.17 (q, J=7.2 Hz, 2H), 3.97 (s, 3H), 1.41-1.36 (t, J=7.2 Hz, 2H)

EXAMPLE 79

5-(4-fluoro-3-methoxyphenyl)-3-(1-methyl-1H-pyrazol-5-yl)pyrazolo[1,5-a]pyrimidin-7(4H)-one

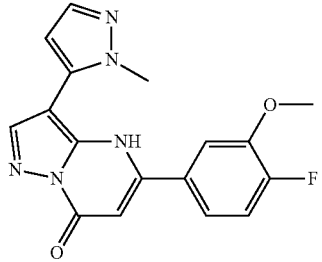 [SMILES: COc1cc(-c2cc(=O)n3ncc(-c4ccnn4C)c3[nH]2)ccc1F]

Step 1: Methyl 4-fluoro-3-methoxybenzoate

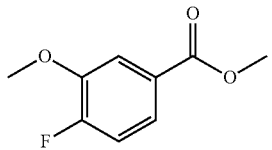

To a solution of 4-fluoro-3-hydroxybenzoic acid (15 g, 100 mmol) in DMF (100 mL) was added MeI (34 g, 250 mmol) and potassium carbonate (34 g, 250 mmol) at room temperature. After 10 hours of stirring, the solution was concentrated in vacuo to afford a residue, which was dissolved in ethyl acetate (400 mL), washed with brine (4×100 mL) and dried over anhydrous sodium sulfate. Concentration in vacuo afforded methyl 4-fluoro-3-methoxybenzoate as a yellow solid (11 g, 85%), which was purified by a silica gel column chromatography eluting with 1%-5% ethyl acetate in petroleum ether.

$^1$H-NMR (300 MHz, CDCl$_3$) δ 7.67-7.61 (m, 2H), 7.15-7.08 (m, 1H), 3.94 (s, 3H), 3.91 (s, 3H)

Step 2: 4-fluoro-3-methoxybenzoic acid

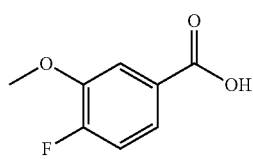

A solution of methyl 4-fluoro-3-methoxybenzoate (11 g, 59.8 mmol) in methanol (100 mL) was treated with sodium hydroxide (9.5 g, 240 mmol) in water (20 mL) for 4 h at room temperature. The solvent was removed in vacuo to afford a residue, which was dissolved in water (100 mL) and the pH value was adjusted to 4 with HCl (1N). The solids were collected by filtration, washed with water (3×50 mL) and dried to afford 4-fluoro-3-methoxybenzoic acid as a white solid (9 g, 97%).

$^1$H-NMR (300 MHz, DMSO) δ 7.66-7.55 (m, 2H), 7.37-7.30 (m, 1H), 3.91 (s, 3H)

Step 3: Ethyl 3-(4-fluoro-3-methoxyphenyl)-3-oxopropanoate

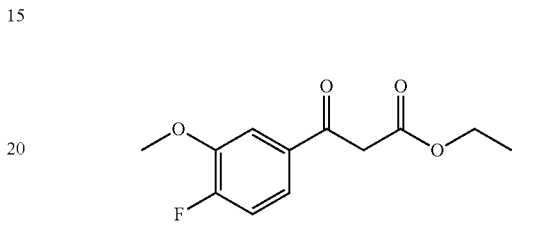

To a solution 4-fluoro-3-methoxybenzoic acid (9 g, 53 mmol) in THF (100 ml) was added CDI (13 g, 80 mmol) and the reaction was stirred at room temperature for 3 hours. Then a solution of the magnesium salt of malonic acid monoethyl ester [prepared via the addition of Et$_3$N (16 g, 158 mmol) and MgCl$_2$ (23 g, 238 mmol) to a solution of potassium monoethylonate (27 g, 158 mmol) in acetonitrile (200 ml) followed by stirring at room temperature for 2 h] was added dropwise at 0° C. The reaction mixture was stirred overnight at RT, quenched by the addition of water (100 ml) and adjusted to pH 3-4 with HCl (1N). The mixture was extracted with ethyl acetate with (4×100 ml) and the organic layers were combined, dried over anhydrous magnesium sulfate and concentrated in vacuo to afford a residue, which was purified by silica gel column chromatography with 50% ethyl acetate in petroleum ether to afford ethyl 3-(4-fluoro-3-methoxyphenyl)-3-oxopropanoate as yellow oil (10 g, 79%)

$^1$H NMR (300 MHz, CDCl$_3$) δ 7.64-7.7.39 (m, 2H), 7.17-7.07 (m, 1H), 4.30-4.19 (m, 2H), 3.96-3.94 (m, 5H), 1.32-1.28 (m, 3H)

Step 4: 5-(4-fluoro-3-methoxyphenyl)-3-(1-methyl-1H-pyrazol-5-yl)pyrazolo[1,5-a]pyrimidin-7(4H)-one

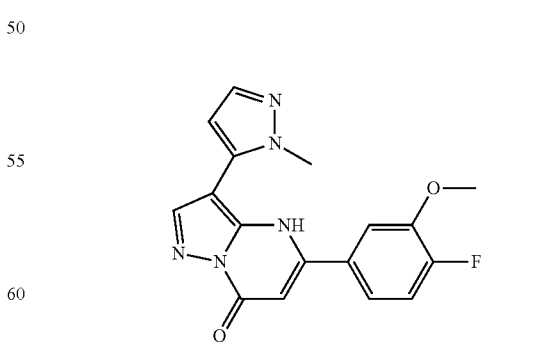

To a solution of 2-methyl-1'H,2H-3,4'-bipyrazol-5'-amine (50 mg, 0.3 mmol) in n-BuOH (0.2 mL) was added ethyl 3-(4-fluoro-3-methoxyphenyl)-3-oxopropanoate (118 mg, 0.45 mmol) and p-TsOH (5 mg) at room temperature. After refluxing 1 hour, the solids were collected by filtration and washed with methanol (3×5 mL) to afford 5-(4-fluoro-3-methoxyphenyl)-3-(1-methyl-1H-pyrazol-5-yl)pyrazolo[1,5-a]pyrimidin-7(4H)-one as a white solid (46.9 mg, 30%).

LCMS (ES, m/z): [M+H]+ 339.9

¹H NMR (300 MHz, DMSO+NH₃ (saturated D2O solution)) δ 12.38 (s, 1H), 8.06 (s, 1H), 7.56-7.51 (m, 2H), 7.43-7.37 (m, 2H), 6.46 (d, J=1.5 Hz, 1H), 6.16 (s, 1H), 3.94 (s, 3H), 3.74 (s, 3H)

EXAMPLE 80

2-[5-(4-chloro-3-methoxyphenyl)-7-oxo-4H,7H-pyrazolo[1,5-a]pyrimidin-3-yl]-N-ethylacetamide

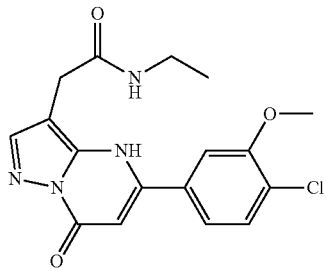 [SMILES: CCNC(=O)Cc1cnn2c(=O)cc(-c3ccc(Cl)c(OC)c3)[nH]c12]

Step 1: potassium 2,3-dicyanoprop-1-en-1-olate

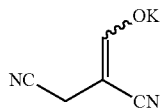

A solution of t-BuOK (4.2 g, 37.43 mmol) in tert-butanol (10 mL) was added dropwise to a solution of butanedinitrile (3 g, 37.46 mmol) in toluene (20 mL) at 0° C. and the reaction was stirred for 6 h at room temperature. The solids were collected by filtration, washed with ethanol (2×20 mL) to afford potassium 2,3-dicyanoprop-1-en-1-olate as a white solid (3 g, 55%).

Step 2: 2-((dimethylamino)methylene)succinonitrile

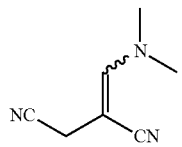

To a solution of potassium 2,3-dicyanoprop-1-en-1-olate (1 g, 6.84 mmol) in AcOH (2 mL) was added a solution of dimethylamine hydrochloride (560 mg, 6.87 mmol) in ethanol (10 mL) and the reaction was stirred for 2 h at 80° C. The resulting mixture was concentrated in vacuo to afford 2-((dimethylamino)methylene)succinonitrile as light yellow oil (2 g, crude).

Step 3: 2-(5-amino-1H-pyrazol-4-yl)acetonitrile

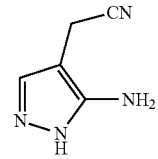

A solution of N₂H₄.H₂O (3 g, 4.00 equiv) in AcOH (5 mL) was added to a solution of 2-((dimethylamino)methylene)succinonitrile (2 g, 16.11 mmol) in ethanol (25 mL) and the reaction was stirred for 1 h at 80° C. The resulting mixture was concentrated in vacuo, diluted with H₂O (100 mL), extracted with ethyl acetate (20×10 mL), and the organic layers were combined, dried over anhydrous sodium sulfate and concentrated in vacuo. The residue was purified by a silica gel column chromatography with 1% methanol in dichloromethane to afford 2-(5-amino-1H-pyrazol-4-yl)acetonitrile as a white solid (100 mg, 5%).

Step 4: 2-[5-(4-chloro-3-methoxyphenyl)-7-oxo-4H,7H-pyrazolo[1,5-a]pyrimidin-3-yl]acetonitrile

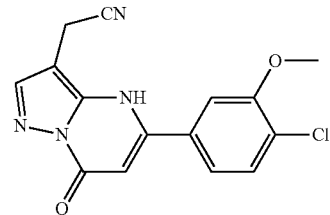 [SMILES: COc1cc(-c2cc(=O)n3ncc(CC#N)c3[nH]2)ccc1Cl]

To a solution of 2-(5-amino-1H-pyrazol-4-yl)acetonitrile (100 mg, 0.82 mmol) in n-BuOH (1 mL) was added ethyl 3-(4-chloro-3-methoxyphenyl)-3-oxopropanoate (315 mg, 1.23 mmol) and p-TsOH (7 mg, 0.04 mmol) and the reaction was stirred for 1 h at 130° C. The solids were collected by filtration and washed with methanol (3×2 mL) to afford 2-[5-(4-chloro-3-methoxyphenyl)-7-oxo-4H,7H-pyrazolo[1,5-a]pyrimidin-3-yl]acetonitrile as a light yellow solid (180 mg, 70%).

LCMS: (ES, m/z): [M+H]⁺ 315.0

¹H NMR (300 MHz, DMSO-d₆, ppm) δ 7.79 (d, J=1.50 Hz, 1H), 7.67-7.61 (m, 2H), 7.46 (d, J=8.40 Hz, 1H), 7.25 (s, 1H), 6.00 (s, 1H), 4.09 (s, 3H), 3.95 (s, 2H)

Step 5: 2-[5-(4-chloro-3-methoxyphenyl)-7-oxo-4H,7H-pyrazolo[1,5-a]pyrimidin-3-yl]acetic acid

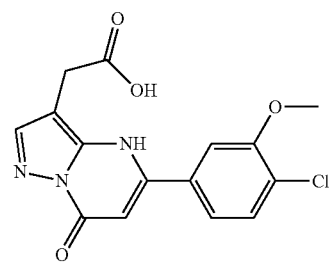 [SMILES: COc1cc(-c2cc(=O)n3ncc(CC(=O)O)c3[nH]2)ccc1Cl]

To a solution of 2-[5-(4-chloro-3-methoxyphenyl)-7-oxo-4H,7H-pyrazolo[1,5-a]pyrimidin-3-yl]acetonitrile (150 mg, 0.48 mmol) in EtOH (3 mL) was added aq. potassium hydroxide (2N) (3 mL) with stirring for 1 h at 70° C. in an oil bath. The resulting mixture was concentrated in vacuo. The residue was dissolved in H₂O (1 mL). The solution was adjusted to pH 4 with aq. HCl (4N). The solids were collected by filtration, washed with water (3×2 mL) and dried in an oven under reduced pressure to afford 2-[5-(4-chloro-3-methoxyphenyl)-7-oxo-4H,7H-pyrazolo[1,5-a]pyrimidin-3-yl]acetic acid as a light yellow solid (130 mg, 82%).

LCMS: (ES, m/z): [M+H]⁺ 334.0

¹H NMR (300 MHz, DMSO-d₆, ppm) δ 12.37 (s, 1H), 12.16 (s, 1H), 7.84 (s, 1H), 7.67 (d, J=8.40 Hz, 1H), 7.51 (d, J=1.80 Hz, 1H), 7.39-735 (dd, J=1.80, 8.40 Hz, 1H), 6.08 (s, 1H), 3.99 (s, 3H), 3.73 (s, 2H)

Step 6: 2-[5-(4-chloro-3-methoxyphenyl)-7-oxo-4H,7H-pyrazolo[1,5-a]pyrimidin-3-yl]-N-ethylacetamide

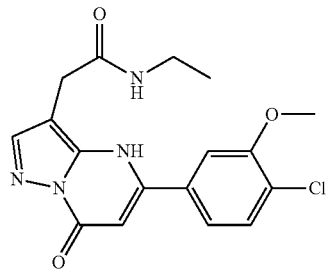 [SMILES: CCNC(=O)Cc1cnn2c(=O)cc(-c3ccc(Cl)c(OC)c3)[nH]c12]

To a solution of 2-[5-(4-chloro-3-methoxyphenyl)-7-oxo-4H,7H-pyrazolo[1,5-a]pyrimidin-3-yl]acetic acid (50 mg, 0.15 mmol) in DMF (1.5 mL) was added ethanamine hydrochloride (16 mg, 0.20 mmol), EDC (46 mg, 0.24 mmol), HOBT (33 mg, 0.24 mmol) and triethylamine (33 mg, 0.33 mmol) and the reaction was stirred for 2 h at room temperature. The resulting mixture was concentrated in vacuo. The solids were precipitated by the addition of H₂O (10 mL). The products were collected by filtration and dried in an oven under reduced pressure to afford 2-[5-(4-chloro-3-methoxyphenyl)-7-oxo-4H,7H-pyrazolo[1,5-a]pyrimidin-3-yl]-N-ethylacetamide as a light yellow solid (45.7 mg, 85%).

LCMS: (ES, m/z): [M+H]⁺ 361.0

¹H NMR (300 MHz, DMSO-d₆, ppm) δ 7.82 (s, 1H), 7.67 (d, J=1.80 Hz, 1H), 7.48-7.45 (m, 2H), 6.15 (s, 1H), 4.00 (s, 3H), 3.65 (s, 2H), 3.29-3.20 (q, J=7.20 Hz, 2H), 1.08 (t, J=7.20 Hz, 3H)

EXAMPLE 81

2-(5-(4-chloro-3-methoxyphenyl)-7-oxo-4,7-dihydropyrazolo[1,5-a]pyrimidin-3-yl)-N-methylacetamide

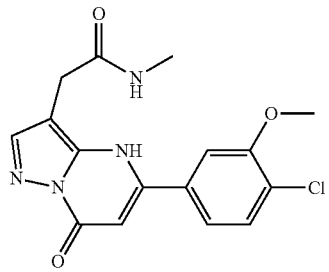

To a solution of 2-(5-(4-chloro-3-methoxyphenyl)-7-oxo-4,7-dihydropyrazolo[1,5-a]pyrimidin-3-yl)acetic acid (50 mg, 0.15 mmol) in DMF (5 mL) was added methanamine hydrochloride (15 mg, 0.20 mmol), EDC (43 mg, 0.23 mmol), HOBT (30 mg, 0.23 mmol) and TEA (30 mg, 0.3 mmol) at room temperature. After 1 hour, the pH value of the solution was adjusted to pH 3-4 with aq. HCl (1N). The precipitate was collected by filtration and washed with methanol (3×5 mL) to afford 2-(5-(4-chloro-3-methoxyphenyl)-7-oxo-4,7-dihydropyrazolo[1,5-a]pyrimidin-3-yl)-N-methylacetamide as a white solid (35.7 mg, 69%).

LCMS: (ES, m/z): [M+H]⁺ 347.0

¹H NMR (300 MHz, DMSO-d₆, ppm) δ 12.19 (s, 1H), 7.82-7.78 (m, 2H), 7.68-7.65 (d, J=8.4 Hz, 1H), 7.52 (s, 1H), 740-7.37 (m, 1H), 6.11 (s, 1H), 3.99 (s, 3H), 3.56 (s, 2H), 2.59 (s, 3H)

EXAMPLE 82

5-(1-methyl-1H-indazol-5-yl)-3-(1-methyl-1H-pyrazol-5-yl)pyrazolo[1,5-a]pyrimidin-7(4H)-one

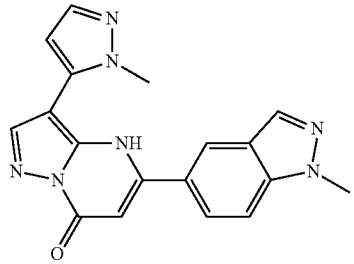 [SMILES: Cn1nccc1-c1cnn2c(=O)cc(-c3ccc4c(cnn4C)c3)[nH]c12]

To a solution of 2-methyl-1'H,2H-3,4'-bipyrazol-5'-amine (50 mg, 0.30 mmol) in n-BuOH (0.2 mL) was added ethyl 3-(1-methyl-1H-indazol-5-yl)-3-oxopropanoate (110 mg, 0.46 mmol) and p-TsOH (5 mg) at room temperature. After refluxing 2 hours, the solids were collected by filtration and washed with methanol (3×2 mL) to afford 5-(1-methyl-1H-indazol-5-yl)-3-(1-methyl-1H-pyrazol-5-yl)pyrazolo[1,5-a]pyrimidin-7(4H)-one as a white solid (78.1 mg, 74%).

LCMS (ES, m/z): [M+H]+ 346.1

¹H NMR (300 MHz, DMSO) δ 12.41 (s, 1H), 8.23 (s, 2H), 8.05 (s, 1H), 7.79 (s, 1H), 7.52 (d, J=1.8 Hz, 1H), 6.46 (d, J=1.8 Hz, 1H), 6.13 (s, 1H), 4.10 (s, 3H), 3.80 (s, 3H)

EXAMPLE 83

5-(1-methyl-1H-indazol-5-yl)-3-(1-methyl-1H-pyrazol-3-yl)pyrazolo[1,5-a]pyrimidin-7(4H)-one

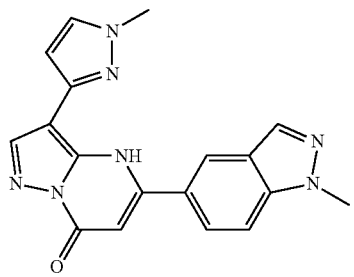 [SMILES: Cn1ccc(-c2cnn3c(=O)cc(-c4ccc5c(cnn5C)c4)[nH]c23)n1]

To a solution of 1-methyl-1H,1'H-3,4'-bipyrazol-5'-amine (50 mg, 0.30 mmol) in n-BuOH (0.2 mL) was added ethyl 3-(1-methyl-1H-indazol-5-yl)-3-oxopropanoate (110 mg, 0.46 mmol) and p-TsOH (5 mg) at room temperature. After refluxing 2 hours, the solids were collected by filtration and washed with methanol (3×2 mL) to afford 5-(1-methyl-1H-indazol-5-yl)-3-(1-methyl-1H-pyrazol-3-yl)pyrazolo[1,5-a]pyrimidin-7(4H)-one as a white solid (67.2 mg, 64%).

LCMS: (ES, m/z): [M+H]+ 346.0

$^1$H-NMR (300 MHz, DMSO-d$_6$, ppm) δ 11.20 (s, 1H), 8.33 (s, 1H), 8.25 (d, J=1.2 Hz, 2H), 7.87 (s, 2H), 7.80 (d, J=2.1 Hz, 1H), 6.68 (d, J=1.8 Hz, 1H), 6.21 (s, 1H), 4.12 (s, 3H), 3.94 (s, 3H)

EXAMPLE 84

5-(1-ethyl-1H-indazol-5-yl)-3-(4-methyl-1H-pyrazol-3-yl)-4H,7H-pyrazolo[1,5-a]pyrimidin-7-one

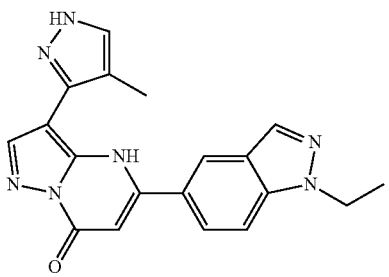 [SMILES: CCn1ncc2cc(-c3cc(=O)n4ncc(-c5n[nH]cc5C)c4[nH]3)ccc21]

Step 1: (E)-1,1,1-trichloro-4-ethoxy-3-methylbut-3-en-2-one

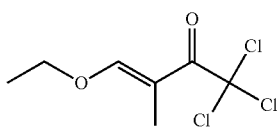

A solution of 2,2,2-trichloroacetyl chloride (116 g, 637.95 mmol) in dichloromethane (200 mL) was added dropwise to a solution of (E)-1-ethoxyprop-1-ene (50 g, 580.50 mmol) in pyridine (200 mL), and the reaction was stirred at room temperature for 3 h. The resulting mixture was concentrated in vacuo. The residue was diluted with water (300 mL) and the pH value of the solution was adjusted to pH 7 with sodium carbonate (sat. aq.). The resulting solution was extracted with ethyl acetate (3×200 mL) and the organic layers were combined and dried over anhydrous sodium sulfate. The organics were concentrated in vacuo to afford (E)-1,1,1-trichloro-4-ethoxy-3-methylbut-3-en-2-one as green oil (100 g, 74%).

LC-MS (ES, m/z): [M+H]+ 233

$^1$H NMR (400 MHz, DMSO-d$_6$, ppm): δ 8.08 (s, 1H), 4.34-4.29 (q, J=8.0 Hz, 2H), 1.84 (s, 3H), 1.33-1.29 (t, J=8.0 Hz, 3H)

Step 2: Ethyl 4-methyl-1H-pyrazole-5-carboxylate

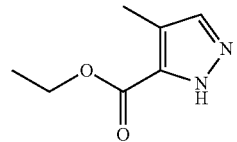

Hydrazine hydrochloride (22 g, 321.14 mmol) was added to a solution of (E)-1,1,1-trichloro-4-ethoxy-3-methylbut-3-en-2-one (50 g, 215.98 mmol) in ethanol (400 mL) and the reaction was stirred overnight at 85° C. in an oil bath. Then it was concentrated in vacuo, diluted with water (300 mL), and extracted with ethyl acetate (3×300 mL). The organic layers were combined and dried over anhydrous sodium sulfate. The organics were concentrated in vacuo to afford ethyl 4-methyl-1H-pyrazole-5-carboxylate as an orange solid (25 g, 75%).

LC-MS (ES, m/z): [M+H]+ 155

$^1$H NMR (400 MHz, DMSO-d$_6$, ppm): δ 7.57 (s, 1H), 4.30-4.24 (q, J=8.0 Hz, 2H), 2.20 (s, 3H), 1.34-1.30 (t, J=8.0 Hz, 3H)

Step 3: (4-methyl-1H-pyrazol-3-yl)methanol

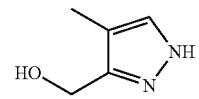

A solution of ethyl 4-methyl-1H-pyrazole-5-carboxylate (5 g, 32.43 mmol) in diethyl ether (20 mL) was added dropwise to a solution of lithium aluminum hydride (1.5 g, 39.53 mmol) in diethyl ether (20 mL) at 0-5° C. under an inert atmosphere of nitrogen. The reaction was stirred for 2 h at room temperature. Then the reaction was quenched by the addition of water (1 mL). The mixture was dried over anhydrous sodium sulfate. The organics were concentrated in vacuo to afford (4-methyl-1H-pyrazol-3-yl)methanol as white solid (3 g, 82%).

LC-MS (ES, m/z): [M+H]+ 113

$^1$H NMR (400 MHz, DMSO-d$_6$, ppm): δ 12.47-12.27 (m, 1H), 7.47-7.24 (m, 1H), 5.08 (s, 1H), 4.41 (s, 1H), 2.01 (s, 3H)

Step 4: 3-(chloromethyl)-4-methyl-1H-pyrazole

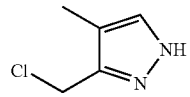

Thionyl chloride (4.8 g, 40.35 mmol) was added dropwise to a solution of (4-methyl-1H-pyrazol-3-yl)methanol (3 g, 26.75 mmol) in dichloromethane (30 mL) at room temperature. After stirring overnight at room temperature, the resulting mixture was concentrated in vacuo. The residue was diluted with water (30 mL), adjusted to pH 8 with sodium carbonate (aq. sat.), and extracted with of dichloromethane (3×30 mL) and the organic layers were combined and dried over anhydrous sodium sulfate. The organic layer was concentrated in vacuo to afford 3-(chloromethyl)-4-methyl-1H-pyrazole (2 g, crude) as colorless oil.

LC-MS (ES, m/z): [M+H]$^+$ 133.

Step 5: 2-(4-methyl-1H-pyrazol-3-yl)acetonitrile

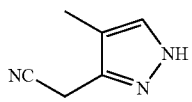

KCN (1.2 g, 18.43 mmol) was added to a solution of 3-(chloromethyl)-4-methyl-1H-pyrazole (2 g, crude) in CH$_3$CN (15 mL)/water (5 mL) and the reaction was stirred overnight at 50° C. in an oil bath. The resulting solution was diluted with water (20 mL), extracted with ethyl acetate (3×30 mL) and the organic layers were combined and dried over anhydrous sodium sulfate. The resulting mixture was concentrated in vacuo to afford a residue, which was purified by silica gel column chromatography with dichloromethane/methanol (200:1-150:1) to afford 2-(4-methyl-1H-pyrazol-3-yl)acetonitrile as a brown solid (800 mg, 43%).

LC-MS (ES, m/z): [M+H]$^+$ 132

$^1$H NMR (300 MHz, DMSO-d$_6$, ppm): δ 12.54 (s, 1H), 7.49 (s, 1H), 3.89 (s, 2H), 1.99 (s, 3H)

Step 6: 3-(dimethylamino)-2-(4-methyl-1H-pyrazol-3-yl)acrylonitrile

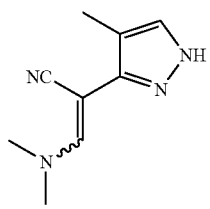

To a solution of 2-(4-methyl-1H-pyrazol-3-yl)acetonitrile (800 mg, 6.60 mmol) in toluene (0.5 mL) was added DMF-DMA (1.2 g, 10.08 mmol) and the reaction was stirred overnight at 85° C. in an oil bath. The resulting mixture was concentrated in vacuo to afford 3-(dimethylamino)-2-(4-methyl-1H-pyrazol-3-yl)acrylonitrile as an orange solid (800 mg crude)

LC-MS (ES, m/z): [M+H]$^+$ 177 .

Step 7: 4-methyl-1H,1'11-3,4'-bipyrazol-5'-amine

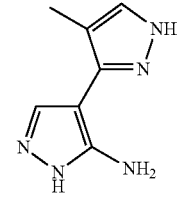

To a solution of 3-(dimethylamino)-2-(4-methyl-1H-pyrazol-3-yl)acrylonitrile (800 mg, crude) in AcOH (2 mL) was added N$_2$H$_4$·H$_2$O (1.2 g, 24.46 mmol) in portions at 0-5° C. and the reaction was stirred for 4 h at 90° C. in an oil bath. The resulting mixture was concentrated in vacuo, diluted with water (30 mL), and extracted with ethyl acetate (5×30 mL). Then the organic layers were combined and dried over anhydrous sodium sulfate. The organics were concentrated in vacuo to afford a residue, which was purified by silica gel column chromatography with dichloromethane/methanol (100:1-80:1) to afford 4-methyl-1H,1'H-3,4'-bipyrazol-5'-amine as a white solid (150 mg, 20%).

LC-MS (ES, m/z): [M+H]$^+$ 164

$^1$H NMR (300 MHz, DMSO): δ 8.92 (s, 1H), 7.97 (s, 1H), 7.58 (s, 1H), 5.15 (s, 2H), 2.09 (s, 3H)

Step 8: 5-(1-ethyl-1H-indazol-5-yl)-3-(4-methyl-1H-pyrazol-3-yl)-4H,7H-pyrazolo[1,5-a]pyrimidin-7-one

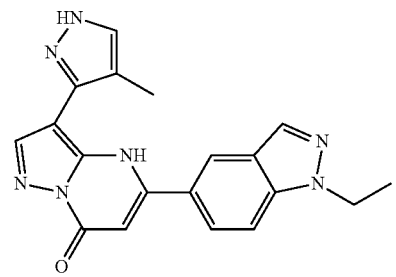 [SMILES: CCn1ncc2cc(-c3cc(=O)n4ncc(-c5n[nH]cc5C)c4[nH]3)ccc21]

To a solution of 4-methyl-1H,1'H-3,4'-bipyrazol-5'-amine (50 mg, 0.31 mmol) in n-BuOH (0.2 mL) was added ethyl 3-(1-ethyl-1H-indazol-5-yl)-3-oxopropanoate (120 mg, 0.46 mmol) and p-TsOH (5 mg) at room temperature. After refluxing 2 hours, the solids were collected by filtration and washed with methanol (3×5 mL) to afford 5-(1-ethyl-1H-indazol-5-yl)-3-(4-methyl-1H-pyrazol-3-yl)-4H,7H-pyrazolo[1,5-a]pyrimidin-7-one as a yellow solid (37.6 mg, 34%).

LC-MS: (ES, m/z): [M+H]$^+$ 360

$^1$H NMR (300 MHz, DMSO): δ 12.86 (s, 1H), 8.30-8.18 (m, 3H), 7.87-7.78 (m, 2H), 7.60 (s, 1H), 6.18 (s, 1H), 4.52 (q, J=6.0 Hz, 2H), 2.19 (s, 3H), 1.39 (t, J=6.0 Hz, 3H)

EXAMPLE 85

3-(1,4-dimethyl-1H-pyrazol-5-yl)-5-(1-ethyl-1H-indazol-5-yl)-4H,7H-pyrazolo[1,5-a]pyrimidin-7-one

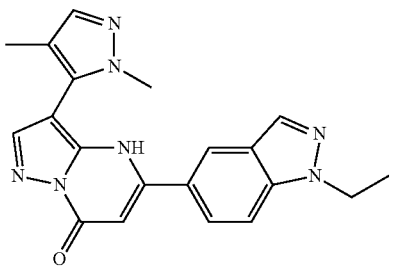 [SMILES: CCn1ncc2cc(-c3cc(=O)n4ncc(-c5c(C)cnn5C)c4[nH]3)ccc21]

Step 1: Ethyl 1,4-dimethyl-1H-pyrazole-5-carboxylate

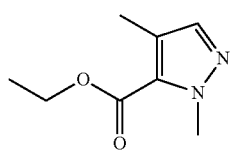

Potassium carbonate (22 g, 159.18 mmol) and MeI (25 g) were added to a solution of ethyl 4-methyl-1H-pyrazole-5-carboxylate (10 g, 64.86 mmol) in DMF (35 mL) and the reaction was stirred for 10 h at room temperature. The resulting mixture was concentrated in vacuo, diluted with H₂O (200 mL), extracted with ethyl acetate (3×50 mL), and the organic layers were combined, dried over anhydrous sodium sulfate and concentrated in vacuo. The product was purified by a silica gel column chromatography with 2% ethyl acetate in petroleum ether to afford ethyl 1,4-dimethyl-1H-pyrazole-5-carboxylate as a light yellow solid (3.2 g, 29%).

LCMS: (ES, m/z): [M+H]⁺ 169.0

¹H NMR (300 MHz, CDCl₃) δ 7.29 (s, 1H), 4.40-4.29 (m, 2H), 4.13 (s, 3H), 2.56 (s, 3H), 1.42-1.25 (m, 3H)

Step 2: (1,4-dimethyl-1H-pyrazol-5-yl)methanol

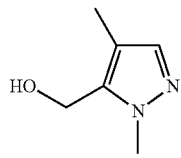

LiAlH₄ (910 mg, 23.98 mmol) was added portion wise to a solution of ethyl 1,4-dimethyl-1H-pyrazole-5-carboxylate (3.2 g, 19.03 mmol) in tetrahydrofuran (20 mL) and the reaction was stirred for 2 h at room temperature. The reaction was then quenched by the addition of water (1 ml). The resulting solution was diluted with sodium hydroxide (15%) (1.82 mL). The mixture was dried over anhydrous sodium sulfate. The solids were filtered out. The resulting mixture was concentrated under vacuum to afford (1,4-dimethyl-1H-pyrazol-5-yl)methanol as a light yellow solid (2.5 g, crude).

LCMS: (ES, m/z): [M+H]⁺ 127.0

¹H NMR (300 MHz, DMSO-d₆, ppm) δ 7.13 (s, 1H), 5.08-5.03 (m, 1H), 4.42 (d, J=5.10 Hz, 2H), 37.5 (s, 3H), 1.97 (s, 3H)

Step 3: 5-(chloromethyl)-1,4-dimethyl-1H-pyrazole

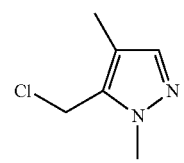

To a solution of (1,4-dimethyl-1H-pyrazol-5-yl)methanol (2.5 g, 19.82 mmol) in dichloromethane (10 mL) was added thionyl chloride (3.5 g) with stirring for 10 h at room temperature. The reaction was then quenched by the addition of water/ice (100 mL). The solution was adjusted to pH 7 with sodium carbonate (sat.), extracted with dichloromethane (3×50 mL), and the organic layers combined and dried over anhydrous sodium sulfate. The solids were filtered out. The resulting mixture was concentrated under vacuum to afford 5-(chloromethyl)-1,4-dimethyl-1H-pyrazole as black crude oil (2 g, 70%).

LCMS: (ES, m/z): [M+H]⁺ 145.0

¹H NMR (300 MHz, DMSO-d₆, ppm) δ 7.22 (d, J=4.20 Hz, 1H), 4.88 (s, 2H), 3.80 (s, 3H), 2.03 (s, 3H)

Step 4: 2-(1,4-dimethyl-1H-pyrazol-5-yl)acetonitrile

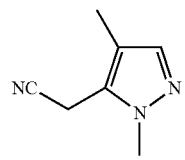

To a solution of 5-(chloromethyl)-1,4-dimethyl-1H-pyrazole (2 g, 13.83 mmol) in CH₃CN (10 mL) was added a solution of KCN (1.35 g, 20.73 mmol) in water (0.5 mL). The resulting solution was stirred for 10 h at 50° C. The reaction was then quenched by the addition of ferrous sulfate (20 g) in water (50 mL). The resulting solution was extracted with ethyl acetate (5×20 mL), and the organic layers combined and dried over anhydrous sodium sulfate and concentrated under vacuum to give the residue, which was purified by a silica gel column with 5% ethyl acetate in petroleum ether to afford 2-(1,4-dimethyl-1H-pyrazol-5-yl)acetonitrile as light yellow oil (1.2 g, 64%).

LCMS: (ES, m/z): [M+H]⁺ 136.0 ¹H NMR (300 MHz, CDCl3) δ 7.29 (s, 1H), 3.89 (s, 3H), 3.68 (s, 2H), 2.08 (s, 3H).

Step 5: 2-(1,4-dimethyl-1H-pyrazol-5-yl)-3-(dimethylamino)acrylonitrile

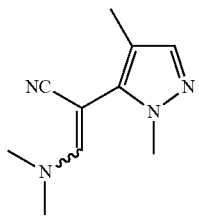

To a solution of 2-(1,4-dimethyl-1H-pyrazol-5-yl)acetonitrile (1.2 g, 8.88 mmol) in toluene (0.5 mL) was added DMF-DMA (1.5 mL) with stirring for 10 h at 85° C. The resulting mixture was concentrated under vacuum to afford 2-(1,4-dimethyl-1H-pyrazol-5-yl)-3-(dimethylamino)acrylonitrile as black crude oil (2 g, crude).

Step 6: 2,4-dimethyl-1'H,2H-3,4'-bipyrazol-5'-amine

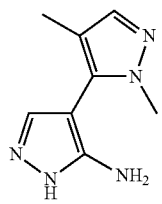

To a solution of 2-(1,4-dimethyl-1H-pyrazol-5-yl)-3-(dimethylamino)acrylonitrile (2 g, 10.51 mmol) in AcOH (10 mL) was added $N_2H_4.H_2O$ (2.1 g) at 0° C. The resulting solution was stirred for 4 h at 85° C. The resulting mixture was concentrated under vacuum, diluted with $H_2O$ (20 mL) and extracted with (20×10 mL) ethyl acetate. The organic layers combined, dried over anhydrous sodium sulfate and concentrated under vacuum to give the residue, which was purified by a silica gel column with 2% methanol in dichloromethane to afford 2,4-dimethyl-1'H,2H-3,4'-bipyrazol-5'-amine as a light yellow solid (550 mg, 30%).

Step 7: 3-(1,4-dimethyl-1H-pyrazol-5-yl)-5-(1-ethyl-1H-indazol-5-yl)-4H,7H-pyrazolo[1,5-a]pyrimidin-7-one

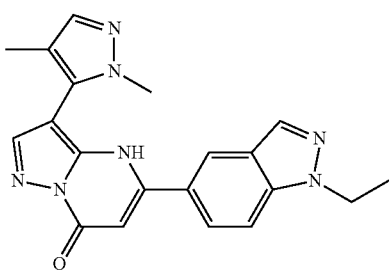 [SMILES: CCn1ncc2cc(-c3cc(=O)n4ncc(-c5c(C)cnn5C)c4[nH]3)ccc21]

To a solution of 2,4-dimethyl-1'H,2H-3,4'-bipyrazol-5'-amine (50 mg, 0.28 mmol) in n-BuOH (0.5 mL) was added ethyl 3-(1-ethyl-1H-indazol-5-yl)-3-oxopropanoate (88 mg, 0.34 mmol), p-TsOH (2.4 mg, 0.01 mmol) with stirred for 2 h at 130° C. The solids were collected by filtration and washed with methanol (2×1 mL) to afford 3-(1,4-dimethyl-1H-pyrazol-5-yl)-5-(1-ethyl-1H-indazol-5-yl)-4H,7H-pyrazolo[1,5-a]pyrimidin-7-one as a white solid (96.0 mg, 91%).

LCMS: (ES, m/z): [M+H]$^+$ 374.0

$^1$H NMR (300 MHz, DMSO-d$_6$, ppm) δ 12.43 (s, 1H), 8.20 (s, 1H), 8.16 (s, 1H), 7.99 (s, 1H), 7.81 (d, J=5.70 Hz, 1H), 7.72-7.68 (dd, J=1.50, 8.70 Hz, 1H), 7.32 (s, 1H), 6.09 (s, 1H), 4.49-4.42 (q, J=7.20 Hz, 2H), 1.93 (s, 3H), 1.36 (t, J=7.20 Hz, 3H)

EXAMPLE 86

5-(1-ethyl-1H-indazol-5-yl)-3-(3-methylisoxazol-5-yl)pyrazolo[1,5-a]pyrimidin-7(4H)-one

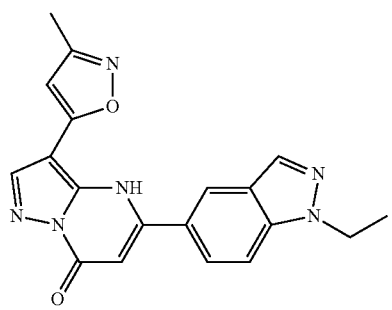 [SMILES: CCn1ncc2cc(-c3cc(=O)n4ncc(-c5cc(C)no5)c4[nH]3)ccc21]

To a solution of 4-(3-methylisoxazol-5-yl)-1H-pyrazol-5-amine (40 mg, 0.24 mmol) in n-BuOH (0.2 mL) was added ethyl 3-(1-ethyl-1H-indazol-5-yl)-3-oxopropanoate (95 mg, 0.37 mmol) and p-TsOH (5 mg) at room temperature. After refluxing 2 hours, the solids were collected by filtration and washed with methanol (3×2 mL) to afford 5-(1-ethyl-1H-indazol-5-yl)-3-(3-methylisoxazol-5-yl)pyrazolo[1,5-a]pyrimidin-7(4H)-one as light yellow solid (28.5 mg, 33%).

LCMS: (ES, m/z): [M+H]$^+$ 361.0

$^1$H-NMR (300 MHz, DMSO-d$_6$, ppm) δ 12.20 (brs, 1H), 8.29-8.22 (m, 3H), 7.85-7.73 (m, 2H), 6.81 (s, 1H), 6.16 (s, 1H), 4.47 (q, J=7.2 Hz, 2H), 2.23 (s, 3H), 1.38 (t, J=7.2 Hz, 3H)

EXAMPLE 87

5-(1-ethyl-1H-indazol-5-yl)-3-(4-methyl-1,2-oxazol-5-yl)-4H,7H-pyrazolo[1,5-a]pyrimidin-7-one

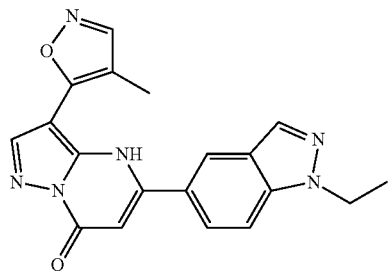 [SMILES: CCn1ncc2cc(-c3cc(=O)n4ncc(-c5oncc5C)c4[nH]3)ccc21]

Step 1: ethyl 4-methylisoxazole-5-carboxylate

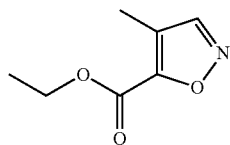

To a solution of (E)-1,1,1-trichloro-4-ethoxy-3-methyl-but-3-en-2-one (40 g, 172.78 mmol) in ethanol (400 mL) was added $NH_2OH \cdot HCl$ (14.5 g, 208.66 mmol) and sulfuric acid (51 g, 519.98 mmol) with stirring overnight at 85° C. in an oil bath. The resulting mixture was concentrated under vacuum, diluted with water (400 mL), and adjusted pH value to 7 with sodium carbonate (sat.). The resulting solution was extracted with ethyl acetate (3×300 mL) and the organic layers combined and dried over anhydrous sodium sulfate. The solids were filtered out. The resulting mixture was concentrated under vacuum to afford ethyl 4-methylisoxazole-5-carboxylate as an orange solid (6 g, 22%).

LC-MS (ES, m/z): $[M+H]^+$ 156
$^1H$ NMR (300 MHz, $CDCl_3$): δ 8.21 (s, 1H), 4.47-4.40 (q, J=7.2 Hz, 2H), 2.31 (s, 3H), 1.45-1.40 (t, J=7.2 Hz, 3H)

Step 2: (4-methylisoxazol-5-yl)methanol

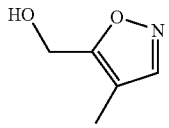

To a solution of lithium aluminum hydride (1.6 g, 42.16 mmol) in diethyl ether (20 mL) was added a solution of ethyl 4-methylisoxazole-5-carboxylate (5.5 g, 35.45 mmol) in diethyl ether (20 mL) dropwise at 0-5° C. under an inert atmosphere of nitrogen. The reaction was stirred for 2 h at room temperature. Then the reaction was quenched by the addition of water (1 mL). The mixture was dried by anhydrous sodium sulfate. Then the solids were filtered out. The resulting solution was concentrated under vacuum to afford (4-methylisoxazol-5-yl)methanol as colorless oil (3 g, 75%).

$^1H$ NMR (300 MHz, CD3OD): δ 8.20 (s, 1H), 4.64 (s, 2H), 2.07 (s, 3H)

Step 3: 5-(chloromethyl)-4-methylisoxazole

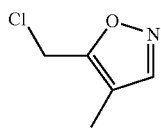

To a solution of (4-methylisoxazol-5-yl)methanol (3 g, 26.52 mmol) in dichloromethane (30 mL) was added thionylchloride (4.7 g, 39.51 mmol) dropwise with stirring at room temperature. After stirring 8 h at room temperature, the resulting mixture was concentrated under vacuum. The residue was diluted with water (30 mL), adjusted pH value to 8 with sodium carbonate (sat.), and extracted with of dichloromethane (3×30 mL) and the organic layers combined and dried over anhydrous sodium sulfate. The solids were filtered out. The resulting mixture was concentrated under vacuum to afford 5-(chloromethyl)-4-methylisoxazole as yellow oil (3 g, 86%).

LC-MS (ES, m/z): $[M+H]^+$ 133
$^1H$ NMR (300 MHz, $CD_3OD$): δ 8.22 (s, 1H), 4.73 (s, 2H), 2.05 (s, 3H)

Step 4: 2-(4-methylisoxazol-5-yl)acetonitrile

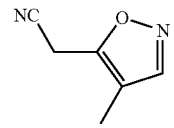

To a solution of 5-(chloromethyl)-4-methylisoxazole (3 g, crude) in $CH_3CN$ (15 mL)/water (5 mL) was added KCN (1.8 g, 27.64 mmol) with stirring overnight at 50° C. in an oil bath. The resulting solution was diluted with water (20 mL), extracted with ethyl acetate (3×30 mL) and the organic layers combined and dried over anhydrous sodium sulfate. The solids were filtered out. The resulting mixture was concentrated under vacuum to give the residue, which was applied onto a silica gel column with dichloromethane/methanol (200:1-150:1) to afford 2-(4-methylisoxazol-5-yl)acetonitrile as a yellow solid (1.2 g, 43%).

LC-MS (ES, m/z): $[M+H]^+$ 123
$^1H$ NMR (300 MHz, $CD_3OD$): δ 8.24 (s, 1H), 4.84 (s, 2H), 2.04 (s, 3H)

Step 5: 3-(dimethylamino)-2-(4-methylisoxazol-5-yl)acrylonitrile

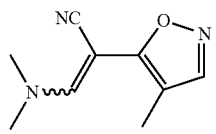

To a solution of 2-(4-methylisoxazol-5-yl)acetonitrile (1 g, 8.19 mmol) in toluene (0.5 mL) was added DMF-DMA (1.5 g, 12.61 mmol) with stirring overnight at 85° C. in an oil bath. The resulting mixture was concentrated under vacuum to afford 3-(dimethylamino)-2-(4-methylisoxazol-5-yl)acrylonitrile as brown oil (1 g, crude).

LC-MS (ES, m/z): $[M+H]^+$ 178.

Step 6:
4-(4-methylisoxazol-5-yl)-1H-pyrazol-5-amine

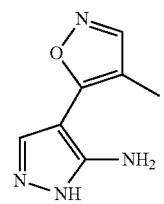

To a solution of 3-(dimethylamino)-2-(4-methylisoxazol-5-yl)acrylonitrile (1 g, crude) in AcOH (2 mL) was added N$_2$H$_4$.H$_2$O (1.4 g, 28.54 mmol) in portions at 0-5° C. with stirring for 4 h at 90° C. in an oil bath. The resulting mixture was concentrated under vacuum, diluted with water (20 mL), and extracted with ethyl acetate (5×30 mL) and the organic layers combined and dried over anhydrous sodium sulfate. The solids were filtered out. The resulting mixture was concentrated under vacuum to give the residue, which was applied onto a silica gel column with dichloromethane/methanol (100:1-80:1) to afford 4-(4-methylisoxazol-5-yl)-1H-pyrazol-5-amine as an off-white solid (500 mg, 54%).

LC-MS (ES, m/z): [M+H]$^+$ 165

$^1$H NMR (400 MHz, DMSO-d$_6$, ppm): δ 12.17-11.88 (m, 1H), 8.60 (s, 1H), 8.36 (s, 1H), 4.97-4.95 (m, 2H), 2.08 (s, 3H)

Step 7: 5-(1-ethyl-1H-indazol-5-yl)-3-(4-methyl-isoxazol-5-yl)pyrazolo[1,5-a]pyrimidin-7(4H)-one

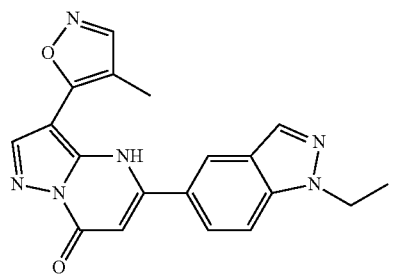 [SMILES: CCn1ncc2cc(-c3cc(=O)n4ncc(-c5oncc5C)c4[nH]3)ccc21]

To a solution of 4-(4-methylisoxazol-5-yl)-1H-pyrazol-5-amine (50 mg, 0.31 mmol) in n-BuOH (0.2 mL) was added ethyl 3-(1-ethyl-1H-indazol-5-yl)-3-oxopropanoate (120 mg, 0.46 mmol) and p-TsOH (5 mg) at room temperature. After refluxing 2 hours, the solids were collected by filtration and washed with methanol (3×1 mL) to afford 5-(1-ethyl-1H-indazol-5-yl)-3-(4-methylisoxazol-5-yl)pyrazolo[1,5-a]pyrimidin-7(4H)-one as an off-white solid (80.3 mg, 73%).

LC-MS (ES, m/z): [M+H]$^+$ 361

$^1$H NMR (400 MHz, DMSO-d$_6$, ppm): δ 12.40 (s, 1H), 8.83-7.79 (m, 6H), 6.23 (s, 1H), 4.56-4.50 (q, J=7.2 Hz, 2H), 2.18 (s, 3H), 1.45-1.41 (t, J=7.2 Hz, 3H)

EXAMPLE 88

5-(1-isopropyl-1H-indazol-5-yl)-3-(1-methyl-1H-pyrazol-5-yl)pyrazolo[1,5-a]pyrimidin-7(4H)-one

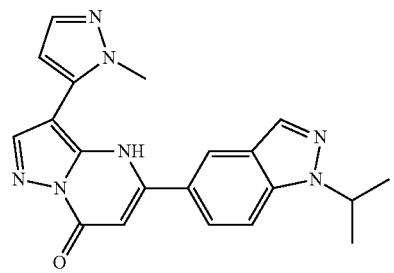 [SMILES: CC(C)n1ncc2cc(-c3cc(=O)n4ncc(-c5ccnn5C)c4[nH]3)ccc21]

Step 1: 4-amino-3-methylbenzoic acid

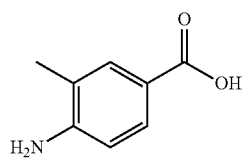

To a solution of 3-methyl-4-nitrobenzoic acid (100 g, 552.04 mmol) in methanol (2000 mL) was added Palladium carbon (5.0 g) at room temperature under an atmosphere of hydrogen. After stirring for 24 h at room temperature, the solids were filtered out. The filtrate was concentrated under vacuum to afford 4-amino-3-methylbenzoic acid as a light yellow solid (80 g, 96%).

Step 2: Methyl 4-amino-3-methylbenzoate

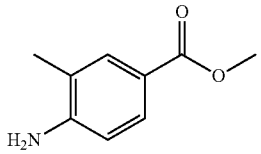

To a solution of 4-amino-3-methylbenzoic acid (80 g, 529.23 mmol) in methanol (1000 mL) was added thionyl chloride (250 g) with stirring for 10 h at 90° C. The resulting mixture was concentrated under vacuum. The resulting mixture was diluted with H$_2$O (200 mL), extracted with dichloromethane (3×150 mL) and the organic layers combined and dried over anhydrous sodium sulfate. The solids were filtered out to give the filtered, which was concentrated under vacuum to afford methyl 4-amino-3-methylbenzoate as a light yellow solid (80 g, 92%).

LCMS (ES, m/z): [M+H]$^+$ 166.0

$^1$H NMR (300 MHz, DMSO) δ 8.25 (brs, 2H), 7.60 (s, 1H), 7.59 (s, 1H), 6.86 (d, J=8.40 Hz, 1H), 3.76 (s, 3H), 2.16 (s, 2H)

Step 3: Methyl 1H-indazole-5-carboxylate

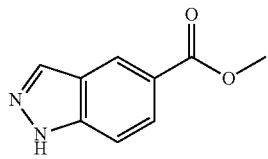

To a solution of methyl 4-amino-3-methylbenzoate (80 g, 484.29 mmol) in HBF$_4$ (500 mL) was followed by the addition of NaNO$_2$ (40 g, 579.71 mmol) dropwise at 0° C. The reaction was allowed to react 4 h at room temperature. The solid was collected by filtration and washed with 3×200 mL of ether. The solids were dried in an oven under reduced pressure. Under an inert atmosphere of nitrogen, was placed CH$_3$COOK (94 g, 698.6 mmol), 18-crown-6 (6.3 g, 23.83 mmol), chloroform (500 mL). This was followed by the addition of the solid at 0° C., in portions. The resulting solution was stirred for 3 h at room temperature. Then to this was added 1 L of H$_2$O. The resulting solution was extracted with 5×100 mL of DCM. The organic layers were dried over anhydrous sodium sulfate. The solids were filtered out. The filtrate was concentrated under vacuum to afford the residue, which was purified by a silica gel column with 20% ethyl acetate in CH$_2$Cl$_2$ to afford of methyl 1H-indazole-5-carboxylate as a yellow solid (40 g, 47%).

LCMS (ES, m/z): [M+H]$^+$ 177.1

Step 4: methyl 1-isopropyl-1H-indazole-5-carboxylate

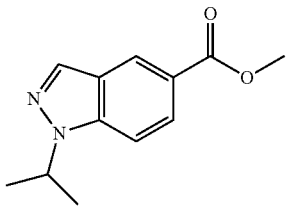 [SMILES: COC(=O)c1ccc2c(cnn2C(C)C)c1]

To a solution of methyl 1H-indazole-5-carboxylate (15 g, 56.8 mmol) in DMF (300 mL) was added potassium carbonate (15.6 g, 113.6 mmol) and isopropyl iodide (19.3 g, 113.6 mmol), and the resulting mixture was stirred for 5 h at room temperature. The resulting mixture was concentrated under vacuum. The residue was diluted with H$_2$O (200 mL), and extracted with ethyl acetate (3×100 mL). The organic layers combined and dried over anhydrous sodium sulfate. The solids were filtered out. The filtrate was concentrated under vacuum to afford the residue, which was purified by a silica gel column with 10% ethyl acetate in petroleum ether to afford methyl 1-isopropyl-1H-indazole-5-carboxylate as a orange solid (8 g, 47%).

(ES, m/z): [M+H]$^+$ 219.0

$^1$H NMR (300 MHz, DMSO) δ8.48 (s, 1H), 8.27 (s, 1H), 7.96-7.92 (dd, J=1.50, 9.00 Hz, 1H), 7.81 (d, J=9.00 Hz, 1H), 5.09-5.00 (m, 1H), 3.88 (s, 3H), 1.50 (d, J=6.60 Hz, 6H)

Step 5: 1-isopropyl-1H-indazole-5-carboxylic acid

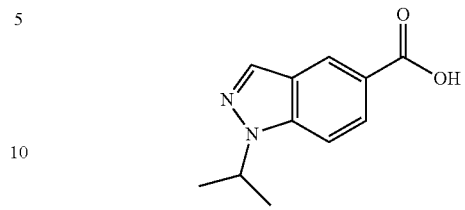

To a solution of methyl 1-isopropyl-1H-indazole-5-carboxylate (8 g, 36.65 mmol) in methanol (100 mL) was added a solution of sodium hydroxide (5.87 g, 146.75 mmol) in water (5 mL) with stirring overnight at room temperature. The resulting mixture was concentrated under vacuum. The resulting solution was diluted with (100 mL) H$_2$O, and adjusted to pH 4 with HCl (4N). The product was precipitated from water and collected by filtration to afford 1-isopropyl-1H-indazole-5-carboxylic acid as an orange solid (6 g, 80%).

Step 6: ethyl 3-(1-isopropyl-1H-indazol-5-yl)-3-oxopropanoate

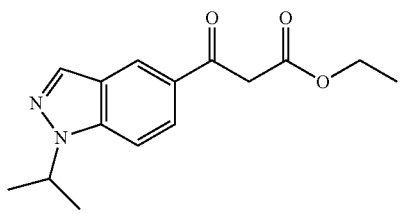 [SMILES: CCOC(=O)CC(=O)c1ccc2c(cnn2C(C)C)c1]

To a solution 1-isopropyl-1H-indazole-5-carboxylic acid (6 g, 29.38 mmol) in THF (100 ml) was added CDI (14.25 g, 87.88 mmol) with stirring at room temperature for 2 hours and then the magnesium salt of malonic acid monoethyl ester (prepared via the addition of Et$_3$N (8.9 g, 87.95 mmol) and MgCl$_2$ (12.35 g) to a solution of potassium monoethylonate (15 g, 88.13 mmol) in acetonitrile (200 ml) followed by stirring at room temperature for 2 h) was added drop wise at 0° C. The reaction mixture was then stirred overnight at r.t, quenched by the addition of water (250 ml) and adjusted to pH 2 with HCl (3N). The mixture was extracted with ethyl acetate with (4×200 ml) and the organic layers combined, dried over anhydrous magnesium sulfate and concentrated under vacuum to give a residue, which was purified by a silica gel column with 10% ethyl acetate in petroleum ether to afford ethyl 3-(1-isopropyl-1H-indazol-5-yl)-3-oxopropanoate as an orange solid (7 g, 87%).

LCMS (ES, m/z): [M+H]$^+$ 275.0

$^1$H NMR (300 MHz, CDCl$_3$) δ 8.39 (s, 1H), 8.26 (s, 1H), 8.01 (d, J=1.50 Hz, 1H), 7.50 (d, J=9.00 Hz, 1H), 4.92-4.83 (m, 1H), 4.30-4.22 (m, 2H), 4.20 (s, 2H), 1.62 (d, J=6.90 Hz, 6H), 1.37-1.31 (m, 3H)

187

Step 7: 5-(1-isopropyl-1H-indazol-5-yl)-3-(1-methyl-1H-pyrazol-5-yl)pyrazolo[1,5-a]pyrimidin-7(4H)-one

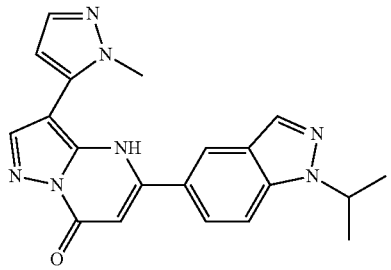 [SMILES: CC(C)n1ncc2cc(-c3cc(=O)n4ncc(-c5ccnn5C)c4[nH]3)ccc21]

To a solution of 2-methyl-1'H,2H-3,4'-bipyrazol-5'-amine (50 mg, 0.3 mmol) in n-BuOH (1 mL) was added ethyl 3-(1-isopropyl-1H-indazol-5-yl)-3-oxopropanoate (150 mg, 0.45 mmol) and p-TsOH (6.3 mg, 0.04 mmol) with stirring for 1 h at 130° C. The solids were collected by filtration and washed with MeOH (3×1 mL) to afford 5-(1-isopropyl-1H-indazol-5-yl)-3-(1-methyl-1H-pyrazol-5-yl)pyrazolo[1,5-a]pyrimidin-7(4H)-one as a light yellow solid (75.9 mg, 66%).

(ES, m/z): [M+H]⁺ 374.0

¹H NMR (300 MHz, DMSO) δ 12.38 (s, 1H), 8.25 (d, J=3.90 Hz, 2H), 8.05 (s, 1H), 7.88 (d, J=8.70 Hz, 1H), 7.77-7.74 (dd, J=1.50, 8.70 Hz, 1H), 7.52 (d, J=1.80 Hz, 1H), 6.47 (d, J=1.80 Hz, 1H), 6.13 (s, 1H), 5.11-5.02 (m, 1H), 3.80 (s, 3H), 1.51 (d, J=6.60 Hz, 6H)

EXAMPLE 89

2-[5-(4-chloro-3-methoxyphenyl)-7-oxo-4H,7H-pyrazolo[1,5-a]pyrimidin-3-yl]acetonitrile

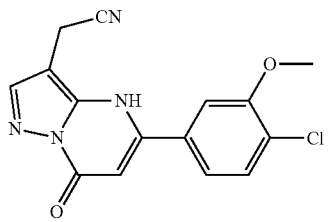 [SMILES: COc1cc(-c2cc(=O)n3ncc(CC#N)c3[nH]2)ccc1Cl]

To a solution of 2-(5-amino-1H-pyrazol-4-yl)acetonitrile (35 mg, 0.29 mmol) in n-BuOH (1 mL) was added ethyl 3-(4-chloro-3-methoxyphenyl)-3-oxopropanoate (95 mg, 0.37 mmol) and p-TsOH (2.5 mg, 0.01 mmol) with stirring for 1 h at 130° C. The solids were collected by filtration and washed with MeOH (3×1 mL) to afford 2-[5-(4-chloro-3-methoxyphenyl)-7-oxo-4H,7H-pyrazolo[1,5-a]pyrimidin-3-yl]acetonitrile as a light yellow solid (57.4 mg, 64%).

(ES, m/z) [M+H]⁺ 314.06

¹H NMR (300 Hz, DMSO): 12.39 (s, 1H), 7.98 (s, 1H), 7.70 (d, J=8.10 Hz, 1H), 7.55 (d, J=1.80 Hz, 1H), 7.43-7.39 (dd, J=1.80, 8.10 Hz, 1H), 6.17 (s, 1H), 4.05 (s, 2H), 3.99 (s, 3H)

188
EXAMPLE 90

5-(3-methylbenzo[d]isoxazol-5-yl)-3-(4-methyloxazol-2-yl)pyrazolo[1,5-a]pyrimidin-7(4H)-one

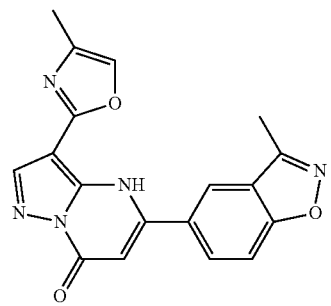 [SMILES: Cc1coc(-c2cnn3c(=O)cc(-c4ccc5onc(C)c5c4)[nH]c23)n1]

Step 1: Methyl 3-acetyl-4-hydroxybenzoate

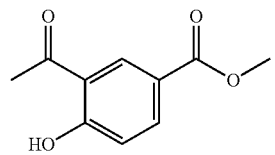

To a solution of 1-(5-bromo-2-hydroxyphenyl)ethanone (10.0 g, 46.50 mmol, 1.00 equiv) in methanol (200 mL) was added Pd(dppf)₂Cl₂ (1.9 g, 2.33 mmol, 0.05 equiv) and triethylamine (9.5 g, 93.88 mmol, 2.00 equiv). To the above CO (g) (10 atm) was introduced. The resulting solution was stirred overnight at 100° C. After the reaction was complete, the mixture was diluted with 300 mL of H₂O. The aqueous phase was extracted with 3×200 mL of dichloromethane and the organic layers were combined. The organic layers were washed with 1×500 mL of brine and then dried with anhydrous sodium sulfate. The organic layers were concentrated in vacuo and purified via silica gel column chromatography with ethyl acetate/petroleum ether (1:10). This resulted in 7.0 g (78%) of methyl 3-acetyl-4-hydroxybenzoate as a light yellow solid.

¹H NMR (300 MHz, CDCl₃): δ 12.65 (s, 1H), 8.45 (s, 1H), 8.10 (d, J=2.1 Hz, 1H), 7.00 (d, J=9.7 Hz, 1H), 3.89 (s, 3H), 2.68 (s, 3H)

Step 2: methyl 4-hydroxy-3-(1-iminoethyl)benzoate

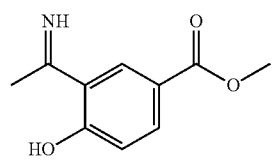

Methyl 3-acetyl-4-hydroxybenzoate (7.0 g, 36.05 mmol, 1.00 equiv) was dissolved in MeOH (saturated with NH₃) (500 mL). The resulting solution was stirred overnight at room temperature. The resulting mixture was concentrated in vacuo. This resulted in 7.4 g (crude) of methyl 4-hydroxy-3-(1-iminoethyl)benzoate as a light yellow solid.

$^1$H NMR (300 MHz, DMSO): δ15.02 (brs, 1H), 10.71 (brs, 1H), 8.10 (s, 1H), 7.68-7.64 (dd, J=2.4 Hz, 9.3 Hz, 1H), 6.50-6.46 (d, J=9.3 Hz, 1H), 3.72 (s, 3H), 2.53 (s, 3H)

Step 3: methyl 3-methylbenzo[d]isoxazole-5-carboxylate

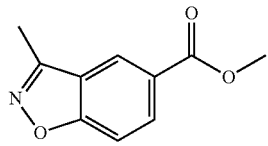

To a solution of methyl 4-hydroxy-3-(1-iminoethyl)benzoate (7.4 g, 38.30 mmol, 1.00 equiv) in THF (150 mL) was added N-chlorosuccinimide (NCS) (3.33 g, 24.94 mmol, 1.50 equiv) and potassium carbonate (11 g, 79.59 mmol, 2.00 equiv). The resulting reaction was stirred for 10 h at room temperature. After the reaction was complete, the mixture was diluted with 300 mL of H$_2$O. The aqueous phase was extracted with 3×200 mL of dichloromethane and the organic layers were combined, washed with 1×500 mL of brine, and dried over anhydrous sodium sulfate. The organics were concentrated in vacuo and purified by silica gel column chromatography with ethyl acetate/petroleum ether (1:10). This resulted in 5.0 g (68%) of methyl 3-methylbenzo[d]isoxazole-5-carboxylate as a light yellow solid.

LC-MS (ES, m/z): [M+H]$^+$ 192.0

$^1$H NMR (300 MHz, DMSO): δ 8.46 (s, 1H), 8.19-8.13 (m, 1H), 7.79 (d, J=9.0 Hz, 1H), 3.86 (s, 3H), 2.58 (s, 3H)

Step 4: 3-methylbenzo[d]isoxazole-5-carboxylic acid

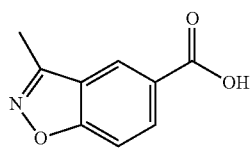

To a solution of methyl 3-methylbenzo[d]isoxazole-5-carboxylate (5.0 g, 26.15 mmol, 1.00 equiv) in methanol (20 mL) was added a solution of sodium hydroxide (4.2 g, 105.00 mmol, 4.00 equiv) in water (2 mL). The resulting solution was stirred overnight at room temperature. The reaction progress was monitored by TLC (ethyl acetate/petroleum ether=1:1). The resulting mixture was concentrated under vacuum. The residue was dissolved in 100 mL of H$_2$O. The pH of the solution was adjusted to pH 4 with HCl (4M). The solids were collected by filtration. The solid was dried in an oven under reduced pressure. This resulted in 4.0 g (86%) of 3-methylbenzo[d]isoxazole-5-carboxylic acid as a light yellow solid.

LC-MS (ES, m/z): [M+H]$^+$ 178.0

$^1$H NMR (300 MHz, DMSO): δ 8.43 (s, 1H), 8.17-8.13 (m, 1H), 7.75 (d, J=8.7 Hz, 1H), 2.57 (s, 3H)

Step 5: ethyl 3-(3-methylbenzo[d]isoxazol-5-yl)-3-oxopropanoate

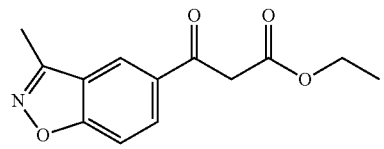 [SMILES: CCOC(=O)CC(=O)c1ccc2onc(C)c2c1]

To a solution of 3-methylbenzo[d]isoxazole-5-carboxylic acid (4.0 g, 22.58 mmol, 1.00 equiv) in tetrahydrofuran (50 mL) was added CDI (11 g, 67.90 mmol, 3.00 equiv). The reaction was stirred for 2 h at 40° C. Separately, to a solution of potassium 3-ethoxy-3-oxopropanoate (10.2 g, 59.93 mmol, 3.00 equiv) in CH$_3$CN (150 mL) was added triethylamine (6.06 g, 59.89 mmol, 3.00 equiv) and MgCl$_2$ (8.55 g, 90.00 mmol, 4.50 equiv). The two solutions were combined and stirred for 1 h at room temperature. The reaction progress was monitored by TLC (ethyl acetate/petroleum ether=1:5). The resulting mixture was concentrated under vacuum. The residue was diluted with 200 mL of H$_2$O. The pH of the solution was adjusted to pH 4 with aq. HCl (4M). The resulting solution was extracted with 4×50 mL of ethyl acetate and the organic layers were combined, dried over anhydrous sodium sulfate, and concentrated in vacuo. The residue was purified by silica gel column chromatography with ethyl acetate/petroleum ether (1:50) to provide 4.5 g (81%) of ethyl 3-(3-methylbenzo[d]isoxazol-5-yl)-3-oxopropanoate as an off-white solid.

LC-MS (ES, m/z): [M+H]$^+$ 248.0

$^1$H NMR (300 MHz, CDCl$_3$): δ 8.33 (s, 1H), 8.21-8.19 (m, 1H), 7.64 (d, J=6.6 Hz, 1H), 4.34-4.23 (m, 2H), 4.10 (s, 2H), 2.69 (s, 3H), 1.40-1.27 (m, 3H)

Step 6: prop-2-ynyl 5-amino-1H-pyrazole-4-carbimidate hydrochloride

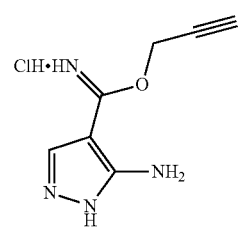

HCl (g) was introduced to a mixture of 5-amino-1H-pyrazole-4-carbonitrile (200 mg, 1.85 mmol, 1.00 equiv), and prop-2-yn-1-ol (2 mL) The reaction was stirred overnight at room temperature. Ether was added to the resulting solution and the solids were collected by filtration. This resulted in 500 mg (crude) of prop-2-ynyl 5-amino-1H-pyrazole-4-carbimidate hydrochloride as a light yellow solid.

Step 7:
4-(4-methyloxazol-2-yl)-1H-pyrazol-5-amine

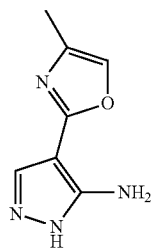

Prop-2-ynyl 5-amino-1H-pyrazole-4-carbimidate hydrochloride (500 mg, 2.49 mmol, 1.00 equiv) was added in portions to a mixture of xylene (2 mL), TsOAg (34.6 mg, 0.12 mmol, 0.05 equiv), and DIEA (485 mg, 3.75 mmol, 1.50 equiv). The reaction was stirred for 1 h at 65° C. After the reaction was completed, the mixture was diluted with 50 mL of H₂O. The aqueous phase was extracted with 3×50 mL of dichloromethane and the organic layers were combined, washed with 1×50 mL of brine, and dried over anhydrous sodium sulfate. Concentration in vacuo and purification via silica gel column chromatography with dichloromethane/methanol (15:1) resulted in 100 mg (24%) of 4-(4-methyloxazol-2-yl)-1H-pyrazol-5-amine as a light yellow oil.

Step 8: 5-(3-methylbenzo[d]isoxazol-5-yl)-3-(4-methyloxazol-2-yl)pyrazolo[1,5-a]pyrimidin-7(4H)-one

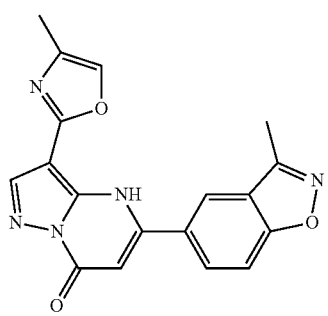 [SMILES: Cc1coc(-c2cnn3c(=O)cc(-c4ccc5onc(C)c5c4)[nH]c23)n1]

To a solution of 4-(4-methyloxazol-2-yl)-1H-pyrazol-5-amine (50 mg, 0.20 mmol, 1.00 equiv) in n-BuOH (0.5 mL) was added ethyl 3-(3-methylbenzo[d]isoxazol-5-yl)-3-oxopropanoate (90 mg, 0.36 mmol, 1.20 equiv), and 4-methylbenzene-1-sulfonic acid (2.6 mg, 0.02 mmol, 0.05 equiv). The resulting solution was stirred for 1 h at 120° C. The reaction progress was monitored by LCMS. The solids were collected by filtration and washed with 3×1 mL of methanol. This resulted in 56 mg (80%) of 5-(3-methylbenzo[d]isoxazol-5-yl)-3-(4-methyloxazol-2-yl)pyrazolo[1,5-a]pyrimidin-7(4H)-one as an off-white solid.

LC-MS (ES, m/z): [M+H]⁺ 348.0

$^1$H NMR (300 MHz, DMSO): δ8.42-8.37 (m, 2H), 8.09-8.06 (m, 1H), 7.94-7.89 (m, 2H), 6.32 (s, 1H), 2.72 (s, 3H), 2.19 (s, 3H)

EXAMPLE 91

5-(3-methylbenzo[d]isoxazol-5-yl)-3-(5-methyloxazol-2-yl)pyrazolo[1,5-a]pyrimidin-7(4H)-one

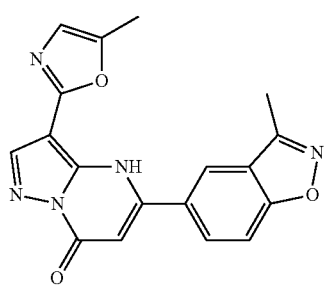 [SMILES: Cc1cnc(-c2cnn3c(=O)cc(-c4ccc5onc(C)c5c4)[nH]c23)o1]

To a solution of 4-(5-methyloxazol-2-yl)-1H-pyrazol-5-amine (50 mg, 0.30 mmol) in n-BuOH (0.2 mL) was added ethyl 3-(3-methylbenzo[d]isoxazol-5-yl)-3-oxopropanoate (110 mg, 0.45 mmol) and p-TsOH (5 mg) at room temperature. After refluxing 2 hours, the solids were collected by filtration and washed with methanol (3×2 mL) to afford 5-(3-methylbenzo[d]isoxazol-5-yl)-3-(5-methyloxazol-2-yl)pyrazolo[1,5-a]pyrimidin-7(4H)-one as an off-white solid (76.8 mg, 73%).

LCMS (ES, m/z): [M+H]⁺ 347.9

$^1$H-NMR (300 MHz, DMSO) δ 8.45-8.42 (m, 1H), 8.36 (s, 1H), 8.05 (dd, J=1.2, 8.7 Hz, 1H), 7.92 (d, J=9.0 Hz, 1H), 7.02 (d, J=1.2 Hz, 1H), 6.32 (s, 1H), 2.67 (s, 3H), 2.40 (s, 3H)

EXAMPLE 92

5-[4-chloro-3-(2,2,2-trifluoroethoxy)phenyl]-3-(3-methyl-1,2,4-oxadiazol-5-yl)-4H,7H-pyrazolo[1,5-a]pyrimidin-7-one

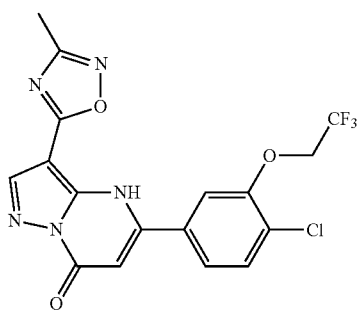 [SMILES: Cc1noc(-c2cnn3c(=O)cc(-c4ccc(Cl)c(OCC(F)(F)F)c4)[nH]c23)n1]

Step 1: 5-[4-chloro-3-(2,2,2-trifluoroethoxy)phenyl]-7-oxo-4H,7H-pyrazolo[1,5-a]pyrimidine-3-carbonitrile

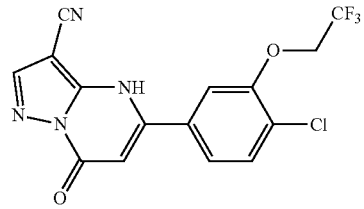 [SMILES: N#Cc1cnn2c(=O)cc(-c3ccc(Cl)c(OCC(F)(F)F)c3)[nH]c12]

A mixture of n-BuOH (0.5 mL), 5-amino-1H-pyrazole-4-carbonitrile (400 mg, 3.70 mmol, 1.00 equiv), ethyl 3-[4-chloro-3-(2,2,2-trifluoroethoxy)phenyl]-3-oxopropanoate (1.4 g, 4.31 mmol, 1.17 equiv), and p-TsOH (10 mg) was heated to reflux for 2 h. The reaction mixture was cooled to room temperature. The resulting solution was diluted with 10 mL of methanol. The solids were collected by filtration. The solid was washed with 4×10 mL of methanol, then dried in an oven under reduced pressure. This resulted in 0.8 g (59%) of 5-[4-chloro-3-(2,2,2-trifluoroethoxy)phenyl]-7-oxo-4H,7H-pyrazolo[1,5-a]pyrimidine-3-carbonitrile as a white solid.

LC-MS (ES, m/z): [M+H]$^+$ 369

$^1$H NMR (300 MHz, DMSO): δ 8.43 (s, 1H), 7.76-7.72 (m, 2H), 7.67-7.56 (m, 1H), 6.44 (s, 1H), 5.08-4.97 (m, 2H)

Step 2: 5-[4-chloro-3-(2,2,2-trifluoroethoxy)phenyl]-7-oxo-4H,7H-pyrazolo[1,5-a]pyrimidine-3-carboxamide

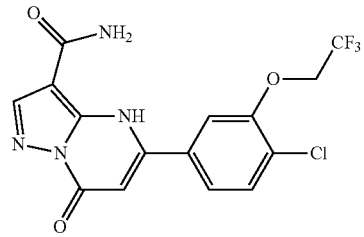 [SMILES: NC(=O)c1cnn2c(=O)cc(-c3ccc(Cl)c(OCC(F)(F)F)c3)[nH]c12]

To a mixture of methanol (18 mL), DMSO (12 mL), 5-[4-chloro-3-(2,2,2-trifluoroethoxy)phenyl]-7-oxo-4H,7H-pyrazolo[1,5-a]pyrimidine-3-carbonitrile (800 mg, 2.17 mmol, 1.00 equiv), and potassium carbonate (3 M) (30 mL) was added H$_2$O$_2$ (30 mL), in portions at 50° C. The reaction was stirred for 2 h at 50° C., and concentrated under vacuum. The residue was diluted with 20 mL of water. The pH of the solution was adjusted to pH 3-4 with HCl (1M). The solids were collected by filtration, washed with 4×20 mL of water and 4×20 of methanol, and dried in an oven under reduced pressure. This resulted in 0.75 g (89%) of 5-[4-chloro-3-(2,2,2-trifluoroethoxy)phenyl]-7-oxo-4H,7H-pyrazolo[1,5-a]pyrimidine-3-carboxamide as a white solid.

LC-MS (ES, m/z): [M+H]$^+$ 387

$^1$H NMR (300 MHz, DMSO): δ 11.379 (bs, 1H), 8.496 (s, 1H), 7.954 (bs, 1H), 7.739-7.600 (m, 2H), 7.478-7.314 (m, 2H), 6.484 (s, 1H), 5.094-4.980 (m, 2H)

Step 3: (E)-5-(4-chloro-3-(2,2,2-trifluoroethoxy)phenyl)-N-(1-(dimethylamino)ethylidene)-7-oxo-4,7-dihydropyrazolo[1,5-a]pyrimidine-3-carboxamide

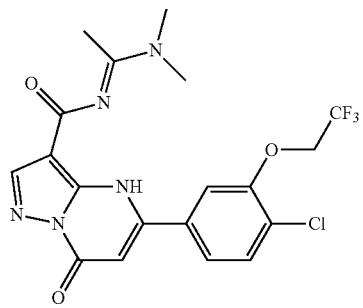 [SMILES: C/C(=N\C(=O)c1cnn2c(=O)cc(-c3ccc(Cl)c(OCC(F)(F)F)c3)[nH]c12)N(C)C]

A mixture of 5-[4-chloro-3-(2,2,2-trifluoroethoxy)phenyl]-7-oxo-4H,7H-pyrazolo[1,5-a]pyrimidine-3-carboxamide (400 mg, 1.03 mmol, 1.00 equiv) and DMADMA (560 mg, 4.21 mmol, 4.00 equiv) in N,N-dimethylformamide (3 mL) was stirred for 3 h at 120° C. The reaction progress was monitored by LCMS. The resulting mixture was concentrated under vacuum. This resulted in 450 mg (crude) of (E)-5-(4-chloro-3-(2,2,2-trifluoroethoxy)phenyl)-N-(1-(dimethylamino)ethylidene)-7-oxo-4,7-dihydropyrazolo[1,5-a]pyrimidine-3-carboxamide as an orange oil.

LC-MS (ES, m/z): [M+H]$^+$ 456

Step 4: 5-[4-chloro-3-(2,2,2-trifluoroethoxy)phenyl]-3-(3-methyl-1,2,4-oxadiazol-5-yl)-4H,7H-pyrazolo[1,5-a]pyrimidin-7-one

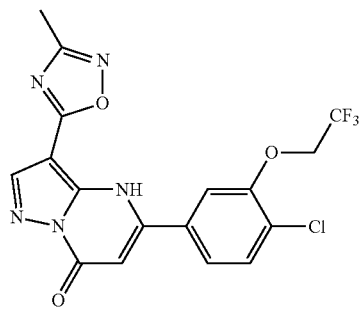

A mixture of (E)-5-(4-chloro-3-(2,2,2-trifluoroethoxy)phenyl)-N-(1-(dimethylamino)ethylidene)-7-oxo-4,7-dihydropyrazolo[1,5-a]pyrimidine-3-carboxamide (450 mg, crude), dioxane (4 mL), NH$_2$OH.HCl (103 mg, 1.48 mmol, 1.50 equiv), and a solution of AcOH (10 mL) in sodium hydroxide (10%) (1 mL) was stirred for 1 h at 100° C. The reaction progress was monitored by LCMS. The resulting mixture was concentrated in vacuo. The residue was applied onto a silica gel column with dichloromethane/methanol (80:1). This resulted in 29.4 mg (7%) of 5-[4-chloro-3-(2,2,2-trifluoroethoxy)phenyl]-3-(3-methyl-1,2,4-oxadiazol-5-yl)-4H,7H-pyrazolo[1,5-a]pyrimidin-7-one as a light yellow solid.

LC-MS (ES, m/z): [M+H]⁺ 426
¹H NMR (300 MHz, CD₃OD): δ 8.413 (s, 1H), 8.009-8.003 (d, J=1.8 Hz, 1H), 7.779-7.745 (dd, J=1.8 Hz, 8.4 Hz, 1H), 7.534-7.506 (d, J=8.4 Hz, 1H), 6.432 (s, 1H), 4.818-4.718 (m, 2H), 2.428 (s, 3H)

EXAMPLE 93

3-(1-ethyl-1H-pyrazol-5-yl)-5-(1-methyl-1H-indazol-5-yl)pyrazolo[1,5-a]pyrimidin-7(4H)-one

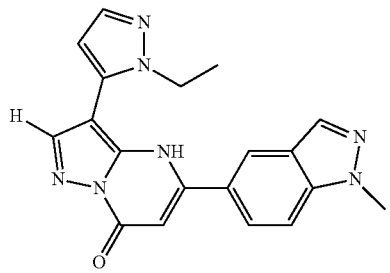 [SMILES: CCn1nccc1-c1cnn2c(=O)cc(-c3ccc4c(cnn4C)c3)[nH]c12]

To a solution of 2-ethyl-1'H,2H-3,4'-bipyrazol-5'-amine (50 mg, 0.28 mmol) in n-BuOH (0.2 mL) was added ethyl 3-(1-methyl-1H-indazol-5-yl)-3-oxopropanoate (105 mg, 0.42 mmol) and p-TsOH (5 mg) at room temperature. After refluxing 2 hours, the solids were collected by filtration and washed with methanol (3×2 mL) to afford 3-(1-ethyl-1H-pyrazol-5-yl)-5-(1-methyl-1H-indazol-5-yl)pyrazolo[1,5-a]pyrimidin-7(4H)-one as a white solid (77.9 mg, 77%).

LCMS (ES, m/z): [M+H]+ 360.1
¹H-NMR (300 MHz, DMSO) δ 12.41 (s, 1H), 8.22 (d, J=4.2 Hz, 2H), 8.03 (s, 1H), 7.81-7.75 (m, 2H), 7.55 (d, J=1.8 Hz, 1H), 6.44 (d, J=1.8 Hz, 1H), 6.12 (s, 1H), 4.09-4.04 (m, 5H), 1.32-1.27 (m, 3H)

EXAMPLE 94

5-(4-chloro-3-(2,2,2-trifluoroethoxy)phenyl)-3-(1-ethyl-1H-pyrazol-5-yl)pyrazolo[1,5-a]pyrimidin-7(4H)-one

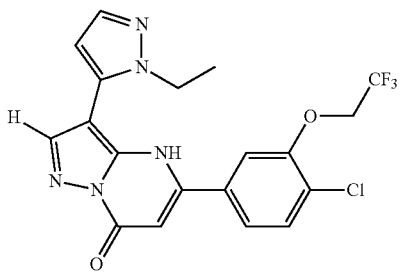 [SMILES: CCn1nccc1-c1cnn2c(=O)cc(-c3ccc(Cl)c(OCC(F)(F)F)c3)[nH]c12]

To a solution of 2-ethyl-1'H,2H-3,4'-bipyrazol-5'-amine (50 mg, 0.28 mmol) in n-BuOH (0.2 mL) was added ethyl 3-(1-methyl-1H-indazol-5-yl)-3-oxopropanoate (130 mg, 0.42 mmol) and p-TsOH (5 mg) at room temperature. After refluxing 2 hours, the solids were collected by filtration and washed with methanol (3×2 mL) to afford 5-(4-chloro-3-(2, 2,2-trifluoroethoxy)phenyl)-3-(1-ethyl-1H-pyrazol-5-yl)pyrazolo[1,5-a]pyrimidin-7(4H)-one as a white solid (91.4 mg, 74%).

LCMS (ES, m/z): [M+H]+ 438.0
¹H-NMR (300 MHz, DMSO) δ 8.02 (s, 1H), 7.65-7.62 (m, 2H), 7.51 (d, J=1.8 Hz, 1H), 7.42-7.40 (m, 1H), 5.02-4.9.3 (m, 2H), 4.06-3.99 (m, 2H), 1.27-1.22 (m, 3H)

EXAMPLE 95

5-(3,4-dichlorophenyl)-3-(1-ethyl-1H-pyrazol-5-yl)pyrazolo[1,5-a]pyrimidin-7(4H)-one

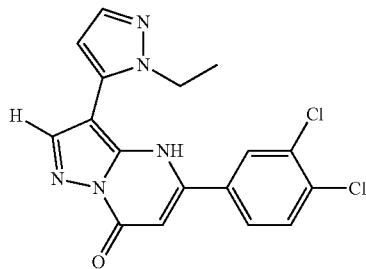 [SMILES: CCn1nccc1-c1cnn2c(=O)cc(-c3ccc(Cl)c(Cl)c3)[nH]c12]

To a solution of 2-ethyl-1'H,2H-3,4'-bipyrazol-5'-amine (50 mg, 0.28 mmol) in n-BuOH (0.2 mL) was added ethyl 3-(3,4-dichlorophenyl)-3-oxopropanoate (110 mg, 0.42 mmol) and p-TsOH (5 mg) at room temperature. After refluxing 2 hours, the solids were collected by filtration and washed with methanol (3×2 mL) to afford 5-(3,4-dichlorophenyl)-3-(1-ethyl-1H-pyrazol-5-yl)pyrazolo[1,5-a]pyrimidin-7(4H)-one as off-white solid (68.5 mg, 65%).

LCMS (ES, m/z): [M+H]⁺ 374.0
¹H-NMR (300 MHz, DMSO) δ 12.44 (brs, 1H), 8.03-8.01 (m, 2H), 7.79-7.70 (m, 2H), 7.51 (d, J=1.8 Hz, 1H), 6.40 (d, J=1.8 Hz, 1H), 6.13 (s, 1H), 4.02 (q, J=7.2 Hz, 2H), 2.23 (s, 3H), 1.24 (t, J=7.2 Hz, 3H)

EXAMPLE 96

5-(4-chloro-3-(2,2,2-trifluoroethoxy)phenyl)-3-(1-methyl-1H-pyrazol-3-yl)pyrazolo[1,5-a]pyrimidin-7(4H)-one

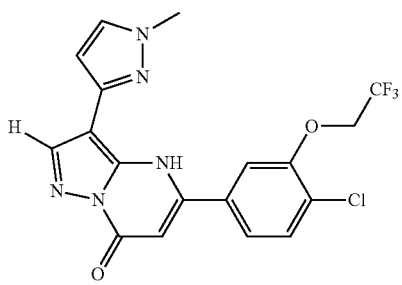 [SMILES: Cn1ccc(-c2cnn3c(=O)cc(-c4ccc(Cl)c(OCC(F)(F)F)c4)[nH]c23)n1]

To a solution of 1-methyl-1H,1'H-3,4'-bipyrazol-5'-amine (50 mg, 0.30 mmol) in n-BuOH (0.2 mL) was added ethyl 3-(4-chloro-3-(2,2,2-trifluoroethoxy)phenyl)-3-oxopropanoate (150 mg, 0.46 mmol) and p-TsOH (5 mg) at room temperature. After refluxing 2 hours, the solids were collected by filtration and washed with methanol (3×2 mL) to afford 5-(4-chloro-3-(2,2,2-trifluoroethoxy)phenyl)-3-(1-methyl-1H-pyrazol-3-yl)pyrazolo[1,5-a]pyrimidin-7(4H)-one as an off-white solid (92.9 mg, 72%).

LCMS (ES, m/z): [M+H]+ 424.0

¹H-NMR (300 MHz, DMSO) δ 11.19 (brs, 1H), 8.23 (s, 1H), 7.76-7.68 (m, 3H), 7.52 (d, J=8.1 Hz, 1H), 6.63 (d, J=1.8 Hz, 1H), 6.30 (s, 1H), 4.02 (q, J=8.7 Hz, 2H), 3.88 (s, 3H)

EXAMPLE 97

5-(2,3-dihydrobenzo[b][1,4]dioxin-6-yl)-3-(3-methyl-1,2,4-oxadiazol-5-yl)pyrazolo[1,5-a]pyrimidin-7(4H)-one

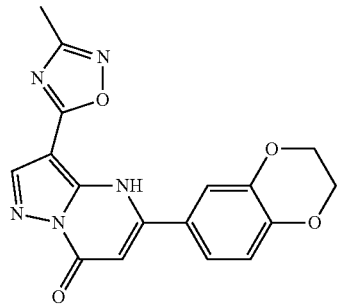 [SMILES: Cc1noc(-c2cnn3c(=O)cc(-c4ccc5c(c4)OCCO5)[nH]c23)n1]

Step 1: 5-(2,3-dihydrobenzo[b][1,4]dioxin-6-yl)-7-oxo-4,7-dihydropyrazolo[1,5-a]pyrimidine-3-carbonitrile

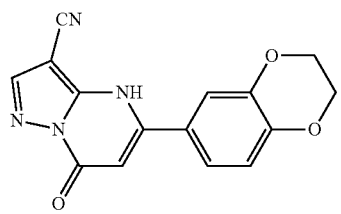 [SMILES: N#Cc1cnn2c(=O)cc(-c3ccc4c(c3)OCCO4)[nH]c12]

To a solution of 5-amino-1H-pyrazole-4-carbonitrile (300 mg, 2.78 mmol, 1.00 equiv) in n-BuOH (0.5 mL) was added ethyl 3-(2,3-dihydrobenzo[b][1,4]dioxin-6-yl)-3-oxopropanoate (1.04 g, 4.16 mmol, 1.50 equiv) and p-TsOH (24 mg, 0.14 mmol, 0.05 equiv) at room temperature. After refluxing for 2 h, the resulting solution was diluted with 5 mL of methanol. The solids were collected by filtration and washed with 3×3 mL of methanol to afford 5-(2,3-dihydrobenzo[b][1,4]dioxin-6-yl)-7-oxo-4,7-dihydropyrazolo[1, 5-a]pyrimidine-3-carbonitrile (700 mg, 86%) as a white solid.

LC-MS (ES, m/z): [M+H]+ 295.0

¹H NMR (300 MHz, DMSO): δ 13.31 (brs, 1H), 8.36 (s, 1H), 7.37 (d, J=2.4 Hz, 1H), 7.30 (dd, J=2.4 Hz, 8.7 Hz, 1H), 7.00 (d, J=2.4 Hz, 1H), 6.16 (s, 1H), 4.29 (m, 4H)

Step 2: 5-(2,3-dihydrobenzo[b][1,4]dioxin-6-yl)-7-oxo-4,7-dihydropyrazolo[1,5-a]pyrimidine-3-carboxamide

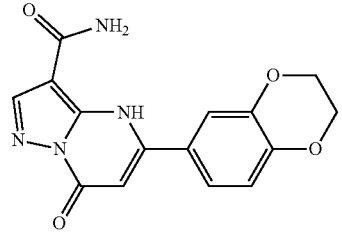 [SMILES: NC(=O)c1cnn2c(=O)cc(-c3ccc4c(c3)OCCO4)[nH]c12]

To a solution of 5-(2,3-dihydrobenzo[b][1,4]dioxin-6-yl)-7-oxo-4,7-dihydropyrazolo[1,5-a]pyrimidine-3-carbonitrile (700 mg, 2.38 mmol, 1.00 equiv) in methanol (12.6 mL)/DMSO (8.4 mL) was added potassium carbonate (3 M) (21 mL) at room temperature. This was followed by the addition of $H_2O_2$ (21 mL) dropwise with stirring at 50° C. over 30 min. After stirring for 2 h at 50° C., the resulting mixture was concentrated under vacuum. The residue was diluted with 20 mL of water. The pH of the solution was adjusted to pH 3-4 with aq. HCl (4N). The solids were collected by filtration and washed with 4×5 mL of methanol to afford 5-(2,3-dihydrobenzo[b][1,4]dioxin-6-yl)-7-oxo-4,7-dihydropyrazolo[1,5-a]pyrimidine-3-carboxamide (600 mg, 81%) as a white solid.

LC-MS (ES, m/z): [M+H]+ 313.0

¹H NMR (400 MHz, DMSO): δ 11.06 (brs, 1H), 8.37 (s, 1H), 7.97 (brs, 1H), 7.45-7.31 (m, 3H), 7.08 (d, J=7.5 Hz, 1H), 6.23 (s, 1H), 4.34 (s, 4H)

Step 3: (E)-5-(2,3-dihydrobenzo[b][1,4]dioxin-6-yl)-N-(1-(dimethylamino)ethylidene)-7-oxo-4,7-dihydropyrazolo[1,5-a]pyrimidine-3-carboxamide

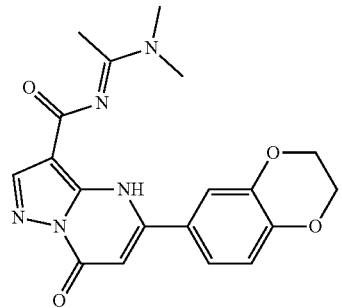 [SMILES: C/C(=N\C(=O)c1cnn2c(=O)cc(-c3ccc4c(c3)OCCO4)[nH]c12)N(C)C]

To a solution of 5-(2,3-dihydrobenzo[b][1,4]dioxin-6-yl)-7-oxo-4,7-dihydropyrazolo[1,5-a]pyrimidine-3-carboxamide (400 mg, 1.28 mmol, 1.00 equiv) in DMF (3 mL) was added DMA-DMA (682 mg, 5.13 mmol, 4.00 equiv). The resulting solution was stirred for 4 h at 130° C. The reaction progress was monitored by LCMS. The resulting mixture was concentrated under vacuum to afford (E)-5-(2,3-dihydrobenzo[b][1,4]dioxin-6-yl)-N-(1-(dimethylamino)ethylidene)-7-oxo-4,7-dihydropyrazolo[1,5-a]pyrimidine-3-carboxamide (450 mg, crude) as yellow oil.

LC-MS (ES, m/z): [M+H]+ 382.0

Step 4: 5-(2,3-dihydrobenzo[b][1,4]dioxin-6-yl)-3-(3-methyl-1,2,4-oxadiazol-5-yl)pyrazolo[1,5-a]pyrimidin-7(4H)-one

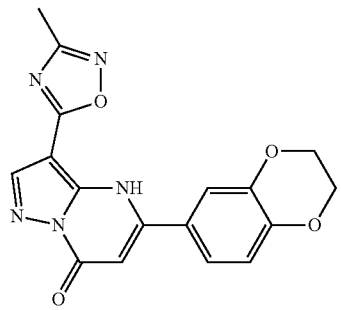 [SMILES: Cc1noc(-c2cnn3c(=O)cc(-c4ccc5c(c4)OCCO5)[nH]c23)n1]

To a solution of (E)-5-(2,3-dihydrobenzo[b][1,4]dioxin-6-yl)-N-(1-(dimethylamino)ethylidene)-7-oxo-4,7-dihydropyrazolo[1,5-a]pyrimidine-3-carboxamide (450 mg, crude) in dioxane (4 mL) was added NH$_2$OH.HCl (123 mg, 1.77 mmol, 1.50 equiv). Then a solution of AcOH (10 mL) in sodium hydroxide (10%) (1 mL) was added dropwise with stirring at room temperature over 10 min The resulting solution was stirred for 1 h at 100° C. The reaction progress was monitored by LCMS. The resulting mixture was concentrated under vacuum to give the residue, which was applied onto a silica gel column with dichloromethane/methanol (150:1-80:1) to afford 5-(2,3-dihydrobenzo[b][1,4]dioxin-6-yl)-3-(3-methyl-1,2,4-oxadiazol-5-yl)pyrazolo[1,5-a]pyrimidin-7(4H)-one (90.8 mg, 22%) as a light green solid.

LC-MS (ES, m/z): [M+H]$^+$ 352.0

$^1$H NMR (300 MHz, DMSO): δ 11.93 (brs, 1H), 8.52 (s, 1H), 7.37-7.32 (m, 2H), 7.07 (d, J=8.4 Hz, 1H), 6.25 (s, 5H), 4.34 (s, 4H), 2.50 (s, 3H)

EXAMPLE 98

5-(3,4-dichlorophenyl)-3-(1-methyl-1H-pyrazol-5-yl)pyrazolo[1,5-a]pyrimidin-7(4H)-one

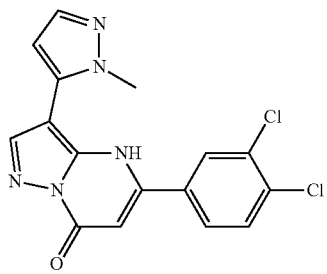 [SMILES: Cn1nccc1-c1cnn2c(=O)cc(-c3ccc(Cl)c(Cl)c3)[nH]c12]

To a solution of 2-methyl-1'H,2H-3,4'-bipyrazol-5'-amine (50 mg, 0.30 mmol) in n-BuOH (0.2 mL) was added ethyl 3-(3,4-dichlorophenyl)-3-oxopropanoate (120 mg, 0.45 mmol) and p-TsOH (5 mg) at room temperature. After refluxing 2 hours, the solids were collected by filtration and washed with methanol (3×2 mL) to afford 5-(3,4-dichlorophenyl)-3-(1-methyl-1H-pyrazol-5-yl)pyrazolo[1,5-a]pyrimidin-7(4H)-one as an off-white solid (39.5 mg, 37%).

LCMS (ES, m/z): [M+H]$^+$ 360.0

$^1$H-NMR (300 MHz, DMSO) δ 12.46 (brs, 1H), 8.10-8.08 (m, 2H), 7.80 (s, 2H), 7.51 (d, J=1.8 Hz, 1H), 6.48 (s, 1H), 6.18 (s, 1H), 3.80 (s, 3H)

EXAMPLE 99

3-(3-methyl-1,2,4-oxadiazol-5-yl)-5-(1-(oxetan-3-yl)-1H-indazol-5-yl)pyrazolo[1,5-a]pyrimidin-7(4H)-one

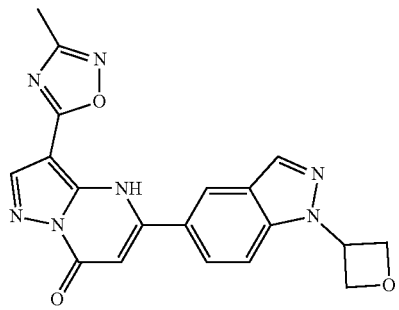 [SMILES: Cc1noc(-c2cnn3c(=O)cc(-c4ccc5c(cnn5C5COC5)c4)[nH]c23)n1]

Step 1: 2-(3-methyl-1,2,4-oxadiazol-5-yl)acetonitrile

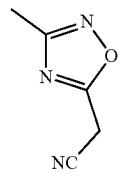

To a solution of 5-(chloromethyl)-3-methyl-1,2,4-oxadiazole (4.5 g, 33.95 mmol, 1.00 equiv) in CH$_3$CN (25 mL) was added a solution of KCN (2.6 g, 39.93 mmol, 1.20 equiv) in water (2.5 mL). The reaction mixture was stirred overnight at 50° C. The resulting solution was diluted with H$_2$O (20 mL), extracted with ethyl acetate (3×30 mL). The organic layers were combined, dried over anhydrous magnesium sulfate and concentrated under vacuum to give the residue, which was purified by silica gel column chromatography with 1% ethyl acetate in petroleum ether to afford 2-(3-methyl-1,2,4-oxadiazol-5-yl)acetonitrile (2 g, 48%) as a colorless oil.

LCMS (ES, m/z): [M+H]$^+$ 213.0

$^1$H NMR (300 MHz, DMSO, ppm): 4.68 (s, 2H), 2.36 (s, 3H)

Step 2: (Z)-3-(dimethylamino)-2-(3-methyl-1,2,4-oxadiazol-5-yl)acrylonitrile

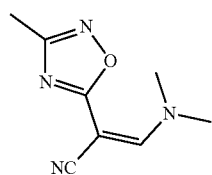

To a solution of 2-(3-methyl-1,2,4-oxadiazol-5-yl)acetonitrile (2.0 g, 16.24 mmol) in toluene (10 mL) was added DMF-DMA (20 mL) and the reaction was stirred for 10 h at 80° C. The reaction mixture was concentrated under vacuum to afford (Z)-3-(dimethylamino)-2-(3-methyl-1,2,4-oxadiazol-5-yl)acrylonitrile (crude) as a yellow solid.

LCMS (ES, m/z): [M+H]⁺ 180.0

Step 3: 3-(3-methyl-1,2,4-oxadiazol-5-yl)-1H-pyrazol-5-amine

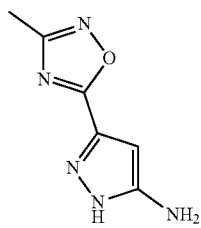

To a solution of (Z)-3-(dimethylamino)-2-(3-methyl-1,2,4-oxadiazol-5-yl)acrylonitrile (crude) in AcOH (10 mL) was added NH$_2$NH$_2$H$_2$O (8 mL) and the reaction was stirred for 6 h at 90° C. The reaction mixture was concentrated under vacuum and diluted with H$_2$O (20 mL). The resulting solution was extracted with EA (5×40 mL). The organic layers were combined, dried over magnesium sulfate and concentrated under vacuum to give the residue, which was purified by silica gel column chromatography (MeOH/DCM 150:1) to afford 3-(3-methyl-1,2,4-oxadiazol-5-yl)-1H-pyrazol-5-amine (1.0 g, 37% of two steps yield) as a white solid.

LCMS (ES, m/z): [M+H]⁺ 166.0

¹H-NMR: (DMSO, ppm): 12.11 (s, 1H), 7.68 (s, 1H), 6.19 (s, 2H), 2.31 (s, 3H)

Step 4: 5-(1H-indazol-5-yl)-3-(3-methyl-1,2,4-oxadiazol-5-yl)pyrazolo[1,5-a]pyrimidin-7(4H)-one

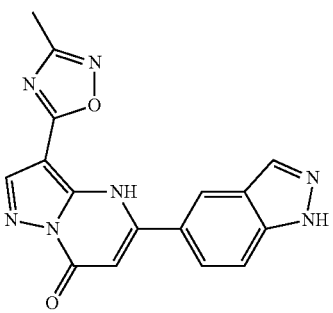 [SMILES: Cc1noc(-c2cnn3c(=O)cc(-c4ccc5[nH]ncc5c4)[nH]c23)n1]

To a solution of 3-(3-methyl-1,2,4-oxadiazol-5-yl)-1H-pyrazol-5-amine (100 mg, 0.6 mmol) in n-BuOH (2 ml) was added ethyl 3-(1-acetyl-1H-indazol-5-yl)-3-oxopropanoate (250 mg, 0.91 mmol) and TsOH (10 mg) and the reaction was stirred for 1 h at 120° C. The product was collected by filtration, and washed with MeOH (3×1 ml) to afford 5-(1H-indazol-5-yl)-3-(3-methyl-1,2,4-oxadiazol-5-yl)pyrazolo[1,5-a]pyrimidin-7(4H)-one (150 mg, 74%) as a yellow solid.

LCMS (ES, m/z): [M+H]⁺ : 334.0

¹H: (DMSO, ppm): δ 13.40 (s, 1H), 12.23 (brs, 1H), 8.51 (s, 1H), 8.40 (s, 2H), 7.72-7.80 (m, 2H), 6.33 (s, 1H), 4.51 (q, J=7.2, 2H), 2.33 (s, 3H)

Step 5: 3-(3-methyl-1,2,4-oxadiazol-5-yl)-5-(1-(oxetan-3-yl)-1H-indazol-5-yl)pyrazolo[1,5-a]pyrimidin-7(4H)-one

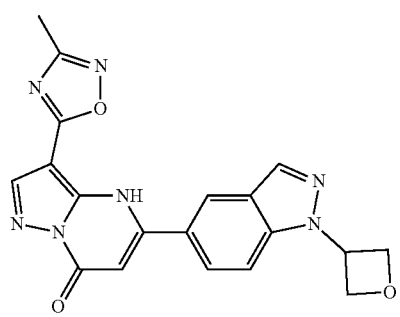 [SMILES: Cc1noc(-c2cnn3c(=O)cc(-c4ccc5c(cnn5C5COC5)c4)[nH]c23)n1]

To a mixture of 5-(1H-indazol-5-yl)-3-(3-methyl-1,2,4-oxadiazol-5-yl)pyrazolo[1,5-a]pyrimidin-7(4H)-one (150 mg, 0.45 mmol) and Cs$_2$CO$_3$ (292 mg, 0.89 mmol) in DMF (5 ml) was added 3-iodooxetane (124 mg, 0.67 mmol) with stirring for 10 h at 100° C. The solids were separated by filtration, and the filtrate was concentrated to afford a residue, which was purified by Prep-HPLC to afford 3-(3-methyl-1,2,4-oxadiazol-5-yl)-5-(1-(oxetan-3-yl)-1H-indazol-5-yl)pyrazolo[1,5-a]pyrimidin-7(4H)-one (34.2 mg, 74%) as a white solid.

LCMS (ES, m/z): [M+H]⁺ 390.0

¹H-NMR: (DMSO, ppm): δ 12.23 (brs, 1H), 8.50 (s, 1H), 8.46 (s, 1H), 8.34 (s, 1H), 7.89 (s, 2H), 6.35 (s, 1H), 6.10-6.19 (m, 1H), 5.02-5.07 (m, 1H), 2.50 (s, 3H)

EXAMPLE 100

5-(3,4-dichlorophenyl)-3-(3-methyl-1,2,4-oxadiazol-5-yl)-4H,7H-pyrazolo[1,5-a]pyrimidin-7-one

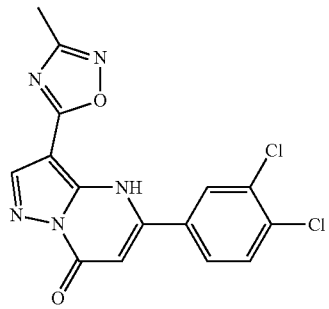 [SMILES: Cc1noc(-c2cnn3c(=O)cc(-c4ccc(Cl)c(Cl)c4)[nH]c23)n1]

Step 1: ethyl 3-(3,4-dichlorophenyl)-3-oxopropanoate

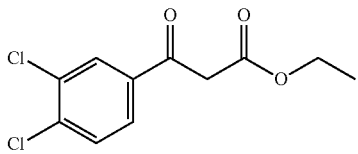 [SMILES: CCOC(=O)CC(=O)c1ccc(Cl)c(Cl)c1]

CDI (41.5 g, 290.32 mmol, 3.70 equiv) was added to a solution of 3,4-dichlorobenzoic acid (15 g, 78.53 mmol, 1.00 equiv) in tetrahydrofuran (200 mL), The resulting solution was stirred for 4 h at 25° C. Separately, to a solution of potassium 3-ethoxy-3-oxopropanoate (37.7 g, 235 mmol, 3.00 equiv) in CH$_3$CN (400 mL) was added MgCl$_2$ (33.5 g, 353 mmol, 4.5 equiv) and triethylamine (23.8 g, 235 mmol, 3.00 equiv). The two solutions were combined and stirred for 2 h at room temperature. The resulting mixture was concentrated under vacuum. The residue was diluted with 200 mL of water. The pH of the solution was adjusted to pH 5 with HCl (1M). The resulting solution was extracted with 4×50 mL of ethyl acetate and the organic layers were combined and dried over magnesium sulfate. The organics were concentrated in vacuo and purified by silica gel column chromatography with petroleum ether/ethyl acetate (50:1). This resulted in 15 g (73%) of ethyl 3-(3,4-dichlorophenyl)-3-oxopropanoate as a colorless oil.

Step 2: 5-(3,4-dichlorophenyl)-7-oxo-4H,7H-pyrazolo[1,5-a]pyrimidine-3-carbonitrile

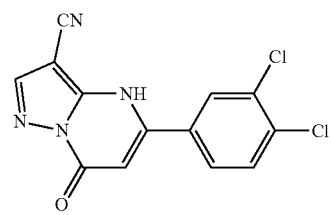 [SMILES: N#Cc1cnn2c(=O)cc(-c3ccc(Cl)c(Cl)c3)[nH]c12]

A mixture of ethyl 3-(3,4-dichlorophenyl)-3-oxopropanoate (1.2 g, 4.60 mmol, 1.20 equiv), 5-amino-1H-pyrazole-4-carbonitrile (400 mg, 3.70 mmol, 1.00 equiv), butan-1-ol (1 mL), and TsOH (10 mg, 0.06 mmol, 0.05 equiv) was stirred for 1 h at 130° C. The reaction progress was monitored by LCMS. The solids were collected by filtration. The solid was washed with 3×1 mL of methanol. This resulted in 0.8 g (71%) of 5-(3,4-dichlorophenyl)-7-oxo-4H,7H-pyrazolo[1,5-a]pyrimidine-3-carbonitrile as a white solid.

$^1$H NMR (300 MHz, DMSO): δ 8.44 (s, 1H), 8.17 (s, 1H), 7.85 (s, 1H), 6.37 (s, 1H)

Step 3: 5-(3,4-dichlorophenyl)-7-oxo-4H,7H-pyrazolo[1,5-a]pyrimidine-3-carboxamide

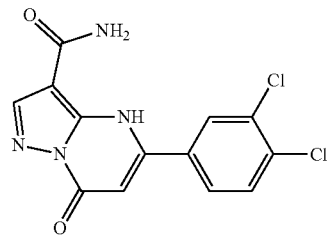 [SMILES: NC(=O)c1cnn2c(=O)cc(-c3ccc(Cl)c(Cl)c3)[nH]c12]

A solution of 5-(3,4-dichlorophenyl)-7-oxo-4H,7H-pyrazolo[1,5-a]pyrimidine-3-carbonitrile (800 mg, 2.62 mmol, 1.00 equiv) in sulfuric acid (3 mL) was stirred for 1 h at 25° C. The reaction was then quenched by the addition of 100 mL of water. The solids were collected by filtration and dried. This resulted in 0.7 g (83%) of 5-(3,4-dichlorophenyl)-7-oxo-4H,7H-pyrazolo[1,5-a]pyrimidine-3-carboxamide as a yellow solid.

LC-MS (ES, m/z): [M+H]$^+$ 323

Step 4: (E)-5-(3,4-dichlorophenyl)-N-(1-(dimethylamino)ethylidene)-7-oxo-4,7-dihydropyrazolo[1,5-a]pyrimidine-3-carboxamide

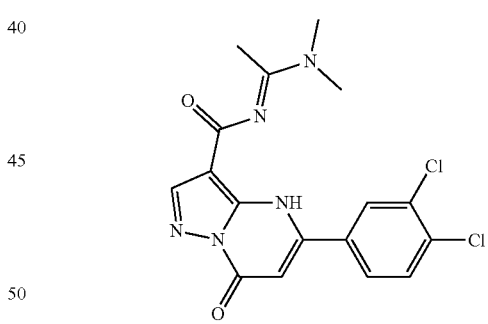

DMA-DMA (2 mL) was added to a solution of 5-(3,4-dichlorophenyl)-7-oxo-4H,7H-pyrazolo[1,5-a]pyrimidine-3-carboxamide (400 mg, 1.24 mmol, 1.00 equiv) in DMF (2 mL). The resulting solution was stirred for 1 h at 120° C. The resulting mixture was concentrated in vacuo. This resulted in 0.5 g (crude) of (E)-5-(3,4-dichlorophenyl)-N-(1-(dimethylamino)ethylidene)-7-oxo-4,7-dihydropyrazolo[1,5-a]pyrimidine-3-carboxamide as red oil.

LC-MS (ES, m/z): [M+H]$^+$ 392.0

Step 5: 5-(3,4-dichlorophenyl)-3-(3-methyl-1,2,4-oxadiazol-5-yl)-4H,7H-pyrazolo[1,5-a]pyrimidin-7-one

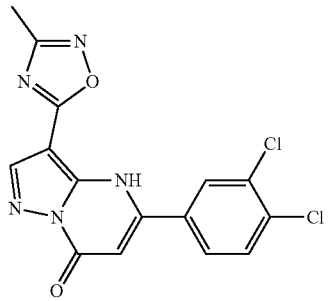 [SMILES: Cc1noc(-c2cnn3c(=O)cc(-c4ccc(Cl)c(Cl)c4)[nH]c23)n1]

NH$_2$OH.HCl (0.7 g, 1.095 mmol, 1.5 equiv) was added to (E)-5-(3,4-dichlorophenyl)-N-(1-(dimethylamino)ethylidene)-7-oxo-4,7-dihydropyrazolo[1,5-a]pyrimidine-3-carboxamide (500 mg, 1.27 mmol, 1.00 equiv, crude) in dioxane (5 mL). The reaction was stirred for 5 min at room temperature, then sodium hydroxide (1 mL, 10%) and AcOH (10 mL) were added. The reaction was stirred for 1 h at 100° C. After the reaction was completed, the mixture was diluted with 300 mL of water. The aqueous phase was extracted with 3×100 mL of dichloromethane and the organic layers were combined. The organic layers were washed with 1×100 mL of brine and then dried over anhydrous sodium sulfate. in vacuo and the product was purified by silica gel column chromatography with dichloromethane/methanol (50:1). This resulted in 22.4 mg (5%) of 5-(3,4-dichlorophenyl)-3-(3-methyl-1,2,4-oxadiazol-5-yl)-4H,7H-pyrazolo[1,5-a]pyrimidin-7-one as an off-white solid.

LC-MS (ES, m/z): [M+H]$^+$ 362.0
$^1$H NMR (300 MHz, CDCl$_3$): δ 8.50 (s, 1H), 8.13 (s, 1H), 7.87-7.80 (m, 2H), 6.36 (s, 1H), 2.41 (s, 1H)

EXAMPLE 101

5-(3,4-dichlorophenyl)-3-(4-methylthiazol-2-yl)pyrazolo[1,5-a]pyrimidin-7(4H)-one

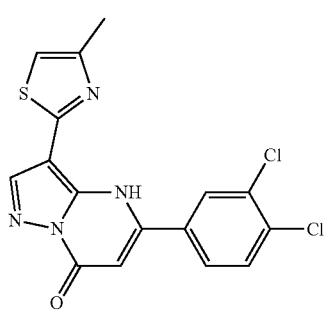 [SMILES: Cc1csc(-c2cnn3c(=O)cc(-c4ccc(Cl)c(Cl)c4)[nH]c23)n1]

To a solution of 4-(4-methylthiazol-2-yl)-1H-pyrazol-5-amine (50 mg, 0.27 mmol) in n-BuOH (1.0 mL) was added p-TsOH (4.7 mg, 0.03 mmol) and ethyl 3-(3,4-dichlorophenyl)-3-oxopropanoate (108 mg, 0.41 mmol). The reaction was stirred for 2 h at reflux, then cooled to room temperature and diluted with methanol (1 mL). The solids were collected by filtration and washed with MeOH (3×1 mL) to afford 5-(3,4-dichlorophenyl)-3-(4-methylthiazol-2-yl)pyrazolo[1,5-a]pyrimidin-7(4H)-one as a white solid (68.9 mg 65%).

LCMS (ES, m/z): [M+H]$^+$: 377.0
$^1$H NMR (300 MHz, CD$_3$OD): δ 8.46 (s, 1H), 8.43 (d, J=2.1 Hz, 1H), 8.11 (dd, J$_1$=2.1 Hz, J$_1$=8.4 Hz, 1H), 7.62 (d, J=8.4 Hz, 1H), 6.97 (s, 1H), 6.38 (s, 1H), 2.45 (s, 3H)

EXAMPLE 102

5-(3,4-dichlorophenyl)-3-(5-methylthiazol-2-yl)pyrazolo[1,5-a]pyrimidin-7(4H)-one

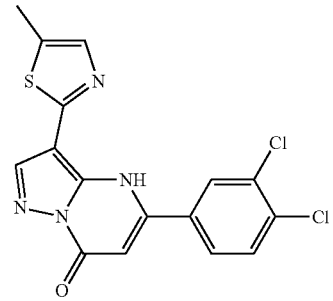 [SMILES: Cc1cnc(-c2cnn3c(=O)cc(-c4ccc(Cl)c(Cl)c4)[nH]c23)s1]

To a solution of 4-(5-methylthiazol-2-yl)-1H-pyrazol-5-amine (100 mg, 0.55 mmol) in n-BuOH (0.2 mL) was added ethyl 3-(3,4-dichlorophenyl)-3-oxopropanoate (220 mg, 0.83 mmol) and p-TsOH (10 mg) at room temperature. After refluxing for 2 hours, the solids were collected by filtration and washed with methanol (3×2 mL) to afford 5-(3,4-dichlorophenyl)-3-(5-methylthiazol-2-yl)pyrazolo[1,5-a]pyrimidin-7(4H)-one as a yellow solid (115.9 mg, 55%).

LCMS (ES, m/z): [M+H]$^+$ 377.0
$^1$H-NMR (300 MHz, DMSO) δ 8.41-8.39 (m, 2H), 8.14-8.10 (dd, J=2.1 Hz, 8.4 Hz, 1H), 7.63 (d, J=8.4 Hz, 1H), 7.35 (d, J=1.2 Hz, 1H), 6.37 (s, 1H), 2.54 (s, 3H)

EXAMPLE 103

3-(5-methyloxazol-2-yl)-5-(1-propyl-1H-indazol-5-yl)pyrazolo[1,5-a]pyrimidin-7(4H)-one

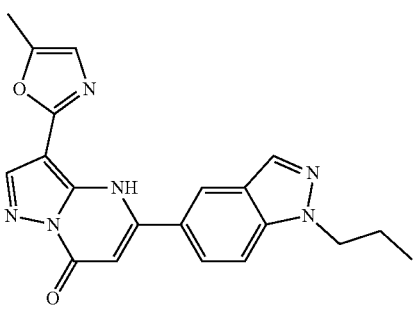 [SMILES: CCCn1ncc2cc(-c3cc(=O)n4ncc(-c5ncc(C)o5)c4[nH]3)ccc21]

To a solution of 4-(5-methyloxazol-2-yl)-1H-pyrazol-5-amine (50 mg, 0.30 mmol) in n-BuOH (0.1 ml) was added ethyl 3-oxo-3-(1-propyl-1H-indazol-5-yl)propanoate (50 mg, 0.18 mmol) and p-TsOH (5 mg) and the reaction was stirred for 2 h at 130° C. The product was collected by filtration, and washed with MeOH (3×1 ml) to afford 3-(5-methyloxazol-2-yl)-5-(1-propyl-1H-indazol-5-yl)pyrazolo[1,5-a]pyrimidin-7(4H)-one as a white solid (41.3 mg, 60%).

LC-MS (ES, m/z): 375 [M+H]+

¹H NMR (300 MHz, DMSO-d₆, ppm): δ 8.42 (s, 1H), 8.30 (d, J=4.5 Hz, 2H), 7.93-7.81 (m, 2H), 7.03 (d, J=1.2 Hz, 1H), 6.29 (s, 1H), 4.48 (t, J=6.9 Hz, 2H), 2.4 (s, 3H), 1.94-1.86 (m, 2H), 1.89-1.78 (m, 3H)

EXAMPLE 104

3-(1-ethyl-1H-pyrazol-5-yl)-5-(1-propyl-1H-indazol-5-yl)-4H,7H-pyrazolo[1,5-a]pyrimidin-7-one

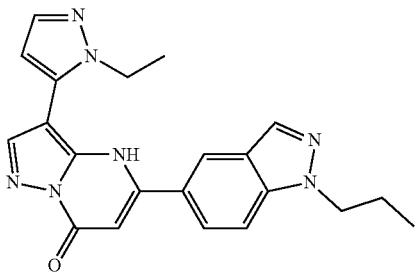 [SMILES: CCCn1ncc2cc(-c3cc(=O)n4ncc(-c5ccnn5CC)c4[nH]3)ccc21]

To a solution of ethyl 3-oxo-3-(1-propyl-1H-indazol-5-yl)propanoate (100 mg, 0.36 mmol) in n-BuOH (1 mL) was added p-TsOH (5 mg) and 2-ethyl-1'H,2H-3,4'-bipyrazol-5'-amine (50 mg, 0.28 mmol) at room temperature. The reaction was stirred for 2 h at 120° C. The solids were collected by filtration and washed with MeOH (3×1 ml). This resulted in 91.7 mg (65%) of 3-(1-ethyl-1H-pyrazol-5-yl)-5-(1-propyl-1H-indazol-5-yl)-4H,7H-pyrazolo[1,5-a]pyrimidin-7-one as a white solid.

LC-MS (ES, m/z): 387 [M+H]+

¹H NMR (300 MHz, DMSO-d₆, ppm): δ 12.40 (s, 1H), 8.21-8.29 (m, 2H), 8.03 (s, 1H, 7.72-7.85 (m, 2H), 7.55 (s, 1H), 6.43 (d, J=1.8 Hz, 1H), 6.11-6.12 (d, J=1.5 Hz, 1H), 4.41-4.45 (t, J=6.9 Hz, 2H), 4.04 (q J=7.5 Hz, 2H), 1.84 (q, J=6.9 Hz, 2H), 1.27 (t, J=5.4 Hz, 3H), 0.85 (t, J=7.2 Hz, 3H)

EXAMPLE 105

5-(1-Ethyl-3-methyl-1H-indazol-5-yl)-3-(5-methyl-oxazol-2-yl)pyrazolo[1,5-a]pyrimidin-7(4H)-one

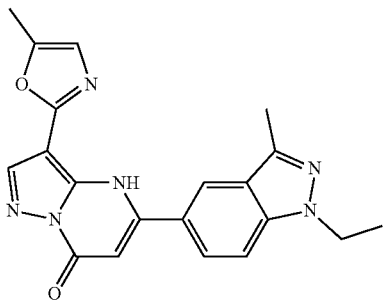 [SMILES: CCn1nc(C)c2cc(-c3cc(=O)n4ncc(-c5ncc(C)o5)c4[nH]3)ccc21]

Step 1: 5-Bromo-3-methyl-1H-indazole

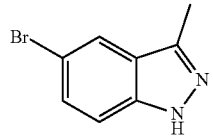

N₂H₄·H₂O (50 mL) was added to a solution of 1-(5-bromo-2-fluorophenyl)ethanone (10 g, 1.00 eq.). The reaction mixture was stirred for 20 h at 50° C. Then it was cooled to room temperature and concentrated in vacuo. The product was purified by silica gel column chromatography with ethyl acetate/hexane (1:90). This afforded 6.2 g (64%) of 5-bromo-3-methyl-1H-indazole as a white solid.

¹H-NMR: (300 MHz, DMSO-d6, ppm): δ 12.82 (s, 1H), 7.96 (s, 1H), 7.43 (m, 2H), 2.48 (s, 3H)

Step 2: Methyl 3-methyl-1H-indazole-5-carboxylate

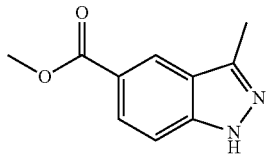

To a solution of 5-bromo-3-methyl-1H-indazole (6.2 g, 1.0 eq) in methanol (700 mL) was added triethylamine (5.9 g, 2.0 eq) and Pd(dppf)Cl₂ (1.2 g, 0.05 eq), and the reaction was placed under an atmosphere of CO (g) at 20 atm. The resulting reaction was stirred overnight at 100° C. Then the mixture was concentrated in vacuo to afford a residue, which was purified by a silica gel column chromatography with ethyl acetate/petroleum ether (1/50) to afford methyl 3-methyl-1H-indazole-5-carboxylate (5.2 g, 93%) as a white solid.

¹H-NMR: (DMSO, ppm): δ 12.99 (s, 1H), 8.40 (s, 1H), 7.90 (dd, J₁=1.2 Hz, J₂=9.0 Hz, 1H), 7.53 (d, J=9.0 Hz, 1H), 3.87 (s, 3H), 2.54 (s, 3H)

Step 3: Methyl 1-ethyl-3-methyl-1H-indazole-5-carboxylate

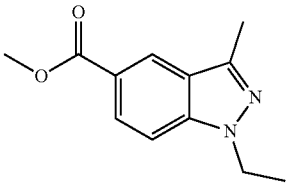 [SMILES: CCn1nc(C)c2cc(C(=O)OC)ccc21]

Potassium carbonate (7.6 g, 54.99 mmol, 2.00 equiv) was added to a solution of methyl 3-methyl-1H-indazole-5-carboxylate (5.2 g, 27.34 mmol, 1.00 equiv) in DMF (50 mL). Then EtI (8.6 g, 54.99 mmol, 2.00 equiv) was added and the reaction was stirred overnight at room temperature and quenched by the addition of 200 mL of water. The resulting solution was extracted with 4×100 mL of ethyl acetate and the organic layers combined and dried over anhydrous sodium sulfate. The organic layer was concentrated in vacuo and the product was purified by a silica gel column chromatography with ethyl acetate/petroleum ether (1/50) to afford methyl 1-ethyl-3-methyl-1H-indazole-5-carboxylate (4.4 g, 73%) as colorless oil.

$^1$H-NMR: (CDCl$_3$, ppm): δ 8.43 (dd, J$_1$=0.6 Hz, J$_2$=1.5 Hz, 1H), 8.03 (dd, J$_1$=1.5 Hz, J$_2$=9.0 Hz, 1H), 7.35 (d, J=0.6 Hz, 1H), 7.27 (q, J=7.2 Hz, 2H), 3.94 (s, 3H), 2.60 (s, 3H), 1.49 (t, J=7.2 Hz, 3H)

Step 4: 1-Ethyl-3-methyl-1H-indazole-5-carboxylic acid

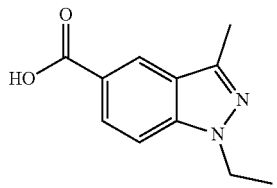

Sodium hydroxide (3.2 g, 80.00 mmol, 4.00 equiv) was added to a solution of methyl 1-ethyl-3-methyl-1H-indazole-5-carboxylate (4.4 g, 20.16 mmol) in methanol (50 mL) and water (10 mL). The resulting solution was stirred overnight at room temperature then concentrated in vacuo. The residue was diluted with 100 mL of H$_2$O and adjusted the pH of the solution to pH 2-3 with HCl (3 N). The product was precipitated by the addition of water and the solid was collected by filtration, to afford 1-ethyl-3-methyl-1H-indazole-5-carboxylic acid (4.0 g, 97%) as a white solid.

$^1$H-NMR: (DMSO, ppm): δ 12.71 (s, 1H), 8.37 (s, 1H), 7.92 (dd, J$_1$=1.5 Hz, J$_2$=9.0 Hz, 1H), 7.65 (d, J=9.0 Hz, 1H), 4.38 (q, J=7.2 Hz, 2H), 2.51 (s, 3H), 1.37 (t, J=7.2 Hz, 3H)

Step 5: Ethyl 3-(1-ethyl-3-methyl-1H-indazol-5-yl)-3-oxopropanoate

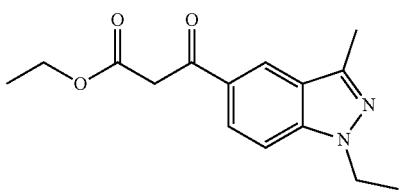 [SMILES: CCOC(=O)CC(=O)c1ccc2c(c1)c(C)nn2CC]

CDI (5.0 g, 1.5 eq) was added to a solution of 1-ethyl-3-methyl-1H-indazole-5-carboxylic acid (4.0 g, 1.0 eq) in THF (80 mL). The reaction was stirred for 3 h at RT. Then a solution of malonic acid monoethyl ester; magnesium salt [prepared via the addition of triethylamine (6.2 g, 61.27 mmol, 3.00 equiv) and MgCl$_2$ (8.8 g, 92.63 mmol, 4.50 equiv) to a solution of potassium 3-ethoxy-3-oxopropanoate (10.5 g, 61.69 mmol, 1.50 equiv) in CH$_3$CN (40 mL)] was added. The resulting solution was stirred overnight at room temperature. The reaction was then quenched by the addition of 250 mL of H$_2$O. Then pH of the solution was adjusted to 2-3 with HCl (3N). The resulting solution was extracted with ethyl acetate (4×200 mL) and the organic layers combined and dried over anhydrous sodium sulfate and concentrated in vacuo. The residue was applied onto a silica gel column with ethyl acetate/petroleum ether (1:10) to afford ethyl 3-(1-ethyl-3-methyl-1H-indazol-5-yl)-3-oxopropanoate (3.5 g, 65%) as light yellow oil.

$^1$H-NMR: (CDCl$_3$, ppm): δ 10.00-11.00 (br s, 1H), 8.32 (d, J=0.6 Hz, 1H), 8.01 (dd, J$_1$=1.5 Hz, J$_2$=6.6 Hz, 1H), 7.38 (d, J=6.6 Hz, 1H), 4.39 (q, J=7.2 Hz, 2H), 4.28 (q, J=7.2 Hz, 2H), 4.07 (s, 2H), 2.62 (s, 3H), 1.50 (t, J=7.2 Hz, 3H), 1.35 (t, J=7.2 Hz, 3H)

Step 6: 5-(1-Ethyl-3-methyl-1H-indazol-5-yl)-3-(5-methyloxazol-2-yl)pyrazolo[1,5-a]pyrimidin-7(4H)-one

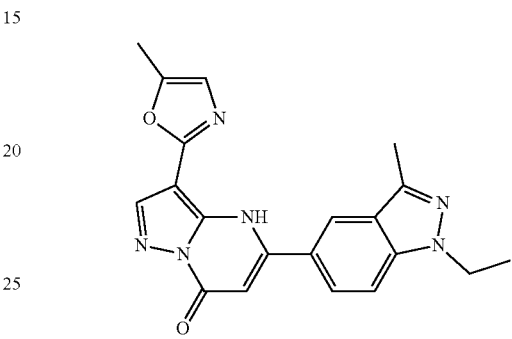

4-(5-Methyloxazol-2-yl)-1H-pyrazol-5-amine (50 mg, 1.0 eq) and TsOH (10 mg) were added to a solution of ethyl 3-(1-ethyl-3-methyl-1H-indazol-5-yl)-3-oxopropanoate (120 mg, 1.5 eq) in n-BuOH (2 ml) and the reaction was stirred for 2 h at 120° C. The reaction mixture was cooled to room temperature and diluted with 2 mL of methanol. The solids were collected by filtration to afford 5-(1-ethyl-3-methyl-1H-indazol-5-yl)-3-(5-methyloxazol-2-yl)pyrazolo[1,5-a]pyrimidin-7(4H)-one (24.2 mg, 21%).

LCMS (ES, m/z): [M+H]+ 375.0

$^1$H-NMR: (DMSO, ppm): δ 8.29 (s, 1H), 7.83 (s, 1H), 7.03-7.80 (m, 2H), 7.03 (s, 1H), 6.32 (s, 1H), 4.28 (q, J=7.2, 2H), 2.73 (s, 3H), 2.40 (s, 3H), 1.39 (t, J=7.2, 3H)

EXAMPLE 106

5-(4-Chlorophenyl)-3-(5-methylthiazol-2-yl)pyrazolo[1,5-a]pyrimidin-7(4H)-one

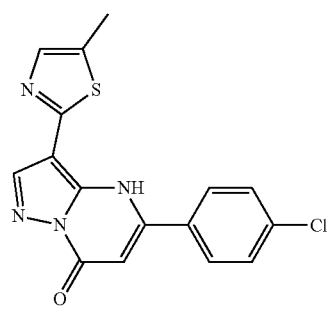 [SMILES: Cc1cnc(-c2cnn3c(=O)cc(-c4ccc(Cl)cc4)[nH]c23)s1]

To a solution of 4-(5-methylthiazol-2-yl)-1H-pyrazol-5-amine (50 mg, 0.28 mmol) in n-BuOH (0.2 mL) was added ethyl 3-(4-chlorophenyl)-3-oxopropanoate (100 mg, 0.42 mmol) and p-TsOH (10 mg) at room temperature. After refluxing 2 hours, the solids were collected by filtration and washed with methanol (3×2 mL) to afford 5-(4-chlorophenyl)-3-(5-methylthiazol-2-yl)pyrazolo[1,5-a]pyrimidin-7(4H)-one as an yellow solid (65.0 mg, 68%).

LCMS (ES, m/z): [M+H]⁺ 343.0

¹H-NMR (300 MHz, CD₃OD) δ 8.38 (s, 1H), 8.24-8.20 (m, 2H), 7.51-7.47 (m, 2H), 7.34 (d, J=1.2 Hz, 1H), 6.37 (s, 1H), 2.53 (s, 3H)

EXAMPLE 107

5-(1-Methyl-1H-indazol-5-yl)-3-(5-methyloxazol-2-yl)pyrazolo[1,5-a]pyrimidin-7(4H)-one

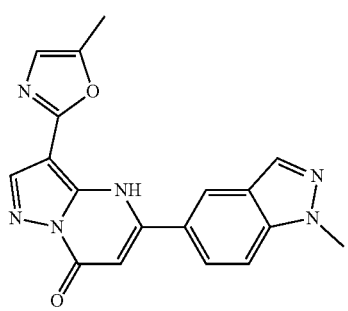 [SMILES: Cc1cnc(-c2cnn3c(=O)cc(-c4ccc5c(cnn5C)c4)[nH]c23)o1]

To a solution of 4-(5-methyloxazol-2-yl)-1H-pyrazol-5-amine (50 mg, 0.3 mmol) in n-BuOH (0.2 mL) was added ethyl 3-(1-methyl-1H-indazol-5-yl)-3-oxopropanoate (110 mg, 0.46 mmol) and p-TsOH (10 mg) at room temperature. After refluxing 2 hours, the solids were collected by filtration and washed with methanol (3×2 mL) to afford 5-(1-methyl-1H-indazol-5-yl)-3-(5-methyloxazol-2-yl)pyrazolo[1,5-a]pyrimidin-7(4H)-one as a yellow solid (27.3 mg, 26%).

LCMS (ES, m/z): [M+H]⁺ 347.0

¹H-NMR (300 MHz, DMSO) δ 8.33 (s, 1H), 8.28 (d, J=7.2 Hz, 2H), 7.86 (s, 2H), 7.03 (d, J=1.5 Hz, 1H), 6.29 (s, 1H), 4.12 (s, 3H), 2.40 (s, 3H)

EXAMPLE 108

5-(1-methyl-1H-indazol-5-yl)-7-oxo-4H,7H-pyrazolo[1,5-a]pyrimidine-3-carbonitrile

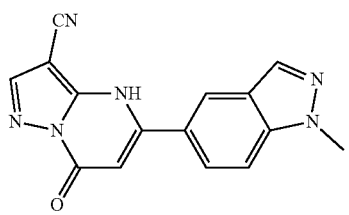 [SMILES: Cn1ncc2cc(-c3cc(=O)n4ncc(C#N)c4[nH]3)ccc21]

To a solution of 5-amino-1H-pyrazole-4-carbonitrile (300 mg, 2.7 mmol) in n-BuOH (1 mL) was added ethyl 3-(1-methyl-1H-indazol-5-yl)-3-oxopropanoate (854 mg, 3.4 mmol) and p-TsOH (10 mg) at room temperature. The resulting solution was stirred for 2 h at 120° C. After the reaction was complete, it was quenched by the addition of 10 mL of methanol. The solids were collected by filtration, and washed with MeOH (3×1 ml). This resulted in 600 mg (74%) of 5-(1-methyl-1H-indazol-5-yl)-7-oxo-4H,7H-pyrazolo[1,5-a]pyrimidine-3-carbonitrile as a yellow solid.

LC-MS (ES, m/z): [M+H]⁺ 291

¹H NMR (300 MHz, DMSO): δ 13.54 (s, 1H), 8.43 (s, 1H), 8.34 (s, 1H), 8.26 (s, 1H), 7.81-7.88 (m, 2H), 6.31 (s, 1H), 4.12 (s, 3H)

EXAMPLE 109

5-(1-ethyl-1H-indazol-6-yl)-3-(oxazol-2-yl)pyrazolo[1,5-a]pyrimidin-7(4H)-one

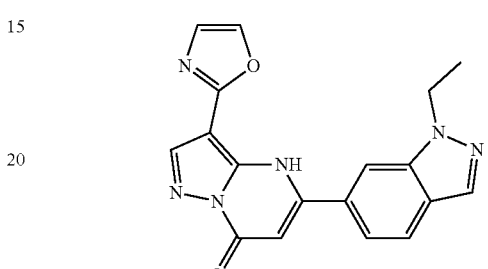

Step 1: Methyl 1-ethyl-1H-indazole-6-carboxylate

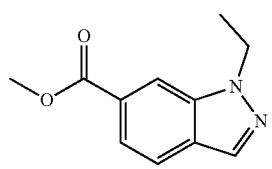

Potassium carbonate (28.2 g) was added to a solution of methyl 1H-indazole-6-carboxylate (18 g) in DMF (80 mL). Then EtI (31.9 g) was added dropwise with stirring and the reaction was stirred for 4 h at room temperature. The reaction was quenched by the addition of 100 mL of water, extracted with 4×100 mL of ethyl acetate and the organic layers were combined, dried over anhydrous sodium sulfate and concentrated in vacuo to provide the product, which was purified by a silica gel column chromatography with 10% ethyl acetate in petroleum ether to afford methyl 1-ethyl-1H-indazole-6-carboxylate (10 g, 48%) as a red solid.

LCMS (ES, m/z): [M+H]⁺ 205

¹H NMR (300 MHz, DMSO): δ 8.33 (d, J=0.9 Hz, 1H), 8.19 (d, J=0.9 Hz, 1H), 7.87 (dd, J=0.9 Hz, 8.7 Hz, 1H), 7.70 (dd, J=1.5 Hz, 8.7 Hz, 1H), 4.54 (q, J=7.2 Hz, 2H), 3.91 (s, 3H), 1.45 (t, J=7.2 Hz, 3H)

Step 2: 1-Ethyl-1H-indazole-6-carboxylic acid

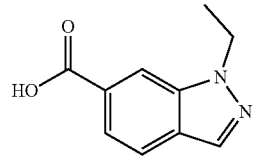

To a solution of methyl 1-ethyl-1H-indazole-6-carboxylate (10 g) in methanol (40 ml) was added sodium hydroxide (7.8 g) and water (10 ml). After stirring 3 h at room temperature, the resulting solution was concentrated in vacuo, dissolved in water (80 ml), and adjusted to pH 6 with aq. HCl (3M). The product was precipitated from water and collected by filtration to afford 1-ethyl-1H-indazole-6-carboxylic acid as an off-white solid (8 g, 86%).

LCMS (ES, m/z): [M+H]$^+$ 191

$^1$H NMR (400 MHz, DMSO): δ 13.07 (s, 1H), 8.29 (s, 1H), 8.17 (s, 1H), 7.84 (d, J=8.4 Hz, 1H), 7.69 (dd, J=1.2 Hz, 8.4 Hz, 1H), 4.53 (q, J=7.2 Hz, 2H), 1.41 (t, J=7.2 Hz, 3H)

Step 3: Ethyl 3-(1-ethyl-1H-indazol-6-yl)-3-oxopropanoate

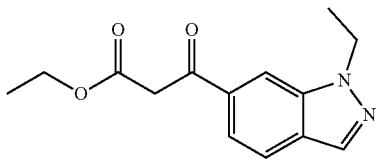 [SMILES: CCOC(=O)CC(=O)c1ccc2cnn(CC)c2c1]

To a solution 1-ethyl-1H-indazole-6-carboxylic acid (8 g) in THF (20 ml) was added CDI (10.2 g). The reaction was stirred at room temperature for 3 h and then a solution of the magnesium salt of malonic acid monoethyl ester [prepared via the addition of Et$_3$N (12.8 g) and MgCl$_2$ (18 g) to a solution of potassium monoethylonate (21.5 g) in acetonitrile (60 ml) and stirred at room temperature for 3 h] was added at room temperature. The reaction mixture was stirred overnight at RT, quenched by the addition of water (150 ml) and adjusted to pH 3 with aq. HCl (3M). The mixture was extracted with ethyl acetate (4×200 ml) and the organic layers were combined, dried over anhydrous magnesium sulfate and concentrated in vacuo to afford a residue, which was purified by a silica gel column chromatography eluting with 50% ethyl acetate in petroleum ether to afford ethyl 3-(1-ethyl-1H-indazol-6-yl)-3-oxopropanoate as a red oil (7.5 g, 69%).

LCMS (ES, m/z): [M+H]$^+$ 261

$^1$H NMR (300 MHz, DMSO): δ 8.42 (s, 1H), 8.19 (s, 1H), 7.89-7.81 (m, 1H), 7.68-7.62 (m, 1H), 4.54 (q, J=7.2 Hz, 2H), 4.32 (s, 2H), 4.17-4.06 (m, 3H), 3.36-3.33 (m, 2H), 1.45-1.38 (m, 3H)

Step 4: 5-(1-ethyl-1H-indazol-6-yl)-7-oxo-4,7-dihydropyrazolo[1,5-a]pyrimidine-3-carbonitrile

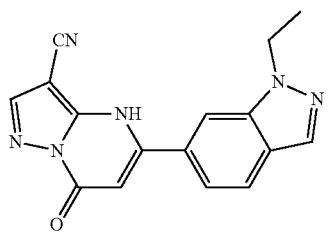 [SMILES: CCn1ncc2ccc(-c3cc(=O)n4ncc(C#N)c4[nH]3)cc21]

To a solution of 5-amino-1H-pyrazole-4-carbonitrile (300 mg) in BuOH (0.7 ml) was added ethyl 3-(1-ethyl-1H-indazol-6-yl)-3-oxopropanoate (1.1 g) and TsOH (24 mg) with stirring for 3 h at 120° C. The product was collected by filtration, and washed with MeOH (3×3 ml) to afford 5-(1-ethyl-1H-indazol-6-yl)-7-oxo-4,7-dihydropyrazolo[1,5-a]pyrimidine-3-carbonitrile (500 mg) as a yellow solid.

LCMS (ES, m/z): [M+H]$^+$ 305

$^1$H NMR (300 MHz, DMSO): δ 13.58 (bs, 1H), 8.46 (s, 1H), 8.24 (s, 1H), 8.19 (d, J=0.9 Hz, 1H), 7.94 (d, J=8.4 Hz, 1H), 7.56 (dd, J=1.2 Hz, 8.4 Hz, 1H), 6.41 (s, 1H), 4.55 (q, J=7.2 Hz, 2H), 1.45 (t, J=7.2 Hz, 3H)

Step 5: 5-(1-ethyl-1H-indazol-6-yl)-7-oxo-4,7-dihydropyrazolo[1,5-a]pyrimidine-3-carboxamide

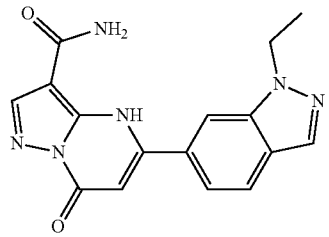 [SMILES: CCn1ncc2ccc(-c3cc(=O)n4ncc(C(N)=O)c4[nH]3)cc21]

5-(1-ethyl-1H-indazol-6-yl)-7-oxo-4,7-dihydropyrazolo[1,5-a]pyrimidine-3-carbonitrile (500 mg, 1.00 equiv) was dissolved in concentrated sulfuric acid (5 mL, 98%) at room temperature. After 1 h, the reaction was cautiously quenched with ice water (20 mL). The solids were collected by filtration, washed with water (5×30 mL) and dried to afford 5-(1-ethyl-1H-indazol-6-yl)-7-oxo-4,7-dihydropyrazolo[1,5-a]pyrimidine-3-carboxamide as an off-white solid (400 mg, 76%).

LCMS: (ES, m/z): [M+H]$^+$ 323

$^1$H NMR (300 MHz, DMSO): δ 11.32 (bs, 1H), 8.40 (s, 1H), 8.33 (s, 1H), 8.28 (s, 1H), 7.98-7.87 (m, 2H), 7.51-7.48 (m, 2H), 6.425 (s, 1H), 4.56 (q, J=7.2 Hz, 2H), 1.44 (t, J=7.2 Hz, 3H)

Step 6: 5-(1-ethyl-1H-indazol-6-yl)-3-(oxazol-2-yl)pyrazolo[1,5-a]pyrimidin-7(4H)-one

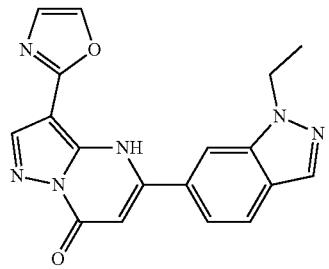 [SMILES: CCn1ncc2ccc(-c3cc(=O)n4ncc(-c5ncco5)c4[nH]3)cc21]

To a solution of 5-(1-ethyl-1H-indazol-6-yl)-7-oxo-4,7-dihydropyrazolo[1,5-a]pyrimidine-3-carboxamide (200 mg, 1.00 equiv) in NMP (0.2 mL) was added TsOH (6 mg) and 2-bromo-1,1-diethoxyethane (183 mg, 1.50 equiv) at room temperature. After stirring for 20 min at 110° C. the reaction was diluted with ether (10 mL) and filtered. The filter cake was washed with ether (3×10 mL) and water (3×10 mL). The solids were collected to give the crude product which was purified by Prep-HPLC under the following conditions (Prep-HPLC-007): Column, XBridge Shield RP18 OBD Column, 5 um, 19*150 mm, mobile phase, WATER WITH 0.05% TFA and MeCN (25.0% MeCN up to 35.0% in 4 min, hold 35.0% in 1 min, up to 97.0% in 1 min); Detector, uv 254 nm. This resulted in 74.6 mg (35%) of 5-(1-ethyl-1H-indazol-6-yl)-3-(oxazol-2-yl)pyrazolo[1,5-a]pyrimidin-7(4H)-one as an off-white solid.

LCMS (ES, m/z): [M+H]$^+$ 347

$^1$H NMR (300 MHz, DMSO): δ 8.42 (s, 1H), 8.28 (s, 1H), 8.21-8.20 (m, 2H), 7.97 (d, J=8.7 Hz, 1H), 7.53 (dd, J=1.5 Hz, 8.7 Hz, 1H), 7.43 (d, J=0.6 Hz, 1H), 6.413 (s, 1H), 4.54 (q, J=7.2 Hz, 2H), 1.45 (t, J=7.2 Hz, 3H)

EXAMPLE 110

5-(3-methylbenzo[d]isoxazol-5-yl)-3-(oxazol-2-yl)pyrazolo[1,5-a]pyrimidin-7(4H)-one

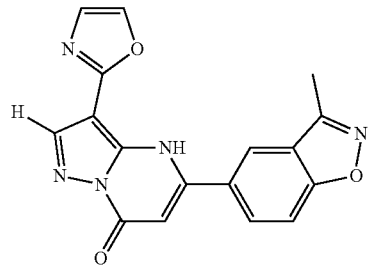 [SMILES: Cc1noc2ccc(-c3cc(=O)n4ncc(-c5ncco5)c4[nH]3)cc12]

Step 1: Methyl 3-acetyl-4-hydroxybenzoate

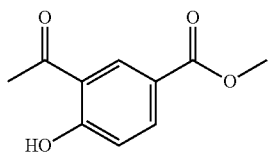

A solution of 1-(5-bromo-2-hydroxyphenyl)ethanone (20.0 g, 93.0 mmol, 1.00 equiv) in methanol (500 mL), Pd(dppf)$_2$Cl$_2$ (4 g, 4.7 mmol, 0.05 equiv) and triethylamine (20 g, 200.00 mmol, 2.00 equiv) were stirred overnight at 100° C. under an atmosphere of CO (g). The reaction progress was monitored by LCMS. The resulting mixture was concentrated in vacuo. The residue was diluted with 200 mL of H$_2$O and the resulting solution was extracted with 5×50 mL of ethyl acetate. The organic layers were combined and dried over anhydrous sodium sulfate. The solids were filtered off. The resulting mixture was concentrated in vacuo and the residue was purified by silica gel column with ethyl acetate/petroleum ether (1:10). This resulted in 15 g (83%) of methyl 3-acetyl-4-hydroxybenzoate as a light yellow solid.

$^1$H NMR (300 MHz, CDCl$_3$): 12.68 (s, 1H), 8.49 (d, 1H), 8.14 (dd, J=2.1 Hz, 1H), 7.02 (d, J=9.6 Hz, 1H), 3.93 (s, 3H), 2.71 (s, 3H)

Step 2: methyl 4-hydroxy-3-(1-iminoethyl)benzoate

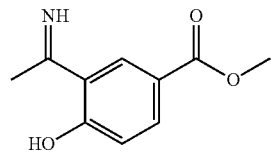

A mixture of methyl 3-acetyl-4-hydroxybenzoate (15 g, 77.25 mmol, 1.00 equiv) and methanol/NH$_3$ (300 mL) was stirred for 10 h at 25° C. The resulting mixture was concentrated in vacuo affording 15 g (crude) of methyl 4-hydroxy-3-(1-iminoethyl)benzoate as a white solid.

Step 3: methyl 3-methylbenzo[d]isoxazole-5-carboxylate

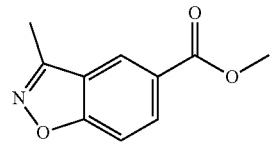

To a solution of methyl 4-hydroxy-3-(1-iminoethyl)benzoate (15 g, 40 mmol, 1.00 equiv) in tetrahydrofuran (300 mL) was added NCS (6.7 g, 50 mmol, 1.50 equiv) and potassium carbonate (22 g, 160 mmol, 2.00 equiv) and the reaction was stirred for 10 h at room temperature, then concentrated in vacuo. The residue was diluted with 200 mL of water. The resulting solution was extracted with 3×250 mL of ethyl acetate and the organic layers were combined. The solids were filtered off. The resulting solution was dried over anhydrous sodium sulfate and concentrated in vacuo. The residue was purified by silica gel column chromatography with ethyl acetate/petroleum ether (1:10). This resulted in 10 g (60%) of methyl 3-methylbenzo[d]isoxazole-5-carboxylate as a light yellow solid.

LC-MS (ES, m/z): 192 [M+H]+

$^1$H NMR (300 MHz, CDCl$_3$): δ 8.43-8.44 (m, 1H), 8.27-8.31 (m, 1H), 7.60-7.63 (m, 1H), 4.01 (s, 3H), 2.66 (s, 3H)

Step 4: 3-methylbenzo[d]isoxazole-5-carboxylic acid

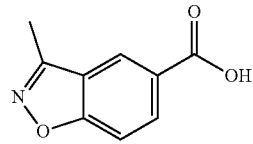

Into a 500-mL round-bottom flask, was placed a solution of methyl 3-methylbenzo[d]isoxazole-5-carboxylate (10 g, 52.3 mmol, 1.00 equiv) in methanol (100 mL), and a solution of sodium hydroxide (8.4 g, 210 mmol, 4.00 equiv) in water (10 mL) was added. The reaction was stirred overnight at room temperature and progress was monitored by TLC (ethyl acetate/petroleum ether=1:1). The resulting mixture was concentrated in vacuo. The residue was dissolved in 100 mL of water. The pH of the solution was adjusted to pH 4 with HCl (4M). The solids were collected by filtration. The solid was dried in an oven in vacuo. This resulted in 8.0 g (90%) of 3-methylbenzo[d]isoxazole-5-carboxylic acid as a light yellow solid.

LC-MS (ES, m/z): 178 [M+H]+

Step 5: ethyl 3-(3-methylbenzo[d]isoxazol-5-yl)-3-oxopropanoate

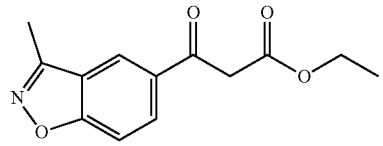 [SMILES: CCOC(=O)CC(=O)c1ccc2onc(C)c2c1]

To a solution of 3-methylbenzo[d]isoxazole-5-carboxylic acid (8.0 g, 45.1 mmol, 1.00 equiv) in tetrahydrofuran (100 mL) was added CDI (22 g, 136 mmol, 3.00 equiv). The reaction was stirred for 2 h at 40° C. Separately, to a solution of potassium 3-ethoxy-3-oxopropanoate (20.4 g, 120 mmol, 3.00 equiv) in CH$_3$CN (300 mL) was added triethylamine (12.1 g, 120 mmol, 3.00 equiv) and MgCl$_2$ (17 g, 180 mmol, 4.50 equiv). The two mixtures were combined, and the resulting reaction was stirred for 1 h at room temperature. The reaction progress was monitored by TLC (ethyl acetate/petroleum ether=1:5). The resulting mixture was concentrated in vacuo and the residue was diluted with 400 mL of H$_2$O. The pH of the solution was adjusted to pH 4 with HCl (4M). The resulting solution was extracted with 4×250 mL of ethyl acetate and the organic layers combined and dried over anhydrous sodium sulfate. The solids were filtered out. The resulting mixture was concentrated in vacuo. The residue was purified by silica gel column chromatography with ethyl acetate/petroleum ether (1:50). This resulted in 8 g (72%) of ethyl 3-(3-methylbenzo[d]isoxazol-5-yl)-3-oxopropanoate as an off-white solid.

LC-MS (ES, m/z): 248 [M+H]+

Step 6: 5-(3-methylbenzo[d]isoxazol-5-yl)-7-oxo-4,7-dihydropyrazolo[1,5-a]pyrimidine-3-carbonitrile

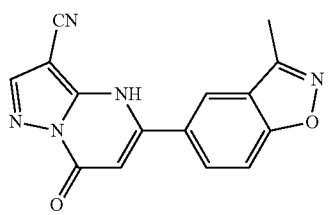 [SMILES: Cc1noc2ccc(-c3cc(=O)n4ncc(C#N)c4[nH]3)cc12]

Ethyl 3-(3-methylbenzo[d]isoxazol-5-yl)-3-oxopropanoate (1.2 g, 4.85 mmol, 1.00 equiv), p-TsOH (5 mg), n-BuOH (5 mL), and 5-amino-1H-pyrazole-4-carbonitrile (400 mg, 3.70 mmol, 0.76 equiv) were placed into a 100-mL round-bottom flask. The resulting solution was stirred for 2 h at 130° C. The solids were collected by filtration, affording 800 mg (57%) of 5-(3-methylbenzo[d]isoxazol-5-yl)-7-oxo-4,7-dihydropyrazolo[1,5-a]pyrimidine-3-carbonitrile as a yellow solid.

LC-MS (ES, m/z): 292 [M+H]+

$^1$H NMR (300 MHz, DMSO): 8.51 (s, 1H), 8.35-8.38 (m, 1H), 8.10 (s, 1H), 7.72 (d, J=9.0 Hz), 6.30 (s, 1H), 2.64 (s, 3H)

Step 7: 5-(3-methylbenzo[d]isoxazol-5-yl)-7-oxo-4,7-dihydropyrazolo[1,5-a]pyrimidine-3-carboxamide

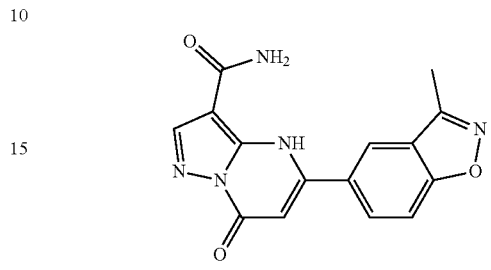

5-(3-Methylbenzo[d]isoxazol-5-yl)-7-oxo-4,7-dihydropyrazolo[1,5-a]pyrimidine-3-carbonitrile (800 mg, 2.75 mmol, 1.00 equiv) and sulfuric acid (10 mL) were stirred for 6 h at 25° C. The reaction was then quenched by the addition of 10 mL of water. The solids were collected by filtration. This resulted in 0.7 g (82%) of 5-(3-methylbenzo[d]isoxazol-5-yl)-7-oxo-4,7-dihydropyrazolo[1,5-a]pyrimidine-3-carboxamide as a white solid.

LC-MS (ES, m/z): 310 [M+H]+

Step 8: 5-(3-methylbenzo[d]isoxazol-5-yl)-3-(oxazol-2-yl)pyrazolo[1,5-a]pyrimidin-7(4H)-one

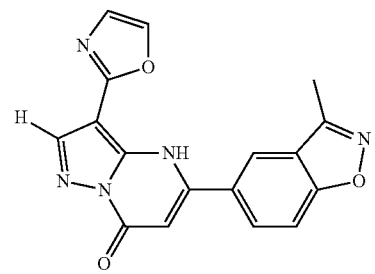 [SMILES: Cc1noc2ccc(-c3cc(=O)n4ncc(-c5ncco5)c4[nH]3)cc12]

A mixture of 5-(3-methylbenzo[d]isoxazol-5-yl)-7-oxo-4,7-dihydropyrazolo[1,5-a]pyrimidine-3-carboxamide (200 mg, 0.65 mmol, 1.00 equiv), NMP (2 mL), and 2-bromo-1,1-diethoxyethane (150 mg, 0.76 mmol, 1.18 equiv) was stirred for 1 h at 110° C. After the reaction was completed, the mixture was diluted with 300 mL of H$_2$O. The aqueous phase was extracted with 3×200 mL of dichloromethane and the organic layers were combined. The organic layers were washed with 1×500 mL of brine and dried with anhydrous sodium sulfate. After filtration, the solvent was removed in vacuo. The residue was concentrated in vacuo and then purified by silica gel column eluting with dichloromethane/methanol (10:1). This resulted in 23.2 mg (11%) of 5-(3-methylbenzo[d]isoxazol-5-yl)-3-(oxazol-2-yl)pyrazolo[1,5-a]pyrimidin-7(4H)-one as a white solid.

LC-MS (ES, m/z): [M+H]+ 334

$^1$H NMR (300 MHz, DMSO): δ 8.21-8.44 (m, 2H), 8.21 (s, 1H), 8.01-8.09 (m, 1H), 7.91-7.94 (m, 1H), 6.33 (s, 1H), 7.42 (d, J=0.6 Hz, 1H), 2.65 (s, 3H)

EXAMPLE 111

5-(1-Ethyl-1H-indazol-6-yl)-3-(3-methyl-1,2,4-oxadiazol-5-yl)pyrazolo[1,5-a]pyrimidin-7(4H)-one

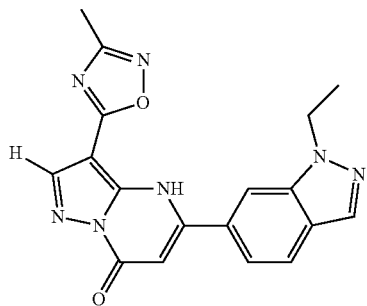 [SMILES: CCn1ncc2ccc(-c3cc(=O)n4ncc(-c5nc(C)no5)c4[nH]3)cc21]

To a solution of 4-(3-methyl-1,2,4-oxadiazol-5-yl)-1H-pyrazol-5-amine (50 mg, 1.0 eq) in n-BuOH (1 mL) was added ethyl 3-(1-ethyl-1H-indazol-6-yl)-3-oxopropanoate (118 mg, 1.5 eq) and p-TsOH (10 mg) at room temperature. After refluxing 2 hours, the solids were collected by filtration and washed with methanol (3×2 mL) to afford 5-(1-ethyl-1H-indazol-6-yl)-3-(3-methyl-1,2,4-oxadiazol-5-yl)pyrazolo[1,5-a]pyrimidin-7(4H)-one as a white solid (77.2 mg, 70%).

LCMS (ES, m/z): [M+H]+ 362.0

$^1$H NMR (300 MHz, CD$_3$OD) δ 8.16 (s, J=3.3 Hz, 1H), 8.61 (d, J=3.9 Hz, 1H), 7.93 (dd, J$_1$=0.9 Hz, J$_2$=7.5 Hz, 1H), 7.85 (dd, J$_1$=0.9 Hz, J$_2$=7.5 Hz, 1H), 6.54 (s, 1H), 4.60 (q, J=7.2 Hz), 2.44 (s, 3H), 1.54 (t, J=7.2 Hz)

EXAMPLE 112

5-(1-ethyl-1H-indazol-6-yl)-3-(5-methyloxazol-2-yl)pyrazolo[1,5-a]pyrimidin-7(4H)-one

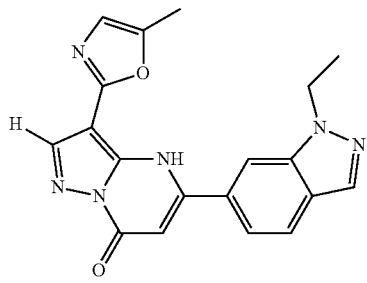 [SMILES: CCn1ncc2ccc(-c3cc(=O)n4ncc(-c5ncc(C)o5)c4[nH]3)cc21]

To a solution of 4-(5-methyloxazol-2-yl)-1H-pyrazol-5-amine (50 mg, 0.30 mmol) in n-BuOH (0.2 mL) was added ethyl 3-(1-ethyl-1H-indazol-6-yl)-3-oxopropanoate (103 mg, 0.40 mmol) and p-TsOH (2.6 mg). The resulting solution was stirred for 2 h at 120° C. The solids were collected by filtration and washed with 5×1 mL of methanol. This afforded 82.1 mg (75%) of 5-(1-ethyl-1H-indazol-6-yl)-3-(5-methyloxazol-2-yl)pyrazolo[1,5-a]pyrimidin-7(4H)-one as an off-white solid.

LCMS (ES, m/z): [M+H]$^+$ 361.1

$^1$H-NMR (400 MHz, CD$_3$OD): δ 8.50 (s, 1H), 8.33 (s, 1H), 8.06 (s, 1H), 7.90-7.84 (m, 2H), 6.86 (s, 1H), 6.47 (s, 1H), 4.65-4.59 (m, 2H), 2.45 (s, 1H), 1.54 (t, 3H)

EXAMPLE 113

5-(5-chloropyridin-2-yl)-3-(1,3-oxazol-2-yl)-4H,7H-pyrazolo[1,5-a]pyrimidin-7-one

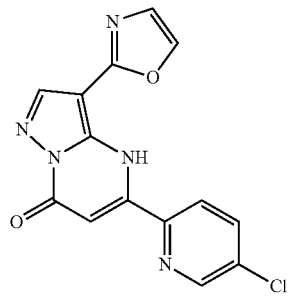 [SMILES: O=c1cc(-c2ccc(Cl)cn2)[nH]c2c(-c3ncco3)cnn12]

Step 1: Ethyl 3-(5-chloropyridin-2-yl)-3-oxopropanoate

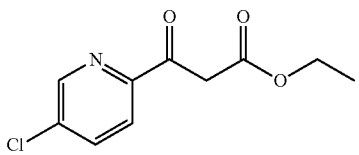

CDI (10.58 g, 65.25 mmol) was added to a solution of 5-chloropyridine-2-carboxylic acid (5 g, 39.35 mmol) in tetrahydrofuran (200 mL) and the reaction was stirred for 2 hours at room temperature. Separately, to a solution of potassium 3-ethoxy-3-oxopropanoate (22 g, 129.41 mmol) in CH$_3$CN (600 mL) was added triethylamine (13.09 g, 129.36 mmol) and MgCl$_2$ (18.47 g) with stirring for 2 hours at room temperature. The second solution was added dropwise to the first solution, and the resulting mixture was stirred for 2 hours at 50° C., then concentrated in vacuo and diluted with water (200 mL). The solution was adjusted to pH 4 with aq. HCl (3 mol/L), extracted with ethyl acetate (4×300 mL) and the organic layers were combined. The residue was purified by silica gel column chromatography with ethyl acetate/petroleum ether (1:100) to afford ethyl 3-(5-chloropyridin-2-yl)-3-oxopropanoate as a white solid (4.5 g, 62%).

LCMS (ES, m/z): [M+H]$^+$ 228.0

$^1$H NMR (300 MHz, DMSO) δ8.61-8.63 (m, 1H), 8.07 (d, J=6.3 Hz, 1H), 7.80-7.92 (m, 1H), 4.17-4.33 (m, 4H), 1.25-1.38 (m, 3H)

Step 2: 5-(5-chloropyridin-2-yl)-7-oxo-4,7-dihydropyrazolo[1,5-a]pyrimidine-3-carbonitrile

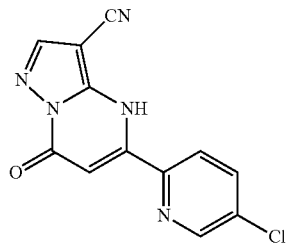 [SMILES: N#Cc1cnn2c(=O)cc(-c3ccc(Cl)cn3)[nH]c12]

To a solution of ethyl 3-(5-chloropyridin-2-yl)-3-oxopropanoate (1.3 g, 5.22 mmol) in n-BuOH (2.5 mL), was added 5-amino-1H-pyrazole-4-carbonitrile (500 mg, 8.56 mmol), and p-TsOH (35 mg, 0.20 mmol) and the reaction was stirred for 2 hours at 125° C. The solids were collected by filtration to afford 5-(5-chloropyridin-2-yl)-7-oxo-4,7-dihydropyrazolo[1,5-a]pyrimidine-3-carbonitrile as a pink solid (600 mg, 49%).

LCMS (ES, m/z): [M+H]+ 272.0

$^1$H NMR (300 MHz, DMSO) δ 8.89 (d, J=2.1 Hz, 1H), 8.44 (s, 1H), 8.33 (d, J=8.7 Hz, 1H), 8.21-8.25 (m, 1H), 6.77 (s, 1H)

Step 3: 5-(5-chloropyridin-2-yl)-7-oxo-4,7-dihydropyrazolo[1,5-a]pyrimidine-3-carboxamide

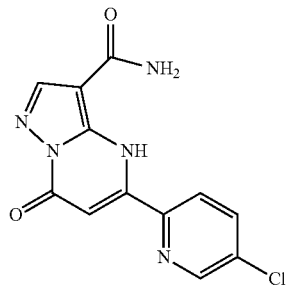 [SMILES: NC(=O)c1cnn2c(=O)cc(-c3ccc(Cl)cn3)[nH]c12]

Sulfuric acid (4.5 mL) was added to 5-(5-chloropyridin-2-yl)-7-oxo-4,7-dihydropyrazolo[1,5-a]pyrimidine-3-carbonitrile (600 mg, 2.58 mmol) and the reaction was stirred for 2 hours at room temperature. The reaction was quenched by ice/water (20 mL). The solids were collected by filtration to afford 5-(5-chloropyridin-2-yl)-7-oxo-4,7-dihydropyrazolo[1,5-a]pyrimidine-3-carboxamide as a light yellow solid (450 mg, 70%).

LCMS (ES, m/z): [M+H]+ 290.0

$^1$H NMR (300 MHz, DMSO) δ 8.70 (d, J=2.1 Hz, 1H), 8.36 (d, J=8.4 Hz, 1H), 8.00-8.05 (m, 2H), 6.58 (s, 1H).

Step 4: 5-(5-chloropyridin-2-yl)-3-(oxazol-2-yl)pyrazolo[1,5-a]pyrimidin-7(4H)-one

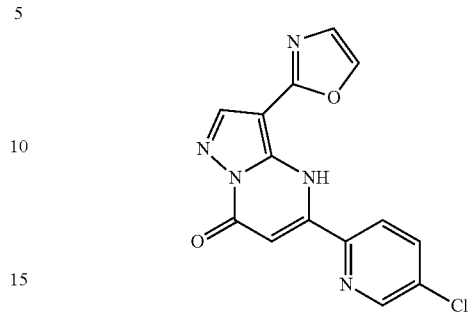

To a solution of 5-(5-chloropyridin-2-yl)-7-oxo-4,7-dihydropyrazolo[1,5-a]pyrimidine-3-carboxamide (200 mg, 0.69 mmol) in NMP (1 mL) was added p-TsOH (285 mg, 1.66 mmol) and 2-bromo-1,1-diethoxyethane (5.9 mg, 0.03 mmol), and the reaction was stirred for 20 min at 80° C. The resulting mixture was concentrated in vacuo. The residue was purified by silica gel column chromatography with DCM/MeOH (100:1) to afford 5-(5-chloropyridin-2-yl)-3-(oxazol-2-yl)pyrazolo[1,5-a]pyrimidin-7(4H)-one as a light yellow solid (39.5 mg, 18%).

LCMS (ES, m/z): [M+H]+ 313.9

$^1$H NMR (300 MHz, DMSO) δ 8.67 (d, J=2.4 Hz, 1H), 8.52 (d, J=8.4 Hz, 1H), 8.14 (s, 1H), 8.02-8.07 (m, 2H), 7.21 (s, 1H), 6.59 (s, 1H)

EXAMPLE 114

2-ethyl-5-(1-ethyl-1H-indazol-5-yl)-3-(3-methyl-1,2,4-oxadiazol-5-yl)pyrazolo[1,5-a]pyrimidin-7(4H)-one

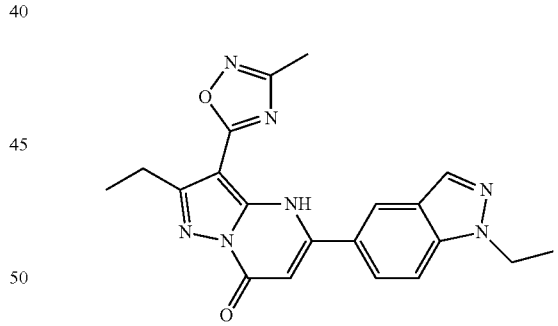

Step 1: 2-(1-ethoxypropylidene)malononitrile

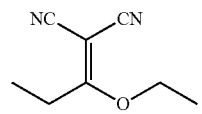

1,1,1-Triethoxypropane (32 g, 181.5 mmol) was added to a solution of malononitrile (10 g, 151.3 mmol) and AcOH (50 mL), in ethanol (50 mL). Then the reaction was heated under reflux overnight. Then resulting mixture was concentrated in vacuo and diluted with 200 mL of water. The resulting solution was extracted with ethyl acetate (4×100 mL) and the organic layers were combined and dried over with anhydrous sodium sulfate. The solution was concentrated in vacuo to afford 2-(1-ethoxypropylidene)propanedinitrile as a yellow solid (10 g, crude).

LCMS (ES, m/z): [M+H]+ 151.0

Step 2: 5-amino-3-ethyl-1H-pyrazole-4-carbonitrile

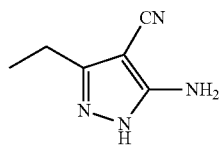

N$_2$H$_4$.H$_2$O (20 mL) was added to a solution of 2-(1-ethoxypropylidene)malononitrile (1.00 equiv) and AcOH (10 mL) in ethanol (50 mL). The resulting solution was heated to reflux overnight. Then the mixture was concentrated in vacuo and was diluted with 200 mL of water. The resulting solution was extracted with ethyl acetate (4×100 mL) and the organic layers were combined and dried over anhydrous sodium sulfate. The solution was concentrated in vacuo and the residue was purified by silica gel column chromatography with dichloromethane/methanol (500:1-100:1) to afford 5-amino-3-ethyl-1H-pyrazole-4-carbonitrile as an off-white solid (5 g, 24% yield of two steps).

LCMS (ES, m/z): [M+H]+ 137.0

Step 3: 2-ethyl-5-(1-ethyl-1H-indazol-5-yl)-7-oxo-4,7-dihydropyrazolo[1,5-a]pyrimidine-3-carbonitrile

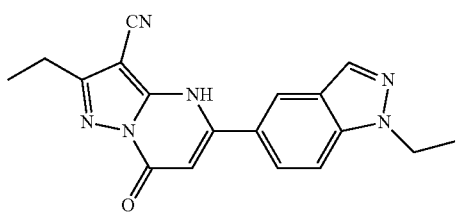 [SMILES: CCc1nn2c(=O)cc(-c3ccc4c(cnn4CC)c3)[nH]c2c1C#N]

p-TsOH (50 mg) was added to a solution of 5-amino-3-ethyl-1H-pyrazole-4-carbonitrile (500 mg, 3.67 mmol) and ethyl 3-(1-ethyl-1H-indazol-5-yl)-3-oxopropanoate (1.2 g, 4.61 mmol) in n-BuOH (1 mL). The reaction was stirred for 2 h at 125° C. Then it was diluted with methanol (5 mL). The solids were collected by filtration and washed with methanol (3×5 mL). The solid was dried in an oven under reduced pressure to afford 2-ethyl-5-(1-ethyl-1H-indazol-5-yl)-7-oxo-4H,7H-pyrazolo[1,5-a]pyrimidine-3-carbonitrile as a yellow solid (900 mg, 74%).

LCMS (ES, m/z): [M+H]+ 333.0

$^1$H NMR (300 MHz, DMSO+NH$_3$ (saturated D$_2$O solution)) δ 13.41 (brs, 1H), 8.31 (s, 1H), 8.26 (s, 1H), 7.87 (d, J=9.0, 1H), 7.81 (dd, J$_1$=1.5 Hz, J$_2$=9.0 Hz, 1H), 6.27 (s, 1H), 4.51 (q, J=7.2 Hz, 2H), 2.80 (q, J=7.5 Hz, 2H), 1.42 (t, J=7.2 Hz, 3H), 1.30 (t, J=7.5 Hz, 3H)

Step 4: 2-ethyl-5-(1-ethyl-1H-indazol-5-yl)-7-oxo-4,7-dihydropyrazolo[1,5-a]pyrimidine-3-carboxamide

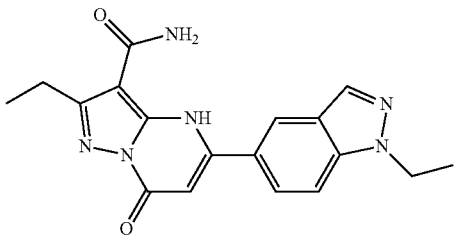 [SMILES: CCc1nn2c(=O)cc(-c3ccc4c(cnn4CC)c3)[nH]c2c1C(N)=O]

2-Ethyl-5-(1-ethyl-1H-indazol-5-yl)-7-oxo-4H,7H-pyrazolo[1,5-a]pyrimidine-3-carbonitrile (900 mg, 2.71 mmol, 1.00 equiv) was added to sulfuric acid (5 mL) in portions. The resulting solution was stirred at 50° C. for 2 h. Then the mixture was poured into ice/water (100 mL) and the solids were precipitated and collected by filtration to afforded 2-ethyl-5-(1-ethyl-1H-indazol-5-yl)-7-oxo-4H,7H-pyrazolo[1,5-a]pyrimidine-3-carboxamide as a yellow solid (800 mg, 84%).

LCMS (ES, m/z): [M+H]+ 351.0

$^1$H NMR (300 MHz, DMSO+NH$_3$ (saturated D$_2$O solution)) δ 8.31 (s, 1H), 8.26 (s, 1H), 7.87 (brs, 2H), 7.40 (brs, 2H), 6.27 (s, 1H), 4.51 (q, J=7.2, 2H), 2.96 (d, J=7.5 Hz, 2H), 1.42 (t, J=7.2 Hz, 3H), 1.26 (t, J=7.5 Hz, 3H)

Step 5: N-(1-(dimethylamino)ethylidene)-5-(1-ethyl-1H-indazol-5-yl)-2-methyl-7-oxo-4,7-dihydropyrazolo[1,5-a]pyrimidine-3-carboxamide

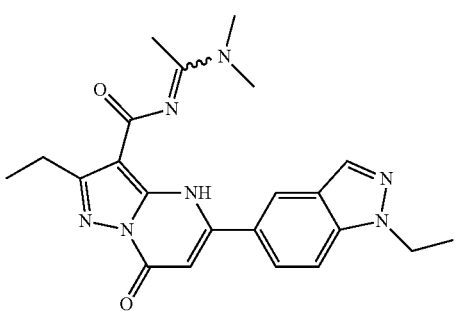 [SMILES: CCc1nn2c(=O)cc(-c3ccc4c(cnn4CC)c3)[nH]c2c1C(=O)N=C(C)N(C)C]

DMA-DMA (1.76 g, 13.23 mmol, 10.00 equiv) was added to a solution of 2-ethyl-5-(1-ethyl-1H-indazol-5-yl)-7-oxo-4H,7H-pyrazolo[1,5-a]pyrimidine-3-carboxamide (400 mg, 1.31 mmol), in DMF (2 mL). The reaction was stirred at 130° C. for 4 h. Then the resulting mixture was concentrated and the residue was washed with 3×10 mL ether (3×10 mL). The solid was collected by filtration and washed with EtOH (3×1 mL) to afford N-(1-(dimethylamino)ethylidene)-2-ethyl-5-(1-ethyl-1H-indazol-5-yl)-7-oxo-4,7-dihydropyrazolo[1,5-a]pyrimidine-3-carboxamide as a dark red solid (crude).

LCMS (ES, m/z): [M+H]+ 420.0

Step 6: 2-ethyl-5-(1-ethyl-1H-indazol-5-yl)-3-(3-methyl-1,2,4-oxadiazol-5-yl)pyrazolo[1,5-a]pyrimidin-7(4H)-one

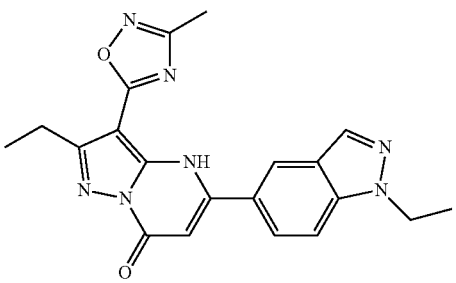 [SMILES: CCc1nn2c(=O)cc(-c3ccc4c(cnn4CC)c3)[nH]c2c1-c1nc(C)no1]

NH₂OH.HCl (130 mg, 1.50 equiv), AcOH (15 mL) and sodium hydroxide (10%) (10 mL) in dioxane (10 mL) were added to a solution of N-(1-(dimethylamino)ethylidene)-2-ethyl-5-(1-ethyl-1H-indazol-5-yl)-7-oxo-4,7-dihydropyrazolo[1,5-a]pyrimidine-3-carboxamide, and the resulting mixture was stirred for 2 h at 100° C. The resulting mixture was concentrated in vacuo and the residue was purified by silica gel column chromatography with dichloromethane/methanol (200:1) to afford 2-ethyl-5-(1-ethyl-1H-indazol-5-yl)-3-(3-methyl-1,2,4-oxadiazol-5-yl)pyrazolo[1,5-a]pyrimidin-7(4H)-one as a white solid (50 mg, 5%).

LCMS (ES, m/z): [M+H]⁺ 390.0

¹H NMR (300 MHz, DMSO+NH₃ (saturated D₂O solution)) δ 8.48 (s, 1H), 8.20 (s, 1H), 8.16 (s, 1H), 7.71 (d, J=7.2 Hz 1H), 6.21 (s, 1H), 4.46 (q, J=7.2 Hz, 2H), 2.96 (d, J=7.5 Hz, 2H), 2.34 (s, 3H) 1.42 (t, J=7.2 Hz, 3H), 1.26 (t, J=7.5 Hz, 3H)

EXAMPLE 115

5-(1-ethyl-1H-indazol-5-yl)-2-methyl-3-(3-methyl-1,2,4-oxadiazol-5-yl)-4H,7H-pyrazolo[1,5-a]pyrimidin-7-one

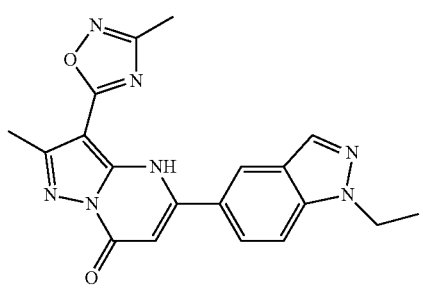 [SMILES: CCn1ncc2cc(-c3cc(=O)n4nc(C)c(-c5nc(C)no5)c4[nH]3)ccc21]

Step 1: 5-(1-ethyl-1H-indazol-5-yl)-2-methyl-7-oxo-4H,7H-pyrazolo[1,5-a]pyrimidine-3-carbonitrile

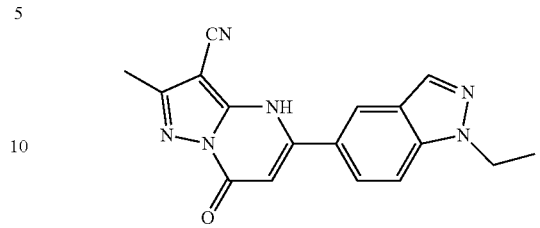

Ethyl 3-(1-ethyl-1H-indazol-5-yl)-3-oxopropanoate (1.02 g, 3.92 mmol) and p-TsOH (28.2 mg, 0.16 mmol) were added to a solution of 5-amino-3-methyl-1H-pyrazole-4-carbonitrile (400 mg, 3.28 mmol) in n-BuOH (1 mL) and the reaction was stirred for 2 h at 130° C. The solids were collected by filtration and washed with MeOH (3×2 mL) to afford 5-(1-ethyl-1H-indazol-5-yl)-2-methyl-7-oxo-4H,7H-pyrazolo[1,5-a]pyrimidine-3-carbonitrile as a light yellow solid (800 mg, 77%).

(ES, m/z) [M+H]⁺ 319.0

Step 2: 5-(1-ethyl-1H-indazol-5-yl)-2-methyl-7-oxo-4H,7H-pyrazolo[1,5-a]pyrimidine-3-carboxamide

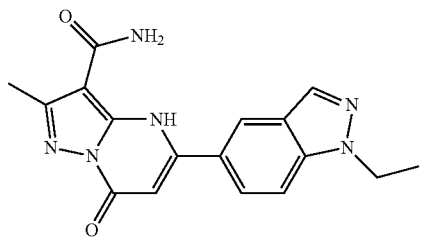 [SMILES: CCn1ncc2cc(-c3cc(=O)n4nc(C)c(C(N)=O)c4[nH]3)ccc21]

5-(1-ethyl-1H-indazol-5-yl)-2-methyl-7-oxo-4H,7H-pyrazolo[1,5-a]pyrimidine-3-carbonitrile (800 g, 2.51 mol) was added to conc. sulfuric acid (10 mL) and the reaction was stirred for 4 h at room temperature. The reaction was then quenched by the addition of ice/water (50 mL). The solids were collected by filtration, dried in an oven under reduced pressure to afford 5-(1-ethyl-1H-indazol-5-yl)-2-methyl-7-oxo-4H,7H-pyrazolo[1,5-a]pyrimidine-3-carboxamide as an off-white solid (700 mg, 83%).

(ES, m/z) [M+H]⁺ 337.0

¹H NMR (300 Hz, DMSO): δ 11.57 (s, 1H), 8.30 (s, 1H), 8.26 (s, 1H), 7.95 (s, 1H), 7.36 (brs, 1H), 6.27 (s, 1H), 4.55-4.48 (q, J=7.20 Hz, 2H), 1.44-1.30 (t, J=7.20 Hz, 3H)

Step 3: (E)-N-(1-(dimethylamino)ethylidene)-5-(1-ethyl-1H-indazol-5-yl)-2-methyl-7-oxo-4,7-dihydropyrazolo[1,5-a]pyrimidine-3-carboxamide

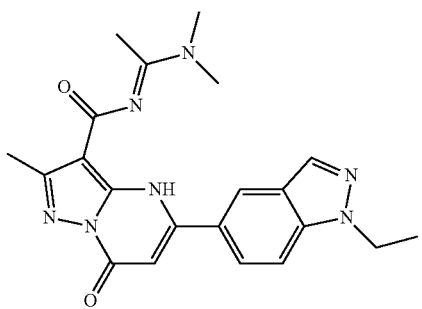 [SMILES: CCn1ncc2cc(-c3cc(=O)n4nc(C)c(C(=O)/N=C(\C)N(C)C)c4[nH]3)ccc21]

DMA-DMA (2 mL) was added to a solution of 5-(1-ethyl-1H-indazol-5-yl)-2-methyl-7-oxo-4H,7H-pyrazolo[1,5-a]pyrimidine-3-carboxamide (500 mg, 1.49 mmol) in DMF (2 mL), and the reaction was stirred for 2 h at 130° C. The resulting mixture was concentrated in vacuo to afford (E)-N-(1-(dimethylamino)ethylidene)-5-(1-ethyl-1H-indazol-5-yl)-2-methyl-7-oxo-4,7-dihydropyrazolo[1,5-a]pyrimidine-3-carboxamide as dark red crude oil (600 mg, 100%).

LCMS (ES, m/z) [M+H]$^+$ 406.0

Step 4: 5-(1-ethyl-1H-indazol-5-yl)-2-methyl-3-(3-methyl-1,2,4-oxadiazol-5-yl)-4H,7H-pyrazolo[1,5-a]pyrimidin-7-one

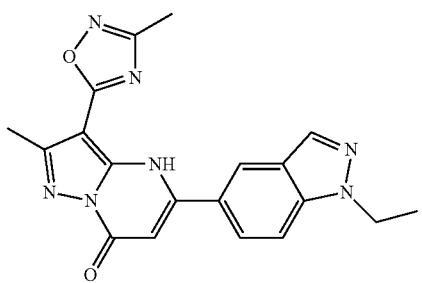 [SMILES: CCn1ncc2cc(-c3cc(=O)n4nc(C)c(-c5nc(C)no5)c4[nH]3)ccc21]

To a solution of (E)-N-(1-(dimethylamino)ethylidene)-5-(1-ethyl-1H-indazol-5-yl)-2-methyl-7-oxo-4,7-dihydropyrazolo[1,5-a]pyrimidine-3-carboxamide (600 mg, 1.48 mmol) in dioxane (5 mL), was added NH$_2$OH.HCl (155 mg) and 10% aq. sodium hydroxide (1 mL) in AcOH (10 mL), and the reaction was stirred for 1 h at 100° C. The resulting mixture was concentrated in vacuo to afford the residue, which was purified by silica gel column chromatography with 1% methanol in dichloromethane to afford of 5-(1-ethyl-1H-indazol-5-yl)-2-methyl-3-(3-methyl-1,2,4-oxadiazol-5-yl)-4H,7H-pyrazolo[1,5-a]pyrimidin-7-one as a light yellow solid (153.9 mg, 28%).

LCMS (ES, m/z) [M+H]$^+$ 376.0.0
$^1$H-NMR (300 Hz, DMSO): δ 11.86 (s, 1H), 8.25 (s, 1H), 7.88 (d, J=8.70 Hz, 1H), 7.80 (d, J=9.00 Hz, 1H), 6.28 (s, 1H), 4.52-4.45 (q, J=6.90 Hz, 2H), 2.61 (s, 3H), 2.40 (s, 3H), 1.38 (t, J=6.90 Hz, 3H)

EXAMPLE 116

5-(1-ethyl-1H-indazol-5-yl)-3-(3-methyl-1,2,4-oxadiazol-5-yl)-2-propyl-4H,7H-pyrazolo[1,5-a]pyrimidin-7-one

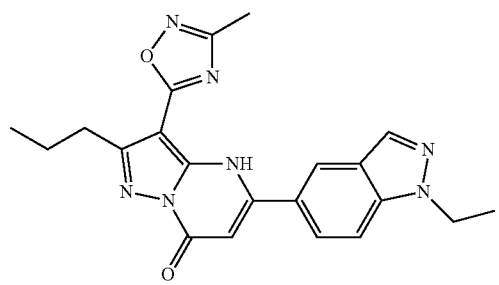 [SMILES: CCCc1nn2c(=O)cc(-c3ccc4c(cnn4CC)c3)[nH]c2c1-c1nc(C)no1]

Step 1: 2-(1-ethoxybutylidene)malononitrile

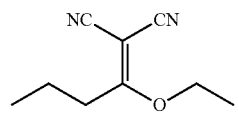

1,1,1-triethoxybutane (69 g, 362.62 mmol) was added to a solution of malononitrile (20 g, 302.75 mmol) in AcOH (70 mL)/ethanol (70 mL), and the reaction was stirred overnight at 95° C. The reaction progress was monitored by TLC (ethyl acetate/petroleum ether=1:2). The resulting mixture was concentrated in vacuo to afford 2-(1-ethoxybutylidene)propanedinitrile as a red oil (45 g, crude).

LC-MS: (ES, m/z): [M+H]$^+$ 165

Step 2: 5-amino-3-propyl-1H-pyrazole-4-carbonitrile

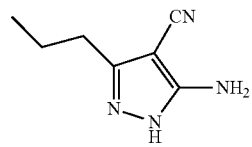

N$_2$H$_4$.H$_2$O (69 g, 1.38 mol) was added in portions to a solution of 2-(1-ethoxybutylidene)malononitrile (45 g, crude) in AcOH (70 mL) at 0-5° C. After stirring for 4 h at 90° C., the reaction mixture was concentrated in vacuo, diluted with water (200 mL), and extracted with ethyl acetate (3×200 mL). The organic layers were combined and dried over anhydrous sodium sulfate, and concentrated in vacuo to provide the product which was purified by silica gel column chromatography with dichloromethane/methanol (100:1-80:1) to afford 5-amino-3-propyl-1H-pyrazole-4-carbonitrile as a red solid (12 g, 29%).

LC-MS: (ES, m/z): [M+H]$^+$ 151
$^1$H NMR (300 MHz, DMSO): δ 11.75 (s, 1H), 5.80 (s, 2H), 2.45-2.40 (t, J=7.5 Hz, 2H), 1.61-1.49 (m, 2H), 0.90-0.85 (t, J=7.5 Hz, 3H)

Step 3: 5-(1-ethyl-1H-indazol-5-yl)-7-oxo-2-propyl-4H,7H-pyrazolo[1,5-a]pyrimidine-3-carbonitrile

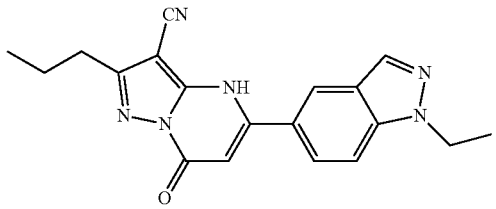 [SMILES: CCCc1nn2c(=O)cc(-c3ccc4c(cnn4CC)c3)[nH]c2c1C#N]

Ethyl 3-(1-ethyl-1H-indazol-5-yl)-3-oxopropanoate (1.3 g, 4.99 mmol) and p-TsOH (30 mg, 0.17 mmol) were added to a solution of 5-amino-3-propyl-1H-pyrazole-4-carbonitrile (500 mg, 3.33 mmol) in n-BuOH (0.5 mL) and the reaction was heated under reflux for 2 hr. The resulting solution was poured into methanol (2 mL). The solids were collected by filtration and washed with methanol (3×2 mL) to afford 5-(1-ethyl-1H-indazol-5-yl)-7-oxo-2-propyl-4H,7H-pyrazolo[1,5-a]pyrimidine-3-carbonitrile as a white solid (1 g, 87%).

LC-MS: (ES, m/z): [M+H]+ 347

$^1$H NMR (300 MHz, DMSO): δ 13.39 (s, 1H), 8.27-7.76 (m, 4H), 6.22 (s, 1H), 4.51-4.43 (q, J=7.2 Hz, 2H), 2.73-2.68 (t, J=7.2 Hz, 2H), 1.78-1.73 (m, 2H), 1.70-1.66 (t, J=7.2 Hz, 3H), 1.40-1.35 (t, J=7.2 Hz, 3H)

Step 4: 5-(1-ethyl-1H-indazol-5-yl)-7-oxo-2-propyl-4H,7H-pyrazolo[1,5-a]pyrimidine-3-carboxamide

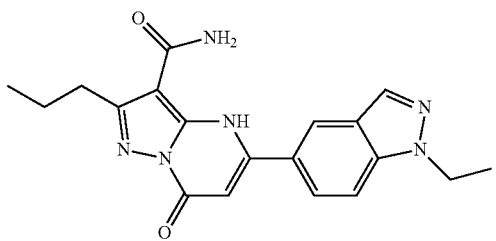 [SMILES: CCCc1nn2c(=O)cc(-c3ccc4c(cnn4CC)c3)[nH]c2c1C(N)=O]

A solution of 5-(1-ethyl-1H-indazol-5-yl)-7-oxo-2-propyl-4H,7H-pyrazolo[1,5-a]pyrimidine-3-carbonitrile (1 g, 2.89 mmol) in sulfuric acid (3 mL) was stirred for 2 h at room temperature. The resulting solution was diluted with water (20 mL). The solids were collected by filtration, and washed with water (6×10 mL) to afford 5-(1-ethyl-1H-indazol-5-yl)-7-oxo-2-propyl-4H,7H-pyrazolo[1,5-a]pyrimidine-3-carboxamide as a pink solid (800 mg, 76%).

LC-MS: (ES, m/z): [M+H]+ 365

$^1$H NMR (300 MHz, DMSO): δ 11.53 (s, 1H), 8.31-7.24 (m, 6H), 6.26 (s, 1H), 4.54-4.47 (q, J=7.2 Hz, 2H), 2.92 (s, 2H), 1.78-1.66 (m, 2H), 1.44-1.39 (t, J=7.2 Hz, 3H), 0.98-0.93 (t, J=7.2 Hz, 3H)

Step 5: (E)-N-(1-(dimethylamino)ethylidene)-5-(1-ethyl-1H-indazol-5-yl)-7-oxo-2-propyl-4,7-dihydropyrazolo[1,5-a]pyrimidine-3-carboxamide

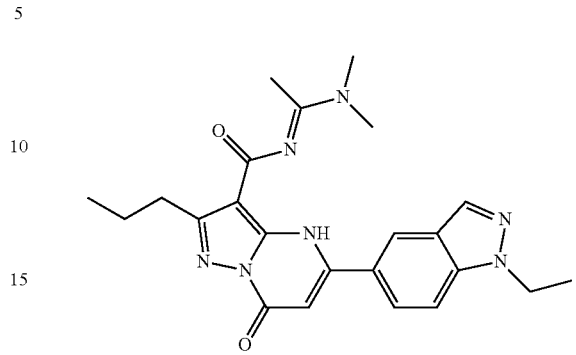

DMA-DMA (585 mg, 4.40 mmol) was added to a solution of 5-(1-ethyl-1H-indazol-5-yl)-7-oxo-2-propyl-4H,7H-pyrazolo[1,5-a]pyrimidine-3-carboxamide (400 mg, 1.10 mmol) in DMF (3 mL) and the reaction was stirred for 3 h at 130° C. The resulting mixture was concentrated in vacuo to afford (E)-N-(1-(dimethylamino)ethylidene)-5-(1-ethyl-1H-indazol-5-yl)-7-oxo-2-propyl-4,7-dihydropyrazolo[1,5-a]pyrimidine-3-carboxamide as yellow oil (450 mg, crude).

LC-MS (ES, m/z): [M+H]+ 434

Step 6: 5-(1-ethyl-1H-indazol-5-yl)-3-(3-methyl-1,2,4-oxadiazol-5-yl)-2-propyl-4H,7H-pyrazolo[1,5-a]pyrimidin-7-one

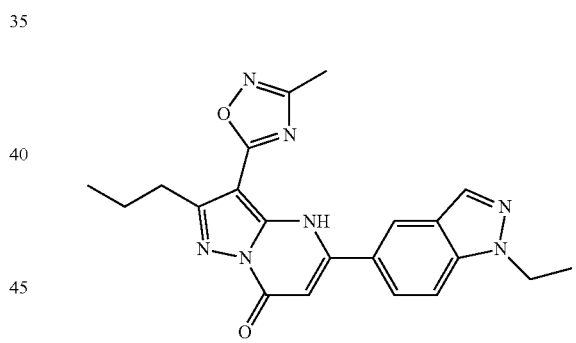

NH$_2$OH.HCl (108 mg, 1.55 mmol) was added to a solution of (E)-N-(1-(dimethylamino)ethylidene)-5-(1-ethyl-1H-indazol-5-yl)-7-oxo-2-propyl-4,7-dihydropyrazolo[1,5-a]pyrimidine-3-carboxamide (450 mg, crude) in dioxane (4 mL) at room temperature. After stirring 5 min, a solution of AcOH (10 mL) in 10% aqueous sodium hydroxide (1 mL) was added. The resulting reaction was stirred for 1 h at 100° C. Then it was concentrated in vacuo to afford the product which was purified by silica gel column chromatography with dichloromethane/methanol (150:1-100:1) to afford 5-(1-ethyl-1H-indazol-5-yl)-3-(3-methyl-1,2,4-oxadiazol-5-yl)-2-propyl-4H,7H-pyrazolo[1,5-a]pyrimidin-7-one as an off-white solid (36.3 mg, 9%).

LC-MS (ES, m/z): [M+H]+ 404

$^1$H NMR (300 MHz, DMSO): δ 8.29-7.80 (m, 4H), 6.34 (s, 1H), 4.56-4.49 (q, J=7.2 Hz, 2H), 3.00-29.5 (t, J=7.5 Hz, 2H), 2.45 (s, 3H), 1.83-1.71 (m, 2H), 1.45-1.40 (t, J=7.2 Hz, 3H), 1.01-0.96 (t, J=7.5 Hz, 3H)

EXAMPLE 117

5-(4-chloro-3-methoxyphenyl)-2-ethyl-3-(3-methyl-1,2,4-oxadiazol-5-yl)-4H,7H-pyrazolo[1,5-a]pyrimidin-7-one

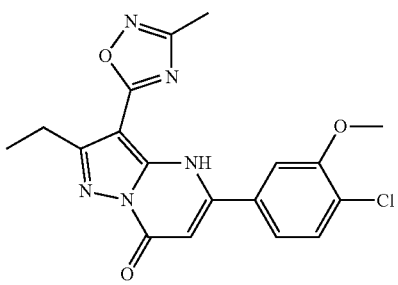 [SMILES: CCc1nn2c(=O)cc(-c3ccc(Cl)c(OC)c3)[nH]c2c1-c1nc(C)no1]

Step 1: 5-(4-chloro-3-methoxyphenyl)-2-ethyl-7-oxo-4H,7H-pyrazolo[1,5-a]pyrimidine-3-carbonitrile

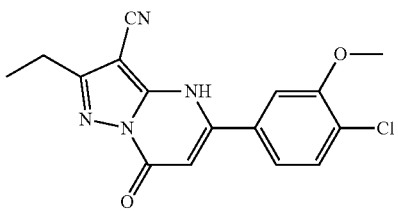 [SMILES: CCc1nn2c(=O)cc(-c3ccc(Cl)c(OC)c3)[nH]c2c1C#N]

p-TsOH (25 mg, 0.1 mmol) and ethyl 3-(4-chloro-3-methoxyphenyl)-3-oxopropanoate (903 mg, 3.52 mmol) were added to a solution of 5-amino-3-ethyl-1H-pyrazole-4-carbonitrile (400 mg, 2.94 mmol) in n-BuOH (1 mL) and the reaction was stirred for 3 h at 130° C. The solids were collected by filtration, washed with MeOH (3×2 mL) and dried in an oven under reduced pressure to afford 5-(4-chloro-3-methoxyphenyl)-2-ethyl-7-oxo-4H,7H-pyrazolo[1,5-a]pyrimidine-3-carbonitrile as a light yellow solid (800 mg, 83%).

LCMS (ES, m/z) [M+H]$^+$ 329.0

H$^1$-NMR (300 Hz, DMSO): δ 11.45 (brs, 1H), 7.66 (d, J=8.10 Hz, 1H), 7.54 (d, J=1.80 Hz, 1H), 7.44-7.40 (dd, J=1.80, 8.10 Hz, 1H), 6.35 (s, 1H), 3.99 (s, 3H), 2.83-2.75 (q, J=7.50 Hz, 2H), 1.29 (t, J=7.50 Hz, 3H)

Step 2: 5-(4-chloro-3-methoxyphenyl)-2-ethyl-7-oxo-4H,7H-pyrazolo[1,5-a]pyrimidine-3-carboxamide

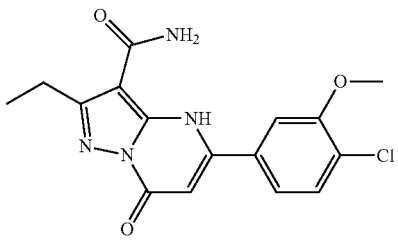 [SMILES: CCc1nn2c(=O)cc(-c3ccc(Cl)c(OC)c3)[nH]c2c1C(N)=O]

A solution of 3M potassium carbonate (15 mL) in methanol (18 mL) and 40% aqueous H$_2$O$_2$ (15 mL) was added to a solution of 5-(4-chloro-3-methoxyphenyl)-2-ethyl-7-oxo-4H,7H-pyrazolo[1,5-a]pyrimidine-3-carbonitrile (800 mg, 2.43 mmol) in DMSO (12 mL) and stirred for 6 h at 50° C. The resulting mixture was concentrated in vacuo, diluted with H$_2$O (200 mL) and adjusted pH 5 with HCl (4M). The solids were collected by filtration, washed with MeOH (3×2 mL) and dried in an oven under reduced pressure to afford 5-(4-chloro-3-methoxyphenyl)-2-ethyl-7-oxo-4H,7H-pyrazolo[1,5-a]pyrimidine-3-carboxamide as a light yellow solid (700 mg, 83%).

LCMS (ES, m/z) [M+H]$^+$ 347.0

$^1$H-NMR (300 Hz, DMSO): δ 7.60-7.39 (m, 4H), 6.30 (s, 1H), 3.93 (s, 3H), 2.95-2.88 (q, J=6.30 Hz, 2H), 1.28 (t, J=6.30 Hz, 3H)

Step 3: (E)-5-(4-chloro-3-methoxyphenyl)-N-(1-(dimethylamino)ethylidene)-2-ethyl-7-oxo-4,7-dihydropyrazolo[1,5-a]pyrimidine-3-carboxamide

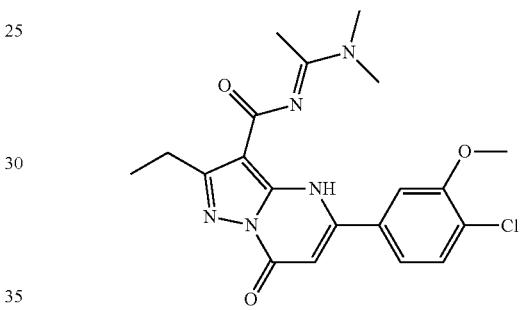

DMA-DMA (1 mL) was added to a solution of 5-(4-chloro-3-methoxyphenyl)-2-ethyl-7-oxo-4H,7H-pyrazolo[1,5-a]pyrimidine-3-carboxamide (200 mg, 0.58 mmol) in DMF (1 mL) and the reaction was stirred for 4 h at 130° C. The resulting mixture was concentrated in vacuo to afford (E)-5-(4-chloro-3-methoxyphenyl)-N-(1-(dimethylamino)ethylidene)-2-ethyl-7-oxo-4,7-dihydropyrazolo[1,5-a]pyrimidine-3-carboxamide as black crude oil (240 mg).

LCMS (ES, m/z) [M+H]$^+$ 416.0

Step 4: 5-(4-chloro-3-methoxyphenyl)-2-ethyl-3-(3-methyl-1,2,4-oxadiazol-5-yl)-4H,7H-pyrazolo[1,5-a]pyrimidin-7-one

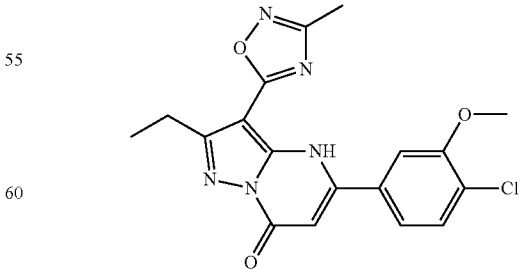

NH$_2$OH.HCl (51 mg) and a solution of 10% aqueous sodium hydroxide (1 mL) in AcOH (10 mL) was added to a solution of (E)-5-(4-chloro-3-methoxyphenyl)-N-(1-(dimethylamino)ethylidene)-2-ethyl-7-oxo-4,7-dihydropyrazolo[1,5-a]pyrimidine-3-carboxamide (200 mg, 0.48 mmol) in dioxane (5 mL) and the reaction was stirred at 100° C. The resulting mixture was concentrated in vacuo to afford the product which was purified by silica gel column chromatography with 1% methanol in dichloromethane to afford 5-(4-chloro-3-methoxyphenyl)-2-ethyl-3-(3-methyl-1,2,4-oxadiazol-5-yl)-4H,7H-pyrazolo[1,5-a]pyrimidin-7-one as a light yellow solid (28.4 mg, 15%).

LCMS (ES, m/z) [M+H]+ 386.0

1H-NMR (300 Hz, DMSO): δ 11.81 (s, 1H), 7.65 (d, J=8.10 Hz, 1H), 7.53 (d, J=1.80 Hz, 1H), 7.38-7.35 (dd, J=1.80, 8.40 Hz, 1H), 6.38 (s, 1H), 3.95 (s, 3H), 3.02-2.94 (q, J=7.50 Hz, 2H), 2.23 (s, 3H), 1.27 (t, J=7.50 Hz, 3H)

EXAMPLE 118

5-(3-methylbenzo[d]isoxazol-6-yl)-3-(oxazol-2-yl)pyrazolo[1,5-a]pyrimidin-7(4H)-one

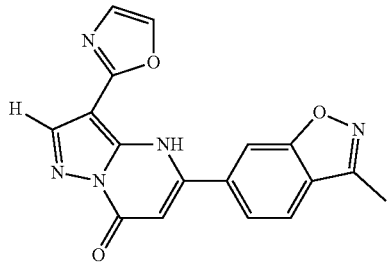 [SMILES: Cc1noc2cc(-c3cc(=O)n4ncc(-c5ncco5)c4[nH]3)ccc12]

Step 1: Methyl 4-acetyl-3-hydroxybenzoate

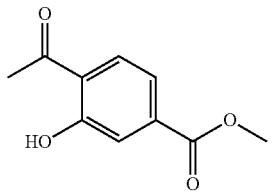

A solution of 1-(4-bromo-2-hydroxyphenyl)ethanone (20 g, 93.00 mmol, 1.00 equiv) in methanol (700 mL), Pd(dppf)Cl2CH2Cl2 (4 g, 5.47 mmol, 0.05 equiv), TEA (19 g, 187.77 mmol, 2.00 equiv) was stirred overnight at 100° C. under an atmosphere of CO (g) (10 atm). The resulting mixture was concentrated in vacuo. The residue was purified by silica gel column chromatography with ethyl acetate/petroleum ether (1:20). This resulted in 16 g (89%) of methyl 4-acetyl-3-hydroxybenzoate as a light yellow solid.

LCMS (ES, m/z): [M+H]+ 195.0

1H-NMR (400 MHz, DMSO) δ 12.17 (s, 1H), 7.82 (d, J=8.4 Hz, 1H), 7.64 (s, 1H), 7.55 (d, J=8.4 Hz, 1H), 7.28 (s, 1H), 3.95 (s, 3H), 2.70 (s, 3H)

Step 2: Methyl 3-hydroxy-4-(1-iminoethyl)benzoate

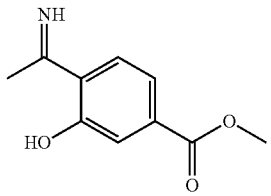

Methyl 4-acetyl-3-hydroxybenzoate (12 g, 61.80 mmol, 1.00 equiv) was dissolved in a solution of methanolic ammonia (150 mL). The resulting solution was stirred overnight at room temperature. The resulting mixture was concentrated in vacuo. This resulted in 12 g (crude) of methyl 3-hydroxy-4-(1-iminoethyl)benzoate as a light yellow solid.

Step 3: Methyl 3-methylbenzo[d]isoxazole-6-carboxylate

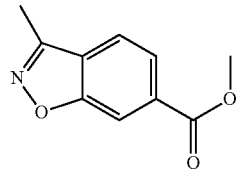

NCS (12.5 g, 1.50 equiv) and potassium carbonate (17 g, 2.00 equiv) were added to a solution of methyl 3-hydroxy-4-(1-iminoethyl)benzoate (12 g, 62.11 mmol) in THF (100 mL). The resulting solution was stirred 10 h at room temperature. The resulting mixture was concentrated in vacuo. The residue was extracted with 3×60 mL of ethyl acetate and the organic layers were combined. The organics were washed with 3×80 mL of brine. The mixture was dried over anhydrous sodium sulfate and purified by silica gel column chromatography with ethyl acetate/petroleum ether (60:1). This resulted in 11 g (93%) of methyl 3-methylbenzo[d]isoxazole-6-carboxylate as an off-white solid.

LCMS (ES, m/z): [M+H]+ 195.0

1H-NMR (400 MHz, CDCl3) δ 8.24 (s, 1H), 8.02 (d, J=8 Hz, 1H), 7.70 (s, J=8.4 Hz, 1H), 4.15 (t, 1H), 3.99 (s, 3H), 2.63 (s, 3H), 2.06 (s, 1H), 1.27 (t, 1H)

Step 4: 3-methylbenzo[d]isoxazole-6-carboxylic acid

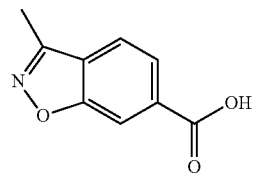

Sodium hydroxide (7 g, 175.00 mmol, 3.00 equiv) was added to a solution of methyl 3-methylbenzo[d]isoxazole-6-carboxylate (11 g, 57.54 mmol, 1.00 equiv) in methanol/

H₂O (90/30 mL). The resulting solution was stirred for 6 h at room temperature. The resulting mixture was concentrated in vacuo and the pH value was adjusted to pH 2 with aqueous HCl. The solids were collected by filtration. This resulted in 7 g (69%) of 3-methylbenzo[d]isoxazole-6-carboxylic acid as an off-white solid.

LCMS (ES, m/z): [M+H]+ 177.0

¹H-NMR (400 MHz, DMSO) δ 8.19 (s, 1H), 7.96 (m, 2H), 2.60 (s, 3H)

Step 5: Ethyl 3-(3-methylbenzo[d]isoxazol-6-yl)-3-oxopropanoate

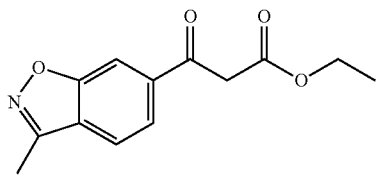 [SMILES: CCOC(=O)CC(=O)c1ccc2c(C)noc2c1]

CDI (9.6 g, 1.50 equiv) was added to a solution of 3-methylbenzo[d]isoxazole-6-carboxylic acid (7 g, 39.51 mmol) in tetrahydrofuran (80 mL) and the resulting solution was stirred for 3 h at room temperature. Then solution of potassium 3-ethoxy-3-oxopropanoate (20 g, 117.51 mmol, 2.97 equiv), MgCl₂ (17 g), triethylamine (12 g, 118.59 mmol, 3.00 equiv) in CH₃CN was added dropwise. The resulting solution was stirred for 3 h at room temperature. The resulting mixture was concentrated in vacuo. The residue was extracted with 3×100 mL of ethyl acetate and the organic layers were combined. The resulting mixture was washed with 4×80 mL of brine. The resulting mixture was concentrated in vacuo. The residue was purified by silica gel column chromatography with ethyl acetate/petroleum ether (1:30). This resulted in 6 g (61%) of ethyl 3-(3-methylbenzo[d]isoxazol-6-yl)-3-oxopropanoate as an off-white solid.

LCMS (ES, m/z): [M+H]+ 248.0

¹H-NMR (300 MHz, CDCl₃): δ 12.64 (s, 1H), 8.12 (s, 1H), 7.70 (m, 2H), 5.78 (s, 1H), 4.29 (q, 2H), 2.61 (s, 3H), 1.36 (t, 3H)

Step 6: 5-(3-methylbenzo[d]isoxazol-6-yl)-7-oxo-4,7-dihydropyrazolo[1,5-a]pyrimidine-3-carbonitrile

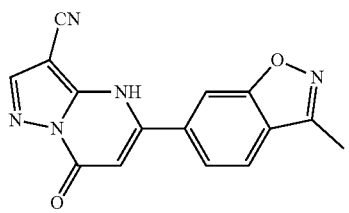 [SMILES: Cc1noc2cc(-c3cc(=O)n4ncc(C#N)c4[nH]3)ccc12]

5-amino-1H-pyrazole-4-carbonitrile (300 mg, 2.78 mmol, 1.00 equiv) was dissolved in n-BuOH (2 mL). Then ethyl 3-(3-methylbenzo[d]isoxazol-6-yl)-3-oxopropanoate (894 mg, 3.62 mmol, 1.30 equiv) and p-TsOH (48 mg, 0.10 equiv) were added. The resulting solution was stirred for 2 h at 120° C. The solids were collected by filtration. This resulted in 700 mg of 5-(3-methylbenzo[d]isoxazol-6-yl)-7-oxo-4,7-dihydropyrazolo[1,5-a]pyrimidine-3-carbonitrile as a light yellow solid.

LCMS (ES, m/z): [M+H]+ 248.0

¹H-NMR (400 MHz, DMSO) δ 8.45 (s, 1H), 8.23 (s, 1H), 8.05 (d, J=8.4 Hz, 1H), 7.85 (d, J=8 Hz, 1H), 6.41 (s, 1H), 2.78 (s, 3H)

Step 7: 5-(3-methylbenzo[d]isoxazol-6-yl)-7-oxo-4,7-dihydropyrazolo[1,5-a]pyrimidine-3-carboxamide

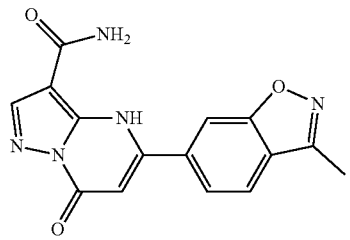 [SMILES: Cc1noc2cc(-c3cc(=O)n4ncc(C(N)=O)c4[nH]3)ccc12]

A solution of 5-(3-methylbenzo[d]isoxazol-6-yl)-7-oxo-4,7-dihydropyrazolo[1,5-a]pyrimidine-3-carbonitrile (700 mg, 2.40 mmol, 1.00 equiv) in sulfuric acid (2 mL) was stirred for 4 h at room temperature. The resulting solution was diluted with 6 mL of water/ice. The solids were collected by filtration. This resulted in 500 mg (67%) of 5-(3-methylbenzo[d]isoxazol-6-yl)-7-oxo-4,7-dihydropyrazolo[1,5-a]pyrimidine-3-carboxamide as a light yellow solid.

LCMS (ES, m/z): [M+H]+ 248.0

¹H-NMR (300 MHz, DMSO) δ 8.27 (s, 1H), 8.15 (s, 1H), 8.08 (d, J=1.2 Hz, 1H), 8.01 (s, 1H), 7.91 (d, J=8.1 Hz, 1H), 6.94 (s, 1H), 6.25 (s, 1H), 2.51 (s, 3H)

Step 8: 5-(3-methylbenzo[d]isoxazol-6-yl)-3-(oxazol-2-yl)pyrazolo[1,5-a]pyrimidin-7(4H)-one

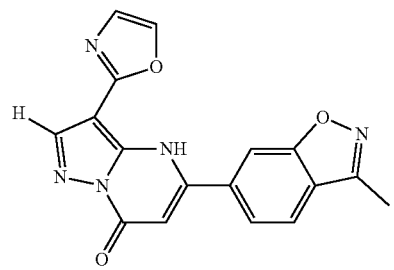 [SMILES: Cc1noc2cc(-c3cc(=O)n4ncc(-c5ncco5)c4[nH]3)ccc12]

2-Bromo-1,1-diethoxyethane (384 mg, 1.9 mmol, 1.50 equiv) was added to a solution of 5-(3-methylbenzo[d]isoxazol-6-yl)-7-oxo-4,7-dihydropyrazolo[1,5-a]pyrimidine-3-carboxamide (400 mg, 1.2 mmol, 1.00 equiv) in NMP (10 mL). The reaction was stirred for 1 h at 110° C. The solid was dried in an oven under reduced pressure. The residue was purified by silica gel column chromatography with dichloromethane/methanol (10:1). This resulted in 84.5 mg (78%) of 5-(3-methylbenzo[d]isoxazol-6-yl)-3-(oxazol-2-yl)pyrazolo[1,5-a]pyrimidin-7(4H)-one as a yellow solid.

LCMS (ES, m/z): [M+H]+ 334.0

¹H-NMR (400 MHz, DMSO) δ 8.42 (s, 1H), 8.21 (d, J=5.6 Hz, 2H), 8.07 (d, J=8.4 Hz, 1H), 7.82 (d, J=9.6 Hz, 1H), 7.42 (s, 1H), 6.38 (s, 1H), 2.79 (s, 3H)

EXAMPLE 119

5-(3-Methylbenzo[d]isoxazol-6-yl)-3-(5-methyloxazol-2-yl)pyrazolo[1,5-a]pyrimidin-7(4H)-one

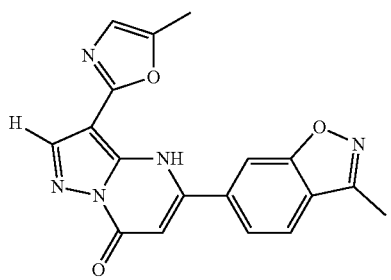 [SMILES: Cc1cnc(-c2cnn3c(=O)cc(-c4ccc5c(C)noc5c4)[nH]c23)o1]

To a solution of 4-(5-methyloxazol-2-yl)-1H-pyrazol-5-amine (50 mg, 0.31 mmol) in n-BuOH (0.2 mL) was added ethyl 3-(3-methylbenzo[d]isoxazol-6-yl)-3-oxopropanoate (98 mg, 0.40 mmol) and p-TsOH (10 mg) at room temperature. After refluxing overnight, the solids were collected by filtration and washed with methanol (3×2 mL) to afford 5-(3-methylbenzo[d]isoxazol-6-yl)-3-(5-methyloxazol-2-yl)pyrazolo[1,5-a]pyrimidin-7(4H)-one as a yellow solid (68.6 mg).

LCMS (ES, m/z): [M+H]+ 348.0

$^1$H-NMR (400 MHz, DMSO) δ 8.37 (s, 1H), 8.20 (s, 1H), 8.08 (d, J=8.4 Hz, 1H), 7.81 (d, J=9.2 Hz, 1H), 7.02 (s, 1H), 6.37 (s, 1H), 2.79 (s, 3H), 2.50 (s, 3H)

EXAMPLE 120

5-(3-Ethylbenzo[d]isoxazol-6-yl)-3-(oxazol-2-yl)pyrazolo[1,5-a]pyrimidin-7(4H)-one

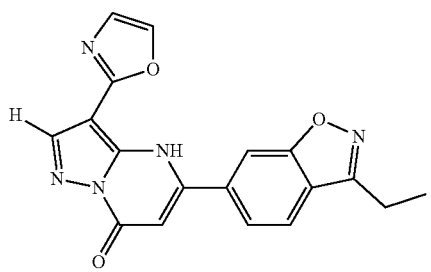 [SMILES: CCc1noc2cc(-c3cc(=O)n4ncc(-c5ncco5)c4[nH]3)ccc12]

Step 1: 1-(4-bromo-2-hydroxyphenyl)propan-1-one

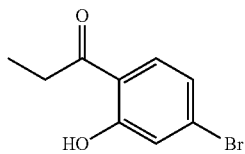

Under an inert atmosphere of nitrogen was placed a solution of 3-bromophenol (20 g, 115.6 mmol, 1.00 equiv) in DCE (200 mL). This was followed by the addition of AlCl$_3$ (20.06 g), in portions. To this was added propionyl chloride (10.75 g, 116.2 mmol, 1.00 equiv). The resulting solution was stirred for 6 h at 70° C. The mixture was poured slowly into a beaker containing ice (150 ml) and aqueous HCl (2N) (150 ml). The resulting solution was extracted with 2×100 mL of dichloromethane and the organic layers were combined and dried over anhydrous sodium sulfate and concentrated in vacuo. The residue was purified by silica gel column chromatography with ethyl acetate/petroleum ether (1:20). This resulted in 20 g (76%) of 1-(4-bromo-2-hydroxyphenyl)propan-1-one as a light yellow solid.

LCMS (ES, m/z): [M+H]+ 229

$^1$H-NMR (400 MHz, CDCl$_3$): δ 12.47 (s, 1H), 7.64 (d, J=8.8 Hz, 1H), 7.21 (d, J=2.0 Hz, 1H), 7.07 (m, 1H), 3.05 (q, J=5.7 Hz, 2H), 1.28 (t, J=5.7 Hz, 3H)

Step 2: Methyl 3-hydroxy-4-propionylbenzoate

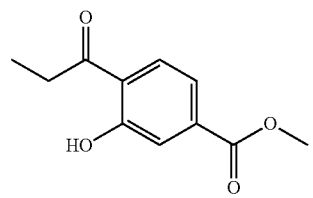

Under an atmosphere of CO (g) was placed a solution of 1-(4-bromo-2-hydroxyphenyl)propan-1-one (30 g, 130.96 mmol, 1.00 equiv) in methanol (1500 mL), Pd(dppf)Cl$_2$ (5.37 g, 7.34 mmol, 0.06 equiv) and TEA (26.58 g, 262.67 mmol, 2.01 equiv). The reaction was stirred for 12 h at 100° C. The resulting mixture was concentrated in vacuo. The residue was purified by silica gel column chromatography with ethyl acetate/petroleum ether (1:20). This resulted in 16 g (58.67%) of methyl 3-hydroxy-4-propionylbenzoate as an off-white solid.

LCMS (ES, m/z): [M+H]$^+$ 209

$^1$H-NMR (300 MHz, CDCl$_3$): δ 7.83 (d, J=8.1 Hz, 1H), 7.63 (s, 1H), 7.54 (d, J=10.2 Hz, 1H), 3.93 (s, 3H), 3.08 (q, J=7.2 Hz, 2H), 1.25 (t, J=7.2 Hz, 3H)

Step 3: Methyl 3-hydroxy-4-(1-iminopropyl)benzoate

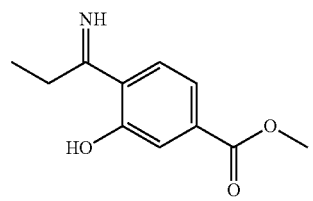

A solution of methyl 3-hydroxy-4-propionylbenzoate (16 g, 76.85 mmol, 1.00 equiv) in methanolic ammonia (160 mL) was stirred for 10 h at room temperature. The resulting mixture was concentrated in vacuo. This resulted in 16 g (crude) of methyl 3-hydroxy-4-(1-iminopropyl)benzoate as a yellow solid.

Step 4: Methyl 3-ethylbenzo[d]isoxazole-6-carboxylate

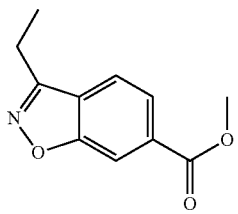

A solution of methyl 3-hydroxy-4-(1-iminopropyl)benzoate (16 g, 77.21 mmol, 1.00 equiv) in tetrahydrofuran (160 mL), potassium carbonate (21.33 g, 154.33 mmol, 2.00 equiv), and NCS (15.46 g, 115.78 mmol, 1.50 equiv) was stirred for 10 h at room temperature. The resulting solution was diluted with 100 mL of H$_2$O. The resulting solution was extracted with 2×100 mL of ethyl acetate and the organic layers combined. The residue was applied onto a silica gel column with ethyl acetate/petroleum ether (1:20). This resulted in 5.2 g (33%) of methyl 3-ethylbenzo[d]isoxazole-6-carboxylate as a yellow solid.

LCMS (ES, m/z): [M+H]+ 206

$^1$H-NMR (300 MHz, CDCl$_3$): δ 8.23 (s, 1H), 8.01 (d, J=9.6 Hz, 1H), 9.71 (d, J=12.9 Hz, 1H), 3.95 (s, 3H), 3.07 (q, J=7.5 Hz, 2H), 1.47 (t, J=7.5 Hz, 3H)

Step 5: 3-ethylbenzo[d]isoxazole-6-carboxylic acid

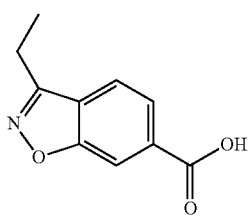

To a solution of methyl 3-ethylbenzo[d]isoxazole-6-carboxylate (5 g, 24.37 mmol, 1.00 equiv) in methanol (50 mL) was added a solution of sodium hydroxide (3 g, 75.00 mmol, 3.08 equiv) in water (10 mL). The reaction was stirred for 6 h at room temperature, then concentrated in vacuo. The resulting residue was diluted with 100 mL of H$_2$O. The pH of the solution was adjusted to pH 3 with HCl (2M). The solids were collected by filtration. This resulted in 4 g (86%) of 3-ethylbenzo[d]isoxazole-6-carboxylic acid as an off-white solid.

LCMS (ES, m/z): [M+H]+ 192

$^1$H-NMR (400 MHz, DMSO): δ 13.43 (s, 1H), 8.19 (s, 1H), 8.02 (d, J=8.2 Hz, 1H), 7.94 (d, J=9.2 Hz, 1H), 3.06 (q, J=7.6 Hz, 2H), 1.36 (t, J=7.6 Hz, 3H)

Step 6: ethyl 3-(3-ethylbenzo[d]isoxazol-6-yl)-3-oxopropanoate

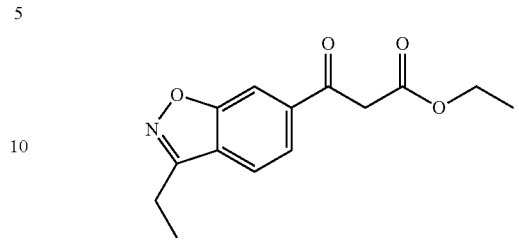

To a solution of 3-ethylbenzo[d]isoxazole-6-carboxylic acid (4 g, 20.92 mmol, 1.00 equiv) in tetrahydrofuran (50 mL) was added CDI (5.1 g, 31.45 mmol, 1.50 equiv). The reaction was stirred for 2 h at 40° C. Separately, to a solution of potassium 3-ethoxy-3-oxopropanoate (10.7 g, 62.87 mmol, 3.00 equiv) in CH$_3$CN (50 mL) was added triethylamine (6.3 g, 62.26 mmol, 2.98 equiv) and MgCl$_2$ (9 g). The two solutions were combined and stirred for 1 h at room temperature. The reaction progress was monitored by TLC (ethyl acetate/petroleum ether=1:5). Then the reaction mixture was concentrated in vacuo. The residue was diluted with 200 mL of H$_2$O. The pH of the solution was adjusted to pH 4 with HCl (2M). The resulting solution was extracted with 4×100 mL of ethyl acetate and the organic layers were combined and dried over anhydrous sodium sulfate. The resulting mixture was concentrated in vacuo and purified by silica gel column chromatography with ethyl acetate/petroleum ether (1:50). This resulted in 4 g (73%) of ethyl 3-(3-ethylbenzo[d]isoxazol-6-yl)-3-oxopropanoate as an off-white solid.

LCMS (ES, m/z): [M+H]+ 262.0

$^1$H-NMR (400 MHz, CDCl$_3$): δ 8.12 (s, 1H), 7.91 (d, J=7.2 Hz, 1H), 7.77 (d, J=8.4 Hz, 1H), 7.68 (s, 1H), 4.29-4.26 (m, 3H), 4.07 (s, 2H), 3.07-3.05 (m, 3H), 1.30-1.24 (m, 6H)

Step 7: 5-(3-ethylbenzo[d]isoxazol-6-yl)-7-oxo-4,7-dihydropyrazolo[1,5-a]pyrimidine-3-carbonitrile

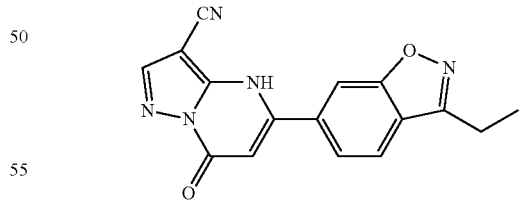

p-TsOH (30 g). was added to a solution of ethyl 3-(3-ethylbenzo[d]isoxazol-6-yl)-3-oxopropanoate (1.2 g, 4.59 mmol, 1.30 equiv) and 5-amino-1H-pyrazole-4-carbonitrile (382 mg, 3.53 mmol, 1.00 equiv) in n-BuOH (0.5 mL). The resulting solution was stirred for 1 h at 110° C. The solids were collected by filtration and washed with 5×1 mL of methanol. This resulted in 800 mg (74%) of 5-(3-ethylbenzo[d]isoxazol-6-yl)-7-oxo-4,7-dihydropyrazolo[1,5-a]pyrimidine-3-carbonitrile as an off-white solid.

Step 8: 5-(3-ethylbenzo[d]isoxazol-6-yl)-7-oxo-4,7-dihydropyrazolo[1,5-a]pyrimidine-3-carboxamide

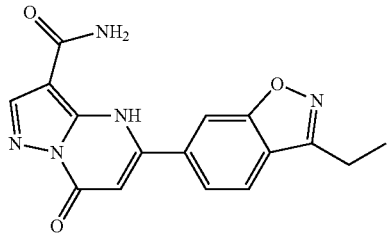 [SMILES: CCc1noc2cc(-c3cc(=O)n4ncc(C(N)=O)c4[nH]3)ccc12]

A solution of 5-(3-ethylbenzo[d]isoxazol-6-yl)-7-oxo-4,7-dihydropyrazolo[1,5-a]pyrimidine-3-carbonitrile (700 mg, 2.29 mmol, 1.00 equiv) in sulfuric acid (5 mL) was stirred for 1 h at room temperature. The resulting solution was diluted with 10 mL of ice/water. The solids were collected by filtration. This resulted in 700 mg (94%) of 5-(3-ethylbenzo[d]isoxazol-6-yl)-7-oxo-4,7-dihydropyrazolo[1,5-a]pyrimidine-3-carboxamide as a yellow solid.

LCMS (ES, m/z): [M+H]+ 324.0

$^1$H-NMR (300 MHz, DMSO): δ 8.41 (s, 1H), 8.19 (s, 1H), 8.10 (d, 1H, J=4.0 Hz), 7.78 (d, 2H, J=4.0 Hz), 6.38 (s, 1H), 3.09 (q, 2H, J=22.5 Hz), 1.38 (t, 3H, J=22.5 Hz)

Step 9: 5-(3-ethylbenzo[d]isoxazol-6-yl)-3-(oxazol-2-yl)pyrazolo[1,5-a]pyrimidin-7(4H)-one

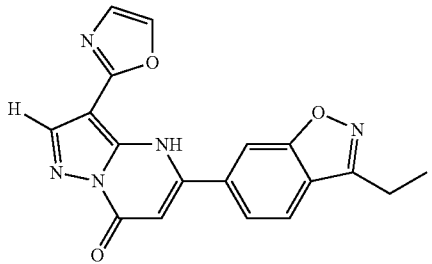 [SMILES: CCc1noc2cc(-c3cc(=O)n4ncc(-c5ncco5)c4[nH]3)ccc12]

2-bromo-1,1-diethoxyethane (91.5 mg, 0.46 mmol, 1.50 equiv) was added to a solution of 5-(3-ethylbenzo[d]isoxazol-6-yl)-7-oxo-4,7-dihydropyrazolo[1,5-a]pyrimidine-3-carboxamide (100 mg, 0.31 mmol, 1.00 equiv) in NMP (0.5 mL). The resulting solution was stirred for 1 h at 110° C. The crude product was purified by Prep-HPLC under the following conditions: Column, XBridge Shield RP18 OBD Column, 5 um, 19*150 mm; mobile phase, water with 0.05% TFA and MeCN (25.0% MeCN up to 35.0% in 4 min, hold 35.0% in 1 min, up to 97.0% in 1 min); Detector, uv 254 nm. This resulted in 55.7 mg (52%) of 5-(3-ethylbenzo[d]isoxazol-6-yl)-3-(oxazol-2-yl)pyrazolo[1,5-a]pyrimidin-7(4H)-one as a white solid.

LCMS (ES, m/z): [M+H]+ 348

$^1$H-NMR (DMSO, 400 MHz): δ 8.43 (s, 1H), 8.21 (d, J=4 Hz, 2H), 8.12 (d, J=8 Hz, 1H), 7.82 (d, J=9.6 Hz, 1H), 7.42 (s, 1H), 3.09 (q, 2H, J=7.6 Hz), 1.39 (t, 3H, J=7.6 Hz)

EXAMPLE 121

5-(3-ethylbenzo[d]isoxazol-6-yl)-3-(5-methyloxazol-2-yl)pyrazolo[1,5-a]pyrimidin-7(4H)-one

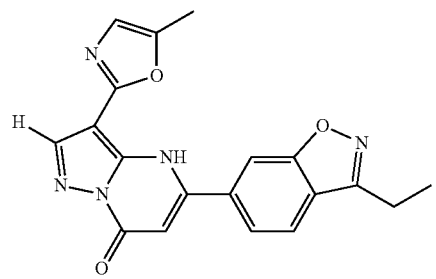 [SMILES: CCc1noc2cc(-c3cc(=O)n4ncc(-c5ncc(C)o5)c4[nH]3)ccc12]

To a solution of 4-(5-methyloxazol-2-yl)-1H-pyrazol-5-amine (50 mg, 0.31 mmol) in n-BuOH (0.2 mL) was added ethyl 3-(3-ethylbenzo[d]isoxazol-6-yl)-3-oxopropanoate (113.6 mg, 0.46 mmol) and p-TsOH (10 mg) at room temperature. After refluxing overnight, the solids were collected by filtration and washed with methanol (3×2 mL) to afford 5-(3-ethylbenzo[d]isoxazol-6-yl)-3-(5-methyloxazol-2-yl)pyrazolo[1,5-a]pyrimidin-7(4H)-one as a yellow solid (28.9 mg).

LCMS (ES, m/z): [M+H]+ 362.0

$^1$H-NMR (300 MHz, DMSO) δ 8.36 (s, 1H), 8.20 (s, 1H), 8.12 (d, J=8.4 Hz, 1H), 7.79 (m, 1H), 7.02 (d, J=1.2 Hz, 1H), 6.37 (s, 1H), 3.08 (q, J=7.5 Hz, 2H), 2.39 (s, 3H), 1.39 (t, J=7.5 Hz, 3H)

EXAMPLE 122

5-(3-methylbenzo[d]isoxazol-6-yl)-7-oxo-4,7-dihydropyrazolo[1,5-a]pyrimidine-3-carboxamide

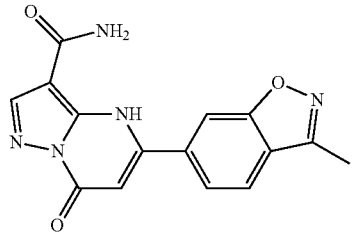 [SMILES: Cc1noc2cc(-c3cc(=O)n4ncc(C(N)=O)c4[nH]3)ccc12]

5-(3-Methylbenzo[d]isoxazol-6-yl)-7-oxo-4,7-dihydropyrazolo[1,5-a]pyrimidine-3-carbonitrile (100 mg, 0.34 mmol, 1.00 equiv) was dissolved in H$_2$SO$_4$ (2 mL). The resulting solution was stirred for 4 h at room temperature. The resulting mixture was concentrated in vacuo. The residue was purified by silica gel column chromatography with dichloromethane/methanol (10:1). This resulted in 22.7 mg (21%) of 5-(3-methylbenzo[d]isoxazol-6-yl)-7-oxo-4,7-dihydropyrazolo[1,5-a]pyrimidine-3-carboxamide as a light yellow solid.

LCMS (ES, m/z): [M+H]+ 310.0

$^1$H-NMR (400 MHz, DMSO) δ 8.26 (s, 1H), 8.05 (d, J=8 Hz, 1H), 8.00 (s, 1H), 7.90 (d, J=8 Hz, 1H), 6.25 (s, 1H), 2.58 (s, 3H)

EXAMPLE 123

5-(3-ethylbenzo[d]isoxazol-6-yl)-7-oxo-4,7-dihydro-pyrazolo[1,5-a]pyrimidine-3-carboxamide

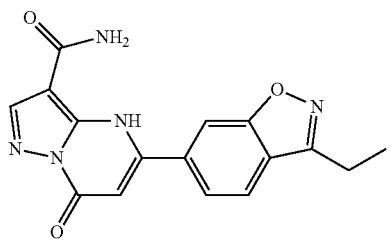 [SMILES: CCc1noc2cc(-c3cc(=O)n4ncc(C(N)=O)c4[nH]3)ccc12]

5-(3-Ethylbenzo[d]isoxazol-6-yl)-7-oxo-4,7-dihydropyrazolo[1,5-a]pyrimidine-3-carbonitrile (100 mg, 0.33 mmol, 1.00 equiv) was dissolved in sulfuric acid (2 mL). The resulting solution was stirred for 1 h at room temperature. The resulting solution was diluted with 10 mL of water/ice. The solids were collected by filtration. The crude product was purified by Prep-HPLC under the following conditions: Column, XBridge Shield RP18 OBD Column,5 um,19*150 mm; mobile phase, water with 0.05% TFA and MeCN (25.0% MeCN up to 35.0% in 4 min, hold 35.0% in 1 min, up to 97.0% in 1 min; Detector, uv 254 nm. This resulted in 7.9 mg (7%) of 5-(3-ethylbenzo[d]isoxazol-6-yl)-7-oxo-4,7-dihydropyrazolo[1,5-a]pyrimidine-3-carboxamide as an off-white solid.

LCMS (ES, m/z): [M+H]+ 324

$^1$H-NMR (400 MHz, DMSO): δ 8.27 (s, 1H), 8.05 (d, J=8 Hz, 1H), 7.99 (s, 1H), 7.94 (d, J=8.2 Hz, 1H), 6.24 (s, 1H), 3.04 (q, J=7.6 Hz, 2H), 1.38 (t, J=7.6 Hz, 3H)

The following compounds can generally be made using the methods known in the art and described above. It is expected that these compounds when made will have activity similar to those that have been made in the examples above.

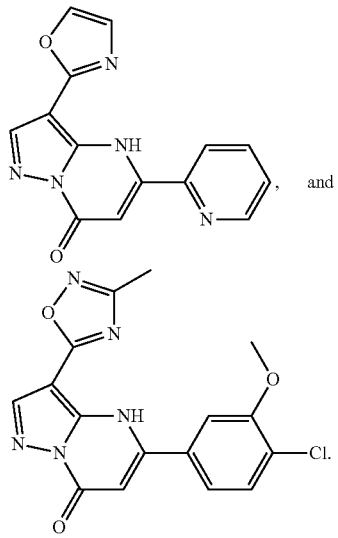

The activity of the compounds in Examples 1-123 as PASK modulators and PIM1 and CK2 inhibitors is illustrated in the following assays.

Biochemical Assay for hPASK Activity

PASK ATP Radiochemical Assay

Purified PASK (UniProt #Q96RG2; human recombinant N-terminal GST tagged construct, residues 879-1323) from insect cells (final concentration 5 nM) is added to freshly prepared Base Reaction Buffer containing 20 mM HEPES (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and Myelin Basic Protein (20 μM final). Test compounds in DMSO are then added and the mixture, followed by delivery of $^{33}$P-ATP (specific activity 0.01 μCi/μl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results for this assay are shown below in Table 1. Examples not listed in the table were not tested.

TABLE 1

| Example # | IC$_{50}$ Kinase Domain<br>+ indicates ≤10 μm<br>− indicates >10 μm |
|---|---|
| 1 | + |
| 2 | + |
| 3 | + |
| 4 | + |
| 5 | + |
| 13 | + |
| 15 | + |
| 16 | + |
| 17 | + |
| 18 | + |
| 19 | + |
| 20 | + |
| 21 | + |
| 23 | + |
| 24 | + |
| 27 | + |
| 54 | + |
| 55 | + |
| 56 | + |
| 57 | + |
| 58 | + |
| 59 | + |
| 64 | + |
| 65 | + |
| 66 | + |
| 67 | + |
| 68 | + |
| 69 | + |
| 70 | + |
| 71 | + |
| 73 | + |
| 74 | + |
| 79 | + |
| 83 | + |
| 84 | + |
| 85 | + |
| 86 | + |
| 87 | + |
| 89 | + |
| 91 | + |
| 93 | + |
| 94 | + |
| 95 | + |
| 96 | + |
| 98 | + |
| 100 | + |

PAS Kinase FRET Assay

The aim of the FRET assay is to determine the inhibition potential of test compounds on targeted kinase. This assay platform provides a homogenous screening method for measuring kinase activity by quantitating the amount of phospho-substrate in solution following a kinase reaction.

In the presence of kinase and ATP, the Ulight-peptide is phosphorylated and captured by an anti-phospho-substrate antibody, which brings the Eu chelate donor and Ulight acceptor dyes into close proximity. Upon excitation at 340 nm, the Eu chelate transfers its energy to the Ulight dye, resulting in a fluorescent light emission at 665 nm.

Titration of kinase at 1 mM ATP was achieved via the following protocol. After making serial three-fold dilutions of PASK (Invitrogen) in reaction buffer across the plate; 5 μl of kinase dilution and 5 μl substrate/ATP mix were added to the wells of the white Optiplate-384 (PerkinElmer). The contents of the plate were and incubated at RT for 1 h. The reaction was stopped by adding 5 μl of stop solution to each test well followed by mixing and incubation at RT for 10 minutes. 5 μl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$.

Titration of ATP at the $EC_{50}$ concentration of kinase to determine ATP Km,app. was performed using the following method. After making serial dilutions of ATP (Invitrogen), 5 μl of ATP dilution and 5 μl substrate/kinase mix were added to the wells of the white Optiplate-384 (PerkinElmer). The contents of the plate were and incubated at RT for 1 h. The reaction was stopped by adding 5 μl of stop solution to each test well followed by mixing and incubation at RT for 10 minutes. 5 μl of detection mix (detection antibody diluted in detection buffer) was added; the contents of the plate were mixed and then incubated in the dark for 1 hour at RT. The signal was recorded at TR-FRET mode (665 nm/615 nm). The results were graphed to calculate the $EC_{50}$ as the ATP Km,app.

Compound screening was done via the following method. 10 mM stock solution of test compound in DMSO was prepared by dissolving test compound in DMSO at RT for 1 hour, and then sonicating at 100% output for 8 minutes. If compound is not soluble under this condition, it was diluted to 3 mM. Kinase reaction buffer was prepared containing 10 mM $MgCl_2$, 50 mM HEPES, 1 mM EGTA, 0.01% TWEEN-20, 2 mM DTT. Serial dilutions of the test compounds were prepared at 4× final assay concentrations using Freedom EVO200® dispensing system as follows: $12 \times 10^{-5}$ M, $4 \times 10^{-5}$ M, $1.33 \times 10^{-5}$ M, $4.44 \times 10^{-6}$ M, $1.48 \times 10^{-6}$ M, $4.92 \times 10^{-7}$ M, $1.65 \times 10^{-7}$ M, $5.48 \times 10^{-7}$ M, $1.82 \times 10^{-8}$ M, $6.09 \times 10^{-9}$, $2.03 \times 10^{-9}$ M. Test compounds (2.5 μl at 4× the final assay concentration) was added to wells using Freedom EVO200® dispensing system. As a positive control, 2.5 μl of positive compound was added to assay wells, and 2.5 μl of DMSO to assay wells as vehicle control. Kinase solution was prepared in reaction buffer at 2× final assay concentration. Kinase solution (5 μl) was added to each well of the assay plate. The substrate and ATP solution was prepared in kinase reaction buffer at 4× final assay concentration. The kinase reaction was started by adding 2.5 μl of substrate+ATP mix solution to each well of the assay plate. The plate is mixed on a plate shaker; then covered and allowed to react for 2 hours in the dark at 25° C. without shaking. The reaction was stopped by adding 5 μl of stop solution to each test well followed by mixing and incubation at RT for 10 minutes in the dark. 5 μl of detection mix (detection antibody diluted in detection buffer) was added; the contents of the plate were mixed and then incubated in the dark for 1 hour at RT. The signal was recorded at TR-FRET mode (665 nm/615 nm).

Results are shown below in Table 2. Examples not listed in the table were not tested.

TABLE 2

| Example # | $IC_{50}$ Kinase Domain<br>+ indicates ≤10 μm<br>− indicates >10 μm |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 62 | + |
| 63 | + |
| 64 | + |
| 65 | + |
| 66 | + |
| 67 | + |
| 69 | + |
| 70 | + |
| 71 | + |

TABLE 2-continued

| Example # | IC$_{50}$ Kinase Domain<br>+ indicates ≤10 μm<br>− indicates >10 μm |
|---|---|
| 72 | + |
| 73 | + |
| 74 | + |
| 75 | + |
| 76 | + |
| 78 | + |
| 79 | + |
| 80 | + |
| 81 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 105 | + |
| 106 | + |
| 107 | + |
| 108 | + |
| 109 | + |
| 110 | + |
| 111 | + |
| 112 | + |
| 113 | − |
| 114 | + |
| 115 | + |
| 116 | + |
| 117 | + |
| 118 | + |
| 119 | + |
| 120 | + |
| 121 | + |
| 122 | + |
| 123 | + |

TABLE 3

| Example # | IC$_{50}$ CK2a2<br>+ indicates ≤10 μm<br>− indicates >10 μm |
|---|---|
| 2 | + |
| 3 | + |
| 4 | + |
| 5 | + |
| 13 | + |
| 15 | + |
| 16 | + |
| 17 | + |
| 18 | + |
| 19 | + |
| 20 | + |
| 21 | − |
| 23 | + |
| 24 | + |
| 27 | + |
| 54 | + |
| 55 | + |
| 56 | + |
| 57 | + |
| 58 | + |
| 59 | + |
| 64 | + |
| 65 | + |
| 66 | + |
| 67 | + |
| 68 | + |
| 69 | + |
| 70 | + |
| 71 | + |
| 73 | + |
| 74 | + |
| 79 | + |
| 83 | + |
| 84 | + |
| 85 | + |
| 86 | + |
| 87 | + |
| 89 | + |
| 91 | + |
| 93 | + |
| 94 | + |
| 95 | + |
| 96 | − |
| 98 | + |
| 100 | + |

Biochemical Assay for CK2 Activity

Purified CK2a2 (NP_001887; human full-length protein, GST tagged) from insect cells (final concentration 1.2 nM) is added to freshly prepared Base Reaction Buffer containing 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and CK2 sub [RRRDDDSDDD] (20 μM final). Test compounds in DMSO are then added and the mixture, followed by delivery of $^{33}$P-ATP (specific activity 0.01 μCi/μl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results are shown below in Table 3. Examples not listed in the table were not tested.

Biochemical Assay for PIM1 Activity

Purified PIM1 (NP_002639; human full-length protein, 6×His tagged) from insect cells (final concentration 1.0 nM) is added to freshly prepared Base Reaction Buffer containing 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO and substrate S6K/Rsk2 peptide 2 [KKRNRTLTK] (20 μM final). Test compounds in DMSO are then added and the mixture, followed by delivery of $^{33}$P-ATP (specific activity 10 μCi/μl final) to initiate the reaction. The kinase reaction is incubated for 120 min at room temperature. The entire reaction mixture is washed through onto a P81 Phosphocellulose paper and washed three times for 10 minutes in 75 mM phosphoric acid and once in methanol prior to drying and scintillation counting.

Results are shown below in Table 4. Examples not listed in the table were not tested.

TABLE 4

| Example # | IC$_{50}$ PIM1<br>+ indicates ≤10 μm<br>− indicates >10 μm |
|---|---|
| 2 | + |
| 3 | + |
| 4 | + |
| 5 | + |
| 13 | + |
| 15 | + |
| 16 | + |
| 17 | + |
| 18 | + |
| 19 | + |
| 20 | + |
| 21 | + |
| 23 | + |
| 24 | + |
| 27 | + |
| 54 | + |
| 55 | + |
| 56 | + |
| 57 | + |
| 58 | + |
| 59 | + |
| 64 | + |
| 65 | + |
| 66 | + |
| 67 | + |
| 68 | + |
| 69 | + |
| 70 | + |
| 71 | + |
| 73 | + |
| 74 | + |
| 79 | + |
| 83 | + |
| 84 | + |
| 85 | + |
| 86 | + |
| 87 | + |
| 89 | + |
| 91 | + |
| 93 | + |
| 94 | + |
| 95 | + |
| 96 | + |
| 98 | + |
| 100 | + |

Pharmacokinetics of a PASK Inhibitor

The in vivo pharmacokinetics of Examples 12, 17, 43, and 51 were evaluated in the Sprague Dawley rat. The test compounds were formulated as indicated in the table below. Blood samples were collected at 0.083, 0.25, 0.5, 1, 2, 4, 6, 8, and 24 hours and the samples were analyzed for test compounds content using LC/MS/MS. The data was submitted to pharmacokinetic analysis using WinNonLin software and the observed and calculated pharmacokinetic parameters are shown in Table 5 for each compound. Examples not listed in the table were not tested.

TABLE 5

| Ex. # | Route | Dosing Level (mg/kg) | Formulation | Cl (ml/min/kg) | $t_{1/2}$ (hr) | $V_{ss}$ (L/kg) | F (%) | $T_{max}$ (hr) |
|---|---|---|---|---|---|---|---|---|
| 12 | IV | 3 | 30% PEG400 and 10% solutol in saline (solution) | 8.76 | 3.75 | 0.35 | NA | NA |
| 12 | PO | 10 | 30% PEG400 and 10% solutol in saline (solution) | NA | 2.38 | NA | 46.5 | 0.5 |
| 17 | IV | 3 | 10% Ethanol and 50% PEG400 and 10% Tween 80 in "10% HP-β-CD in Saline" | 6.19 | 8.3 | 0.61 | NA | NA |
| 17 | PO | 10 | 30% PEG400 and 10% solutol in saline | NA | 2.12 | NA | 42 | 4 |
| 43 | IV | 3 | Saline (1M Na$_2$CO$_3$) (solution) | 23.9 | 1.62 | 0.719 | NA | NA |
| 43 | PO | 10 | Saline (adjust with 1M Na$_2$CO$_3$) (solution) | NA | 3.35 | NA | 44.7 | 0.5 |
| 51 | IV | 3 | Saline (adjust 1M Na$_2$CO$_3$) (solution) | 62 | 0.38 | 0.71 | NA | NA |
| 51 | PO | 10 | Saline (adjust 1M Na$_2$CO$_3$) (solution) | NA | 2.62 | NA | 1.17 | 0.25 |

Cl = clearance;
$t_{1/2}$ = half-life;
$V_{ss}$ = volume of distribution;
F = oral bioavailability;
$T_{max}$ = Time to maximum blood concentration after an oral dose From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula II

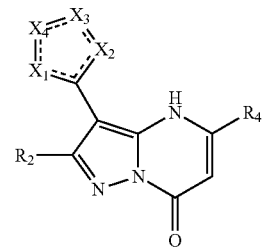

(II)

or a pharmaceutically acceptable salt or ester thereof, wherein:

$X_1$ is chosen from $NR_{16}$, O, and $CR_{10}$;
$X_2$ is chosen from $NR_{17}$, O, and $CR_{11}$;
$X_3$ is chosen from $NR_{14}$ and $CR_{12}$;
$X_4$ is chosen from O, $NR_{15}$ and $CR_{13}$;
$R_2$ is chosen from hydrogen, hydroxy, alkoxy, $NHCOR_{20}$, lower alkyl, lower haloalkyl, aryl, arylalkyl, heteroaryl and heteroarylalkyl, any of which may be optionally substituted;
$R_4$ is chosen from $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{10}$, $R_{11}$, $R_{12}$, and $R_{13}$, are each independently chosen from absent, hydrogen, lower alkyl, aryl, lower alkoxy, hydroxy, and halo, or optionally, $R_{12}$ and $R_{13}$ can be taken together to form an aryl or heteroaryl, or $R_{11}$ and $R_{12}$ can be taken together to form an aryl or heteroaryl;

$R_{14}$ and $R_{15}$ are each independently chosen from absent, hydrogen, lower alkyl, aryl, lower alkoxy, hydroxy, halo, $COR_{20}$, and $SO_2R_{20}$;

$R_{16}$ and $R_{17}$ are each independently chosen from absent, hydrogen, and lower alkyl; and $R_{20}$ is chosen from lower alkyl, arylalkyl, aryl, heteroaryl, and heteroarylalkyl;

wherein at least two of $X_1$, $X_2$, $X_3$, and $X_4$ are heteroatoms.

2. A compound as recited in claim 1 wherein $R_2$ is chosen from hydrogen, hydroxyl, alkoxy, lower alkyl, and lower haloalkyl, any of which may be optionally substituted.

3. A compound as recited in claim 1 wherein $R_4$ is chosen from aryl and heteroaryl, either of which may be optionally substituted.

4. A compound as recited in claim 1, having structural Formula III

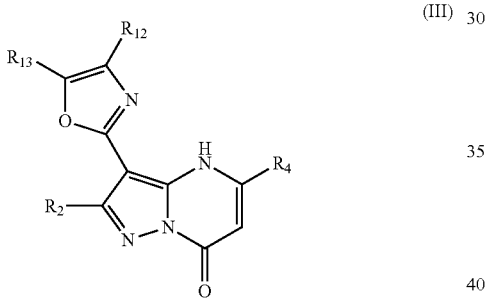

(III)

or a pharmaceutically acceptable salt or ester thereof, wherein:

$R_2$ is chosen from hydrogen, hydroxy, alkoxy, $NHCOR_{20}$, lower alkyl, lower haloalkyl, aryl, arylalkyl, heteroaryl and heteroarylalkyl, any of which may be optionally substituted;

$R_4$ is chosen from $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{12}$ and $R_{13}$ are each independently chosen from hydrogen, lower alkyl, aryl, lower alkoxy, hydroxy, and halo, or optionally, $R_{12}$ and $R_{13}$ can be taken together to form an aryl or heteroaryl; and $R_{20}$ is chosen from lower alkyl, arylalkyl, aryl, heteroaryl, and heteroarylalkyl.

5. A compound as recited in claim 4 wherein $R_2$ is chosen from hydrogen, hydroxyl, alkoxy, lower alkyl, and lower haloalkyl, any of which may be optionally substituted.

6. A compound as recited in claim 4 wherein $R_4$ is chosen from aryl and heteroaryl, either of which may be optionally substituted.

7. A compound as recited in claim 1, having structural Formula V

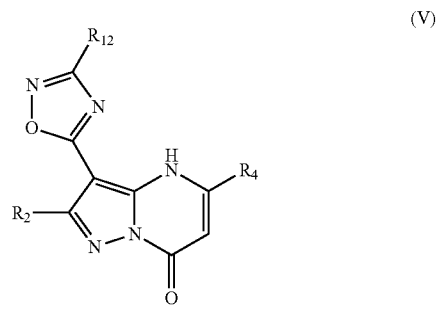

(V)

or a pharmaceutically acceptable salt or ester thereof, wherein:

$R_2$ is chosen from hydrogen, hydroxy, alkoxy, $NHCOR_{20}$, lower alkyl, lower haloalkyl, aryl, arylalkyl, heteroaryl and heteroarylalkyl, any of which may be optionally substituted;

$R_4$ is chosen from $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{12}$ is chosen from hydrogen, lower alkyl, aryl, lower alkoxy, hydroxy, and halo; and $R_{20}$ is chosen from lower alkyl, arylalkyl, aryl, heteroaryl, and heteroarylalkyl.

8. A compound as recited in claim 1, having structural Formula IX

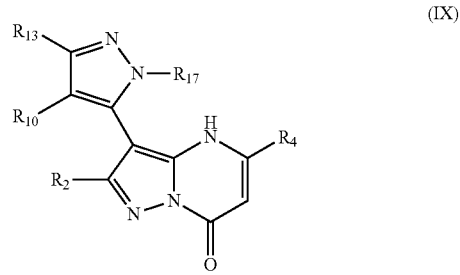

(IX)

or a pharmaceutically acceptable salt or ester thereof, wherein:

$R_2$ is chosen from hydrogen, hydroxy, alkoxy, $NHCOR_{20}$, lower alkyl, lower haloalkyl, aryl, arylalkyl, heteroaryl and heteroarylalkyl, any of which may be optionally substituted;

$R_4$ is chosen from $CH_2CO_2R_5$, alkoxyalkyl, aryl, heteroaryl, cycloalkyl, arylalkyl, heteroarylalkyl, and cycloalkylalkyl, any of which may be optionally substituted;

$R_5$ is chosen from hydrogen and lower alkyl;

$R_{10}$ and $R_{13}$ are each independently chosen from hydrogen, lower alkyl, aryl, lower alkoxy, hydroxy, and halo;

$R_{17}$ is chosen from hydrogen and lower alkyl; and $R_{20}$ is chosen from lower alkyl, arylalkyl, aryl, heteroaryl, and heteroarylalkyl.

9. A pharmaceutical composition comprising a compound as recited in claim 1 together with a pharmaceutically acceptable carrier.

10. A method of inhibiting PASK comprising contacting PASK with a compound as recited in claim 1.

11. A method for achieving an effect in a patient comprising the administration of a therapeutically effective amount of a compound as recited in claim 1 to a patient in need thereof, wherein the effect is selected from the group consisting of reduction of triglycerides, reduction of cholesterol, and reduction of hemoglobin A1c.

12. The method of claim 11 wherein said cholesterol is chosen from LDL and VLDL cholesterol.

13. The method of claim 11 wherein said triglycerides are chosen from plasma triglycerides and liver triglycerides.

14. A compound as recited in claim 1, wherein said compound is chosen from
- 5-(1-ethyl-1H-indazol-5-yl)-3-(5-methyl-1,3-oxazol-2-yl)-4H,7H-pyrazolo[1,5-a]pyrimidin-7-one;
- 5-(4-chloro-3-methoxyphenyl)-3-(5-methyl-1,3-oxazol-2-yl)-4H,7H-pyrazolo[1,5-a]pyrimidin-7-one;
- 5-(1-ethyl-1H-indazol-5-yl)-3-(3-methyl-1,2,4-oxadiazol-5-yl)-4H,7H-pyrazolo[1,5-a]pyrimidin-7-one; and
- 5-(4-chloro-3-methoxyphenyl)-3-(1-methyl-1H-pyrazol-5-yl)pyrazolo[1,5-a]pyrimidin-7(4H)-one.

* * * * *